United States Patent
Palmer et al.

(10) Patent No.: US 9,642,996 B2
(45) Date of Patent: May 9, 2017

(54) METHODS AND APPARATUS FOR ADMINISTERING SMALL VOLUME ORAL TRANSMUCOSAL DOSAGE FORMS

(71) Applicant: AcelRx Pharmaceuticals, Inc., Redwood City, CA (US)

(72) Inventors: Pamela Palmer, San Francisco, CA (US); Andrew Poutiatine, Mill Valley, CA (US); Charles Rampersaud, Castro Valley, CA (US); Bruce Edwards, Menlo Park, CA (US); Edmond Chiu, San Francisco, CA (US); Thomas Schreck, Portola Valley, CA (US); Stelios Tzannis, Petaluma, CA (US); Lawrence Hamel, Pacific Grove, CA (US); William Kolosi, Stow, OH (US); Sascha Retailleau, San Francisco, CA (US)

(73) Assignee: AcelRx Pharmaceuticals, Inc., Redwood City, CA (US)

( * ) Notice: Subject to any disclaimer, the term of this patent is extended or adjusted under 35 U.S.C. 154(b) by 173 days.

(21) Appl. No.: 14/305,422

(22) Filed: Jun. 16, 2014

(65) Prior Publication Data
US 2015/0038898 A1    Feb. 5, 2015

Related U.S. Application Data

(63) Continuation of application No. 13/678,141, filed on Nov. 15, 2012, now Pat. No. 8,753,308, which is a (Continued)

(51) Int. Cl.
*A61M 31/00* (2006.01)
*A61J 7/00* (2006.01)
*A61J 7/04* (2006.01)

(52) U.S. Cl.
CPC .......... *A61M 31/007* (2013.01); *A61J 7/0053* (2013.01); *A61J 7/0418* (2015.05);
(Continued)

(58) Field of Classification Search
CPC ...... A61J 7/0445; A61J 7/0481; A61J 7/0409; A61J 2205/60; A61J 7/0053;
(Continued)

(56) References Cited

U.S. PATENT DOCUMENTS 2,621,655 A    12/1952  Olson et al.
3,162,322 A    12/1964  Gilbertson
(Continued)

FOREIGN PATENT DOCUMENTS

CN    2776369 Y    5/2006
EP    1174363      1/2002
(Continued)

OTHER PUBLICATIONS

Abrams, R. et al., "Safety and effectiveness of intranasal administration of sedative medications (ketamine, midazolam, or sufentanil) for urgent brief pediatric dental procedures," Anesth. Prog., 40:63-66 (1993).
(Continued)

*Primary Examiner* — Bhisma Mehta
*Assistant Examiner* — Brandy S Lee

(57) ABSTRACT

Systems and methods for administration of small volume sufentanil drug dosage forms to the sublingual mucosa of a subject using a device are disclosed. The dispensing device includes a lock-out feature and a means to retard or prevent saliva and/or moisture ingress such that the drug dosage forms in the device remain dry prior to administration.

27 Claims, 54 Drawing Sheets

Related U.S. Application Data continuation-in-part of application No. 11/980,216, filed on Oct. 30, 2007, now Pat. No. 9,289,583, which is a continuation-in-part of application No. 11/825,212, filed on Jul. 3, 2007, now Pat. No. 9,066,847, and a continuation-in-part of application No. 11/650,174, filed on Jan. 5, 2007, now Pat. No. 8,202,535, said application No. 11/825,212 is a continuation-in-part of application No. 11/650,230, filed on Jan. 5, 2007, now Pat. No. 8,357,114, said application No. 13/678,141 is a continuation-in-part of application No. 11/825,212, which is a continuation-in-part of application No. 11/650,230, said application No. 13/678,141 is a continuation-in-part of application No. 11/650,230.

(60) Provisional application No. 60/756,937, filed on Jan. 6, 2006.

(52) U.S. Cl.
CPC ........... *A61J 7/0436* (2015.05); *A61J 7/0445* (2015.05); *A61J 2205/60* (2013.01); *A61J 2205/70* (2013.01)

(58) Field of Classification Search
CPC .... A61J 2205/70; A61J 7/0418; A61J 7/0436; A61K 9/006; A61K 9/20; A61K 9/0056; A61M 15/0081; A61M 15/0083; A61M 2205/276; A61M 31/007; A61M 37/0069
See application file for complete search history.

(56) References Cited

U.S. PATENT DOCUMENTS

| | | |
|---|---|---|
| 3,238,941 A | 3/1966 | Klein et al. |
| 3,444,858 A | 5/1969 | Russell |
| 3,757,781 A | 9/1973 | Smart |
| 3,780,735 A | 12/1973 | Crouter et al. |
| 3,789,845 A | 2/1974 | Long |
| 4,020,558 A | 5/1977 | Cournut et al. |
| 4,060,083 A | 11/1977 | Hanson |
| 4,226,848 A | 10/1980 | Nagai et al. |
| 4,229,447 A | 10/1980 | Porter |
| 4,237,884 A | 12/1980 | Erickson |
| 4,465,191 A | 8/1984 | Darbo |
| 4,474,308 A | 10/1984 | Bergeron |
| 4,489,853 A | 12/1984 | Korte et al. |
| 4,582,835 A | 4/1986 | Lewis et al. |
| 4,671,953 A | 6/1987 | Stanley et al. |
| 4,764,378 A | 8/1988 | Keith et al. |
| 4,782,981 A | 11/1988 | Schuster |
| 4,785,969 A | 11/1988 | McLaughlin |
| 4,863,737 A | 9/1989 | Stanley et al. |
| 4,873,076 A | 10/1989 | Fishman et al. |
| 4,880,634 A | 11/1989 | Speiser |
| 4,950,234 A | 8/1990 | Fujioka et al. |
| 5,080,903 A | 1/1992 | Ayache et al. |
| 5,112,616 A | 5/1992 | McCarty |
| 5,122,127 A | 6/1992 | Stanley |
| 5,132,114 A | 7/1992 | Stanley et al. |
| 5,178,878 A | 1/1993 | Wehling et al. |
| 5,190,185 A | 3/1993 | Blechl |
| 5,223,264 A | 6/1993 | Wehling et al. |
| 5,236,714 A | 8/1993 | Lee et al. |
| 5,263,596 A | 11/1993 | Williams |
| 5,288,497 A | 2/1994 | Stanley et al. |
| 5,288,498 A | 2/1994 | Stanley et al. |
| 5,292,307 A | 3/1994 | Dolzine et al. |
| 5,296,234 A | 3/1994 | Hadaway et al. |
| 5,348,158 A | 9/1994 | Honan et al. |
| 5,366,112 A | 11/1994 | Hinterreiter |
| 5,366,113 A | 11/1994 | Kim et al. |
| 5,489,025 A | 2/1996 | Romick |
| 5,489,689 A | 2/1996 | Mathew |
| 5,507,277 A | 4/1996 | Rubsamen et al. |
| 5,507,807 A | 4/1996 | Shippert |
| 5,549,560 A | 8/1996 | Van de Wijdeven |
| 5,584,805 A | 12/1996 | Sutton |
| 5,657,748 A | 8/1997 | Braithwaite |
| 5,660,273 A | 8/1997 | Discko, Jr. |
| 5,694,919 A | 12/1997 | Rubsamen et al. |
| 5,710,551 A | 1/1998 | Ridgeway |
| 5,724,957 A | 3/1998 | Rubsamen et al. |
| 5,735,263 A | 4/1998 | Rubsamen et al. |
| 5,752,620 A | 5/1998 | Pearson |
| 5,762,631 A | 6/1998 | Klein |
| 5,785,989 A | 7/1998 | Stanley et al. |
| 5,800,832 A | 9/1998 | Tapolsky et al. |
| 5,827,525 A | 10/1998 | Liao et al. |
| 5,850,937 A | 12/1998 | Rauche |
| 5,855,908 A | 1/1999 | Stanley et al. |
| 5,860,946 A | 1/1999 | Hofstatter |
| 5,945,651 A | 8/1999 | Chorosinski et al. |
| 5,950,632 A | 9/1999 | Reber et al. |
| 5,954,641 A | 9/1999 | Kehr et al. |
| 5,968,547 A | 10/1999 | Reder et al. |
| 5,981,552 A | 11/1999 | Alam |
| 5,984,888 A | 11/1999 | Nielsen et al. |
| 5,992,742 A | 11/1999 | Sullivan et al. |
| 5,995,938 A | 11/1999 | Whaley |
| 5,997,518 A | 12/1999 | Laibovitz et al. |
| 6,010,483 A * | 1/2000 | Spencer ............ A61M 5/172 604/151 |
| 6,024,981 A | 2/2000 | Khankari et al. |
| 6,039,251 A | 3/2000 | Holowko et al. |
| 6,116,414 A | 9/2000 | Discko, Jr. |
| 6,131,765 A | 10/2000 | Barry et al. |
| 6,171,294 B1 | 1/2001 | Southam et al. |
| 6,190,326 B1 | 2/2001 | McKinnon et al. |
| 6,200,288 B1 | 3/2001 | Heaton et al. |
| 6,200,604 B1 | 3/2001 | Pather et al. |
| 6,210,699 B1 | 4/2001 | Acharya et al. |
| 6,216,033 B1 | 4/2001 | Southam et al. |
| 6,224,908 B1 | 5/2001 | Wong et al. |
| 6,230,927 B1 | 5/2001 | Schoonen et al. |
| 6,234,343 B1 | 5/2001 | Papp |
| 6,248,789 B1 | 6/2001 | Weg et al. |
| 6,251,418 B1 * | 6/2001 | Ahern ............ A61K 9/0024 424/423 |
| 6,258,056 B1 | 7/2001 | Turley et al. |
| 6,264,981 B1 * | 7/2001 | Zhang ............ A61K 9/0056 424/451 |
| 6,284,512 B1 | 9/2001 | Jones et al. |
| 6,294,999 B1 | 9/2001 | Yarin et al. |
| 6,310,072 B1 | 10/2001 | Smith et al. |
| 6,319,510 B1 | 11/2001 | Yates |
| 6,328,159 B1 | 12/2001 | Discko, Jr. |
| 6,350,470 B1 | 2/2002 | Pather et al. |
| 6,358,944 B1 | 3/2002 | Lederman et al. |
| 6,364,158 B1 | 4/2002 | Dimoulis |
| 6,391,335 B1 | 5/2002 | Pather et al. |
| 6,417,184 B1 | 7/2002 | Ockert |
| 6,425,495 B1 | 7/2002 | Senda et al. |
| 6,425,892 B2 | 7/2002 | Southam et al. |
| 6,484,718 B1 | 11/2002 | Schaeffer et al. |
| 6,488,953 B2 | 12/2002 | Halliday et al. |
| 6,495,120 B2 | 12/2002 | McCoy et al. |
| 6,500,456 B1 | 12/2002 | Capella et al. |
| 6,509,036 B2 | 1/2003 | Pather et al. |
| 6,529,446 B1 * | 3/2003 | de la Huerga ........ A61J 7/0084 368/10 |
| 6,541,021 B1 | 4/2003 | Johnson et al. |
| 6,564,967 B1 | 5/2003 | Stringfield et al. |
| 6,572,891 B1 | 6/2003 | Ugarkovic |
| 6,576,250 B1 | 6/2003 | Pather et al. |
| 6,605,060 B1 | 8/2003 | O'Neil |
| 6,641,838 B2 | 11/2003 | Pather et al. |
| 6,642,258 B1 | 11/2003 | Bourrie et al. |
| 6,645,528 B1 | 11/2003 | Straub et al. |
| 6,651,651 B1 | 11/2003 | Bonney et al. |
| 6,660,295 B2 | 12/2003 | Watanabe et al. |

(56) References Cited

U.S. PATENT DOCUMENTS

| | | |
|---|---|---|
| 6,680,071 B1 | 1/2004 | Johnson et al. |
| 6,682,716 B2 | 1/2004 | Hodges et al. |
| 6,685,951 B2 | 2/2004 | Cutler et al. |
| 6,689,373 B2 | 2/2004 | Johnson et al. |
| 6,726,053 B1 | 4/2004 | Harrold |
| 6,752,145 B1 | 6/2004 | Bonney et al. |
| 6,759,059 B1 | 7/2004 | Pettersson et al. |
| 6,761,910 B1 | 7/2004 | Pettersson et al. |
| 6,762,684 B1 | 7/2004 | Camhi et al. |
| 6,764,696 B2 | 7/2004 | Pather et al. |
| 6,776,978 B2 | 8/2004 | Rabinowitz et al. |
| 6,793,075 B1 | 9/2004 | Jeter |
| 6,796,429 B2 | 9/2004 | Cameron et al. |
| 6,824,512 B2 | 11/2004 | Warkentin et al. |
| 6,835,194 B2 | 12/2004 | Johnson et al. |
| 6,855,310 B2 | 2/2005 | Rabinowitz et al. |
| 6,881,208 B1 | 4/2005 | Phipps et al. |
| 6,914,668 B2 | 7/2005 | Brestel et al. |
| 6,932,983 B1 | 8/2005 | Straub et al. |
| 6,959,808 B2 | 11/2005 | Discko, Jr. |
| 6,961,541 B2 | 11/2005 | Overy et al. |
| 6,963,289 B2 | 11/2005 | Aljadeff et al. |
| 6,969,508 B2 | 11/2005 | Dugger, III |
| 6,974,590 B2 | 12/2005 | Pather et al. |
| 6,999,028 B2 | 2/2006 | Egbert et al. |
| 7,004,111 B2 | 2/2006 | Olson et al. |
| 7,018,370 B2 | 3/2006 | Southam et al. |
| 7,018,619 B2 | 3/2006 | Rabinowitz et al. |
| 7,042,357 B2 | 5/2006 | Girvin et al. |
| 7,044,125 B2 | 5/2006 | Vedrine et al. |
| 7,044,302 B2 | 5/2006 | Conley et al. |
| 7,070,762 B2 | 7/2006 | Rabinowitz et al. |
| 7,070,764 B2 | 7/2006 | Rabinowitz et al. |
| 7,070,765 B2 | 7/2006 | Rabinowitz et al. |
| 7,072,738 B2 | 7/2006 | Bonney et al. |
| 7,073,685 B1 | 7/2006 | Giraud et al. |
| 7,074,935 B2 | 7/2006 | Mathew et al. |
| 7,078,018 B2 | 7/2006 | Rabinowitz et al. |
| 7,078,019 B2 | 7/2006 | Rabinowitz et al. |
| 7,078,218 B2 | 7/2006 | Smith et al. |
| 7,090,830 B2 | 8/2006 | Hale |
| 7,090,866 B2 | 8/2006 | Johnson et al. |
| 7,118,550 B2 | 10/2006 | Loomis |
| 7,119,690 B2 | 10/2006 | Lerch et al. |
| 7,168,626 B2 | 1/2007 | Lerch et al. |
| 7,169,378 B2 | 1/2007 | Rabinowitz et al. |
| 7,172,573 B1 | 2/2007 | Lamb |
| 7,198,172 B2 | 4/2007 | Harvey et al. |
| 7,208,604 B2 | 4/2007 | Mathew et al. |
| 7,215,295 B2 | 5/2007 | Egbert |
| 7,248,165 B2 | 7/2007 | Collins et al. |
| 7,264,139 B2 | 9/2007 | Brickwood et al. |
| 7,276,246 B2 | 10/2007 | Zhang et al. |
| 7,295,890 B2 | 11/2007 | Jean-Pierre |
| 7,306,812 B2 | 12/2007 | Zhang et al. |
| 7,458,374 B2 | 12/2008 | Hale et al. |
| 7,468,179 B2 | 12/2008 | Rabinowitz et al. |
| 7,484,642 B2 | 2/2009 | Bonney |
| 7,500,444 B2 | 3/2009 | Bonney et al. |
| 7,537,005 B2 | 5/2009 | Dave |
| 7,540,998 B2 | 6/2009 | Terwilliger et al. |
| 7,552,728 B2 | 6/2009 | Bonney et al. |
| 7,581,657 B2 | 9/2009 | Dickmann |
| 7,743,923 B2 | 6/2010 | Conley |
| 7,744,558 B2 | 6/2010 | Maag |
| 7,896,192 B2 | 3/2011 | Conley et al. |
| 8,062,248 B2 | 11/2011 | Kindel |
| 8,073,548 B2 | 12/2011 | Colvin, Jr. et al. |
| 8,142,733 B2 | 3/2012 | Creaven |
| 8,357,114 B2 | 1/2013 | Poutiatine et al. |
| 8,499,966 B2 | 8/2013 | Palmer et al. |
| 8,548,623 B2 | 10/2013 | Poutiatine et al. |
| 8,570,838 B2 | 10/2013 | Fujisawa |
| 8,706,288 B2 | 4/2014 | Alpay |
| 8,753,308 B2 | 6/2014 | Palmer et al. |
| 8,778,393 B2 | 7/2014 | Palmer et al. |
| 8,778,394 B2 | 7/2014 | Palmer et al. |
| 8,905,964 B2 | 12/2014 | Poutiatine et al. |
| 8,972,048 B2 | 3/2015 | Canora et al. |
| 9,066,847 B2 | 6/2015 | Poutiatine et al. |
| 9,289,583 B2 | 3/2016 | Palmer et al. |
| 9,320,710 B2 | 4/2016 | Palmer et al. |
| 2001/0020147 A1 | 9/2001 | Staniforth et al. |
| 2002/0026330 A1 | 2/2002 | Klein |
| 2002/0071857 A1 | 6/2002 | Kararli et al. |
| 2002/0110578 A1 | 8/2002 | Pather et al. |
| 2002/0142050 A1 | 10/2002 | Straub et al. |
| 2002/0160043 A1 | 10/2002 | Coleman |
| 2003/0008005 A1 | 1/2003 | Cutler |
| 2003/0015196 A1 | 1/2003 | Hodges et al. |
| 2003/0015197 A1 | 1/2003 | Hale et al. |
| 2003/0017175 A1 | 1/2003 | Cutler |
| 2003/0022910 A1 | 1/2003 | Cutler |
| 2003/0052135 A1 | 3/2003 | Conley et al. |
| 2003/0052787 A1 | 3/2003 | Zerhusen et al. |
| 2003/0077300 A1 | 4/2003 | Wermeling et al. |
| 2003/0099158 A1 | 5/2003 | De La Huerga |
| 2003/0130314 A1 | 7/2003 | Druzgala |
| 2003/0132239 A1 | 7/2003 | Konig et al. |
| 2003/0173408 A1 | 9/2003 | Mosher et al. |
| 2003/0185872 A1 | 10/2003 | Kochinke |
| 2003/0190290 A1 | 10/2003 | Ross |
| 2003/0232080 A1 | 12/2003 | Pather et al. |
| 2004/0017567 A1 | 1/2004 | Loicht et al. |
| 2004/0025871 A1 | 2/2004 | Davies |
| 2004/0034059 A1 | 2/2004 | Grarup et al. |
| 2004/0037882 A1 | 2/2004 | Johnson et al. |
| 2004/0080515 A1 | 4/2004 | Hagiwara |
| 2004/0092531 A1 | 5/2004 | Chizh et al. |
| 2004/0094564 A1 | 5/2004 | Papp |
| 2004/0111053 A1 | 6/2004 | Nicolette |
| 2004/0120896 A1 | 6/2004 | Dugger |
| 2004/0133305 A1 | 7/2004 | Jean-Pierre |
| 2004/0158349 A1 | 8/2004 | Bonney et al. |
| 2004/0170567 A1 | 9/2004 | Sackler |
| 2004/0180080 A1 | 9/2004 | Furusawa et al. |
| 2004/0248964 A1 | 12/2004 | Crooks et al. |
| 2004/0253307 A1 | 12/2004 | Hague et al. |
| 2005/0038062 A1 | 2/2005 | Burns et al. |
| 2005/0049464 A1 | 3/2005 | Lassers et al. |
| 2005/0054942 A1 | 3/2005 | Melker |
| 2005/0065175 A1 | 3/2005 | Gonzales et al. |
| 2005/0089479 A1 | 4/2005 | Rabinowitz et al. |
| 2005/0101936 A1 | 5/2005 | Gonzales et al. |
| 2005/0122219 A1 | 6/2005 | Petersen et al. |
| 2005/0131386 A1 | 6/2005 | Freeman et al. |
| 2005/0142197 A1 | 6/2005 | Moe et al. |
| 2005/0142198 A1 | 6/2005 | Moe et al. |
| 2005/0150488 A1 | 7/2005 | Dave |
| 2005/0150489 A1 | 7/2005 | Dunfield et al. |
| 2005/0163838 A1 | 7/2005 | Moe |
| 2005/0169989 A1 | 8/2005 | Moe et al. |
| 2005/0176790 A1 | 8/2005 | Bartholomaus |
| 2005/0177275 A1 | 8/2005 | Harvey et al. |
| 2005/0258066 A1* | 11/2005 | Conley ............... A61J 7/0472 206/538 |
| 2006/0026035 A1 | 2/2006 | Younkes et al. |
| 2006/0028727 A1 | 2/2006 | Moon et al. |
| 2006/0031099 A1 | 2/2006 | Vitello et al. |
| 2006/0039959 A1 | 2/2006 | Wessling et al. |
| 2006/0045865 A1 | 3/2006 | Jacob et al. |
| 2006/0062812 A1 | 3/2006 | Ross et al. |
| 2006/0067978 A1 | 3/2006 | Heiler et al. |
| 2006/0089858 A1 | 4/2006 | Ling |
| 2006/0134200 A1 | 6/2006 | Vandoni et al. |
| 2006/0216352 A1 | 9/2006 | Nystrom et al. |
| 2006/0229570 A1 | 10/2006 | Lovell et al. |
| 2006/0247578 A1 | 11/2006 | Arguedas et al. |
| 2007/0020186 A1 | 1/2007 | Stroppolo et al. |
| 2007/0036853 A1 | 2/2007 | Agarwal et al. |
| 2007/0071806 A1 | 3/2007 | McCarty |
| 2007/0074722 A1 | 4/2007 | Giroux et al. |
| 2007/0104763 A1 | 5/2007 | Jobdevairakkam et al. |
| 2007/0185084 A1 | 8/2007 | McKinney et al. |

(56) References Cited

U.S. PATENT DOCUMENTS

| | | |
|---|---|---|
| 2007/0186923 A1 | 8/2007 | Poutiatine et al. |
| 2007/0190130 A1 | 8/2007 | Mark et al. |
| 2007/0207207 A1 | 9/2007 | Tzannis et al. |
| 2007/0260491 A1 | 11/2007 | Palmer et al. |
| 2007/0286900 A1 | 12/2007 | Herry et al. |
| 2007/0299687 A1 | 12/2007 | Palmer et al. |
| 2008/0147044 A1 | 6/2008 | Palmer et al. |
| 2008/0164275 A1 | 7/2008 | Poutiatine et al. |
| 2008/0166404 A1 | 7/2008 | Tzannis et al. |
| 2008/0203107 A1 | 8/2008 | Conley et al. |
| 2008/0268023 A1 | 10/2008 | Palmer et al. |
| 2009/0010992 A1 | 1/2009 | Palmer et al. |
| 2009/0048237 A1 | 2/2009 | Palmer et al. |
| 2009/0131479 A1 | 5/2009 | Palmer et al. |
| 2010/0105735 A1 | 4/2010 | Palmer et al. |
| 2010/0130551 A1 | 5/2010 | Pushpala et al. |
| 2010/0137836 A1 | 6/2010 | Palmer et al. |
| 2010/0253476 A1 | 10/2010 | Poutiatine et al. |
| 2010/0256190 A1 | 10/2010 | Palmer et al. |
| 2011/0091544 A1 | 4/2011 | Palmer |
| 2011/0288128 A1 | 11/2011 | Palmer et al. |
| 2012/0035216 A1 | 2/2012 | Palmer et al. |
| 2012/0232473 A1 | 9/2012 | Poutiatine et al. |
| 2013/0158074 A1 | 6/2013 | Palmer et al. |
| 2013/0165481 A1 | 6/2013 | Palmer et al. |
| 2015/0105424 A1 | 4/2015 | Palmer et al. |

FOREIGN PATENT DOCUMENTS

| | | |
|---|---|---|
| EP | 1648327 A2 | 4/2006 |
| EP | 1261316 B1 | 4/2008 |
| EP | 1968539 A2 | 9/2008 |
| EP | 1257311 B1 | 12/2008 |
| EP | 2114383 B1 | 7/2010 |
| GB | 2309966 | 8/1997 |
| JP | 2000-53174 | 2/2000 |
| JP | 2000-142841 | 5/2000 |
| JP | 2000-511158 | 8/2000 |
| JP | 2003-525081 | 8/2003 |
| JP | 2007-517636 | 7/2007 |
| WO | WO 00/16750 | 3/2000 |
| WO | WO 00/57858 | 10/2000 |
| WO | WO 00/66458 | 11/2000 |
| WO | WO 02/32487 | 4/2002 |
| WO | WO 02/074372 | 9/2002 |
| WO | WO 02/078594 | 10/2002 |
| WO | WO 03/070304 | 8/2003 |
| WO | WO 03/092575 | 11/2003 |
| WO | WO 2004/067004 | 8/2004 |
| WO | WO 2004/069198 | 8/2004 |
| WO | WO 2004/080515 | 9/2004 |
| WO | WO 2006/097361 | 9/2006 |
| WO | WO 2008/085764 | 7/2008 |

OTHER PUBLICATIONS

AcelRx Pharmaceuticals, Inc., "AcelRx Pharmaceuticals Reports Positive Results from a Clinical Trial of Sublingual Sufentanil/Triazolam NanoTab™ Combination (ARX-03) in Treating Procedural Pain and Anxiety," Jan. 12, 2009, pp. 1-2.

ACTIQ® Fact Sheet (Mar. 2004).

AHFS Drug Information, Sufentanil Citrate, 28:08.08, 2157-2160 (2007).

Ahmad, S. et al., "Fentanyl HCl iontophoretic transdermal system versus intravenous morphine pump after gynecologic surgery," Arch Gynecol Obstet 276:251-258 (2007).

Albert, J. M. et al., "Patient-controlled analgesia vs. conventional intramuscular analgesia following colon surgery," Diseases of the Colon & Rectum, 31(2):83-86 (1988).

Anlar, S. et al., "Formulation and in vitro-in vivo evaluation of buccoadhesive morphine sulfate tablets," Pharmaceutical Research, 11(2):231-236 (1994).

Bayrak, F. et al., "A comparison of oral midazolam, oral tramadol, and intranasal sufentanil premedication in pediatric patients," Journal of Opioid Management, 3(2):74-78 (2007).

Berthold, C. W. et al., "Comparison of sublingually and orally administered triazolam for premedication before oral surgery," Oral Surg Oral Med Oral Pathol Oral Radiol Endod, 84(2):119-124 (1997).

Bethune-Volters, A. et al., "A randomized double-blind trial assessing the efficacy and safety of sublingual metopimazine and ondansetron in the prophylaxis of chemotherapy-induced delayed emesis," Anti-Cancer Dugs, 17(2):217-224 (2006).

Bovill, J. G. et al., "The pharmacokinetics of sufentanil in surgical patients," Anesthesiology, 61:502-506 (1984).

Bredenberg, S., "New concepts in administration of drugs in tablet form—Formulation and evaluation of a sublingual tablet for rapid absorption, and presentation of an individualised dose administration system," Comprehensive Summaries of Uppsala Dissertations from the Faculty of Pharmacy 287, ACTA Universitatis Upsaliensis Uppsala (2003).

Bredenberg, S. et al., "In vitro and in vivo evaluation of a new sublingual tablet system for rapid oromucosal absorption using fentanyl citrate as the active substance," European Journal of Pharmaceutical Sciences, 20:327-334 (2003).

Brusset, A. et al., "Comparative pharmacokinetic study of fentanyl and sufentanil after single high-bolus doses," Clin Drug Invest, 18(5):377-389 (1999).

Chauvin, M. et al., "Sufentanil pharmacokinetics in patients with cirrhosis," Anesth. Analg., 68(1):1-4 (1989).

Chelly, J. E. et al., "The safety and efficacy of a fentanyl patient-controlled transdermal system for acute postoperative analgesia: a multicenter, placebo-controlled trial," Anesth. Analg., 98:427-433 (2004).

Christie, J. M. et al., "Dose-titration, multi-center study of oral transmucosal fentanyl citrate for the treatment of breakthrough pain in cancer patients using transdermal fentanyl for persistent pain," J Clin Oncol., 16(10):3238-45 (1998).

Coda, B. A. et al., "Comparative efficacy of patient-controlled administration of morphine, hydromorphone, or sufentanil for the treatment of oral mucositis pain following bone marrow transplantation," Pain, 72:333-346 (1997).

Collins, L. M. C. et al., "The surface area of the adult human mouth and thickness of the salivary film covering the teeth and oral mucosa," J. Dent. Res., 66(8):1300-1302 (1987).

Coluzzi, P. H. et al., "Breakthrough cancer pain: a randomized trial comparing oral transmucosal fentanyl citrate (OTFC) and morphine sulfate immediate release (MSIR)," Pain, 91(1-2):123-130 (2001).

Culling et al., "Haemodynamics and plasma concentrations following sublingual GTN and intravenous, or inhaled isosorbide dinitrate," Br. J. Clin. Pharm., 17:125-131 (1984).

Dale, O. et al., "Nasal Administration of Opioids for Pain Management in Adults," Acta Anaesthesiol. Scand., 46:759-770 (2002).

Darwish, M. et al., "Single-Dose and Steady-State Pharmacokinetics of Fentanyl Buccal Tablet in Healthy Volunteers," Journal of Clinical Pharmacology, 47(1):56-63 (2007).

Darwish, M. et al., "Pharmacokinetics and dose proportionality of fentanyl effervescent buccal tablets in healthy volunteers," Clinical Pharmacokinetics, 44(12):1279-1286 (2005).

Darwish, M. et al., "Comparison of equivalent doses of fentanyl buccal tablets and arteriovenous differences in fentanyl pharmacokinetics," Clinical Pharmacokinetics, 45(8):843-350 (2006).

Darwish, M. et al., "Pharmacokinetic properties of fentanyl effervescent buccal tablets: a phase I, open-label, crossover study of single-dose 100, 200, 400, and 800 μg in healthy adult volunteers," Clinical Therapeutics, 28(5):707-714 (2006).

Darwish, M. et al., "Relative bioavailability of the fentanyl effervescent buccal tablet (FEBT) 1080 μg versus oral transmucosal fentanyl citrate 1600 μg and dose proportionality of FEBT 270 to 1300 μg: a single-dose, randomized, open-label, three-period study in healthy adult volunteers," Clinical Therapeutics, 28(5):715-724 (2006).

(56) References Cited

OTHER PUBLICATIONS

Darwish, M. et al., "Effect of buccal dwell time on the pharmacokinetic profile of fentanyl buccal tablet," Expert Opin. Pharmacother., 8(13):2011-2016 (2007).
Darwish, M. et al., "Bioequivalence following buccal and sublingual placement of fentanyl buccal tablet 400 µg in healthy subjects," Clin. Drug Invest., 28(1):1-7 (2008).
Darwish, M. et al., "Absolute and Relative Bioavailability of Fentanyl Buccal Tablet and Oral Transmucosal Fentanyl Citrate," Journal of Clinical Pharmacology, 47:343-350 (2007).
De Castro, J. et al., "Practical applications and limitations of analgesic anesthesia," Acta Anesthesiologica Belgica, 3:107-128 (1976).
De Vries, M. E. et al., "Developments in buccal drug delivery," Critical Reviews in Therapeutic Drug Carrier Systems, 8(3):271-303 (1991).
Demeules, J. et al., "Clinical pharmacology and rationale of analgesic combinations," European Journal of Anaesthesiology, 20(28):7-12 (2003).
Drug Information Bulletin [online], 37(4) (Sep./Oct. 2004), [Retrieved on Jun. 5, 2008.] Retrieved from the Internet: <URL: http://www.kgh.on.ca/pharmacy/diBulletinSeptOct2004.pdf>, 4 pages.
Durfee, S. et al., "Fentanyl effervescent buccal tablets. Enhanced buccal absorption," American Journal of Drug Delivery, 4(1):1-5 (2006).
Egan, T. D. et al., "Multiple dose pharmacokinetics of oral transmucosal fentanyl citrate in healthy volunteers," Anesthesiology, 92:665-673 (2000).
Ellmauer, S., "Sufentanil: An alternative to fentanyl/alfentanil?" Anaesthesist, 43(3):143-158 (1994).
Enting, R. H. et al., "The 'pain pen' for breakthrough cancer pain: a promising treatment," Journal of Pain and Symptom Management, 29(2):213-217 (2005).
Farnsworth, S. T. et al., "Ocular Transmucosal Absorption and Toxicity of Sufentanil in Dogs," Anesth. Analg., 86:138-140 (1998).
FDA Guidance for Industry: Container Closure Systems for Packaging Human Drugs and Biologics, pp. 1-E2 (1999).
Fentora™ Package Insert (2006).
Fentora®, 2008 Red Book, p. 174.
Fisher, D. M. et al., "Pharmacokinetics of an implanted osmotic pump delivering sufentanil for the treatment of chronic pain," Anesthesiology, 99(4):929-937 (2003).
Gardner-Nix, J., "Oral transmucosal fentanyl and sufentanil for incident pain," Journal of Pain and Symptom Management, 22(2):627-630 (2001).
Geldner, G. et al., "Comparison between three transmucosal routes of administration of midazolam in children," Paediatric Anaesthesia, 7(2):103-109 (1997).
Gerak. L. R. et al., "Studies on benzodiazepines and opioids administered alone and in combination in rhesus monkeys: ventilaion and drug discrimination," Psychopharmacology, 137(2):164-174 (1998).
Gordon, D. B., "Oral transmucosal fentanyl citrate for cancer breakthrough pain: a review," Oncology Nursing Forum, 33(2):257-264 (2006).
Gram-Hansen, P. et al., "Plasma concentrations following oral and sublingual administration of lorazepam," Int. J. Clin. Pharmacol. Ther. Toxicol., 26(6):323-324 (1988).
Grass, J., "Patient-controlled analgesia," Anesth. Analg., 101:S44-S61 (2005).
Griffin, D. et al., Reg. Anesth. Pain Med., vol. 10, American Society of Regional Anesthesia Spring Meeting (2010).
Guay, J. et al., "Pharmacokinetics of sufentanil in normal children," Canadian Journal of Anaesthesia, 39(1):14-20 (1992).
Halliburton, J. R., "The pharmacokinetics of fentanyl, sufentanil and alfentanil: a comparative review," Journal of the American Association of Nurse Anesthetists, 56(3):229-233 (1988).
Haynes, G. et al., "Plasma sufentantil concentration after intranasal administration to paediatric outpatients," Canadian Journal of Anaesthesia, 40(3):286-288 (1993).
Hazardous Substances Data Bank (HSDB) [online] [Retrieved from the Internet]. URL: http://toxnet.nlm.nih.gov. Apr. 9, 2007, Name: Sufentanil; RN: 56030-54-7, 26 pages.
Helmers, J. H. et al., "Sufentanil pharmacokinetics in young adult and elderly surgical patients," European Journal of Anaesthesiology, 11(3):181-185 (1994).
Helmers, J. H. et al., "Comparison of intravenous and intranasal sufentanil absorption and sedation," Canadian Journal of Anaesthesia, 36(5):494-497 (1989).
Henderson, J. M. et al., "Pre-induction of anesthesia in pediatric patients with nasally administered sufentanil," Anesthesiology, 68:671-675 (1988).
Heshmati, F. et al., "Intranasal sufentanil for postoperative pain control in lower abdominal pediatric surgery," Iranian Journal of Pharmacology & Therapeutics, 5:131-133 (2006).
Hicks, R. et al., "USP Medication Safety Forum: Medication Errors Involving Patient-Controlled Analgesia," Joint Commission on Quality and Patient Safety, 34(12):734-742 (2008).
Ikinci, G. et al., "Development of buccal bioadhesive nicotine tablet formulation for smoking cessation," International Journal of Pharmaceutics, 277(1-2):173-178 (2004).
Infusion Pump Improvement Initiative, Center for Devices and Radiological Health, U.S. Food and Drug Administration, Apr. 2010, 7 pages.
Jackson, D. L. et al., "Pharmacokinetics and clinical effects of multidose sublingual triazolam in healthy volunteers," Journal Clinical Psychopharmacology, 26(1):4-8 (2006).
Jackson, K. et al., "Pilot dose finding study of intranasal sufentanil for breakthrough and incident cancer-associated pain," Journal of Pain and Symptom Management, 23(6):450-452 (2002).
James, J. J. et al., "The use of a short-acting benzodiazepine to reduce the risk of syncopal episodes during upright sterotactic breast biopsy," Clinical Radiology, 60(3):394-396 (2005).
Jeannet, P-Y et al., "Home and hospital treatment of acute seizures in children with nasal midazolam," European Journal of Paediatric Neurology, 3(2):73-77 (1999).
Kaplan, G. B. et al., "Single-dose pharmacokinetics and pharmacodynamics of alprazolam in elderly and young subjects," The Journal of Clinical Pharmacology, 38(1):14-21 (1998).
Karl, H. W. et al., "Comparison of the safety and efficacy of intranasal midazolam or sufentanil for preinduction of anesthesia in pediatric patients," Anesthesiology, 76:209-215 (1992).
Karl, H. W. et al., "Transmucosal administration of midazolam for premedication of pediatric patients," Anesthesiology, 78(5):885-891 (1993).
Karl, H. W. et al., "Pharmacokinetics of oral triazolam in children," Journal Clinical Psychopharmacology, 17(3):169-172 (1997).
Keohane, C. A. et al., "Intravenous medication safety and smart infusion systems," Journal of Infusion Nursing, 28(5):321-328 (Sep./Oct. 2005).
KGH Drug Information Bulletin, "Sublingual Sufentanil for Incident Pain," KGH Drug Information Bulletin, 37(4):2 (2004).
Khalil, S. et al., "Sublingual midazolam premedication in children: a dose response study," Paediatric Anaesthesia, (8):461-465 (1998).
Kogan, A. et al., "Premedication with midazolam in young children: a comparison of four routes of administration," Paediatric Anaesthesia, 12(8):685-689 (2002).
Kontinen, V. K. et al, "Premedication with sublingual triazolam compared with oral diazepam," Canadian Journal of Anesthesia, 40(9):829-834 (1993).
Kotey, G. A. et al., "Iontophoretic delivery of fentanyl for acute post-operative pain management," The European Journal of Hospital Pharmacy Science, 13(1):3-9 (2007).
Kress, H. G. et al., "Efficacy and tolerability of intranasal fentanyl spray 50 to 200 µg for breakthrough pain in patients with cancer: a phase III, multinantional, randomized, double-blind, placebo-controlled, crossover trial with a 10-month, open-label extension treatment period," Clinical Therapeutics, 31(6): 1171-1191 (2009).

(56) References Cited

OTHER PUBLICATIONS

Kroboth, P. D. et al., "Triazolam pharmacokinetics after intravenous, oral and sublingual administration," J. Clin. Psychopharmacol., 15(4):259-262 (1995).
Kunz, K. M., et al., "Severe episodic pain: management with sublingual sufentanil," Journal of Pain and Symptom Management, 8(4):189-190 (1993).
Lehmann, K. A. et al., "Postoperative patient-controlled analgesia with sufentanil: analgesic efficacy and minimum effective concentrations," Acta Anaesthesiol Scand., 35:221-226 (1991).
Lehmann, K. A. et al., "Pharmacokinetics of sufentanil in general surgical patients under different conditions of anesthesia," Acta Anaesthesiol Scand., 37:176-180 (1993).
Lennernas, B. et al., "Pharmacokinetics and tolerability of different doses of fentanyl following sublingual administration of a rapidly dissolving tablet to cancer patients: a new approach to treatment of incident pain," British Journal of Clinical Pharmacology, 59(2):249-253 (2004).
Lichtor, J. L., "The relative potency of oral transmucosal fentanyl citrate compared with intravenous morphine in the treatment of moderate to severe postoperative pain," Anesth. Analg., 89(3):732-738 (1999).
Lim, T. W. et al., "Premedication with midazolam is more effective by the sublingual than oral route," Canadian Journal of Anaesthesia, 44(7):723-726 (1997).
Lin, L. et al., "Applying human factors to the design of medical equipment: patient-controlled analgesia," J. Clin. Monitoring and Computing, 14:253-263 (1998).
Lipworth, B. J. et al., "Pharmacokinetics, effacacy and adverse effects of sublingual salbutamol in patients with asthma," Europoean Journal of Clinical Pharmacology, 37(6):567-571 (1989).
Mather, L. E., "Clinical pharmacokinetics of fentanyl and its newer derivatives," Clinical Pharmacokinetics, 8:422-446 (1983).
Mathieu, N. et al., "Intranasal sufentanil is effective for postoperative analgesia in adults," Canadian Journal of Anesthesia, 53(1):60-66 (2006).
McCann, M. E. et al., "The management of preoperative anxiety in children: an update," Anesthesia & Analgesia, 93:98-105 (2001).
McInnes, F. et al., "Evaluation of the clearance of a sublingual buprenorphine spray in the beagle dog using gamma scintigraphy," Pharmaceutical Research, (2007), 6 pages.
Mendelson, J. et al., "Bioavailability of Sublingual Buprenorphine," The Journal of Clinical Pharmacology, 37:31-37 (1997).
Miaskowski, C., "Patient-controlled modalities for acute postoperative pain management," Journal of PeriAnesthesia Nursing, 20(4):255-267 (Aug. 2005).
Miller, R. D., "The pursuit of excellence. The 47th Annual Rovenstine Lecture," Anesthesiology, 110(4):714-720 (Apr. 2009).
Minkowitz et al., Reg. Anesth. Pain Med., vol. 8, American Society of Regional Anesthesia Spring Meeting (2010).
Molander, L. et al., "Pharmacokinetic investigation of a nicotine sublilngual tablet," Eur. J. Clin. Pharmacol., 56(11):813-819 (2001).
Momeni, M. et al., "Patient-controlled analgesia in the management of postoperative pain," Drugs, 66(18):2321-2337 (2006).
Monk, J. P. et al., "Sufentanil: A Review of Its Pharmacological Properties and Therapeutic Use," Drugs, 36:286-313 (1988).
Motwani, J. G. et al., "Clinical pharmacokinetics of drugs administered buccally and sublingually," Clin. Pharmacokinet., 21(2):83-94 (1991).
Mystakidou, K. et al., "Oral transmucosal fentanyl citrate: overview of pharmacological and clinical characteristics," Drug Delivery, 13(4):269-276 (2006).
Naguib, M. et al., "The comparative dose-response effects of melatonin and midazolam for premedication of adult patients: A double-blinded, placebo-controlled study," Anesth. Analg., 91(2):473-479 (2000).
Nath, R. P. et al., "Buprenorphine pharmacokinetics: relative bioavailability of sublingual tablet and liquid formulations," The Journal of Clinical Pharmacology, 39:619-623 (1999).
Odou, P. et al., "Development of midazolam sublingual tablets: in vitro study," European Journal of Drug Metabolism Pharmacokinetics, 23(2):87-91 (1998).
Odou, P. et al., "Pharmacokinetics of midazolam: comparison of sublingual and intravenous routes in rabbit," European Journal of Drug Metabolism Pharmacokinetics, 24(1):1-7 (1999).
Okayama, M. et al., "Bronchodilator effect of sublingual isosorbide dinitrate in asthma," European Journal of Clinical Pharmacology, 26(2):151-155 (1984).
Onsolis Package Insert (Jul. 2009), 11 pages.
Paix, A. et al., "Subcutaneous fentanyl and sufentanil infusion substitution for morphine intolerance in cancer pain management," Pain, 63:263-269 (1995).
Paradis et al., "Solid-phase microextraction of human plasma samples for determination of sufentanil by gas chromatography-mass spectrometry," Therapeutic Drug Monitoring, 24:768-774 (2002).
Pavlin, D. J. et al., "Effects of combining propofol and alfentanil on ventilation, analgesia, sedation, and emesis in human volunteers," Anesthesiology, 84(1):23-37 (1996)—Abstract.
Portenoy, R. K. et al., "A randomized, placebo-controlled study of fentanyl buccal tablet for breakthrough pain in opioid-treated patients with cancer," The Clinical Journal of Pain, 22(9):805-811 (2006).
Portenoy, R. K. et al., "Oral transmucosal fentanyl citrate (OTFC) for the treatment of breakthrough pain in cancer patients: a controlled dose titration study," Pain, 79:303-312 (1999).
Puig, M. M. et al., "Sufentanil pharmacokinetics in neurosurgical patients," International Journal of Clinical Pharmacology, Therapy and Toxicology, 27(5):229-234 (1989).
Rawal, N. et al., "Current practices for postoperative pain management in Europe and the potential role of the fentanyl HCl iontophoretic transdermal system," European Journal of Anaesthesiology, 24:299-308 (2007).
Raza, S. M. A. et al., "Haemodynamic stability with midazolam-ketamine-sufentanil analgesia in cardiac patients," Can. J. Anaesth., 36(6):617-623 (1989).
Reisfield, G. M. et al., "Rational use of sublingual opioids in palliative medicine," Journal of Palliative Medicine, 10(2):465-475 (2007).
Reynolds, L. et al., "Relative analgesic potency of fentanyl and sufentanil during intermediate-term infusions in patients after long-term opiod treatment for chronic pain," Pain, 110:182-188 (2004).
Rosati, J. et al., "Evaluation of an oral patient-controlled analgesia device for pain management in oncology inpatients," J. Support. Oncol., 5(9):443-448 (2007).
Rosow, C. E., "Sufentanil Citrate: A New Opioid Analgesic for Use in Anesthesia," Pharmacotherapy, 4:11-19 (1984).
Rothschild, J. M. et al., "A controlled trial of smart infusion pumps to improve medication safety in critically ill patients," Crit. Care Med., 33(3):533-540 (2005).
Roy, S. D., "Transdermal delivery of narcotic analgesics: pH, anatomical, and subject influences on cutaneous permeability of fentanyl and sufentanil," Pharmaceutical Research, 7(8):842-847 (1990).
Roy, S. D. et al., "Solubility behavior of narcotic analgesics in aqueous media: solubilities and dissociation constants of morphine, fentanyl and sufentanil," Pharmaceutical Research, 6(2):147-151 (1989).
Sanford et al., "A comparison of morphine, fentanyl, and sufentanil anesthesia for cardiac surgery: induction, emergence, and extubation," Anesthesia and Analgesia, 65:259-266 (1986).
Savoia, G. et al., "Sufentanil: an overview of its use for acute pain management," Minerva Anestesiologica, 67(9 Suppl 1):206-216 (2001).
Scavone, J. M. et al., "Enhanced bioavailability of triazolam following sublingual versus oral administration," The Journal of Clinical Pharmacology, 26(3):208-210 (1986).
Scavone, J. M. et al., "Alprazolam kinetics following sublingual and oral administration," J. Clin. Psychpharmacol., 7(5):332-334 (1987).

(56) References Cited

OTHER PUBLICATIONS

Scavone, J. M. et al., "The pharmacokinetics and pharmacodynamics of sublingual and oral alprazolam in the post-prandial state," European Journal of Clinical Pharmacology, 42(4):439-443 (1992).
Scholz, J. et al., "Clinical pharmacokinetics of alfentanil, fentanyl and sufentanil," Clin. Pharmacokinet., 31(4):275-292 (1996).
Schreiber, K. M. et al., "The association of preprocedural anxiety and the success of procedural sedation in children," The American Journal of Emergency Medicine, 24(4):397-401 (2006).
Schwagmeier, R. et al., "Midazolam pharmacokinetics following Intravenous and buccal administration," Br. J. Clin. Pharmacol., 46:203-206 (1998).
Shojaei, A. H. et al., "Buccal mucosa as a route for systemic drug delivery: a review," Journal of Pharmacy and Pharmaceutical Sciences, 1:15-30 (1998).
Siepmann, J. et al., "Calculation of the required size and shape of hydroxypropyl methylcellulose matrices to achieve desired drug release profiles," International Journal of Pharmaceutics, 201(1):151-164 (2000).
Sinatra, R. S. et al., "Patient-controlled analgesia with sufentanil: a comparison of two different methods of administration," Journal of Clinical Anesthesia, 8:123-129 (1996).
Slatkin et al., "Fentanyl Buccal Tablet for Relief of Breakthrough Pain in Opioid-Tolerant Patients With Cancer-Related Chronic Pain," J. of Supportive Oncol., vol. 5, No. 7, Jul./Aug. 2007, pp. 327-334.
Smith, R. B. et al., "Temporal variation in traizolam pharmacokinetics and pharmacodynamics after oral administration," The Journal of Clinical Pharmacology, 26(2):120-124 (1986).
Stopperich, P. S. et al., "Oral triazolam pretreatment for intravenous sedation," Anesth. Prog., 40(4):117-121 (1993).
Streisand, J. B. et al., "Absorption and bioavailability of oral transmucosal fentanyl citrate," Anesthesiology, 75:223-229 (1991).
Streisand, J. B. et al., "Dose proportionality and pharmacokinetics of oral transmucosal fentanyl citrate," Anesthesiology, 88(2):305-309 (1998).
Striebel, H. W. et al., "Patient-controlled intranasal analgesia (PCINA) for the management of postoperative pain: a pilot study," Journal of Clinical Anesthesia, 8:4-8 (1996).
Striebel, H. W. et al., "Patient-controlled intranasal analgesia: a method for noninvasive postoperative pain management," Anesth Analg, 83:548-851 (1996).
SUFENTA® Package Insert (2006), 3 pages.
Tweedy, C. M. et al., "Pharmacokinetics and clinical effects of sublingual triazolam in pediatric dental patients," Journal of Clinical Psychopharmacology, 21(3):268-272 (2001).
Vadivelu, N. et al., "Recent advances in postoperative pain management," Yale Journal of Biology and Medicine, 83:11-25 (2010).
Van de Walle, J. et al., "Double blind comparison of fentanyl and sufentanil in anesthesia," Acta Anaesthesiologica Belgica, 27(3):129-138 (1976).
Van Raders, P. et al., "Nurses' views on ease of patient care in postoperative pain management," British Journal of Nursing, 16(5):312-317 (2007).
Vasight, N. et al., "Formulation selection and pharmacokinetic comparison of fentanyl buccal soluble film with oral transmucosal fentanyl citrate," Clin. Drug Investig., 29(10):647-654 (2009).
Vercauteren, M., "Intranasal sufentanil for pre-operative sedation," Anaesthesia, 43(4):270-273 (1988).
Vercauteren, M. P. et al., "Epidural sufentanil for postoperative patient-controlled analgesia (PCA) with or without background infusion: a double-blind comparison," Anesth. Analg., 80:76-80 (1995).
Viitanen, H. et al., "Midazolam premedication delays recovery from propofol-induced sevoflurane anesthesia in children 1-3 yr," Canadian Journal of Anesthesia, 46(8):766-771 (1999).
Viscusi, E. R. et al., "An iontophoretic fentanyl patient-activated analgesic delivery system for postoperative pain: a double-blind, placebo-controlled trial," Anesth Analg., 102(1):188-194 (2006).

Viscusi, E. R. et al., "Patient-controlled transdermal fentanyl hydrochloride vs intravenous morphine pump for postoperative pain: a randomized controlled trial," JAMA, 291(11):1333-1341 (2004).
Viscusi, E. R., "Patient-controlled drug delivery for acute postoperative pain management: a review of current and emerging technologies," Regional Anesthesia and Pain Medicine, 33(2):146-158 (2008).
Walder, B. et al., "Analgesia and sedation in critically ill patients," Swiss Med. Wkly., 134(23-24):333-346 (2004).
Weinberg, D. S. et al., "Sublingual absorption of selected opioid analgesics," Clin. Pharmacol. Ther., 44(3):335-342 (1988).
Wheeler, M. et al., "Uptake pharmacokinetics of the fentanyl oralet in children scheduled for central venous access removal: implications for the timing of initiating painful procedures," Paediatric Anesthesia, 12:594-599 (2002).
Willens, J. S. et al., "Pharmacodynamics, pharmacokinetics, and clinical uses of fentanyl, sufentanil, and alfentanil," Heart and Lung, 22:239-251 (1993).
Yager, J. Y. et al., "Sublingual lorazepam in childhood serial seizures," Am J Dis Child, 142:931-932 (1988).
Yeomans, W. et al., "Sublingual Sufentanil," Vancouver Hospital and Health Science Center Drug and Therapeutics Newsletter, 8(1):2 (2001).
Zedie, N. et al., "Comparison of intranasal midazolam and sufentanil premedication in pediatric outpatients," Clin. Pharmacol. Ther., 59:341-348 (1996).
Zhang, H. et al., "Oral mucosal drug delivery: clinical pharmacokinetics and therapeutic applications," Clinical Pharmacokinetics, 41(9):661-680 (2002).
International Search Report and Written Opinion for International Application No. PCT/US2011/037401, mailed Aug. 19, 2011.
Office Action for U.S. Appl. No. 12/580,930, mailed Oct. 21, 2011.
International Search Report and Written Opinion for International Application No. PCT/US2010/027437, mailed Jun. 21, 2010.
Office Action for U.S. Appl. No. 13/416,236, mailed Feb. 4, 2013.
Office Action for U.S. Appl. No. 12/275,485, mailed Mar. 2, 2011.
Office Action for U.S. Appl. No. 12/275,485, mailed Nov. 23, 2011.
International Search Report and Written Opinion for International Application No. PCT/US2009/064232, mailed Mar. 17, 2010.
Office Action U.S. Appl. No. 11/429,904, mailed Sep. 17, 2008.
Office Action U.S. Appl. No. 11/429,904, mailed Mar. 5, 2009.
Office Action U.S. Appl. No. 11/429,904, mailed Aug. 20, 2009.
International Search Report and Written Opinion for International Application No. PCT/US2007/010822, mailed Aug. 5, 2008.
Office Action U.S. Appl. No. 11/473,551, mailed Sep. 26, 2008.
Office Action U.S. Appl. No. 11/473,551, mailed Mar. 16, 2009.
Office Action U.S. Appl. No. 11/473,551, mailed Sep. 11, 2009.
International Search Report and Written Opinion for International Application No. PCT/US2007/011337, mailed Aug. 21, 2008.
Office Action for U.S. Appl. No. 12/187,937, mailed Sep. 16, 2010.
International Search Report and Written Opinion for International Application No. PCT/US2008/072445, mailed Oct. 20, 2008.
Office Action for U.S. Appl. No. 11/650,227, mailed Dec. 9, 2008.
Office Action for U.S. Appl. No. 11/650,227, mailed Jul. 6, 2009.
Office Action for U.S. Appl. No. 11/650,227, mailed Dec. 15, 2009.
Office Action for U.S. Appl. No. 11/650,227, mailed Aug. 5, 2010.
Office Action for U.S. Appl. No. 11/825,251, mailed Sep. 21, 2009.
Office Action for U.S. Appl. No. 11/825,251, mailed Dec. 15, 2009.
Office Action for U.S. Appl. No. 11/825,251, mailed Aug. 5, 2010.
International Search Report and Written Opinion for International Application No. PCT/US2007/000528, mailed Feb. 4, 2008.
Office Action for U.S. Appl. No. 11/650,174, mailed Oct. 13, 2010.
Office Action for U.S. Appl. No. 11/650,174, mailed Jun. 14, 2011.
Written Opinion for International Application No. PCT/US2007/000529, mailed Sep. 11, 2007.
International Preliminary Report on Patentability for International Application No. PCT/US2007/000529, dated Jul. 8, 2008.
Office Action for Canadian Application No. 2,636,115, dated Feb. 12, 2013.
Supplementary European Search Report for European Application No. 07716450, mailed Apr. 6, 2011.
Office Action for Japanese Patent Application No. 2008-549610, mailed Nov. 25, 2011.

(56) References Cited

OTHER PUBLICATIONS

Office Action for Japanese Patent Application No. 2008-549610, mailed Nov. 15, 2012.
Office Action for U.S. Appl. No. 11/650,230, mailed Sep. 25, 2008.
Office Action for U.S. Appl. No. 11/650,230, mailed Mar. 10, 2009.
Office Action for U.S. Appl. No. 11/650,230, mailed Aug. 4, 2009.
Office Action for U.S. Appl. No. 11/650,230, mailed Feb. 2, 2010.
Office Action for U.S. Appl. No. 11/650,230, mailed Jun. 16, 2010.
Office Action for U.S. Appl. No. 11/650,230, mailed Mar. 1, 2011.
Office Action for U.S. Appl. No. 11/650,230, mailed Mar. 27, 2012.
International Search Report and Written Opinion for International Application No. PCT/US2007/000527, mailed Dec. 17, 2007.
International Preliminary Report on Patentability for International Application No. PCT/US2007/000527, dated Feb. 24, 2009.
Office Action for Canadian Application No. 2,673,880, mailed May 6, 2014.
Office Action for Chinese Patent Application No. 200780051996.7, mailed Feb. 23, 2012.
Office Action for Japanese Patent Application No. 2009-544898, mailed Jul. 24, 2012.
Restriction Requirement for U.S. Appl. No. 11/825,212, mailed Dec. 9, 2009.
Office Action for U.S. Appl. No. 11/825,212, mailed Mar. 24, 2010.
Office Action for U.S. Appl. No. 11/825,212, mailed Aug. 31, 2010.
Office Action for U.S. Appl. No. 11/825,212, mailed Aug. 22, 2014.
International Search Report and Written Opinion for International Application No. PCT/US2007/089016, mailed Jun. 17, 2008.
International Preliminary Report on Patentability for International Application No. PCT/US2007/089016, dated Jul. 7, 2009.
Office Action for U.S. Appl. No. 11/974,092, mailed Sep. 30, 2009.
Office Action for U.S. Appl. No. 11/974,092, mailed Mar. 31, 2010.
Office Action for U.S. Appl. No. 11/974,092, mailed Jun. 13, 2011.
Office Action for Canadian Application No. 2,673,837, mailed Apr. 24, 2014.
First Examination Report for Indian Application No. 2436/KOLNP/2009 dated Aug. 5, 2014.
Notice of Reasons for Rejection for Japanese Application No. 2009-544899, mailed Aug. 1, 2012.
Notice of Final Rejection for Japanese Application No. 2009-544899, mailed Jul. 29, 2013.
Office Action for U.S. Appl. No. 11/980,216, mailed Dec. 24, 2008.
Office Action for U.S. Appl. No. 11/980,216, mailed Jul. 20, 2009.
Office Action for U.S. Appl. No. 11/980,216, mailed Jan. 5, 2010.
Office Action for U.S. Appl. No. 11/980,216, mailed Jul. 2, 2010.
Office Action for U.S. Appl. No. 11/980,216, mailed Jun. 19, 2014.
Office Action for U.S. Appl. No. 11/980,216, mailed Feb. 17, 2015.
International Search Report and Written Opinion for International Application No. PCT/US2007/089017, mailed Jun. 23, 2008.
International Preliminary Report on Patentability for International Application No. PCT/US2007/089017, dated Jul. 7, 2009.
Office Action for U.S. Appl. No. 11/985,162, mailed Dec. 20, 2010.
International Search Report and Written Opinion for International Application No. PCT/US2007/089018, mailed Oct. 15, 2008.
European Search Report for European Application No. 13161632, mailed Feb. 6, 2014.
Office Action for Japanese Application No. 2013-246090, mailed Dec. 2, 2014 [Translation].
Notice of Grounds for Rejection for Korean Patent Application No. 2014-7008364, issued May 28, 2014.
European Search Report for European Application No. 14177156.8, mailed Nov. 5, 2014, 6 pages.
Office Action for U.S. Appl. No. 12/521,983, mailed Feb. 15, 2012.
Office Action for U.S. Appl. No. 13/744,448, mailed Jul. 15, 2013.
Office Action for U.S. Appl. No. 13/744,448, mailed Apr. 9, 2014.
Kress, J. P. et al., "Sedation and analgesia in the intensive care unit," Am. J. Respir. Crit. Care Med., 166:1024-1028 (2002).
Office Action for U.S. Appl. No. 14/041,963, mailed Oct. 23, 2015, 6 pages.
Office Action for U.S. Appl. No. 14/041,963, mailed Apr. 13, 2016, 7 pages.
Notice of Reasons for Rejection for Japanese Application No. 2015-111874, mailed Apr. 18, 2016, 10 pages.
International Search Report and Written Opinion for International Application No. PCT/US2015/067404, mailed Mar. 7, 2016, 10 pages.
Examination Report for Indian Patent Application No. 2873/KOLNP/2008, mailed on Mar. 7, 2017, 6 pages.

* cited by examiner

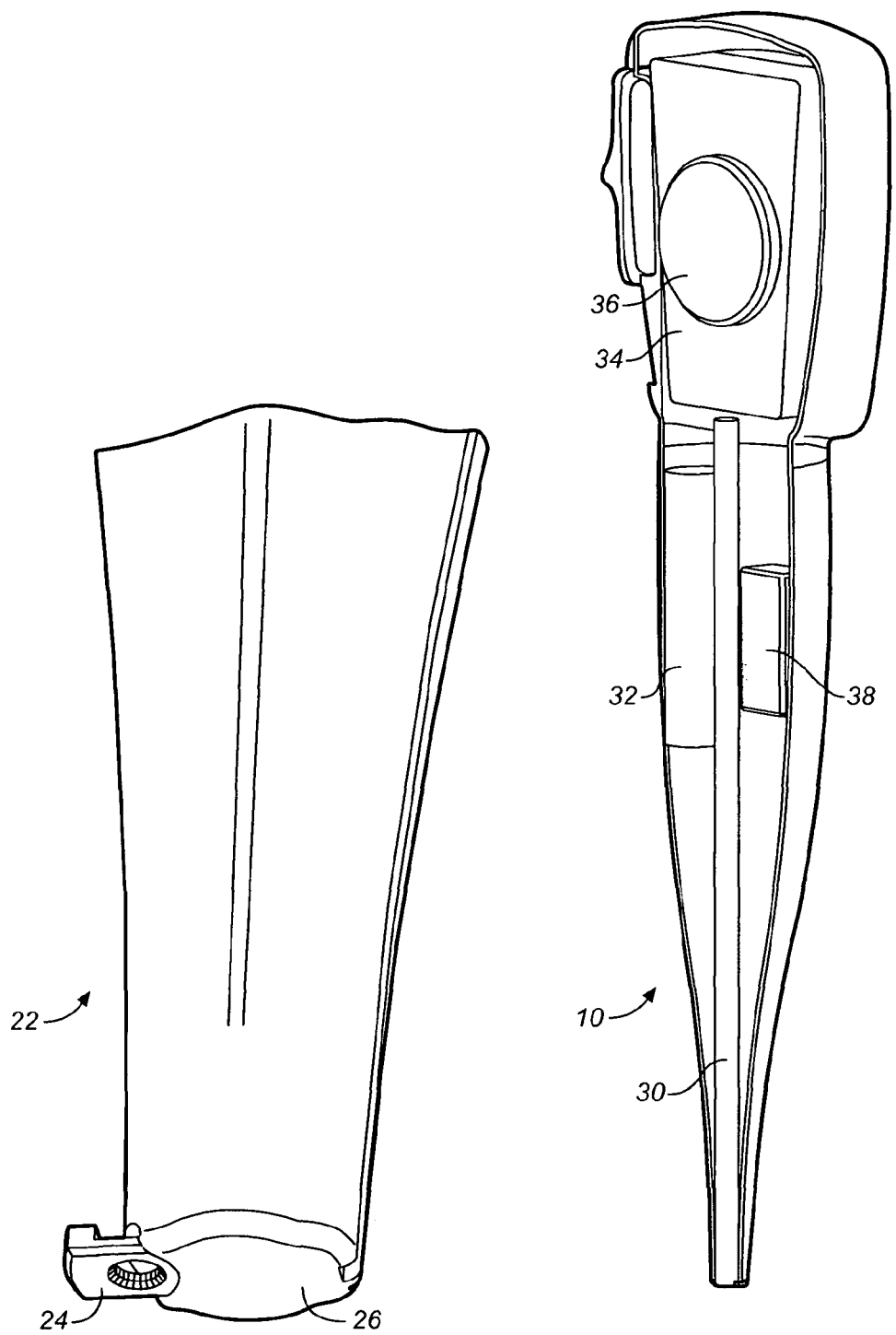

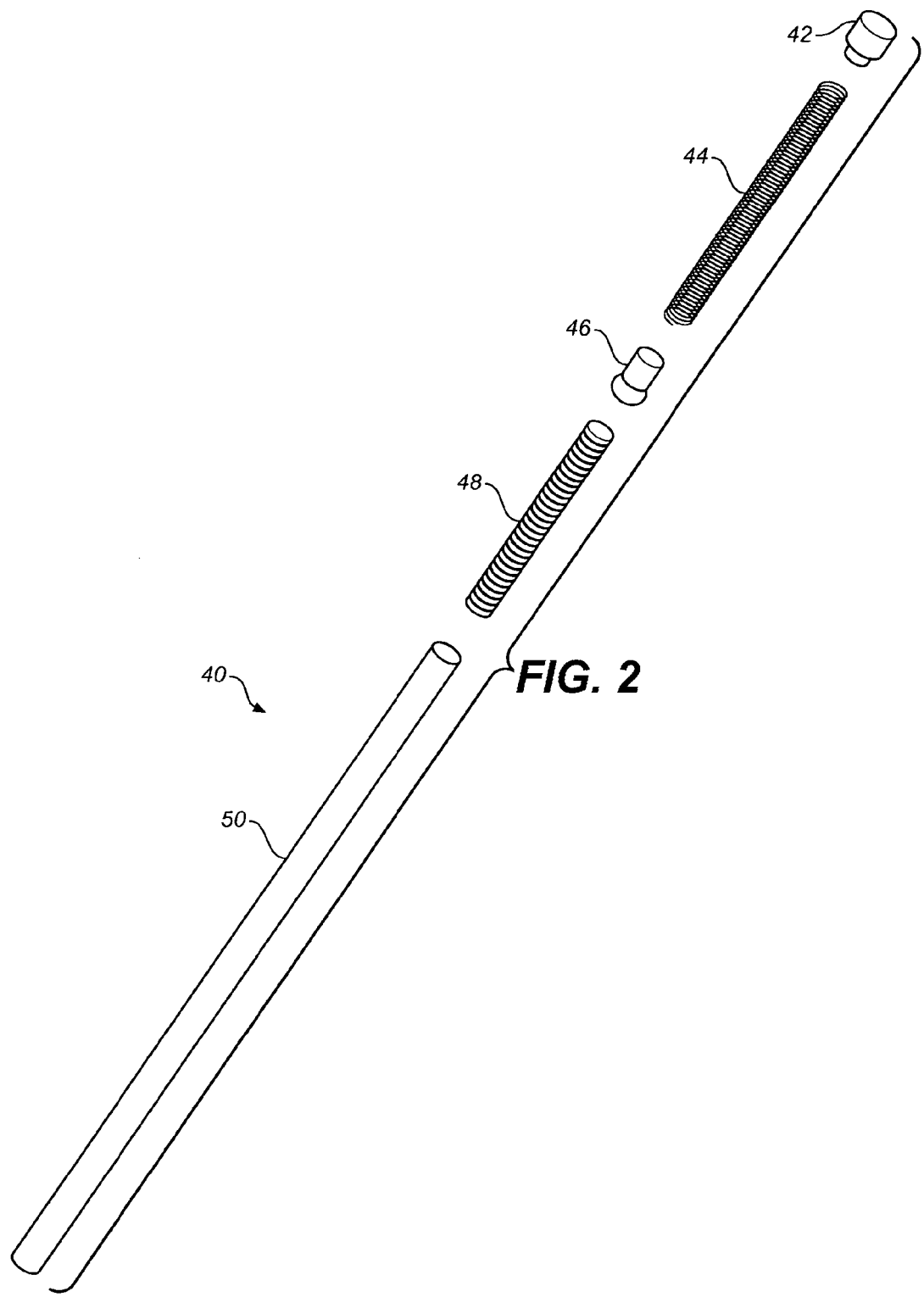

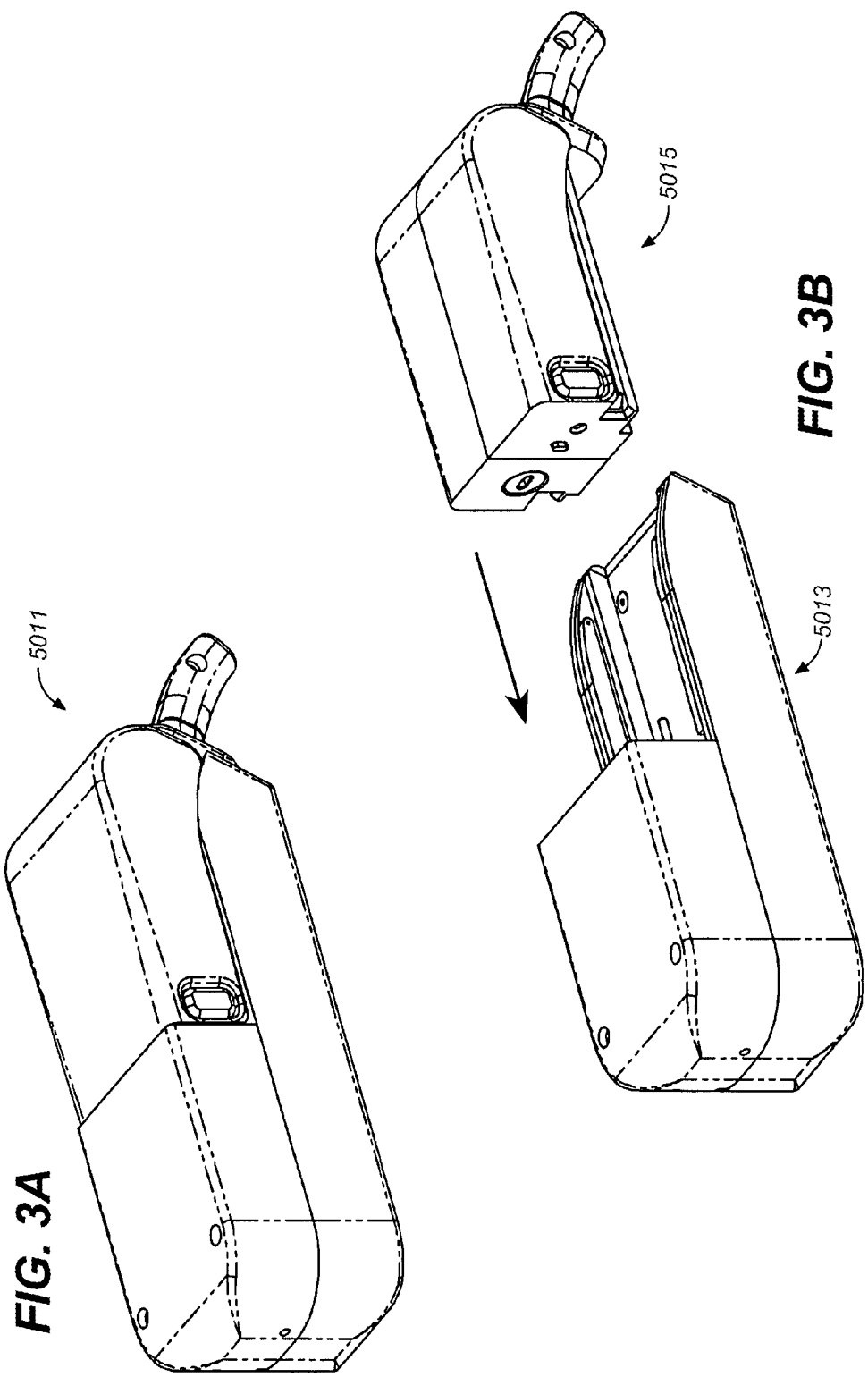

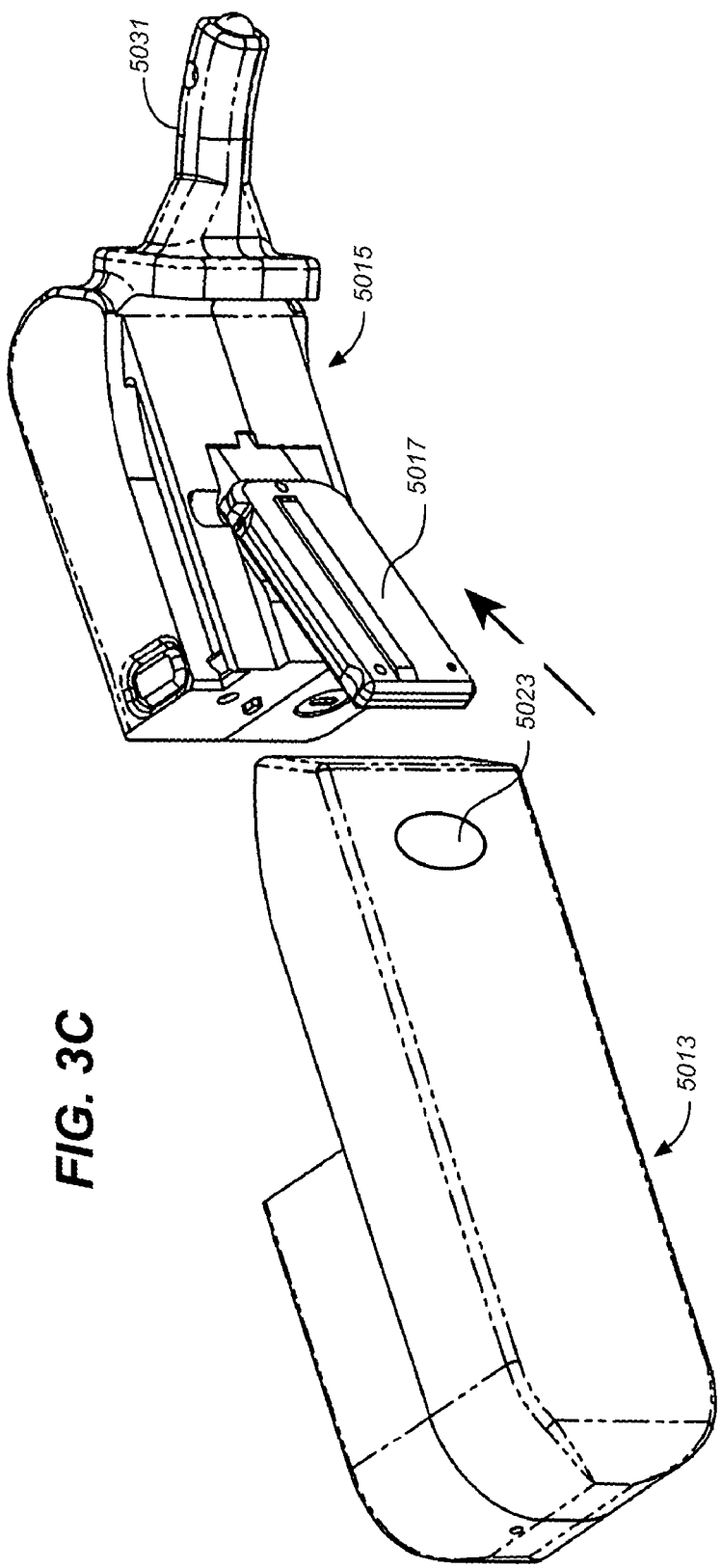

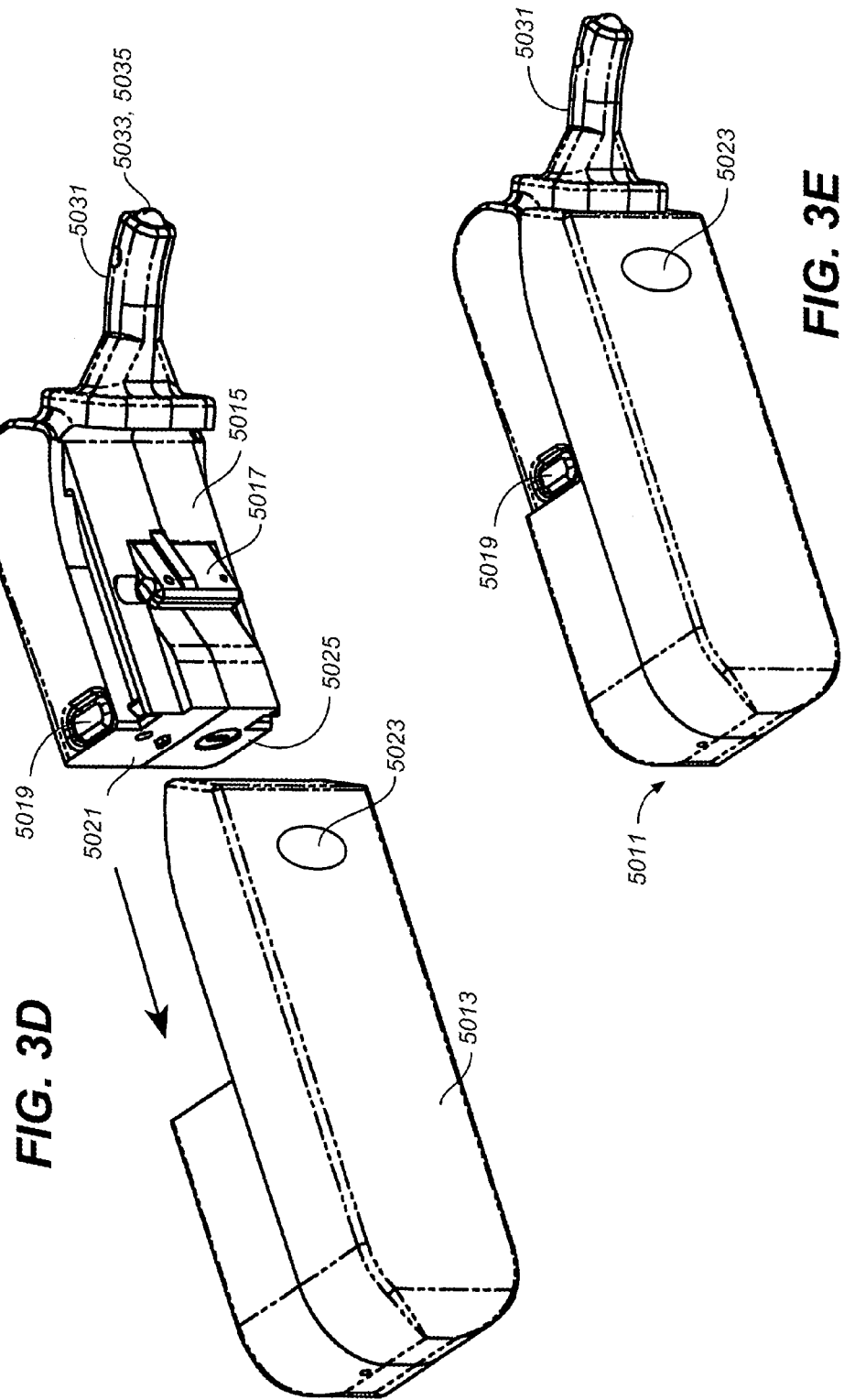

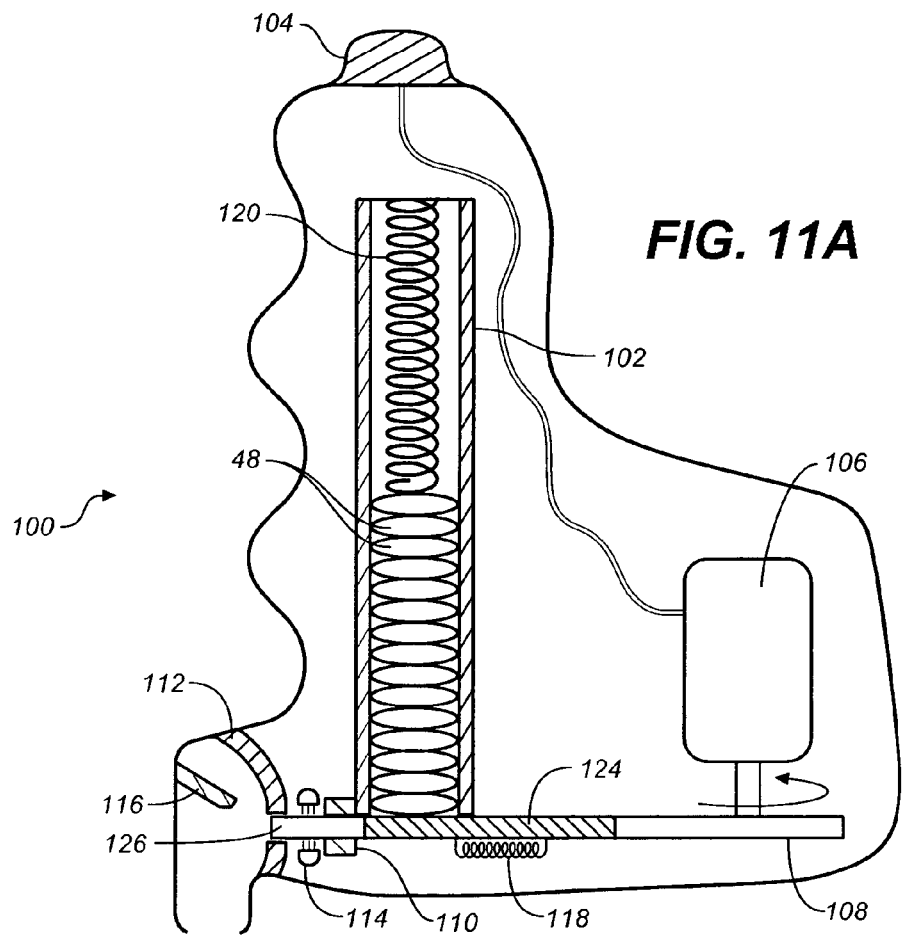
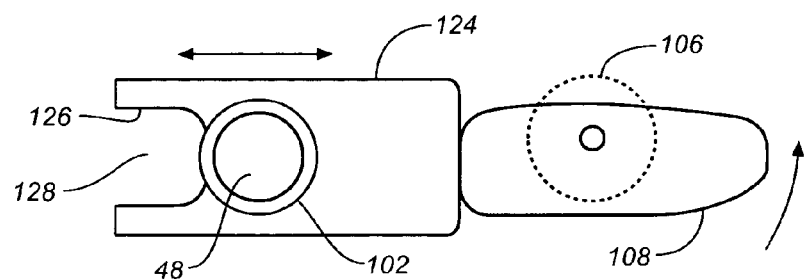

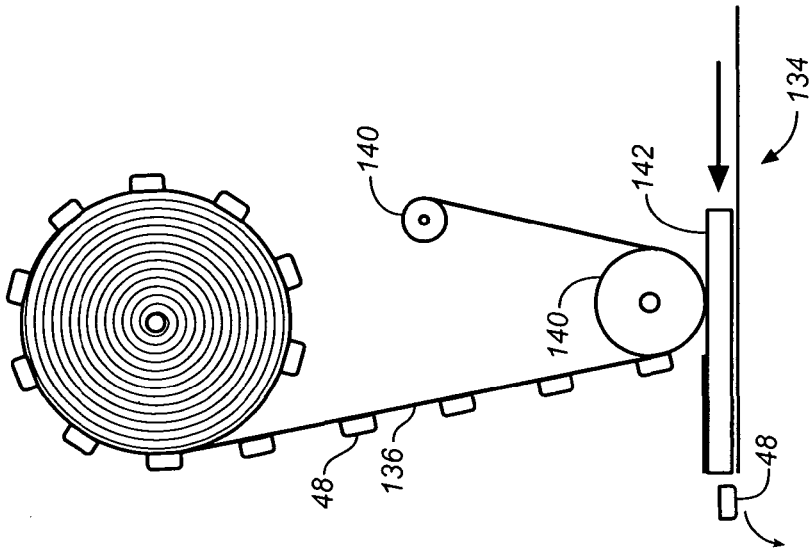
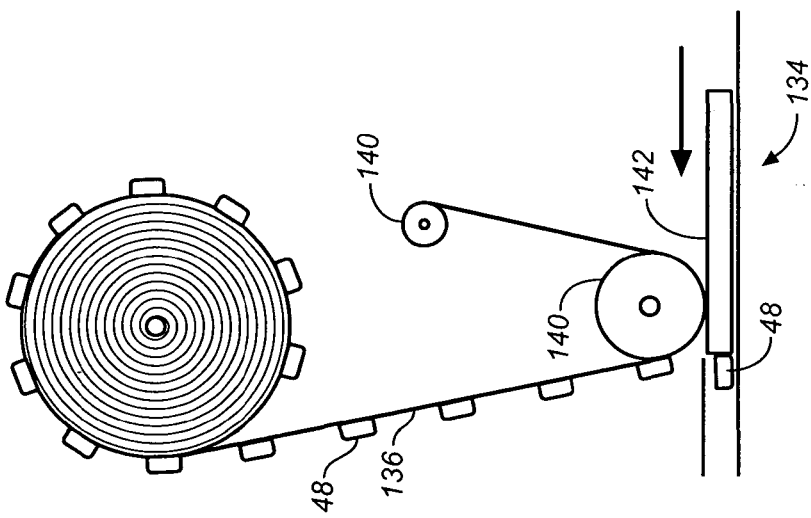
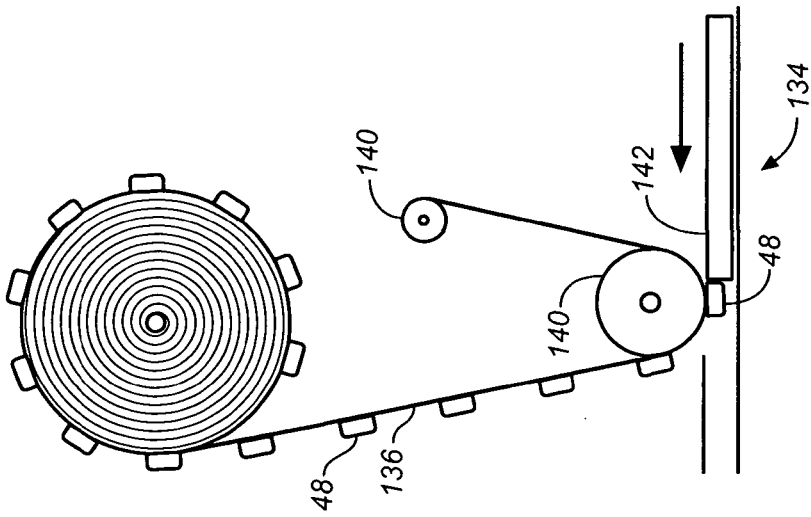

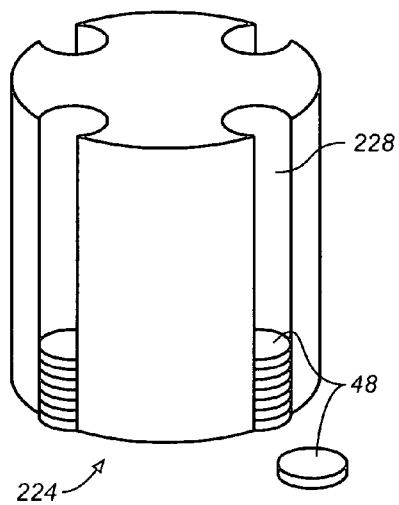
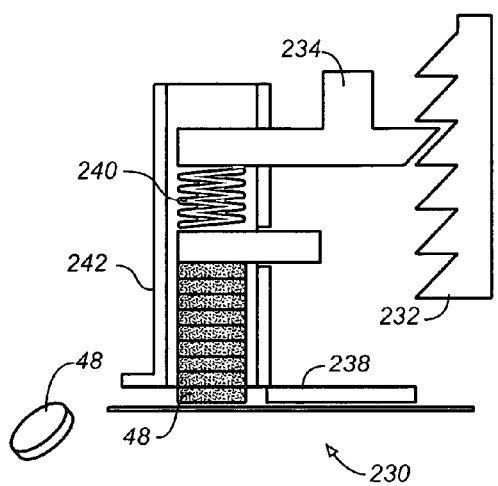
FIG. 19A    FIG. 19B
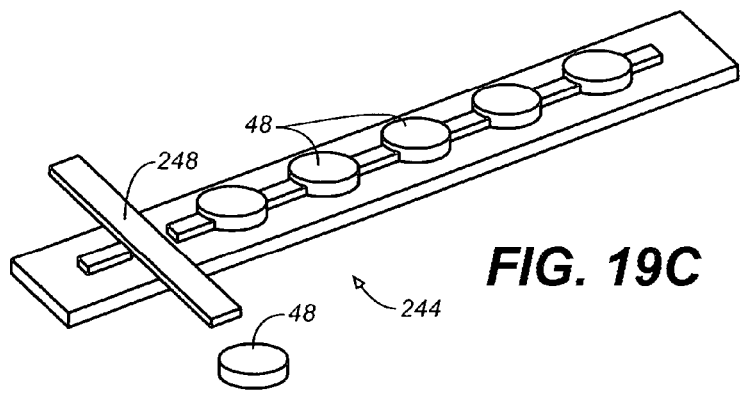
FIG. 19C
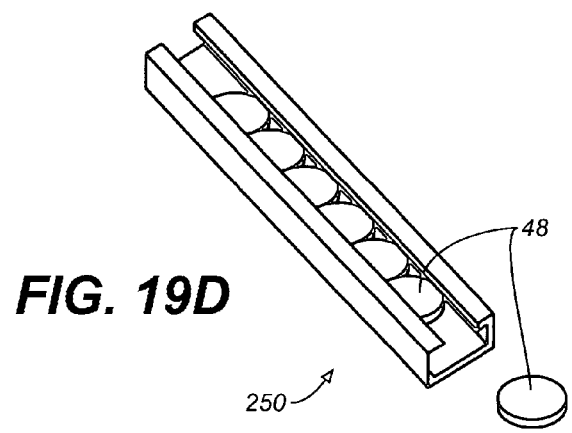
FIG. 19D

368

370

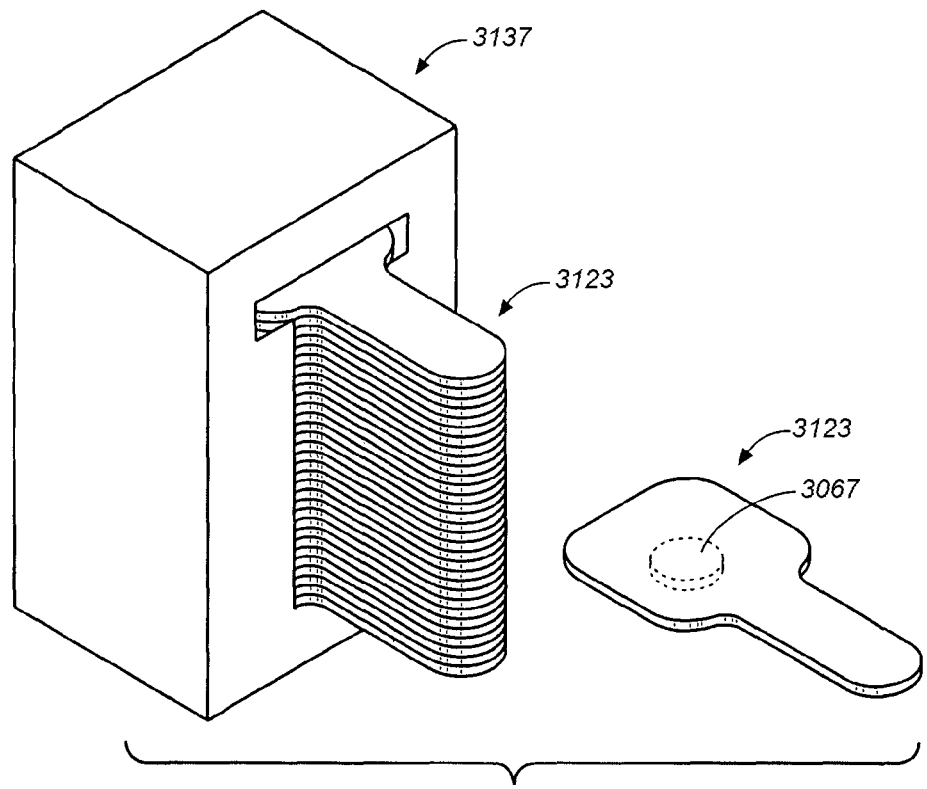
FIG. 24
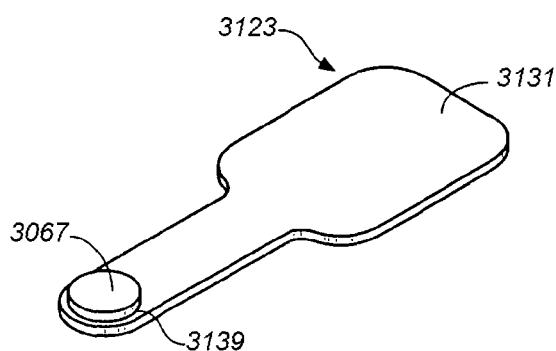 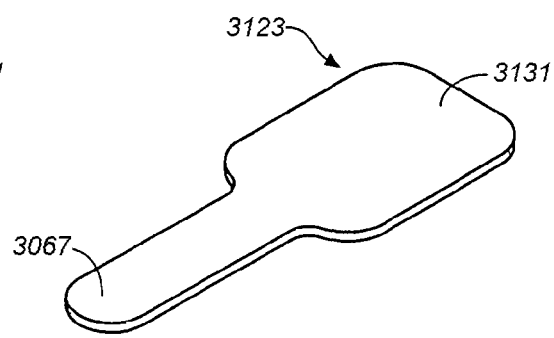
FIG. 25A          FIG. 25B

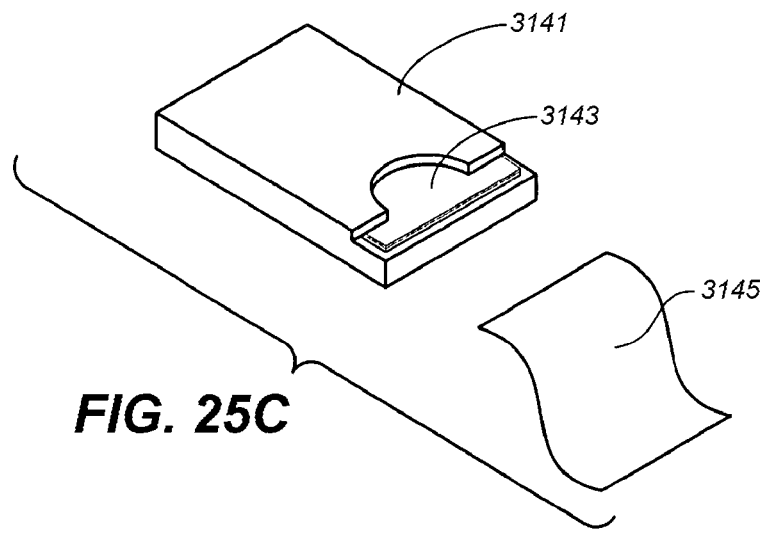
FIG. 25C
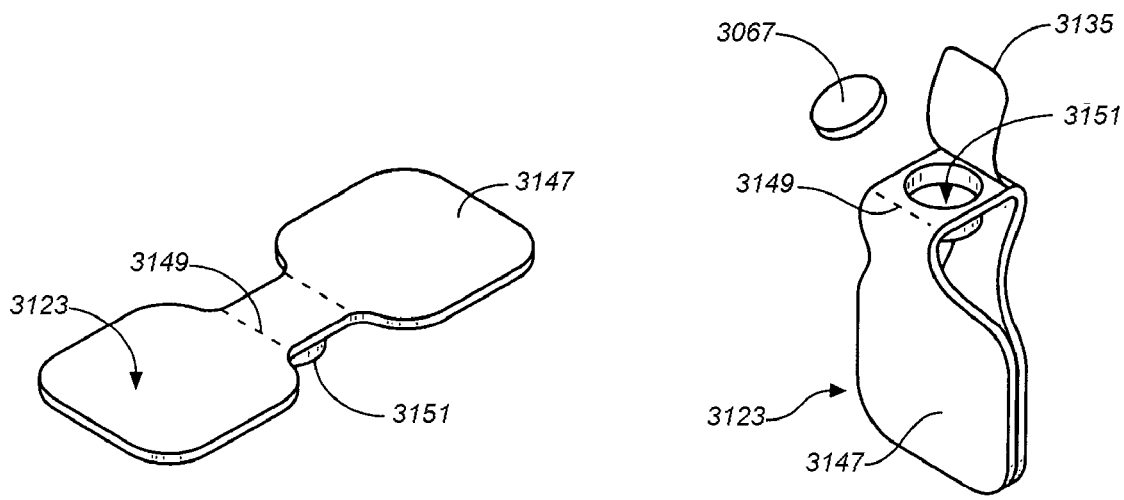
FIG. 26A  FIG. 26B

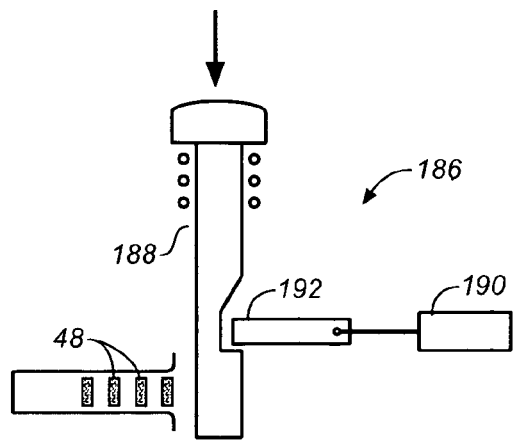
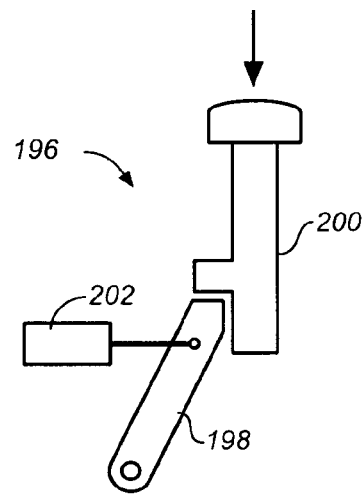
FIG. 30A  FIG. 30B
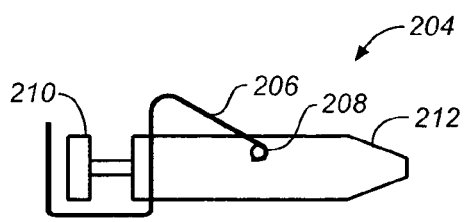
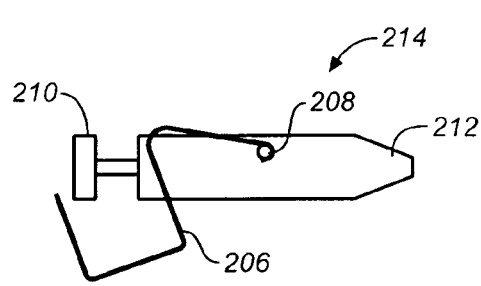
FIG. 30C  FIG. 30D
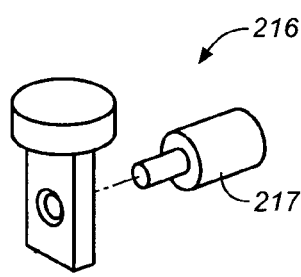
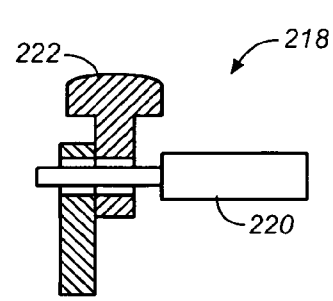
FIG. 30E  FIG. 30F

METHODS AND APPARATUS FOR ADMINISTERING SMALL VOLUME ORAL TRANSMUCOSAL DOSAGE FORMS

CROSS REFERENCE TO OTHER APPLICATIONS

This application is a continuation of U.S. patent application Ser. No. 13/678,141, filed Nov. 15, 2012 (now U.S. Pat. No. 8,753,308), which is a continuation-in-part of U.S. patent application Ser. No. 11/980,216, filed Oct. 30, 2007, which is a continuation-in-part of U.S. patent application Ser. No. 11/825,212, filed Jul. 3, 2007 and of U.S. patent application Ser. No. 11/650,174, filed Jan. 5, 2007 (now U.S. Pat. No. 8,202,535), each of which is incorporated by reference herein in its entirety. U.S. patent application Ser. No. 11/650,174 claims priority benefit of U.S. provisional application Ser. No. 60/756,937, filed Jan. 6, 2006, which is incorporated by reference herein in its entirety. U.S. patent application Ser. No. 11/825,212 is a continuation-in-part of U.S. patent application Ser. No. 11/650,230, filed Jan. 5, 2007 (now U.S. Pat. No. 8,357,114), which claims priority benefit of U.S. provisional application Ser. No. 60/756,937, each of which is incorporated by reference herein in its entirety.

U.S. patent application Ser. No. 13/678,141 (now U.S. Pat. No. 8,753,308) is a continuation-in-part of U.S. patent application Ser. No. 11/825,212, filed Jul. 3, 2007, which is a continuation-in-part of U.S. patent application Ser. No. 11/650,230, filed Jan. 5, 2007 (now U.S. Pat. No. 8,357,114), which claims priority benefit of U.S. provisional application Ser. No. 60/756,937, each of which is incorporated by reference herein in its entirety.

U.S. patent application Ser. No. 13/678,141 (now U.S. Pat. No. 8,753,308) is a continuation-in-part of U.S. patent application Ser. No. 11/650,230, filed Jan. 5, 2007 (now U.S. Pat. No. 8,357,114), which claims priority benefit of U.S. provisional application Ser. No. 60/756,937, each of which is incorporated by reference herein in its entirety.

FIELD OF THE INVENTION

The invention relates to drug dispensing devices and systems for oral transmucosal administration of small volume drug dosage forms to a subject, wherein the drug dosage forms comprise an opioid for treatment of pain.

BACKGROUND OF THE INVENTION

Oral dosage forms account for approximately eighty percent of all the drug dosage forms on the market. Oral dosage forms are non-invasive, easily administered and have high patient compliance.

Orally administered therapeutic agents are rapidly transported to the stomach and small intestine for absorption across the gastrointestinal (GI) mucosal membranes into the blood. The efficiency of absorption of a drug following oral administration can be low because of metabolism within the GI tract and first-pass metabolism within the liver resulting in relatively lengthy onset times or erratic absorption characteristics that are not well suited to control acute disorders. The majority of oral dosage forms on the market are designed for GI delivery. Relatively few oral dosage forms are designed for delivery through the oral mucosa.

However, oral transmucosal delivery offers a number of advantages in that it can provide a shorter onset time to maximal plasma concentration ($C_{max}$) than oral delivery, in particular for lipophilic drugs. This is because the drug rapidly passes directly and efficiently through the epithelium of the highly vascularized mucosal tissue to the plasma, thus rapidly reaching the circulation while avoiding the slower, often inefficient and variable GI uptake. It is therefore advantageous for a drug to be delivered through the mucus membranes of the oral cavity, (e.g., via the sublingual route), when rapid onset, consistent $T_{max}$ and $C_{max}$ are advantageous.

In carrying out oral transmucosal drug delivery, the drug is absorbed through the epithelial membranes of the oral cavity. However, frequently the key risk associated with oral transmucosal delivery is the enhanced potential for swallowing the medication owing to the continuous generation, backward flow and swallowing of the saliva. This becomes a particular risk when the used dosage forms are large enough to produce a significant saliva response, which, in turn, leads to swallowing or drug and/or removal of the dosage form from the oral mucosa.

Various solid dosage forms, such as sublingual tablets, troches, lozenges, lozenges-on-a-stick, chewing gums, and buccal patches have been used to deliver drugs via the oral mucosal tissue. Solid dosage forms such as lozenges and tablets have been used for oral transmucosal delivery of drugs, e.g., nitroglycerin sublingual tablets.

The relevant art does not describe a dispensing device for delivery of a drug dosage form to the oral mucosa, such as the sublingual space, where the device facilitates proper placement of the drug dosage form.

Reproducible and effective drug delivery technology represents an area of active research, in particular, as it applies to controlled substances such as opioids. Controlled access oral transmucosal drug dispensing systems offer numerous advantages over conventional means of drug administration such as oral and intravenous routes, the most important of which is enhanced safety, with additional advantages being rapid and consistent onset of action, more consistent and predictable plasma concentrations and higher and more consistent bioavailability than currently available dosage forms.

This is particularly relevant to the treatment of pain, more specifically, acute, intermittent and breakthrough pain.

Therefore, a need exists for a device and system that can be used to administer a controlled substance, such as an opioid (e.g., by patient-controlled administration), for treatment of pain, wherein the device provides for safe and controlled delivery via the oral mucosa, while minimizing the potential for drug abuse and/or diversion.

The present invention addresses these needs.

BRIEF SUMMARY OF THE INVENTION

The invention provides methods, systems and kits for sublingual administration of a bioadhesive small volume sufentanil-containing drug dosage form to a subject using a device.

The device is hand-held and comprises a cartridge containing one or more drug dosage forms (typically from 1 to about 200) dosage forms.

Each dosage form comprises 5 mcg, 10 mcg, 15 mcg, 20 mcg, 30 mcg, 40 mcg, 50 mcg, 60 mcg, 70 mcg, 80 mcg or 100 mcg of sufentanil and has a volume of less than 100 microliters or a mass of less than 100 mg.

In carrying out the method, the dispensing end of the device is inserted into the mouth of the subject and a dosage form is dispensed through the dispensing end of the device such that it is placed on a sublingual membrane (in the sublingual space) of the subject.

The dispensing end of the device has a proboscis comprising a shroud for placing the dosage form and the shroud includes a means to prevent or retard saliva and other moisture ingress into the device, such that the dosage forms remain dry prior to placement on the sublingual membrane.

The device further comprises a lock-out feature for setting a lock-out time wherein a dosage form cannot be dispensed from the device during the lock-out time. The lock-out time may be a fixed time lock-out interval, a predetermined lock-out interval, a predetermined variable lock-out interval, a lock-out interval determined by an algorithm or a variable lock-out interval communicated to the device from a remote computer, docking station or other device.

The cartridge may comprise one or more shipping tablets wherein at least one shipping tablet is dispensed prior to dispensing of a dosage form.

The cartridge may include a smart cartridge recognition system comprising a physical keyed feature on the cartridge, an optically detected feature or pattern, a bar code on the cartridge, a magnetic tag on the cartridge, an RFID tag on the cartridge, an electronic microchip on the cartridge, or a combination thereof.

The dispensing device further comprises a patient identification means wherein the patient identification means is a radio frequency identification (RFID) reader configured to couple with a matching RFID tag on a patient to be identified and the dispensing device is unlocked when the RFID reader on the dispensing device detects a matching RFID tag on a patient.

The dispensing device may also comprise a means for recording dosing, use history, or both, alone or in combination with a means to view or download the dosing and/or use history.

Following placement of a dosage from on the sublingual membrane of the subject, erosion of the dosage form is complete in from about 30 seconds to about 30 minutes.

In carrying out the method, a single sublingual administration of a dosage form to a subject results in a bioavailability of at least 50%, an AUC with a coefficient of variation of less than 40%, a $T_{max}$ with a coefficient of variation of less than 40%; repeated sublingual administration of a dosage form to a subject results in a bioavailability that is greater than the bioavailability following a single sublingual administration to the subject and the $T_{max}$ following repeated sublingual administration and the time of the previous sublingual administration is shorter than the $T_{max}$ following a single sublingual administration to the subject.

When a bioadhesive small volume sufentanil-containing drug dosage form is administered to the sublingual cavity of subject using a device, an amount of drug selected from the group consisting of at least 55%, at least 60%, at least 65%, at least 70%, at least 75%, at least 80%, at least 85%, at least 90%, at least 95%, at least 98% and at least 99% of the total amount of drug in the dosage form is absorbed via the sublingual route.

Administration of a sufentanil-containing drug dosage form using a drug dispensing device may be patient controlled and may be used for treating pain in a subject, wherein following administration of the dosage form, pain relief is evident.

BRIEF DESCRIPTION OF THE DRAWINGS

FIG. 1C is a schematic depiction of an exemplary dispensing device of the invention wherein the device is designed to deliver drug dosage forms to the sublingual space of a patient under treatment, wherein a dispensing shuttle mechanism and a dispensing end are illustrated.

FIG. 1D is a schematic depiction of an exemplary dispensing device of the invention wherein the device is designed to deliver drug dosage forms to the sublingual space of a patient under treatment, wherein a cartridge assembly; batteries; processor and pc board; antenna; and antagonist reservoir are shown.

FIG. 2 is a schematic depiction of a cartridge assembly for use in a dispensing device for delivering drug dosage forms.

FIGS. 3A-E provide a schematic depiction of an exemplary dispensing device wherein the device is designed to deliver drug dosage forms to oral mucosa of a patient under treatment. FIGS. 3A-E illustrate the progression of intact drug dispensing device 5011 (FIG. 3A); the reusable head 5013 and disposable body 5015 of a drug dispensing device (FIG. 3B); a reusable head 5013, disposable body 5015 and cartridge 5017, a dispense button 5023, and a proboscis 5031 of a drug dispensing device (FIG. 3C); various aspects of a drug dispensing device 5011 including a reusable head 5013, disposable body 5015 and cartridge 5017, a proboscis 5031, and a latch 5019 to unlock the device, a hub lock 5021, a distal seal 5033, 5035, and a power train coupling 5025 (FIG. 3D); and a reassembled intact drug dispensing device 5011 (FIG. 3E).

The shroud shields the valve from moisture and saliva ingress from the tongue and other mucosa and provides an area for the dosage form to exit the device without "sticking" to the wetted distal valve or shroud area. The shroud also comprises a cut-out/relief 5055 in order to mitigate the dragging of dosage forms when the device is removed from the oral space. The valve functions with the shroud to control saliva and moisture ingress, as well as aid in delivery of the dosage form.

Figure 7A:
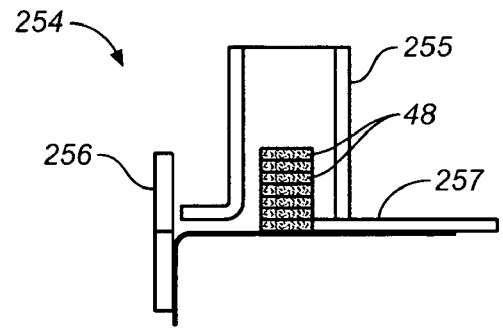
Figure 7B:
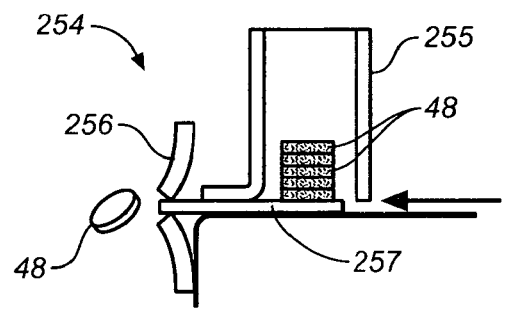

FIGS. 7A and 7B are schematic depictions of dispensing devices of the invention showing a drug dosage form being pushed through a seal by a pushrod, wherein the geometry of the seal is tailored to the shape of the dosage form and pushrod.

Figure 8:
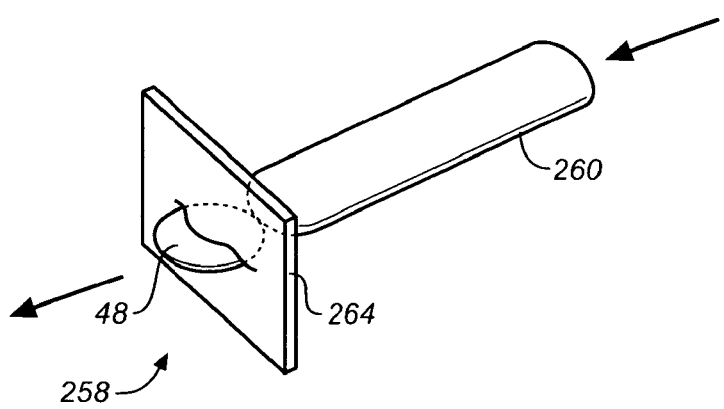
Figure 9A:
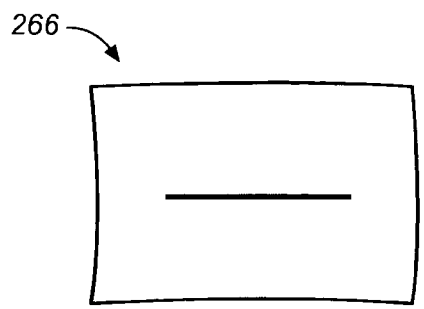
Figure 9B:
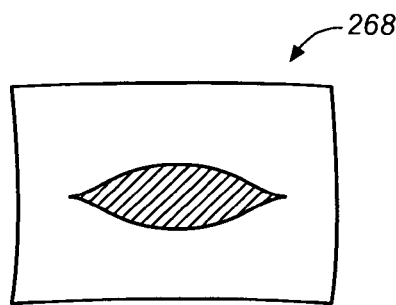
Figure 9C:
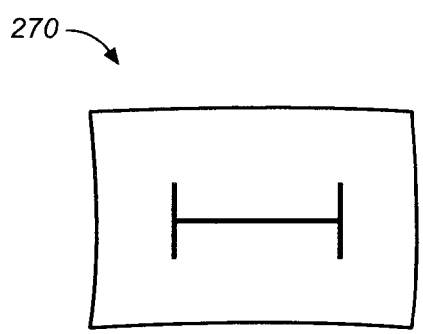
Figure 9D:
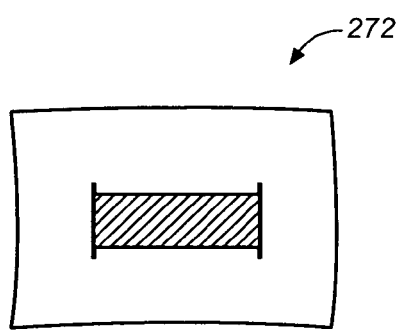
Figure 9E:
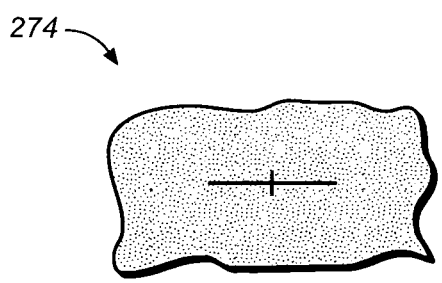
Figure 9F:
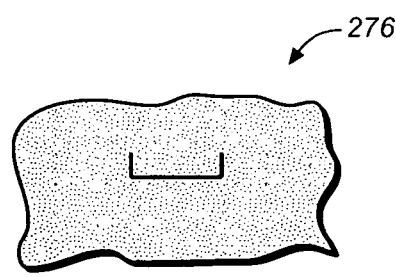

FIG. 8 is a schematic depiction of the geometry of an exemplary pushrod, drug dosage form, and septum-type seal. The exemplary slit type septum seal is designed to maintain a uniform seal around a drug dosage form and a pushrod during delivery.

FIGS. 9A-F are schematic depictions of geometries of other exemplary slit type septum seals designed to maintain a uniform seal around a drug dosage form and a pushrod during delivery of the drug dosage form.

FIGS. 10A-10D are schematic depictions of an exemplary dispensing device for delivering drug dosage forms to the oral mucosa, wherein a means for minimizing saliva influx into the dispensing device during the administration of the dosage forms to the patient is shown.

FIG. 11A is a schematic depiction of an exemplary dispensing mechanism for a dispensing device for delivering drug dosage forms, wherein a column type dispensing mechanism at a rest position is illustrated. The dispensing mechanism comprises one or more of a cartridge assembly, an activation button, a motor, a cam, a desiccant agent, seals, a delivery sensor, a spring clip, and a spring.

FIG. 11B is a schematic depiction of the dispensing device of FIG. 11A wherein the positions of the dispensing mechanism, motor and cam are at a rest position.

Figure 11C:
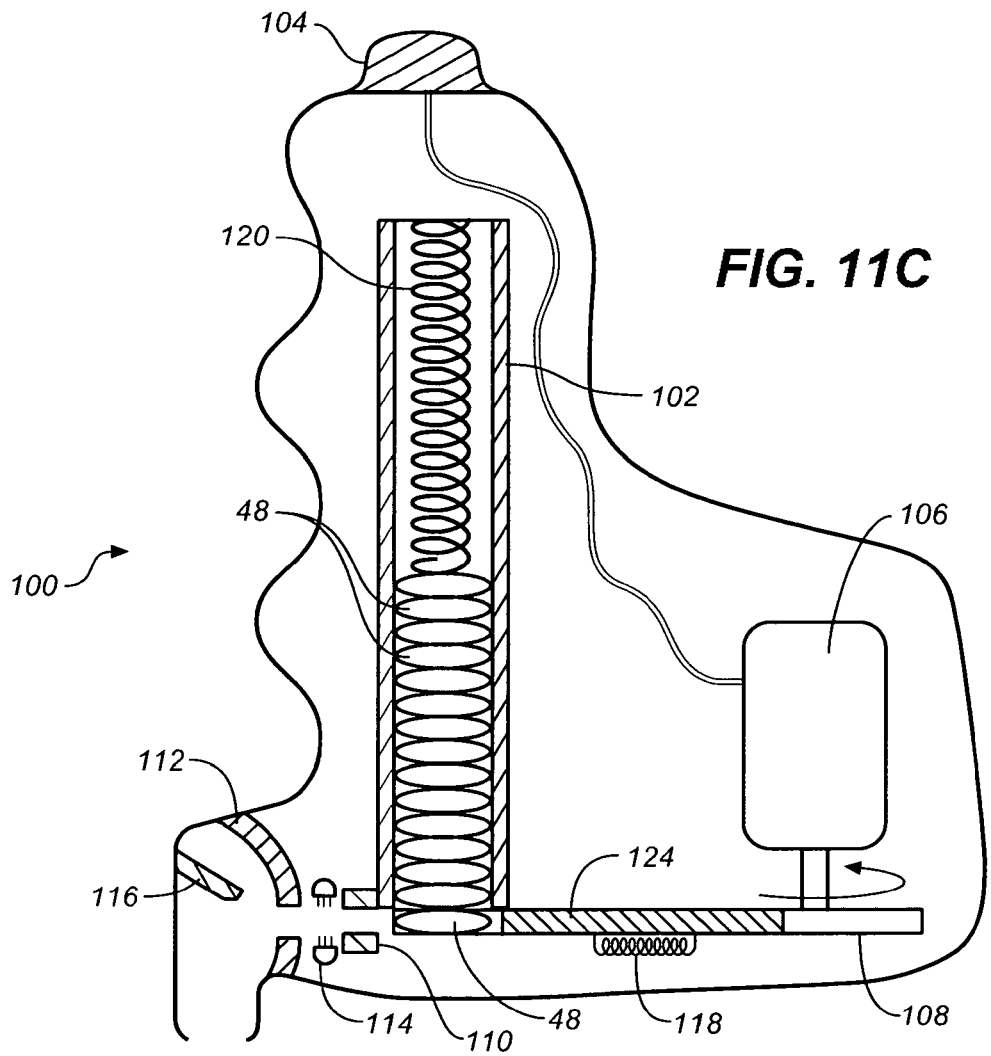
Figure 11D:
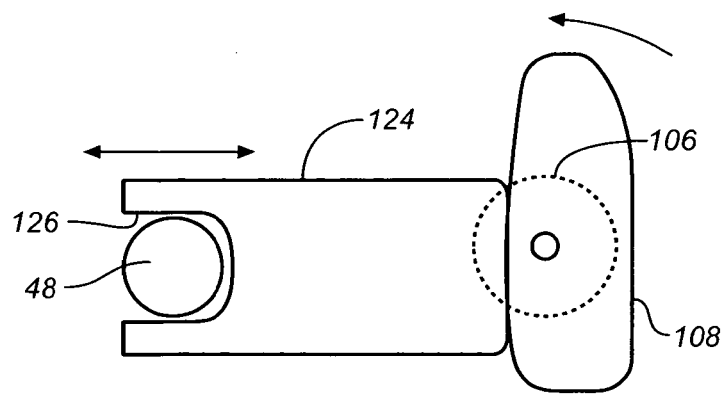

FIGS. 11C and 11D are a schematic depiction of the dispensing device of FIG. 11A wherein the positions of the dispensing mechanism, motor and cam are at a retrieval position.

Figure 11E:
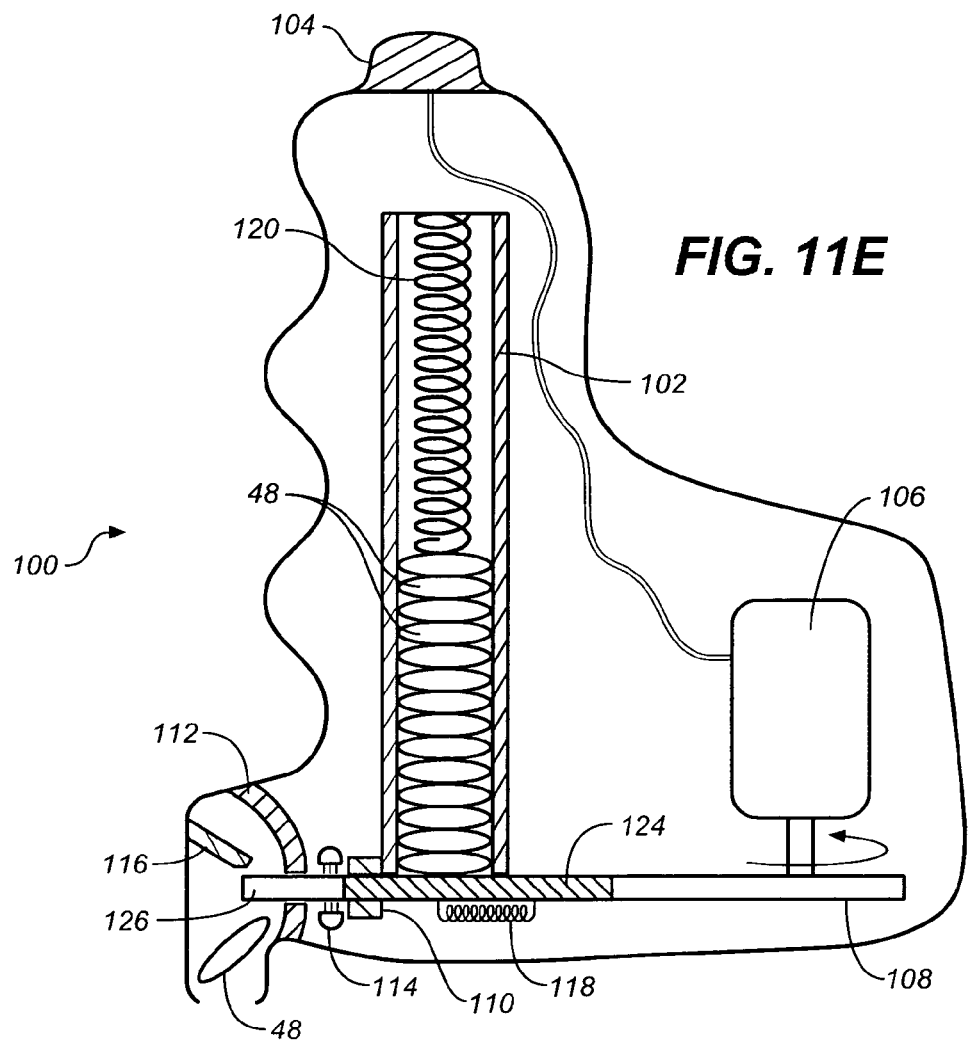
Figure 11F:
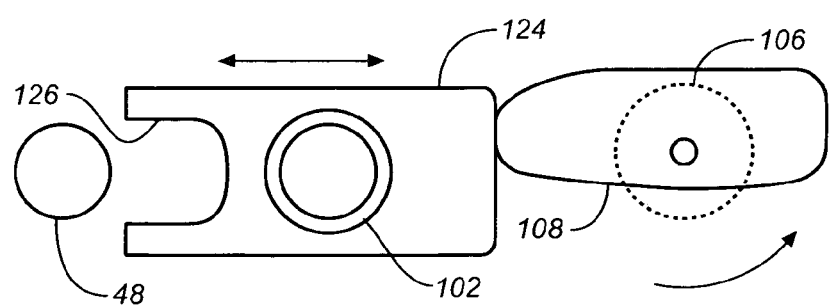

FIGS. 11E and 11F are a schematic depiction of the dispensing device of FIG. 11A wherein the positions of the dispensing mechanism, motor and cam are at a dispensing position.

Figure 11G:
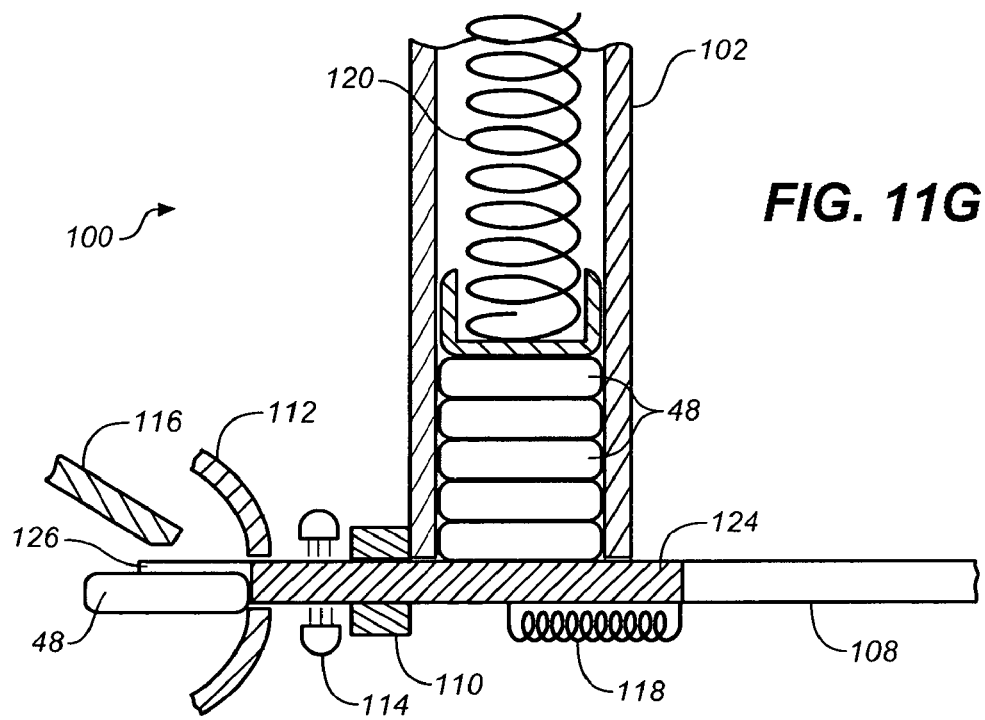
Figure 11H:
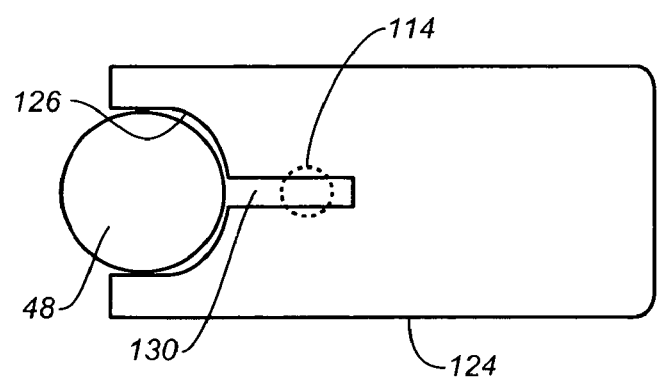

FIGS. 11G and 11H are depictions of the optical sensing mechanism for detecting delivery of drug dosage forms of the dispensing device. The dispensing mechanism comprises one or more cartridge assembly, cam, desiccant, seals, delivery sensor, and a spring clip.

Figure 12A:
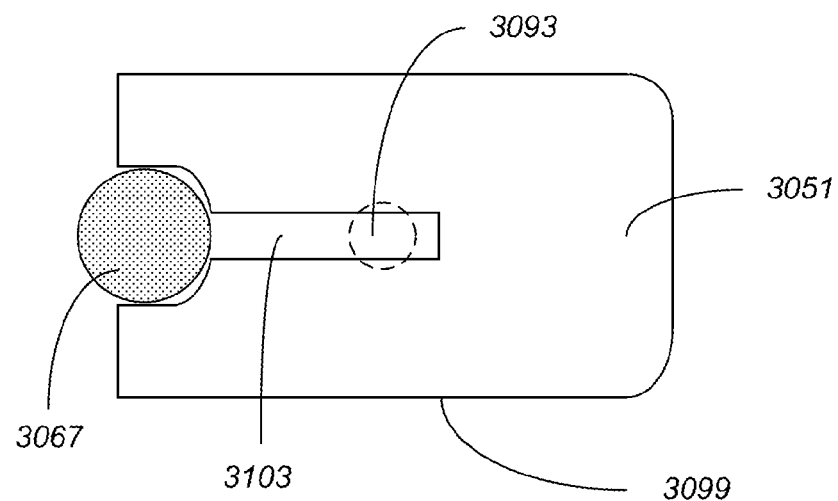
Figure 12B:
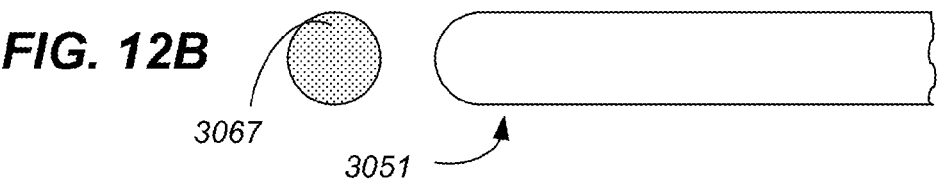
Figure 12C:
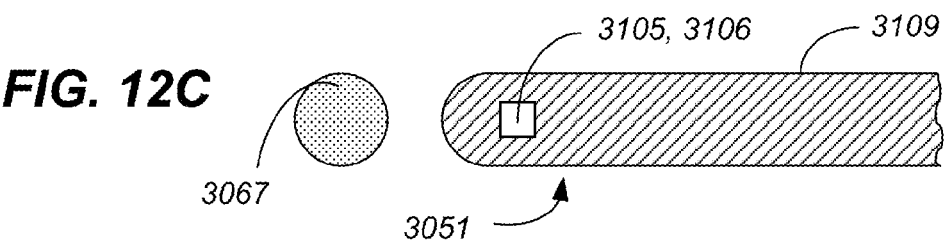
Figure 12D:
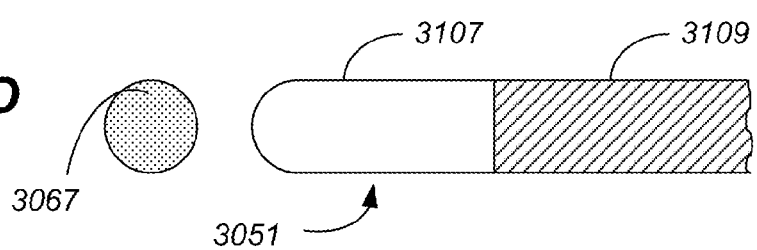

FIG. 12A is a schematic depiction of the dispensing end of a push rod 3051 used to deliver a drug dosage form 3067 using a dispensing device 3011 of the invention.

Figure 12E:
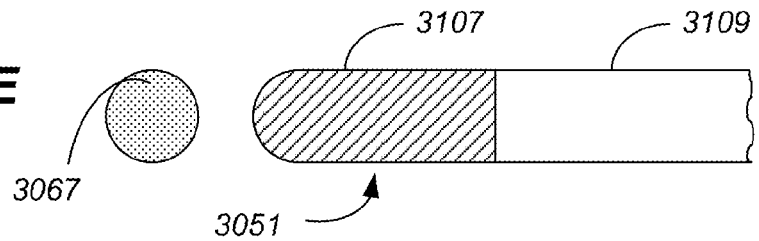

FIGS. 12B-E provide a schematic depiction of push rod embodiments for use in a dispensing device of the invention wherein the push rod may have transparent and/or reflective portions; the push rod 3051 may be entirely transparent (FIG. 12B); the push rod 3051 may have be opaque with or without a window 3105 and with or without a reflector 106 (FIG. 12C); have a transparent tip portion 3107 and an opaque push rod portion 3109 (FIG. 12D); or have a transparent push rod portion 3107 and an opaque tip portion 3109 (FIG. 12E).

FIG. 13A depicts an additional embodiment of a dispensing device of the invention dispensing mechanism, wherein a ribbon type dispensing mechanism at a rest position is illustrated.

FIG. 13B depicts the dispensing mechanism of FIG. 13A at a retrieval position.

FIG. 13C depicts the dispensing mechanism of FIG. 13A at a dispensing position.

Figure 14:
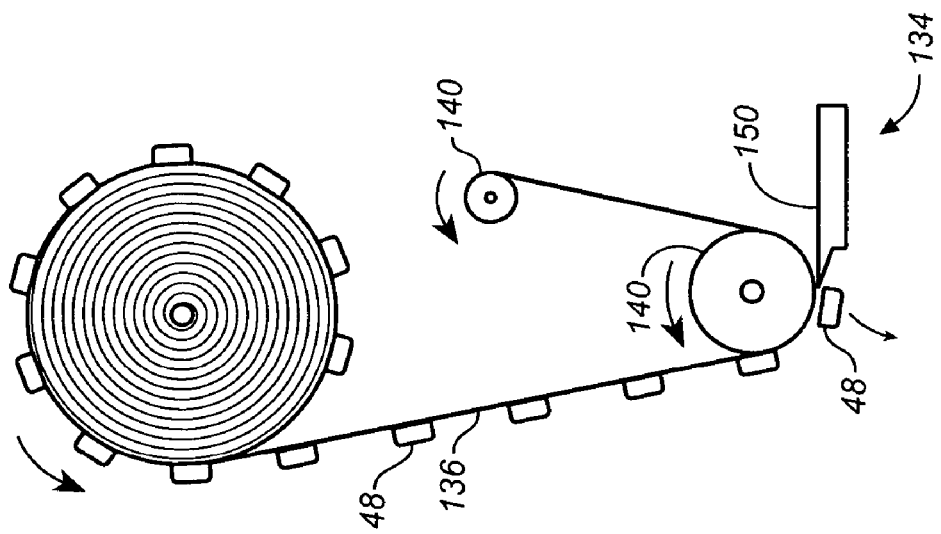

FIG. 14 depicts an additional embodiment of a dispensing mechanism of a dispensing device of the invention, wherein a ribbon type dispensing mechanism using a different type of a pushrod at dispensing position is illustrated.

Figure 15B:
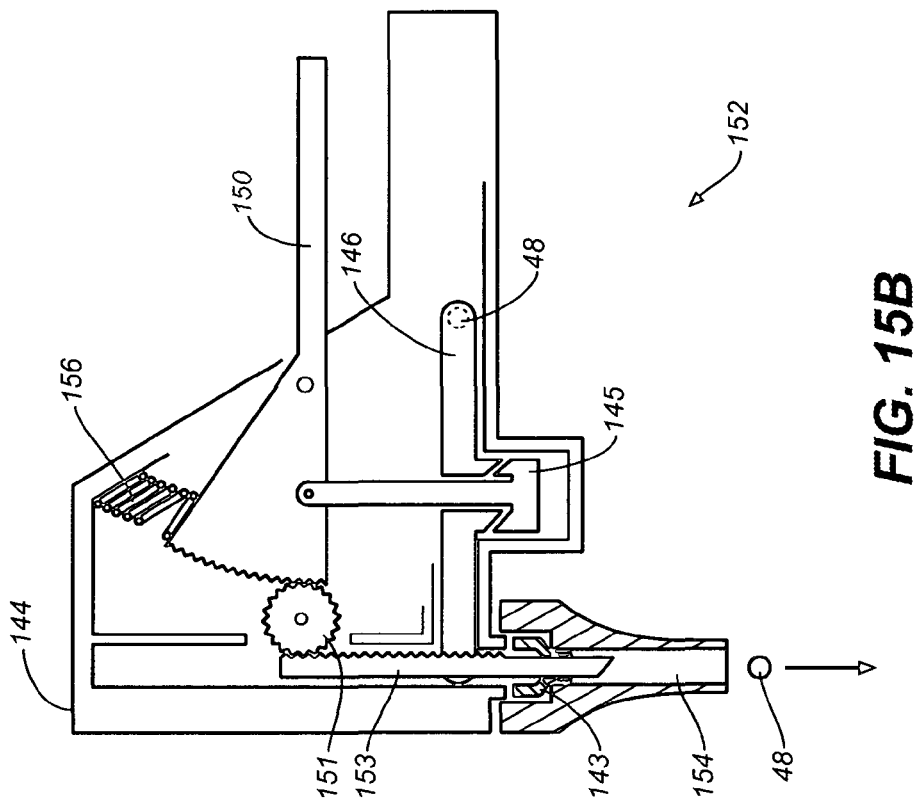
Figure 15A:
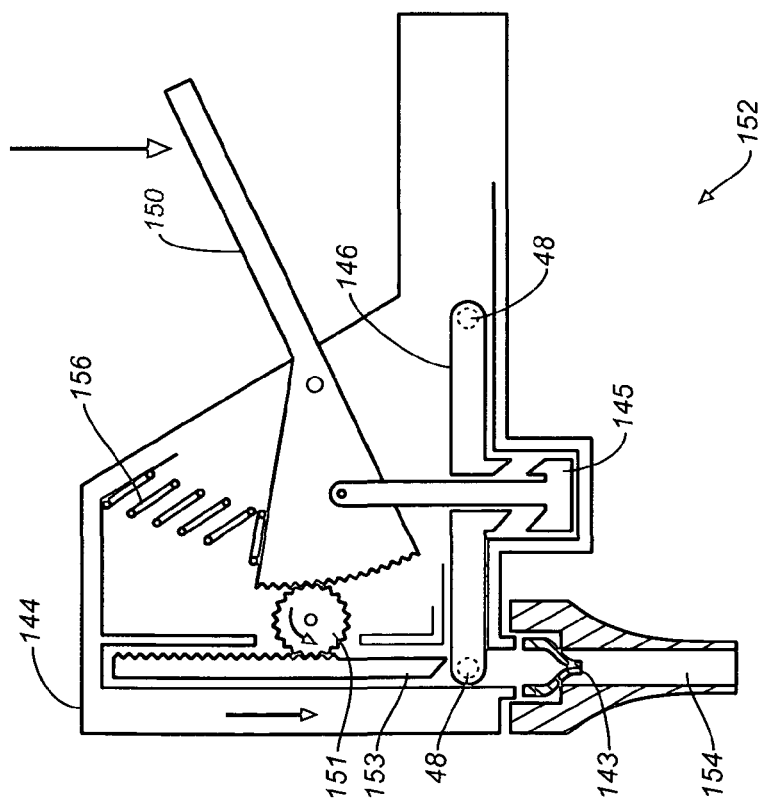

FIG. 15A depicts an additional embodiment of a dispensing device of the invention, wherein a disc type dispensing mechanism at rest position is illustrated.

FIG. 15B depicts the dispensing mechanism of FIG. 13A at a dispensing position.

Figures 16A, 16B, 16C:
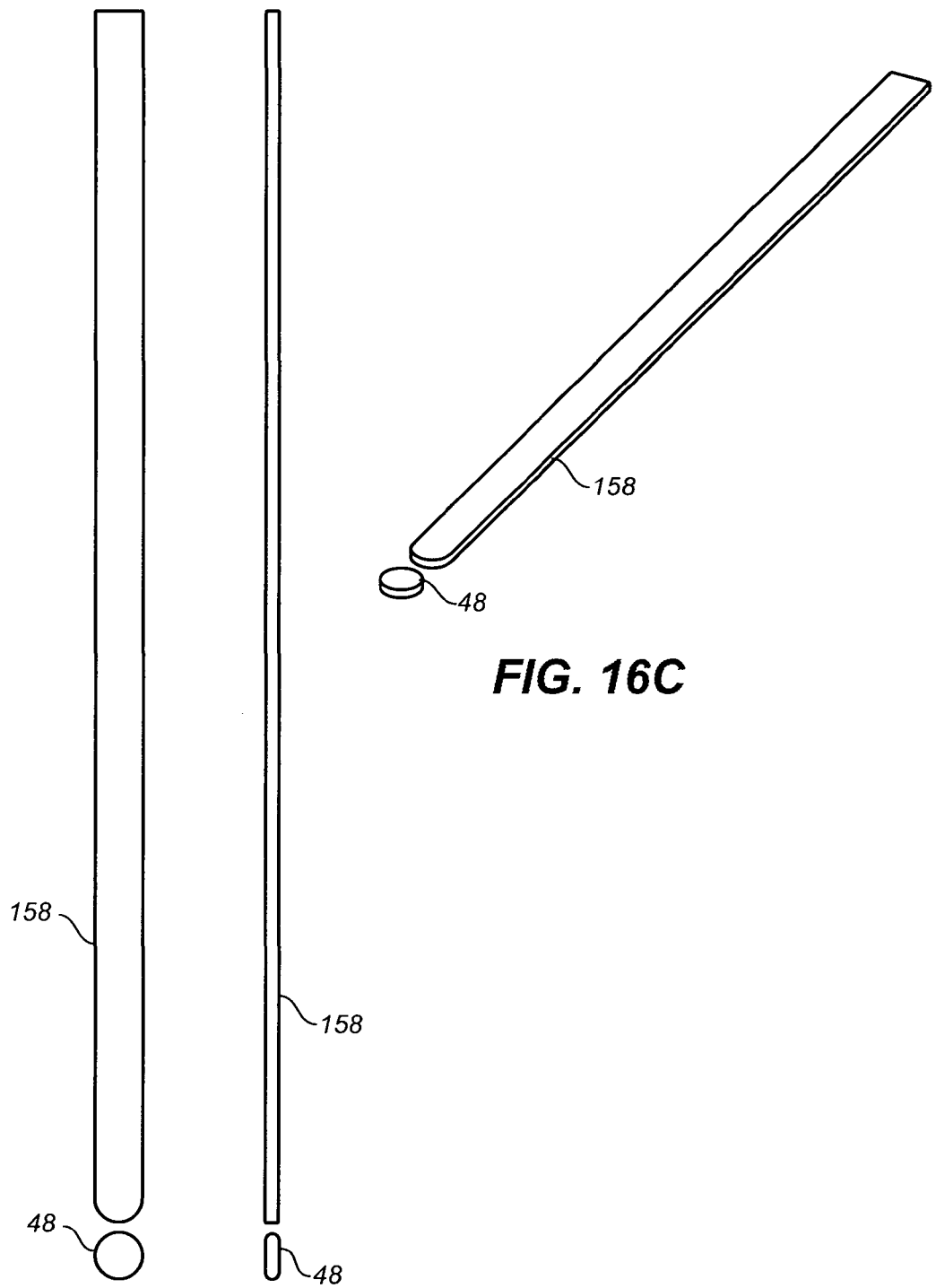

FIGS. 16A-16C depict an exemplary pushrod designed for dispensing a drug dosage form.

Figure 17:
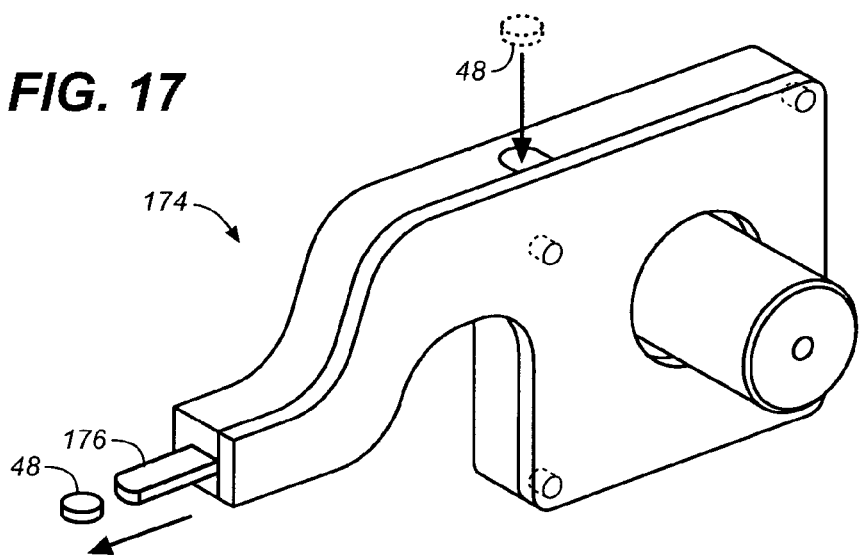
Figure 18:
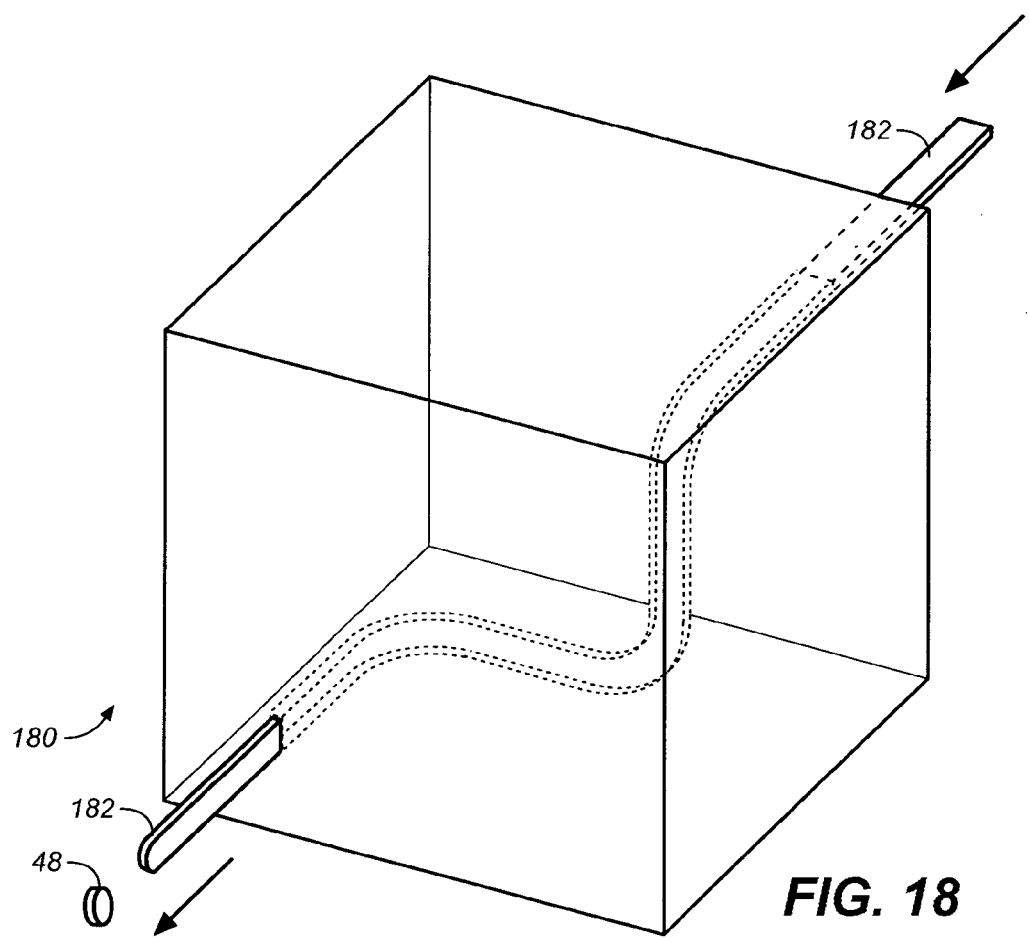

FIGS. 17 and 18 depict additional exemplary pushrod dispensing devices of the invention for dispensing a drug dosage form, wherein the pushrods are designed to be flexible and to afford different geometry.

FIGS. 19A-19D provide schematic depictions of exemplary drug cartridges including barrel, index/springload, snap-out, and track type, respectively.

Figure 20:
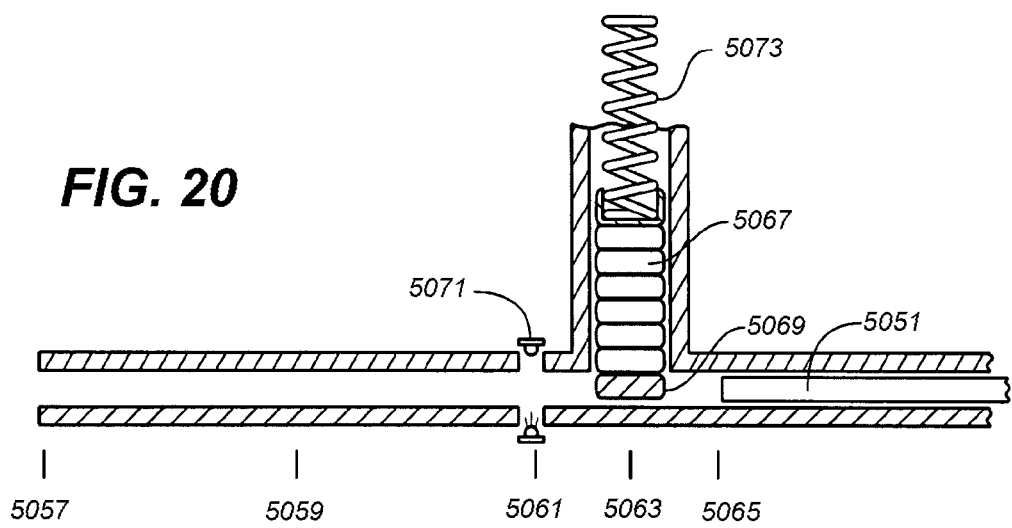

FIG. 20 is a schematic depiction of an exemplary device showing the stages of push rod/tablet interaction during device use. In FIG. 20, the push rod 5051, dosage forms 5067, shipping tablet 5069, spring 5073 and position sensor 5071 are shown. During use, the push rod 5051 moves between positions 5057, 5059, 5061, 5063, 5065 and 5067, also shown in FIG. 20.

Figures 21A, 21B:
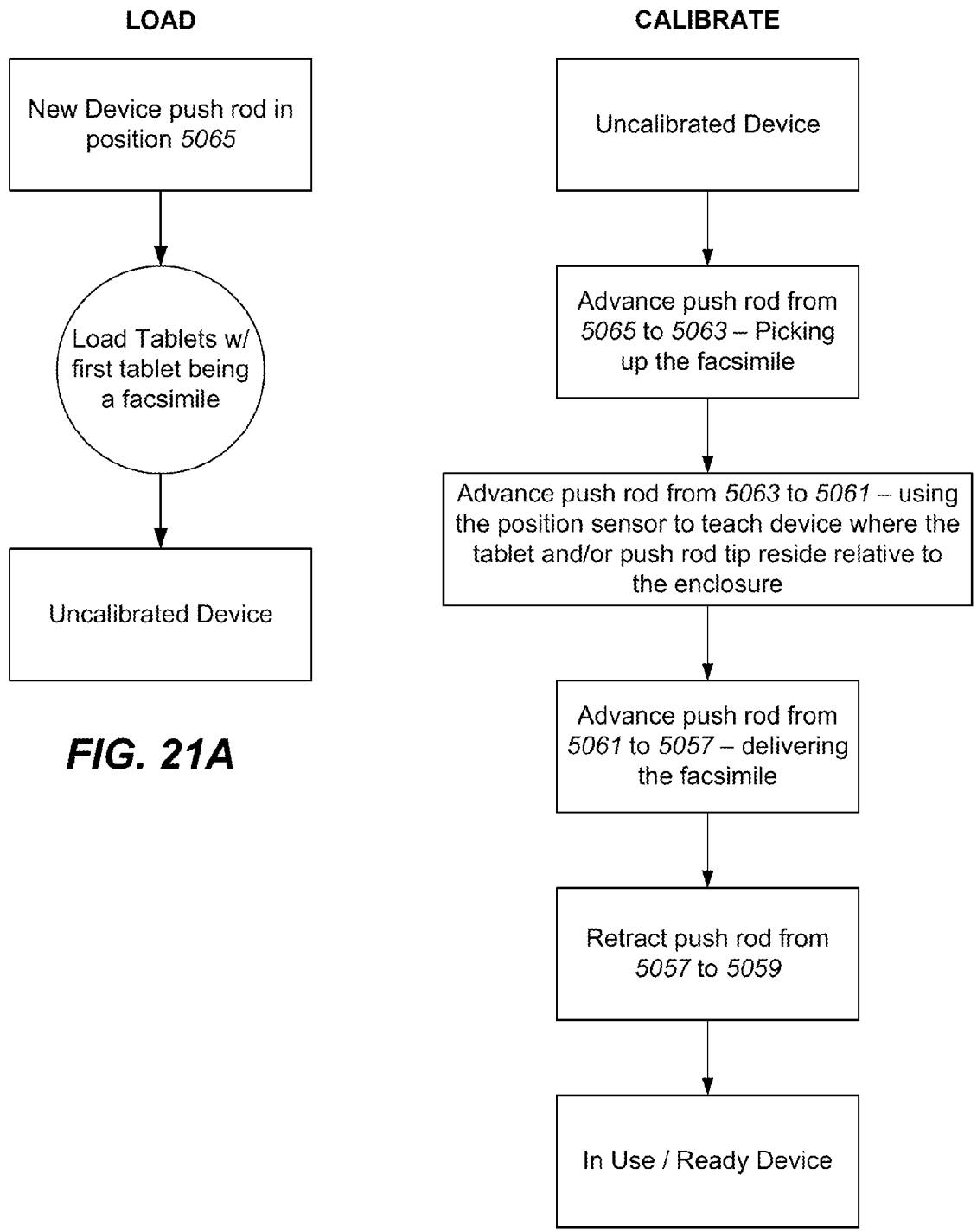
Figure 21C:
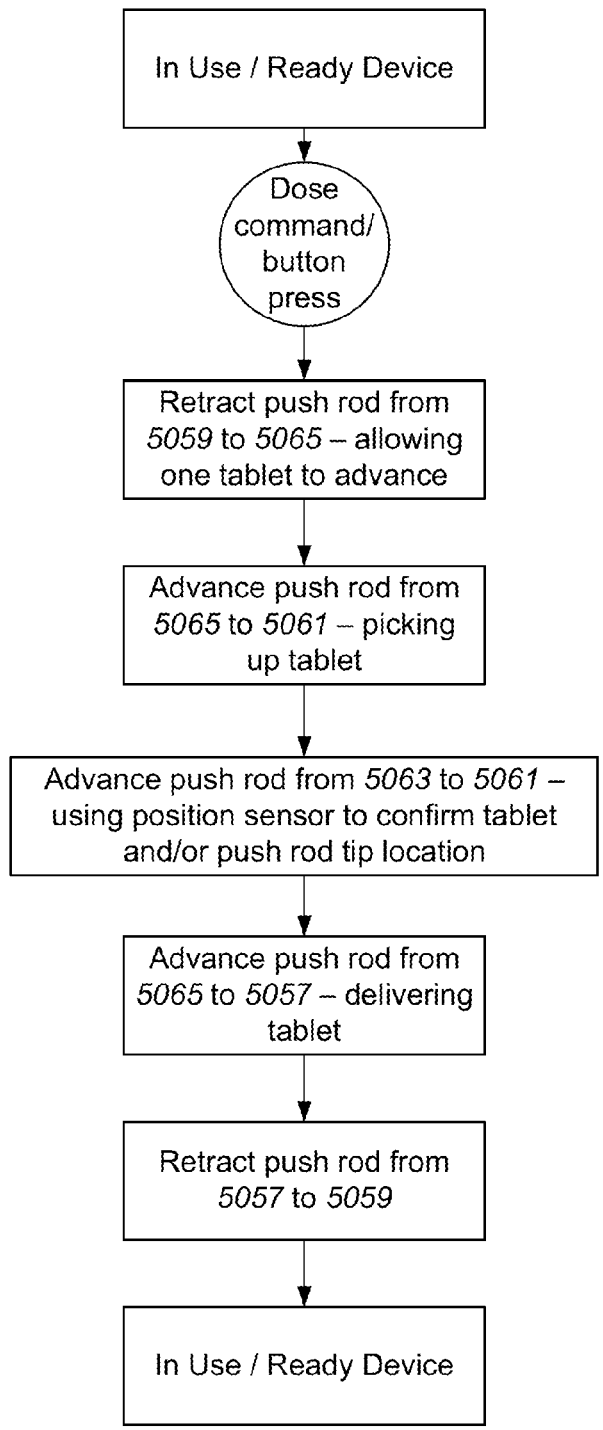
Figure 21D:
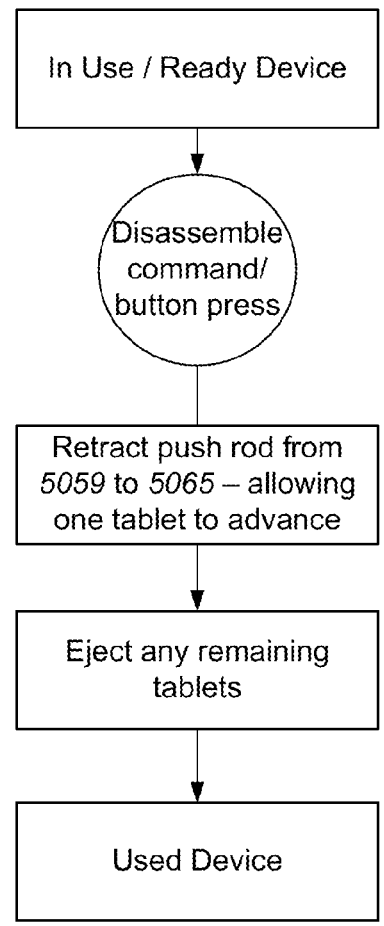

FIGS. 21A-D provide a series of flow diagrams for use of an exemplary device of the invention showing the stages of push rod/tablet interaction during device use, wherein FIG. 21A shows the LOAD feature; FIG. 21B shows the CALIBRATE feature; FIG. 21C shows the DISPENSE feature; and FIG. 21D shows the DISASSEMBLE feature.

Figure 22A:
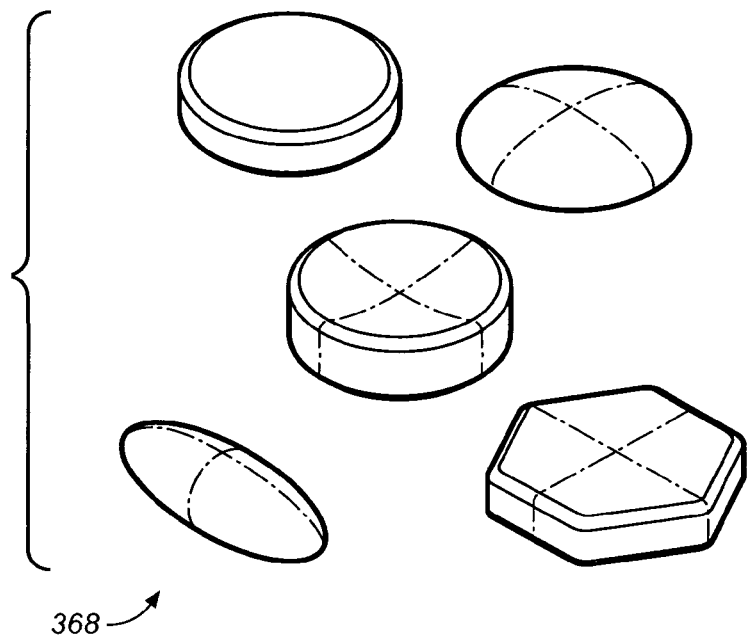
Figure 22B:
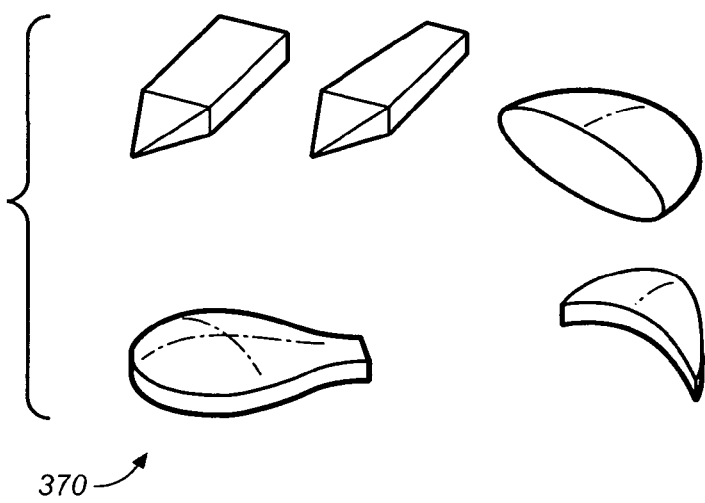

FIGS. 22A and 22B provide depictions of exemplary drug dosage form shapes. FIG. 22A is a schematic depiction of symmetric drug dosage forms including round discs with flat, concave, or convex faces, ellipsoids with flat, concave, or convex faces, spherical, polygons with 3 or more edges and flat, concave, or convex faces, or any other curved solid body. FIG. 22B is a schematic depiction of asymmetric dosage forms.

FIGS. 23A-F provide an illustration of six single dose applicators.

FIG. 24 provides an illustration of a multiple dose applicator where a plurality of single dose applicators are stored prior to use.

FIGS. 25A-C provide an illustration of additional single dose applicator and multiple dose applicator embodiments.

FIGS. 26A-B provide an illustration of two stages of use of one embodiment of a single dose applicator.

Figure 27A:
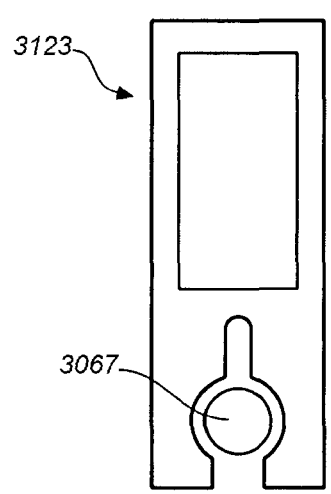
Figure 27B:
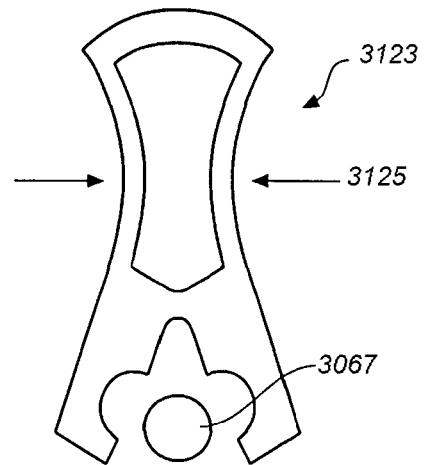

FIGS. 27A and 27B are schematic depictions of an exemplary single dose applicator.

Figure 28A:
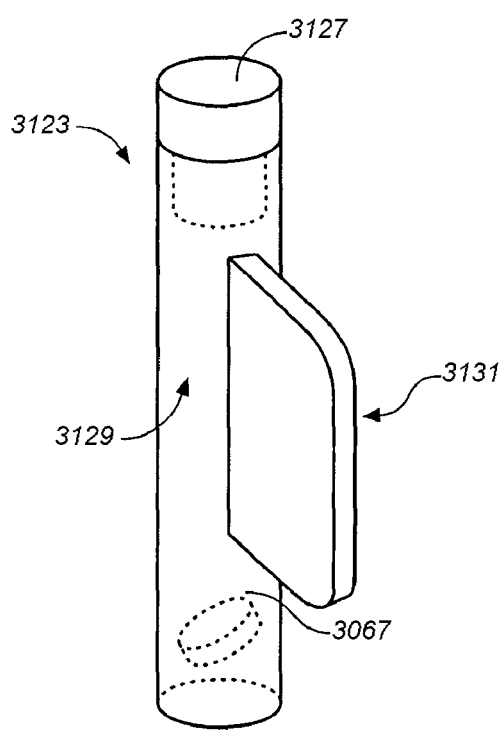
Figure 28B:
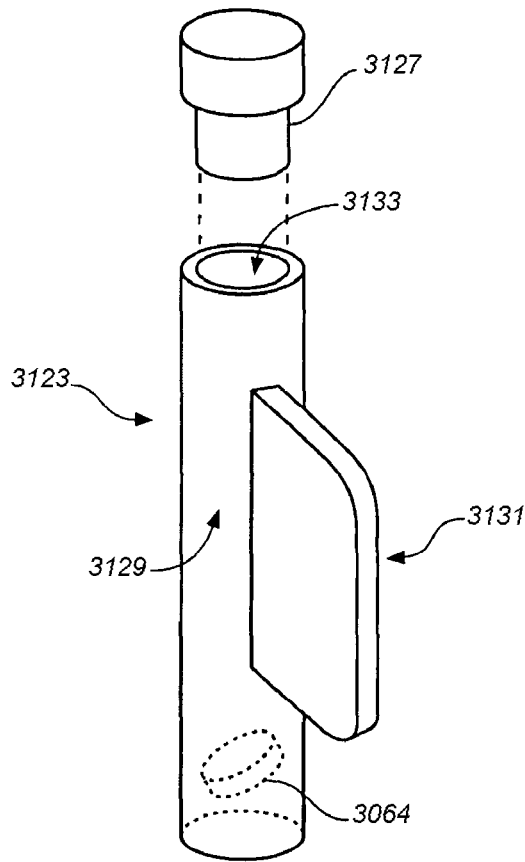
Figure 28C:
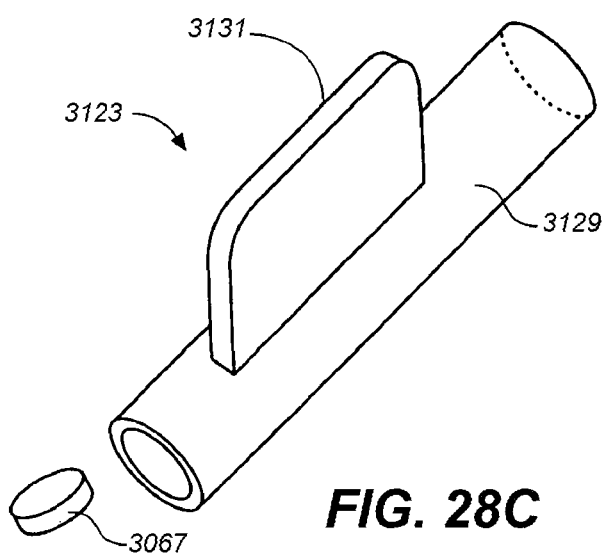

FIGS. 28A-C provide an illustration of one type of single dose applicator and use thereof in delivering a dosage form to a subject.

FIGS. 29A-29D are schematic depictions of an exemplary mechanical lockout means, wherein one exemplary locking mechanism is illustrated. FIGS. 29A through 29D illustrate various stages of the lockout mechanism related to dispensing drug dosage forms.

FIGS. 30A-30F are schematic depictions of exemplary lockout devices, such as a pushrod type device (30A), lockout on actuator type device (30B), safety button/latch type device (30C/30D), solenoid type device (30E), and another solenoid type lockout device (30F), respectively.

Figure 31:
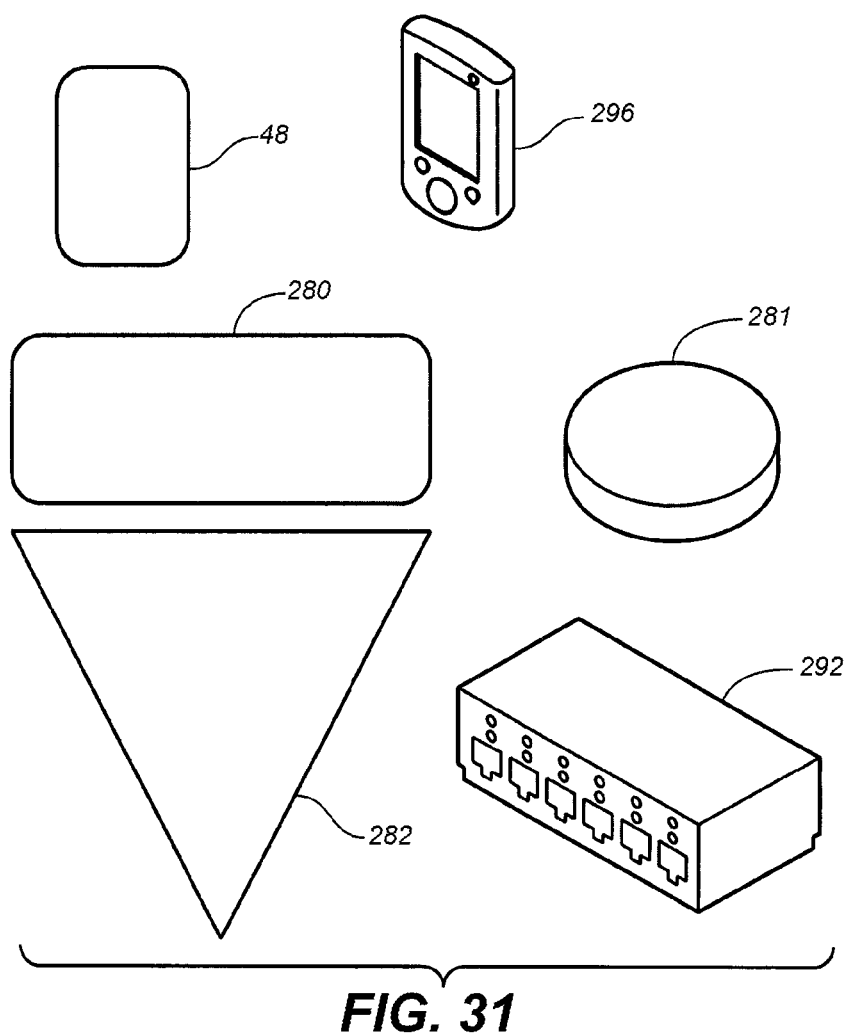

FIG. 31 is a schematic architecture connection diagram illustrating the various components that may be included in a drug dispensing device or system including a device with a separate drug dispensing device head 280, drug dispensing device body 282, disposable drug dosage cartridge 48, a portable docking FOB 296, a patient RFID tag 281, and a base station 292.

Figure 32A:
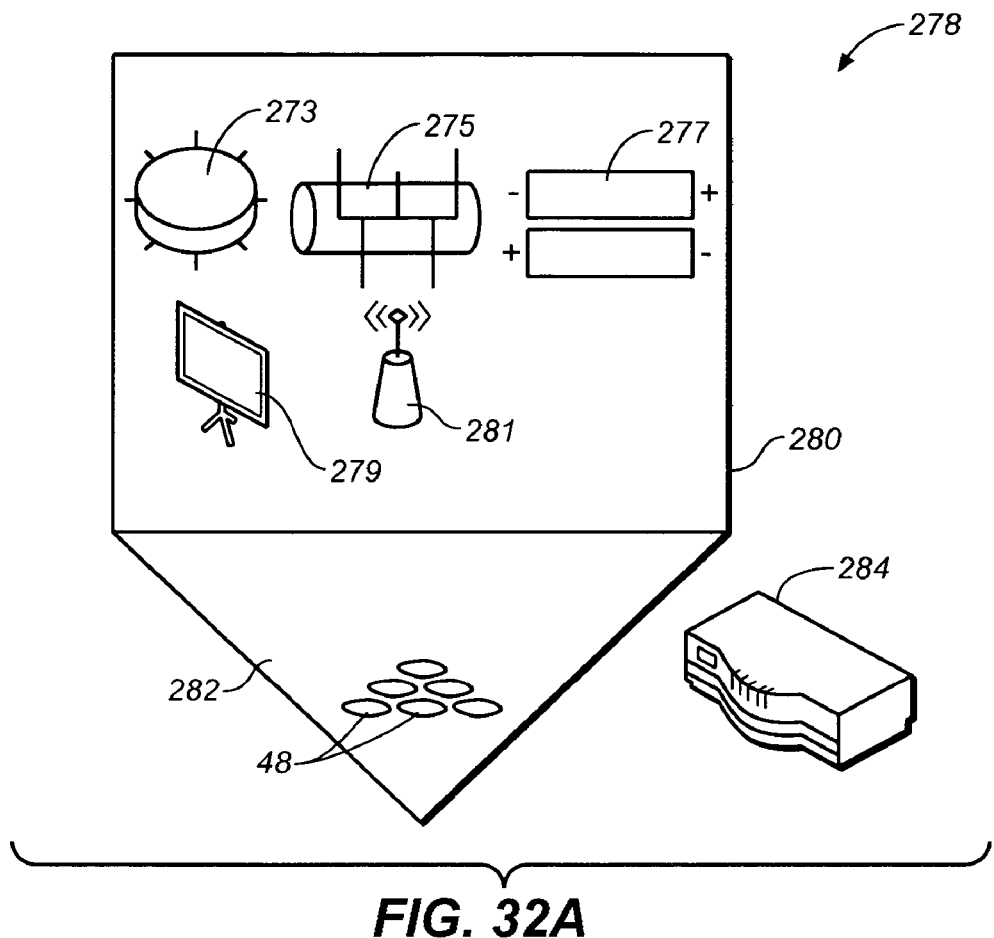

FIG. 32A is a schematic depiction of an exemplary architecture having a reusable head, disposable body, and recharge station.

Figure 32B:
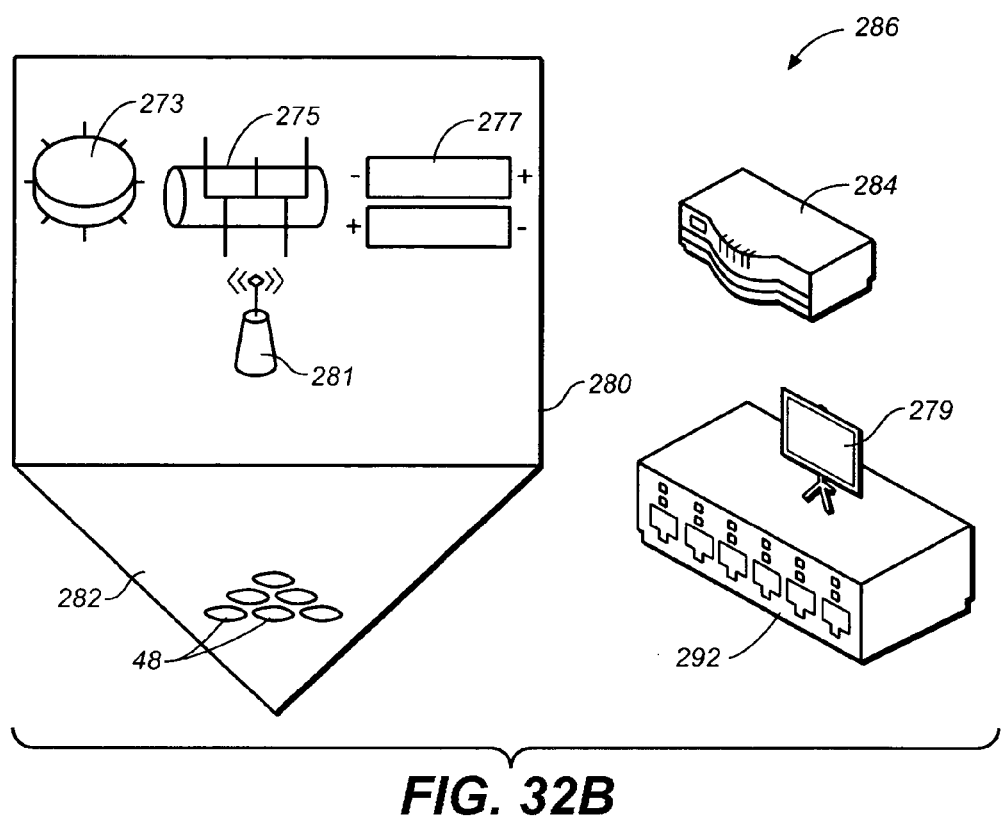

FIG. 32B is a schematic depiction of an exemplary architecture having a reusable head, a disposable body, a docking station, and a docking station.

Figure 32C:
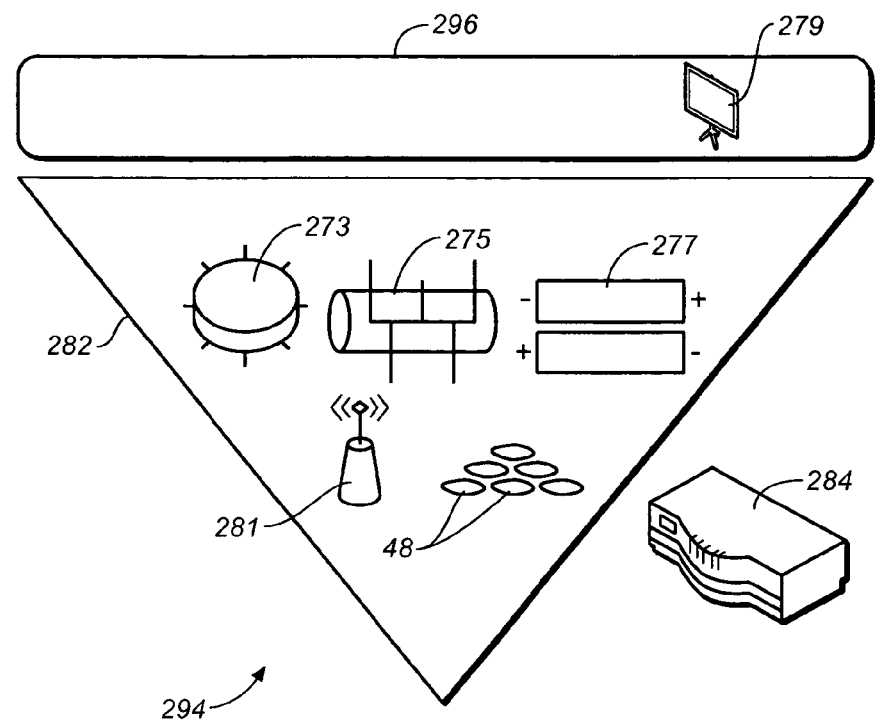

FIG. 32C is a schematic depiction of an exemplary architecture having a disposable body, portable docking station (fob), and a recharge station.

Figure 32D:
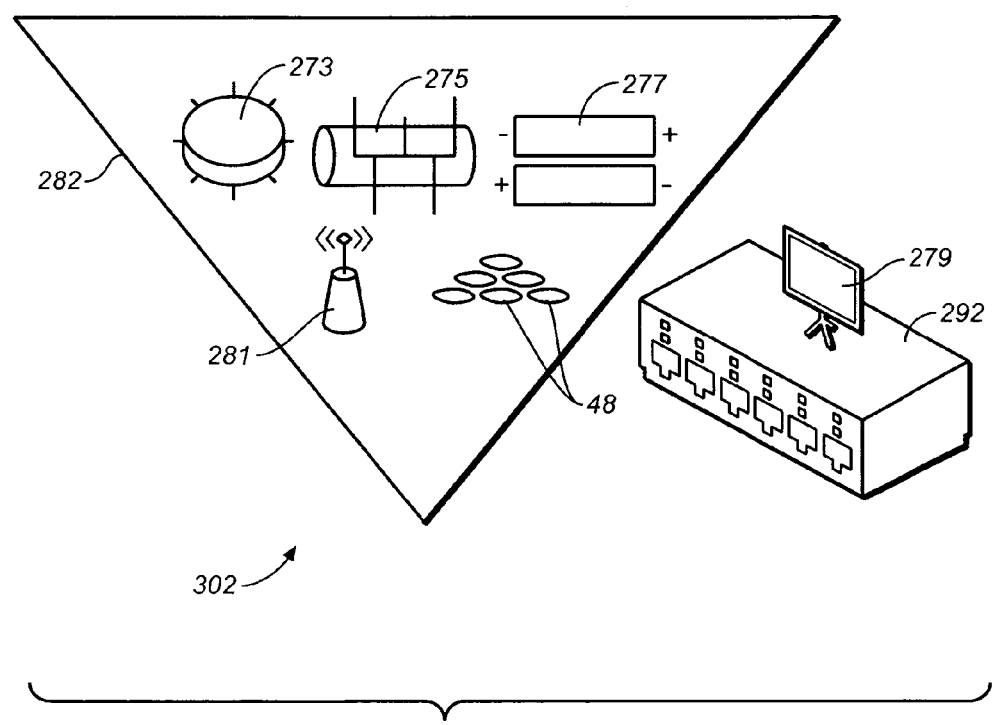

FIG. 32D is a schematic depiction of an exemplary architecture having a disposable body and a docking station.

Figure 32E:
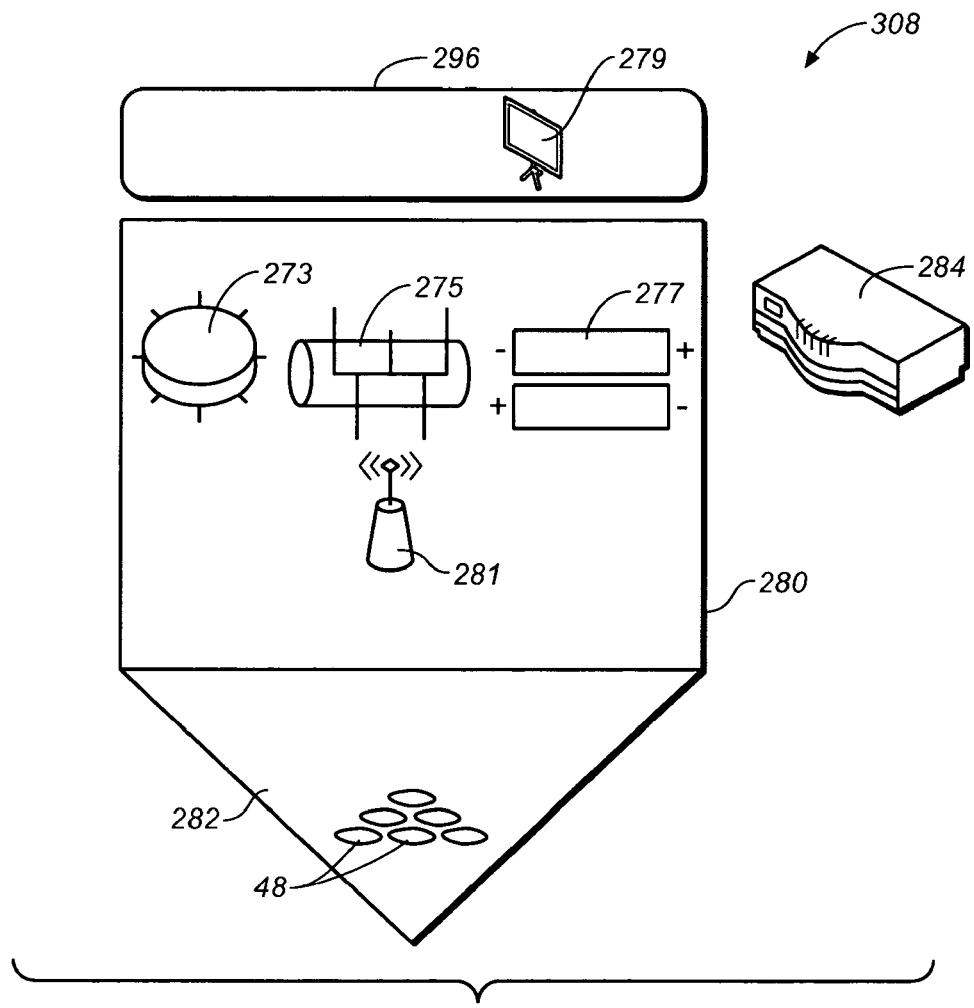

FIG. 32E is a schematic depiction of an exemplary architecture having a reusable head, disposable body, portable docking station, and recharge station.

Figure 32F:
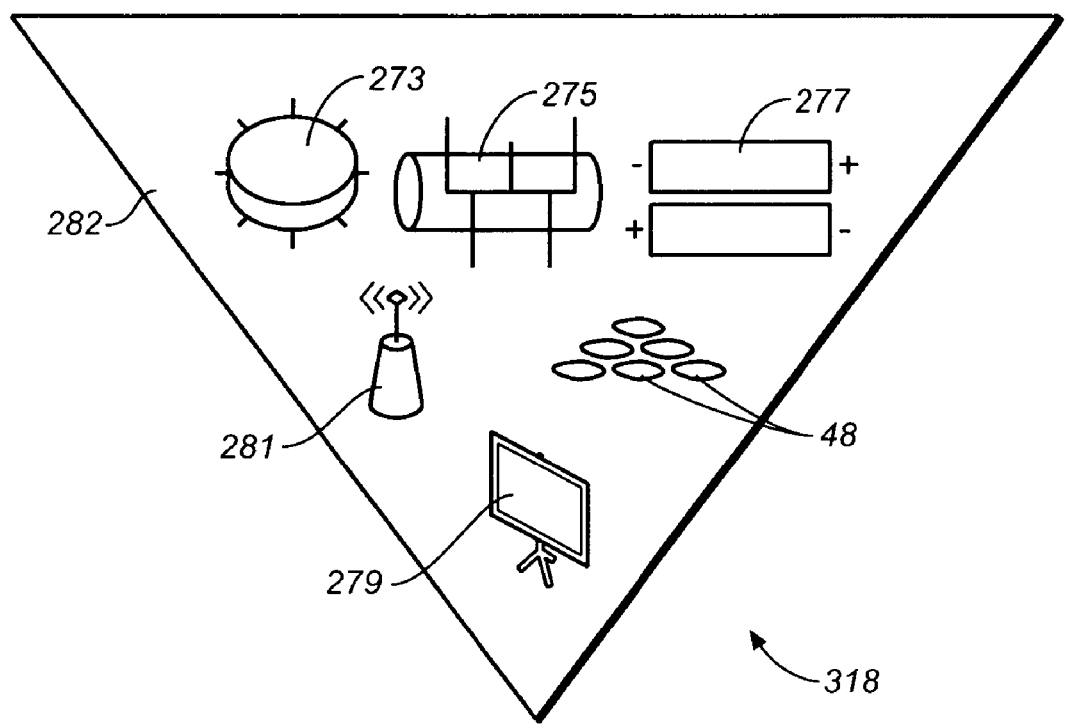

FIG. 32F is a schematic depiction of an exemplary architecture, wherein a fully disposable device is shown.

Figure 33:
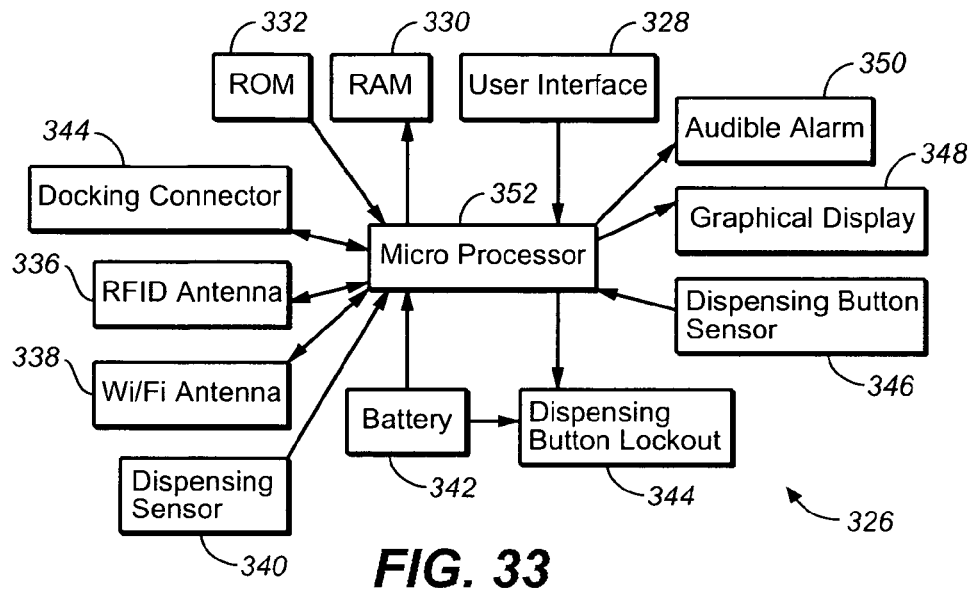

FIG. 33 is a schematic depiction of the functional elements of the drug dispensing system of the invention, including a drug dispensing device and pharmaceutical network with a monitoring and control apparatus coupled via a wireless or other bi-directional communication network. The system includes a battery powered microprocessor which comprises RAM and ROM, is operably connected to a docking connector, and communicates in a bi-directional manner with an RFID antenna, a WI/FI antenna, wherein the drug dispensing device and pharmaceutical network further comprises, a user interface, an audible alarm, a graphic display, a dispensing button and sensor, and a dispensing button lockout.

Figure 34A:
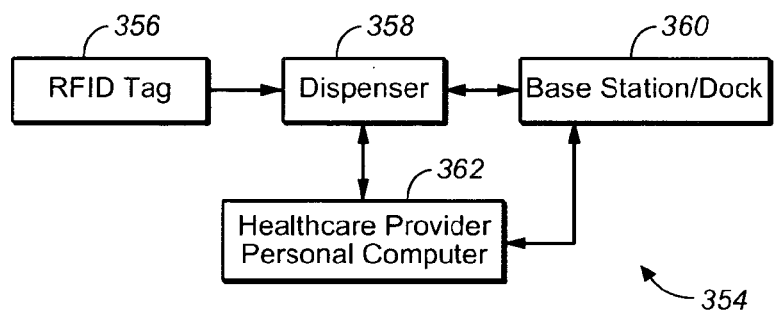
Figure 34B:
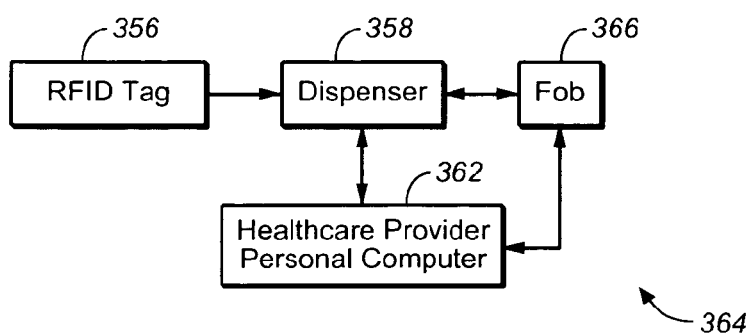

FIGS. 34A and 34B are block diagrams illustrating communication associated with a drug dispensing system of the invention. FIG. 34A depicts a system communication diagram comprising a radio frequency identification (RFID) tag, a dispensing device, a base station/dock and a healthcare provider personal computer. FIG. 34B depicts a system communication diagram comprising an RFID tag, a dispensing device, a fob (or portable handheld docking device) and a healthcare provider personal computer.

Figure 35:
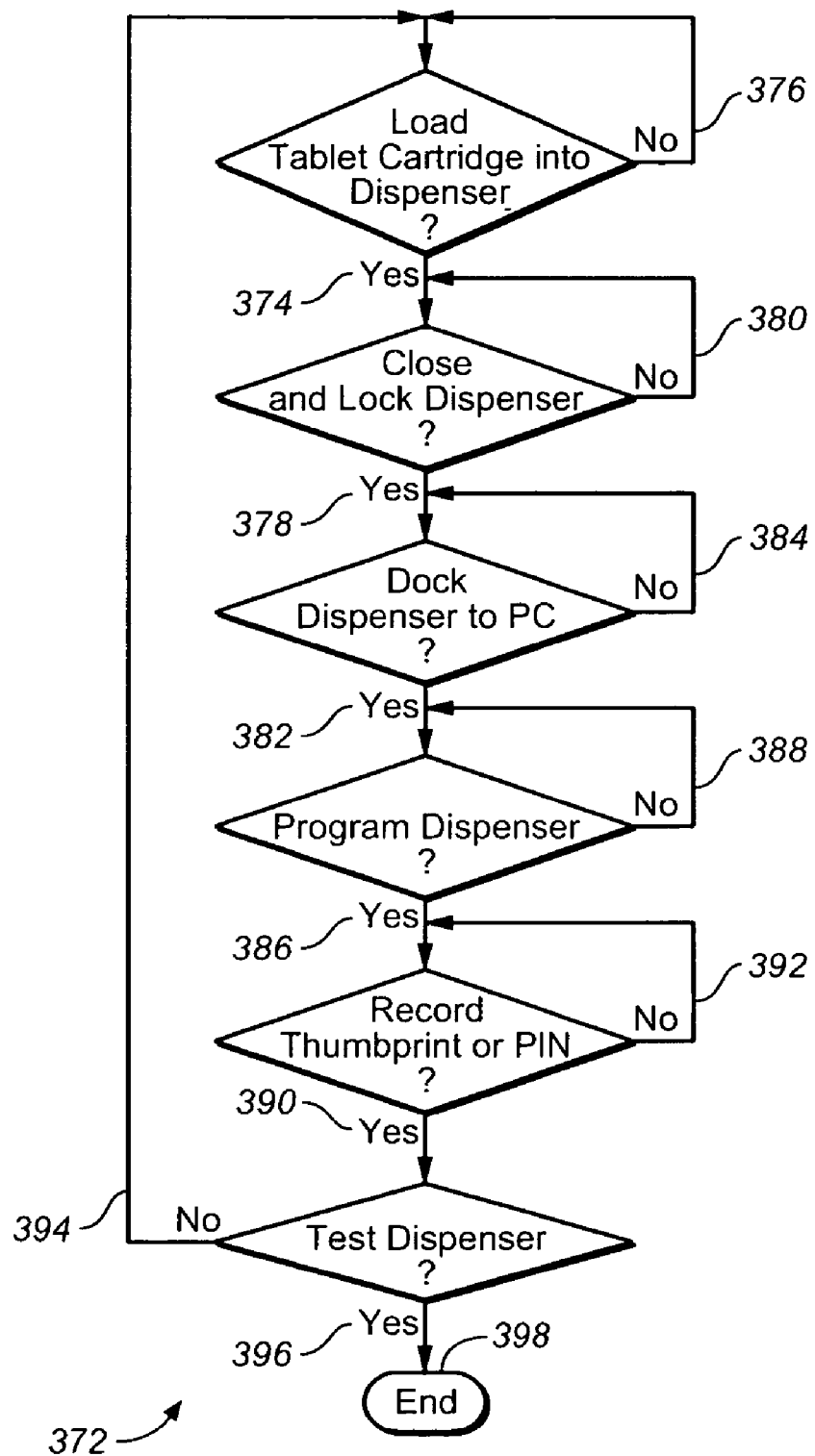

FIG. 35 is a block diagram of a setup and programming flow chart for a drug dispensing system of the invention, wherein the process involves the steps of: loading a dosage form cartridge into the dispensing device; closing and locking the dispensing device; docking the dispensing device into the PC; programming the dispensing device; recording a thumbprint or PIN to identify the appropriate user; and testing the dispensing device.

Figure 36:
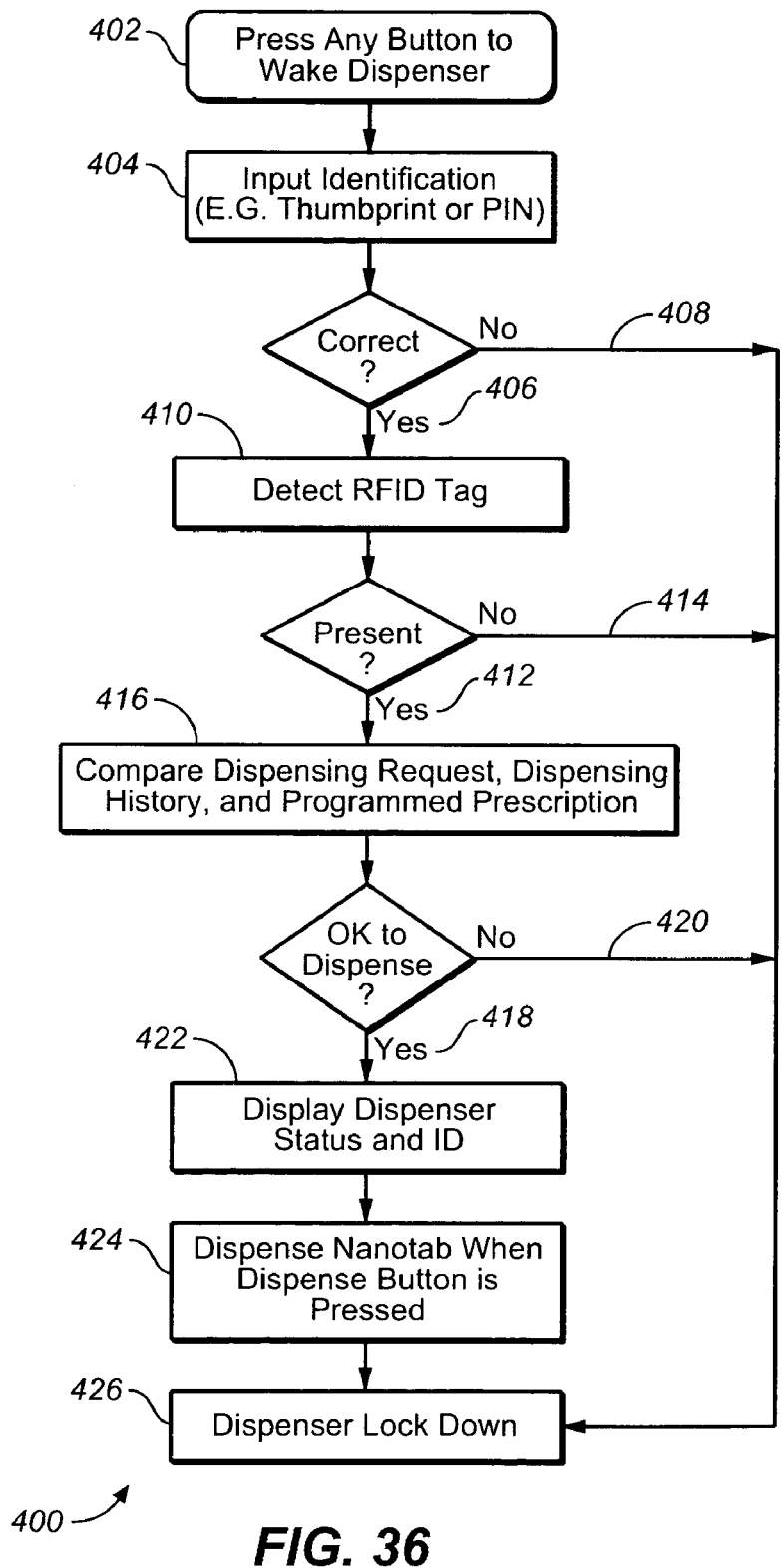

FIG. 36 is a block diagram illustrating a dispensing device operation flow chart, wherein one example of stepwise operation of a drug dispensing device of the invention is provided.

Figure 37:
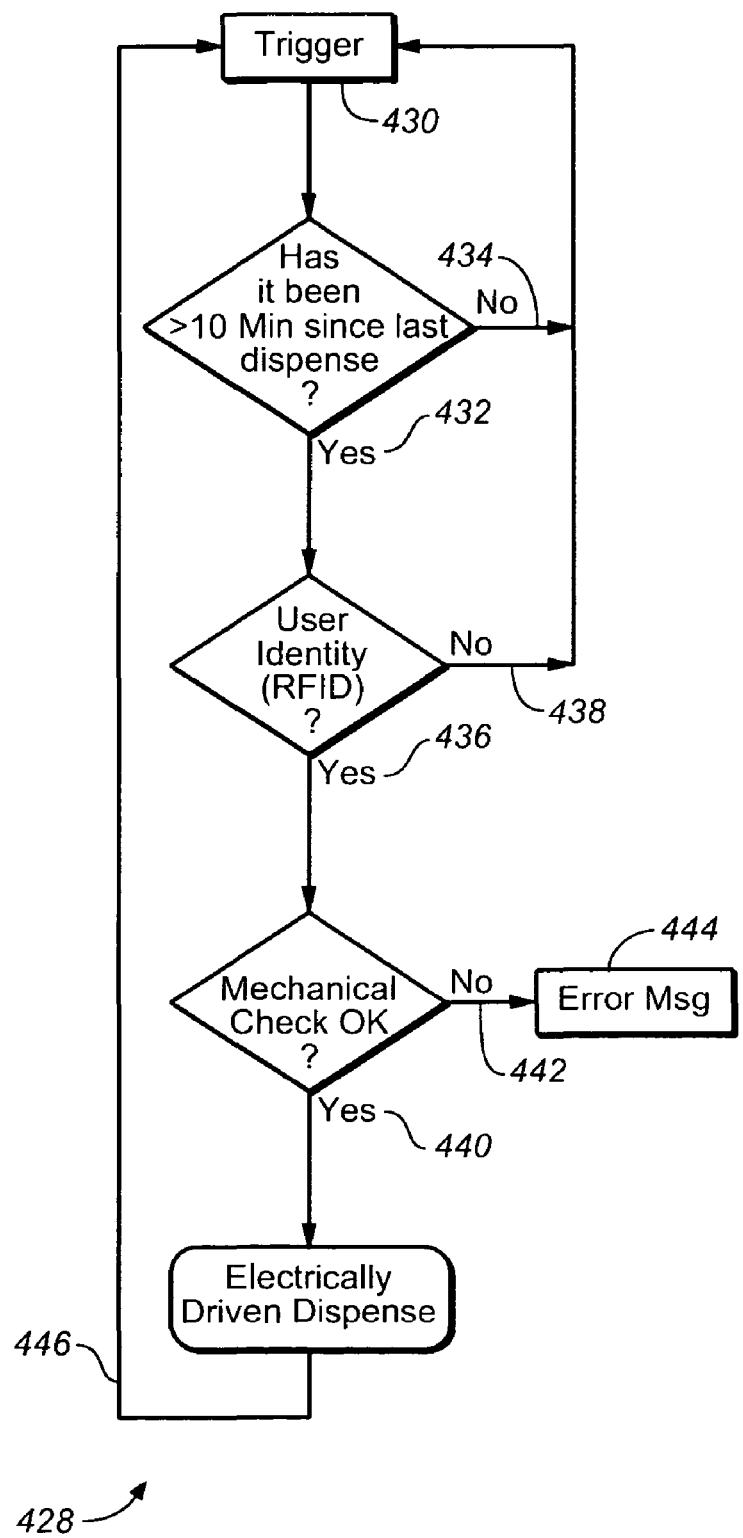

FIG. 37 is a block diagram illustrating another exemplary dispensing device operation flow chart, wherein a second example of stepwise operation of a drug dispensing device of the invention is provided.

Figure 38:
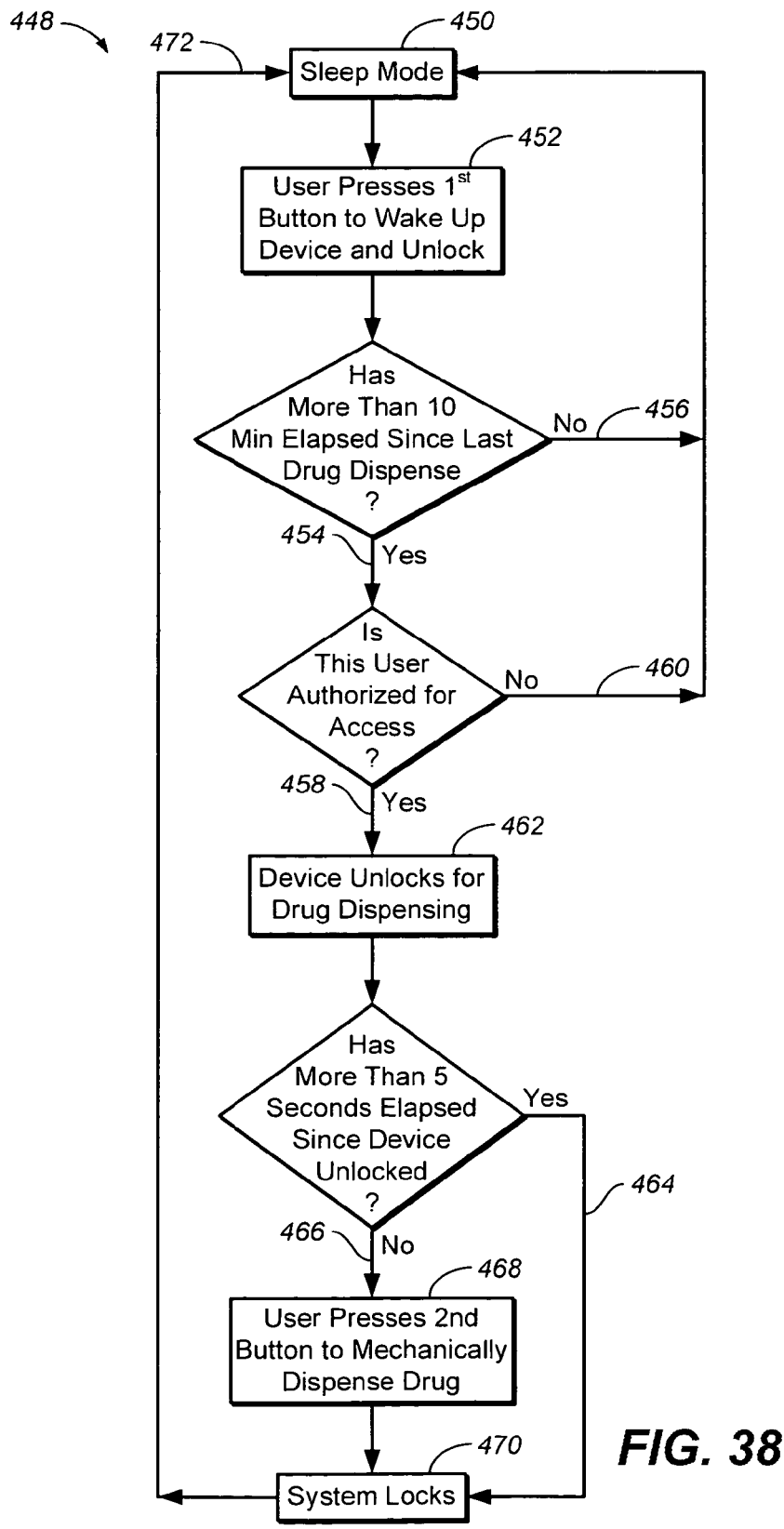

FIG. 38 is a block diagram illustrating another exemplary dispensing device operation flow chart, wherein a third example of stepwise operation of a drug dispensing device of the invention is provided.

Figure 39:
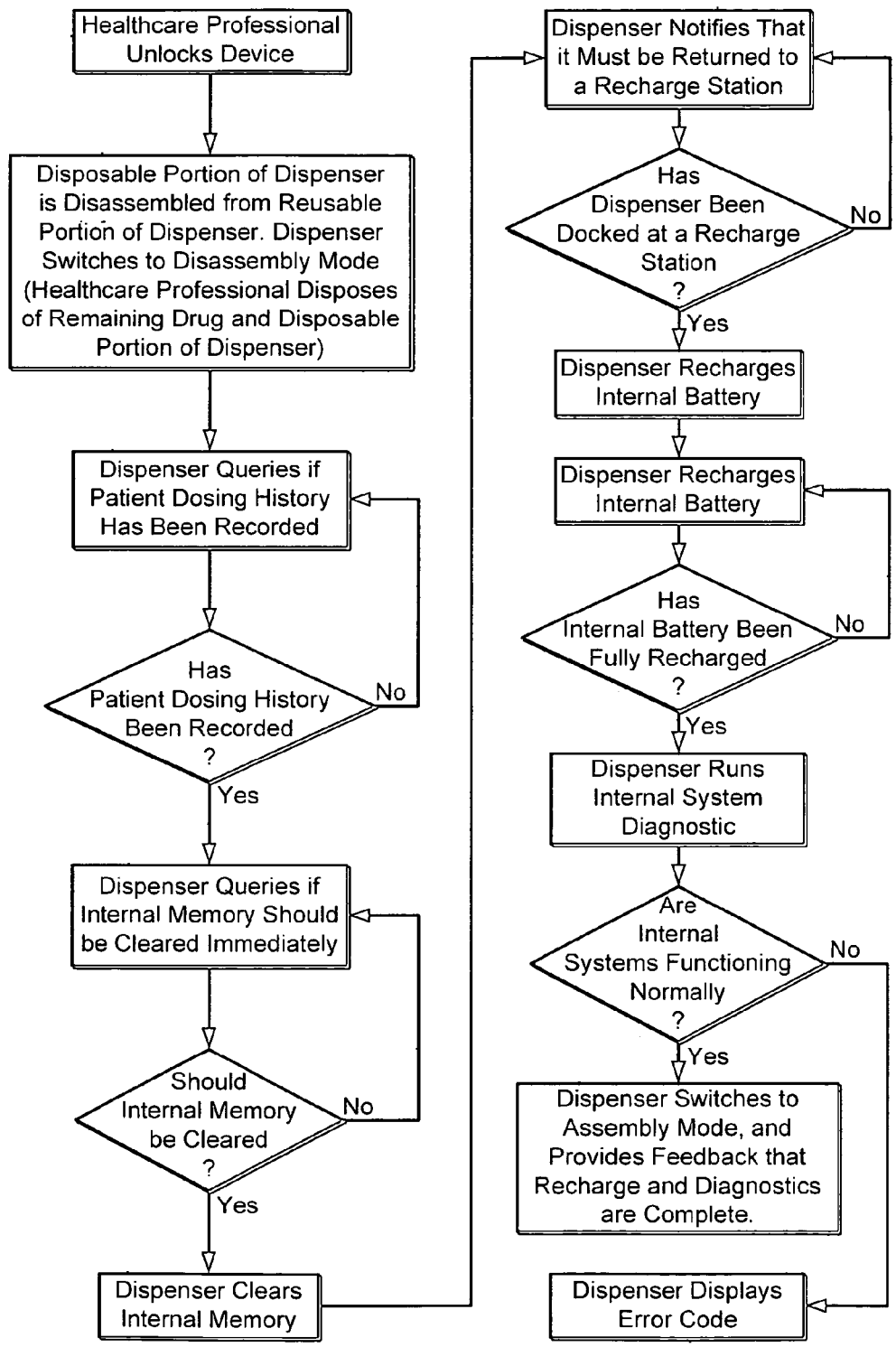

FIG. 39 is a block diagram illustrating exemplary dispensing device disassembly flow chart by a healthcare professional, wherein an example of stepwise disassembly of a drug dispensing device of the invention, following use, is provided.

Figure 40:
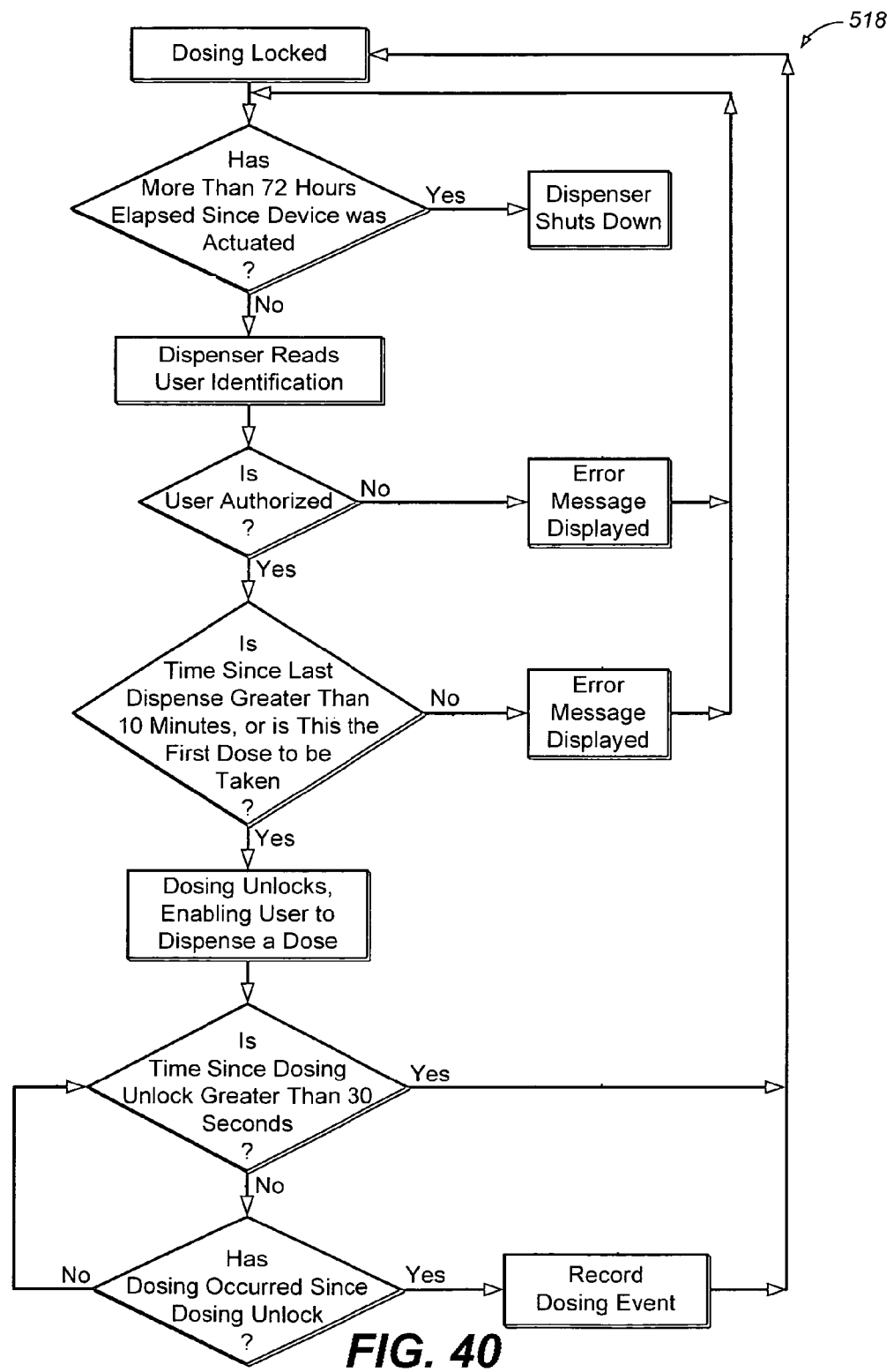

FIG. 40 is a block diagram illustrating an exemplary outpatient acute dispensing device operation flow chart, wherein an example of stepwise operation of a drug dispensing device of the invention is provided.

Figure 41:
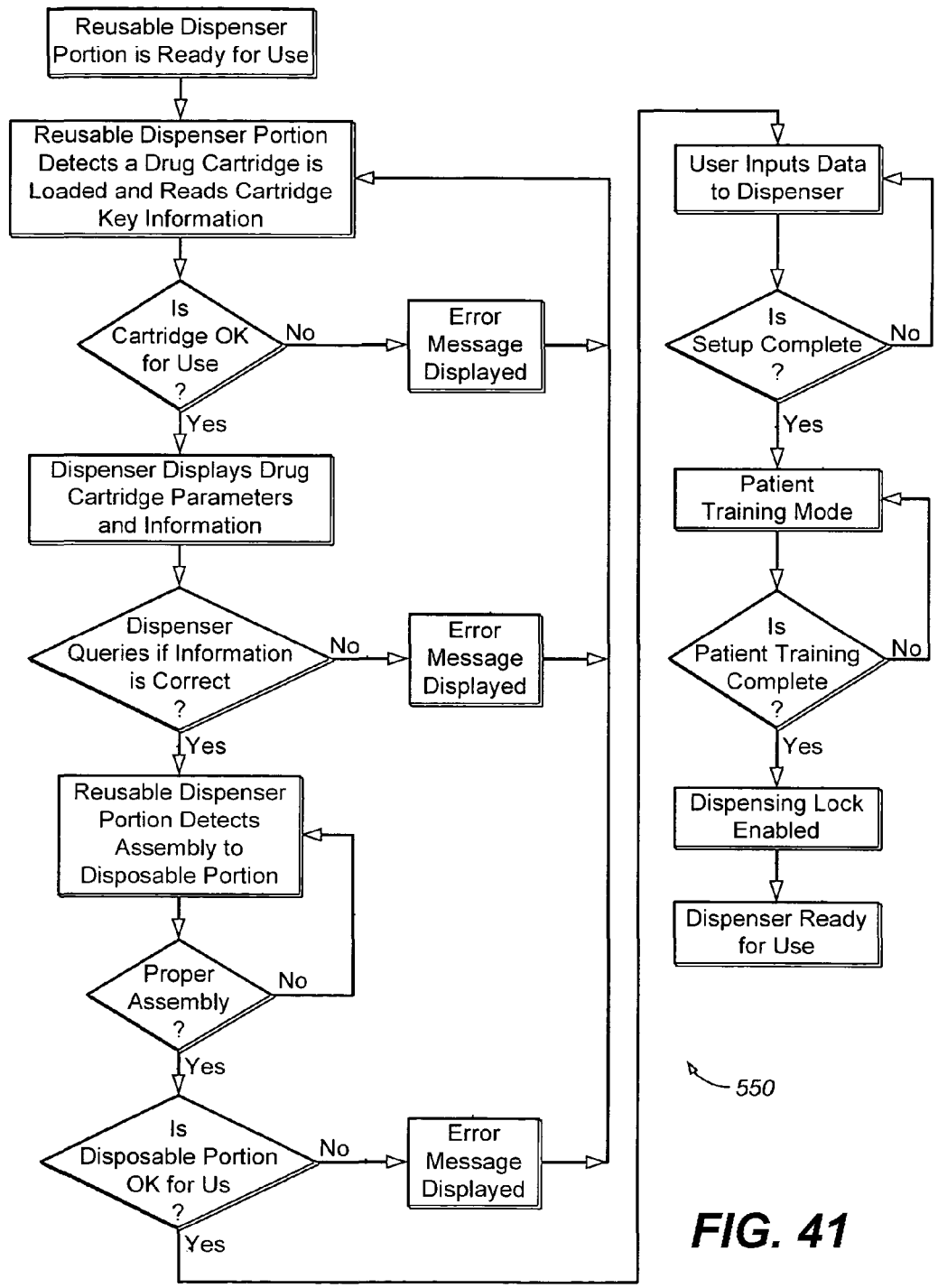

FIG. 41 is a block diagram illustrating an exemplary inpatient dispensing device setup and assembly flow chart, wherein an example of stepwise setup and assembly of a drug dispensing device of the invention, prior to use, is provided.

Figure 42:
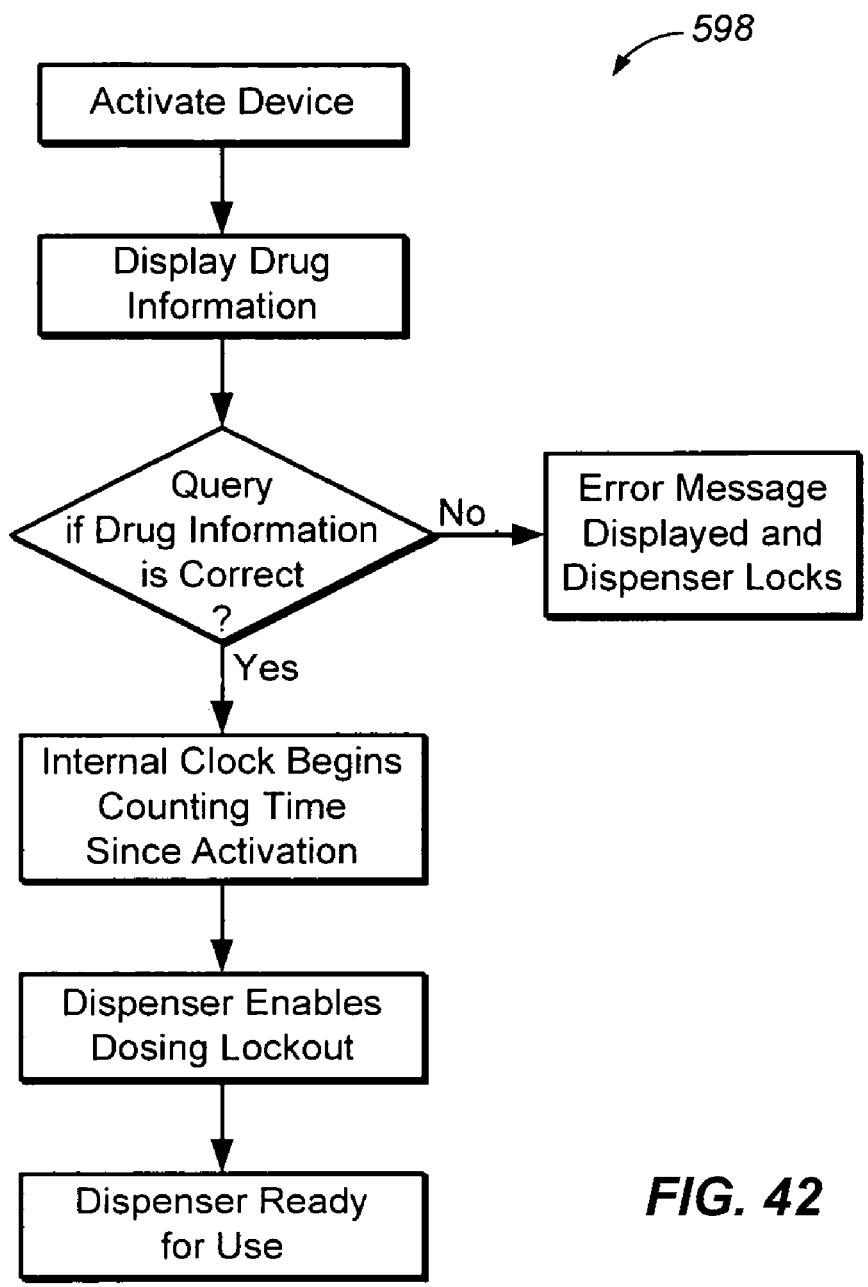

FIG. 42 is a block diagram illustrating an exemplary outpatient chronic dispensing device setup and assembly flow chart, wherein an example of setup and assembly operation of a drug dispensing device of the invention is provided.

Figure 43:
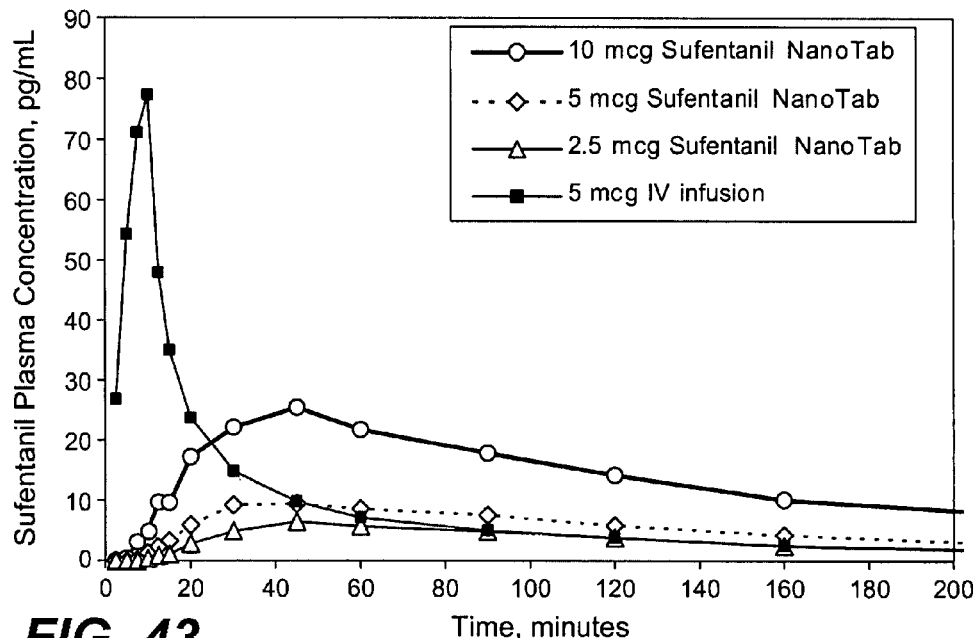

FIG. 43 is a graphic depiction of sufentanil plasma concentrations following intravenous dosing or sublingual single dose administration of three different strengths of sufentanil dosage forms in healthy human volunteers (n=12).

Figure 44:
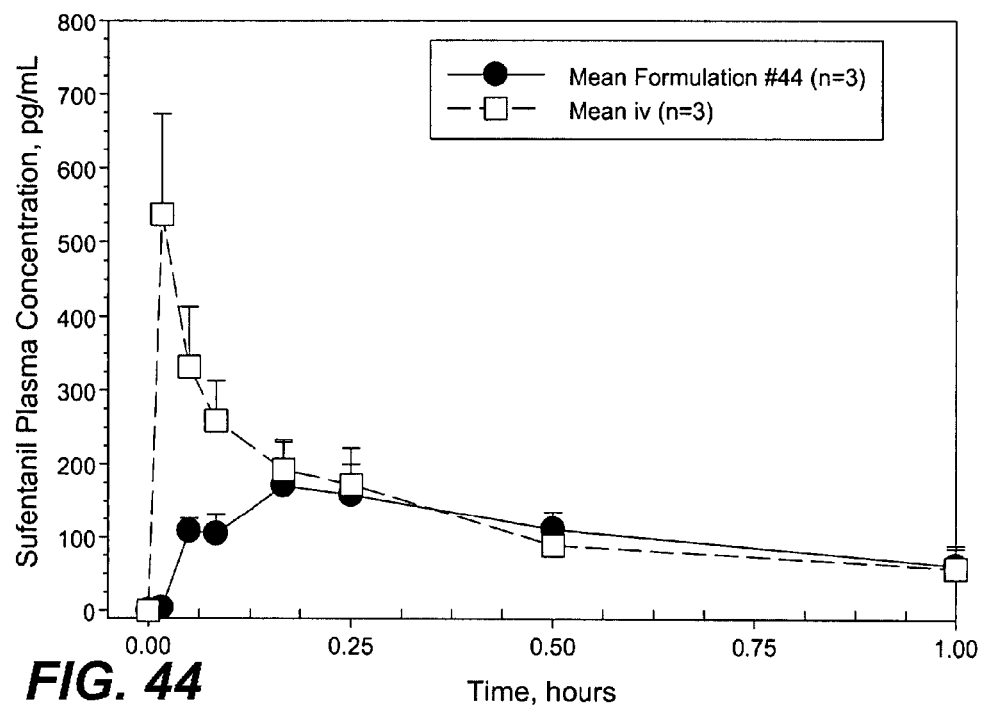

FIG. 44 is a graphic depiction of sufentanil plasma concentrations following sublingual administration of a sufentanil formulation #44 (equivalent to human #47 formulation; n=3) compared to intravenous sufentanil administration (n=3) in a healthy, conscious Beagle dog model. Error bars represents standard errors around the mean (SEM).

Figure 45:
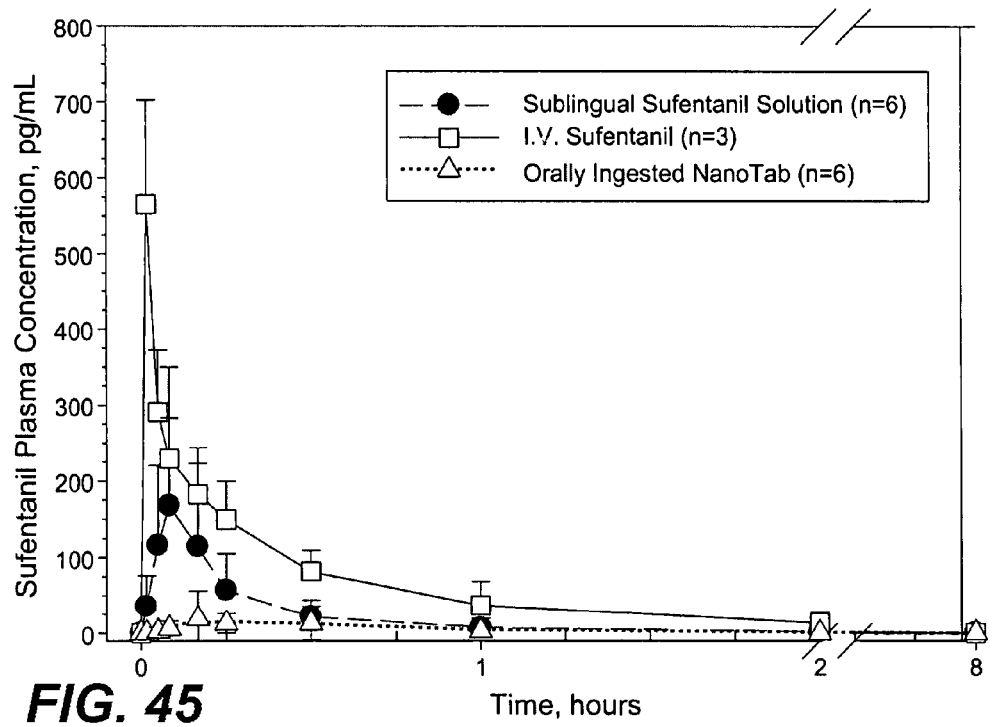

FIG. 45 is a graphic depiction of sufentanil plasma concentrations following sublingual administration of a sufentanil solution (n=6) or following oral ingestion of a sufentanil (n=6) compared to intravenous administration of sufentanil (n=3) in a healthy, conscious Beagle dog model. Error bars represents ±standard error around the mean (SEM).

Figure 46:
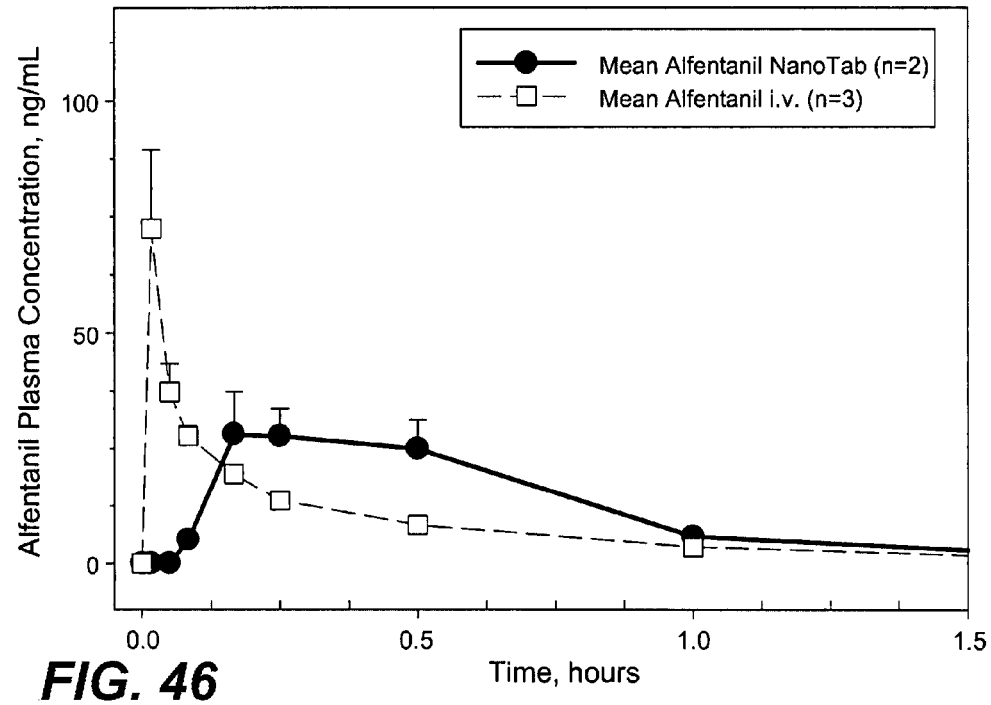

FIG. 46 is a graphic depiction of alfentanil plasma concentrations following sublingual administration of an alfentanil NanoTab® (n=2) compared to intravenous alfentanil administration (n=3) in a healthy, conscious Beagle dog model. Error bars represents ±standard error around the mean (SEM).

DETAILED DESCRIPTION

I. Introduction

Provided herein are compositions, methods, systems and kits for oral transmucosal administration of opioid-containing small volume dosage forms using a device. Oral transmucosal delivery of the dosage forms minimizes the saliva response and therefore minimizes delivery of the drug to the GI tract, such that the majority of drug is delivered across the oral mucosa. The small volume dosage forms have bioadhesive properties which facilitate adherence to the oral mucosa, thus minimizing the risk of ingestion and inefficient delivery due to swallowing.

The following disclosure describes the dosage forms, devices, methods, systems and kits which constitute the invention. The invention is not limited to the specific dosage forms, devices, methodology, systems, kits or medical conditions described herein, as such may, of course, vary. It is also to be understood that the terminology used herein is for the purpose of describing particular embodiments only, and is not intended to limit the scope of the present invention.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug dosage forms and devices for containment, storage and delivery of such dosage forms.

Unless defined otherwise, all technical and scientific terms used herein generally have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in their entirety for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

II. Definitions

The term "active agent" or "active" may be used interchangeably herein with the term "drug" and is meant to refer to any therapeutically active agent.

The term "adhere" is used herein with reference to a drug dosage form or formulation that is in contact with a surface such as a mucosal surface and is retained on the surface without the application of an external force. The term "adhere" is not meant to imply any particular degree of sticking or bonding, nor is it meant to imply any degree of permanency.

The term "drug" as used herein is generally meant to refer to any substance that alters the physiology of an animal. The term "drug" may be used interchangeably herein with the terms "therapeutic agent", "medication", "pharmacologically active agent" and the like. It will be understood that a "drug" formulation of the invention may include more than one therapeutic agent, wherein exemplary combinations of therapeutic agents include a combination of two or more drugs.

The term "analgesic drug" as used herein includes sufentanil or a sufentanil congener, such as alfentanil, fentanyl, lofentanil, carfentanil, remifentanil, trefentanil, or mirfentanil, as well as formulations comprising one or more therapeutic compounds. Use of the phrase "sufentanil or a congener" is not meant to be limiting to use of, or formulations comprising, only one of these selected opioid compounds. Furthermore, reference to sufentanil alone or to a selected sufentanil congener alone, e.g., reference to "alfentanil", is understood to be only exemplary of the drugs suitable for delivery according to the methods of the invention, and is not meant to be limiting in any way.

The term "AUC" as used herein means "area under the curve" in a plot of concentration of drug in plasma versus time. AUC is usually given for the time interval zero to infinity, however, clearly plasma drug concentrations cannot be measured 'to infinity' for a patient so mathematical approaches are used to estimate the AUC from a limited number of concentration measurements. In a practical sense, the AUC (from zero to infinity) represents the total amount of drug absorbed by the body, irrespective of the rate of absorption. This is useful when trying to determine whether two formulations of the same dose release the same dose of drug to the body. The AUC of a transmucosal dosage form compared to that of the same dosage administered intravenously serves as the basis for a measurement of bioavailability.

The term "bioadhesion" as used herein refers to adhesion to a biological surface including mucosal membranes.

The term "bioavailability" or "F" as used herein means "percent bioavailability" and represents the fraction of drug absorbed from a test article as compared to the same drug when administered intravenously. It is calculated from the $AUC_\infty$ of the test article following delivery via the intended route versus the $AUC_\infty$ for the same drug after intravenous administration. It is calculated from the equation: Bioavailability (%)=$AUC_\infty$ (test article)/$AUC_\infty$ (intravenous route/article).

The term "breakthrough pain" as used herein, is a transitory flare of pain of moderate to severe intensity occurring on a background of otherwise controlled pain. "Breakthrough pain" can be intense for short periods of time, as short as 1 or 2 minutes or as long as 30 minutes or more.

The term "cartridge" is used herein with reference to a replaceable, single use disposable cartridge configured to hold one or more drug dosage forms, typically, one up to 200 drug dosage forms. The cartridge typically comprises a smart cartridge recognition system with a physical keyed feature on the cartridge, a bar code on the cartridge, a magnetic tag on the cartridge, an RFID tag on the cartridge, an electronic microchip on the cartridge, or a combination thereof. The cartridge may comprise one or more shipping tablets wherein at least one shipping tablet is dispensed prior to dispensing of a dosage form.

The term "$C_{max}$" as used herein means the maximum observed plasma concentration following administration of a drug.

The term "congener" as used herein refers to one of many variants or configurations of a common chemical structure.

The term "disintegration" is used interchangeably herein with "erosion" and means the physical process by which a dosage form breaks down and pertains to the physical integrity of the dosage form alone. This can occur in a number of different ways including breaking into smaller pieces and ultimately, fine and large particulates or, alternatively, eroding from the outside in, until the dosage form has disappeared.

The term "dispensing device", "drug dispensing device", "dispenser", "drug dispenser", "drug dosage dispenser", "device" and "drug delivery device" are used interchangeably herein and refer to a device that dispenses a drug dosage form. The dispensing device provides for controlled and safe delivery of a pharmaceutically active substance (e.g., an opioid such as sufentanil) formulated in the dosage form. The device may be adapted for storage and/or delivery of a dosage form such as a lozenge, pill, tablet, capsule, membrane, strip, liquid, patch, film, gel, spray or other form.

The term "reservoir" refers to a chamber or containment space within a delivery or storage device for storing a formulation to be delivered from the delivery device.

The term "dispensing end" as used herein with reference to a device means the portion of the device comprising the proboscis and shroud which serves to deliver a drug dosage form to the oral mucosa of a subject.

The term "drug", "medication", "pharmacologically active agent", "therapeutic agent" and the like are used interchangeably herein and generally refer to any substance that alters the physiology of an animal and can be effectively administered by the oral transmucosal route.

The term "erosion time" means the time required for a solid dosage form to break down until the dosage form has disappeared.

"Operatively connected" as used herein means the components are provided in a device so as to function as intended to achieve an aim. For example, a memory device operatively connected to a CPU which is further operatively connected to a release mechanism may be meant to indicate that, upon actuation, the CPU communicates with the memory device to check the status or history of drug delivery, and then further communicates with the release mechanism (e.g., via a solenoid and a switch) to release and dispense a drug.

The term "FOB" refers to a small, portable handheld, powered electronic docking device that can be used in conjunction with the drug dispensing device to upload data, download data, control access to the drug dispensing device, control access to the drug dosage forms, or enhance or otherwise alter the user interface of the drug dispensing device. A FOB may communicate and dock with a drug dispensing device either in a wired or wireless fashion. A FOB may be adapted to attach to a cord so as to allow the FOB to hang from the neck of a healthcare professional such as a physician or caregiver, particularly in the hospital setting. A drug dispensing device may communicate with the physician or care giver via the FOB.

The terms "formulation" and "drug formulation" as used herein refer to a physical composition containing at least one pharmaceutically active substance, which may be provided in any of a number of dosage forms for delivery to a subject. The dosage form may be provided to the patient as a lozenge, pill, capsule, membrane, strip, liquid, patch, film, gum, gel, spray or other form.

The term "hydrogel-forming preparation", means a solid formulation largely devoid of water which upon contact with an aqueous solution, e.g., a bodily fluid, and in particular that of the oral mucosa, absorbs water in such a way that it forms a hydrated gel in situ. The formation of the gel follows unique disintegration (or erosion) kinetics while allowing for release of the therapeutic agent over time.

The term "lock-out feature" is used herein with reference to a feature of the device which provides for a "lock-out time".

The term "lock-out time" is used herein with reference to the period of time during which the device does not allow drug accessibility, i.e., a dosage form cannot be dispensed during the "lock-out time". "Lock-out time" may be programmable, a fixed time interval, a predetermined interval, a predetermined variable interval, an interval determined by an algorithm or a variable interval communicated to the device from a remote computer or docking station.

The term "Log P" as used herein means logarithm of the ratio of equilibrium concentrations of un-ionized compound between octanol and water. P also called the "octanol-water partition coefficient" and serves as a means to quantify the hydrophiobicity or lipophilicity of, a chemical characteristic of a given drug.

The term "mucoadhesion" is used herein in to refer to the adhesion to mucosal membranes which are covered by mucus, such as those in the oral cavity and may be used interchangeably herein with the term "bioadhesion" which refers to adhesion to any biological surface.

The term "mucosal membrane" refers generally to any of the mucus-coated biological membranes in the body. Absorption through the mucosal membranes of the oral cavity is of particular interest. Thus, oral mucosal absorption, i.e., buccal, sublingual, gingival and palatal absorption are specifically contemplated.

The term "mucosal-depot" is used herein in its broadest sense to refer to a reservoir or deposit of a pharmaceutically active substance within or just beneath the mucosal membrane.

The term "non-ordered particulate mixture" or "non-ordered mixture" is used herein with reference to a formulation where the mixture is not ordered with respect to the pharmaceutically active agent and the bioadhesive material or bioadhesion promoting agent, or other formulation components. In addition, it is used herein with reference to any formulation prepared by a process that involves dry mixing wherein drug particles are not uniformly distributed over the surface of larger carrier particles. Such 'non-ordered' mixing may involve dry mixing of particles in a non-ordered fashion, where there is no requirement with respect to the order of addition/mixing of specific excipients with the drug, bioadhesive material or bioadhesion promoting agent and/or disintegrants. Further in the non-ordered mixing process, there is no limitation on the size of the drug particles. The drug particles may be larger than 25 µm. In addition, a "non-ordered mixture" includes any mixing processes in which the primary carrier particles do not incorporate a disintegrant within. Finally the "non-ordered mixture" may be prepared by any 'wet mixing' processes, i.e. processes in which a solvent or non-solvent is added during the mixing process or any mixing process in which the drug is added in a solution or suspension form.

The term "operatively connected" as used herein means the components are provided in a device so as to function as intended to achieve an aim. For example, a memory device operatively connected to a CPU which is further operatively connected to a release mechanism may be meant to indicate that, upon actuation, the CPU communicates with the memory device to check the status or history of drug delivery, and then further communicates with the release mechanism (e.g., via a solenoid and a switch) to release and dispense a drug.

The terms "oral transmucosal dosage form" and "drug dosage form" may be used interchangeably herein and refer to a dosage form which comprises a pharmaceutically active substance, e.g., a drug such as sufentanil. The oral dosage form is used to deliver the pharmaceutically active substance to the circulation by way of the oral mucosa and is typically a "sublingual dosage form", but in some cases other oral transmucosal routes may be employed. The dosage form provides for delivery of the pharmaceutically active substance across the oral mucosa and by controlling the formulation the timing for release of the pharmaceutically active substance can be achieved. The dosage form comprises pharmaceutically acceptable excipients and may be referred to as a NanoTab™, as detailed in U.S. application Ser. No. 11/650,174, expressly incorporated by reference herein. The dosage form comprises a formulation that is neither effervescent nor does it comprise an essentially water-free, ordered mixture of microparticles of drug adhered to the surface of carrier particles, where the carrier particles are substantially larger than the microparticles of drug.

The terms "oral transmucosal drug delivery" and "oral transmucosal administration" as used herein refer to drug delivery that occurs substantially via the transmucosal route and not via swallowing followed by GI absorption. Maximal delivery occurs via the oral mucosa, typically by placement of the dosage form within the sublingual cavity.

The term "proboscis" is used interchangeably with the terms "dispensing tip" a "delivery tip", and refers to a dispensing and/or positioning tip of a drug dosage form dispenser that delivers a dosage form to the oral mucosa (e.g., the sublingual space).

The term "acute pain, and a means for identifying an individual patient for controlled drug access.

The term "chronic pain" is used herein with reference to pain that is typically present for longer than one month.

The term "radio frequency identification device" or "RFID" is used with reference to an automatic identification method, which relies on storing and remotely retrieving data using devices called RFID tags, wherein the RFID tag is applied to, or incorporated into a product, or person for the purpose of identification using radiowaves. Some tags can be read from several meters away and beyond the line of sight of the reader.

The term "replaceable, single use disposable cartridge" is used with reference to a cartridge for housing drug dosage forms which is typically configured to hold up to 200 drug dosage forms, wherein the cartridge is designed to be used one time and discarded.

The term "shipping tablet" is used herein with reference to an "initialization", or "shipping" tablet which is the same size and shape as a drug-containing dosage form but does not contain a pharmaceutically active substance. The "shipping tablet" may comprise a placebo dosage form that does not contain a pharmaceutically active substance or may be made of plastic or other material. It is the first thing dispensed from a new cartridge after insertion into a dispensing device. The device has a means for differentiating between the shipping tablet and a dosage form containing a pharmaceutically active substance.

The term "shroud" is used to describe a partial or complete covering of the dispensing end of the device which protects the delivery port from contact with saliva or other moisture in the oral cavity and forms a barrier between the device, the oral mucosa and tongue, has a relief for dosage form delivery, and an interior that is hydrophobic or hydrophilic which serves to minimize or eliminate saliva ingress or moisture ingress. The "shroud" creates a barrier from the oral mucosa contacting the valve area and dosage form, aiding in dosage form dispensing and discouraging dosage form adherence to the shroud. The shroud may have a rounded interior surface or other geometry to stop the dosage form adhering to the shroud. The shroud limits the ability of the tongue or sublingual mucosa to contact the dosage form dispensing area, thereby controlling saliva contact and ingress.

The term "subject" includes any subject, generally a mammal (e.g., human, canine, feline, equine, bovine, ungulate etc.), adult or child, in which treatment for a disorder is desired. The terms "subject" and "patient" may be used interchangeably herein.

The term "systems that include a drug dosage form and a dispensing device" as used herein refers to a drug dispensing system for delivery and/or monitoring of drug administration. The system may be used to monitor and deliver a pharmaceutically active substance, e.g., an opioid such as sufentanil, wherein the amount of drug delivered, corresponding efficacy and safety are enhanced over currently available systems. The system may have one or more features that provide for improved safety and ease of use over currently available systems including a security feature that prevents unauthorized access to the stored drugs, a dosing lock-out feature, a means for identifying an individual patient for controlled drug access, a dose counting feature, a memory means for retaining information about dose delivery, and an interface for bidirectional exchange of information with a user, a drug cartridge, or another device such as a computer.

The term "small volume drug dosage form" or "small volume dosage form" is used herein with reference to a small volume dosage form that has a volume of less than 100 µl and a mass of less than 100 mg. More specifically, the dosage form has a mass of less than 100 mg, 90 mg, 80 mg, 170 mg, 60 mg, 50 mg, 40 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg or 5 mg or a volume of less than 100 µl, 90 µl, 80 µl, 70 µl, 60 µl, 50 µl, 40 µl, 30 µl, 29 mg, 28 mg, 27 µl, 26 µl, 25 µl, 24 µl, 23 µl, 22 µl, 21 µl, 20 µl, 19 µl, 18 µl, 17 µl, 16 µl, 15 µl, 14 µl, 13 µl, 12 µl, 11 µl, 10 µl, 9 µl, 8 µl, 7 µl, 6 µl or 5 µl. The "dosage form" may or may not have bioadhesive characteristics and may form a hydrogel upon contact with an aqueous solution.

The "dosage form" may be used to deliver any drug that can be administered by the oral transmucosal route in an amount amenable to administration via the small size of the dosage form, i.e. 0.25 µg to 99.9 mg, 1 µg to 50 mg or 1 µg to 10 mg.

The term "small volume sufentanil-containing drug dosage form" is used herein with reference to a small volume dosage form that contains a dose of sufentanil selected from about 2 micrograms (mcg) to about 200 mcg of sufentanil, e.g., 5 mcg, 10 mcg, 15 mcg, 20 mcg, 30 mcg, 40 mcg, 50 mcg, 60 mcg, 70 mcg, 80 mcg or 100 mcg of sufentanil.

The term "solid dosage form" or "solid drug dosage form" is used herein with reference to a small volume dosage form that is a solid, e.g., a lozenge, a pill, a tablet, a membrane or a strip.

The term "sublingual", means literally "under the tongue" and refers to administering a drug dosage form via the mouth in such a way that the pharmaceutically active substance is rapidly absorbed via the blood vessels under the tongue rather than via the digestive tract. Absorption occurs via the highly vascularized sublingual mucosa and allows the pharmaceutically active substance more direct access to the blood circulation, providing for direct systemic administration independent of GI influences.

The term "treatment" or "management" of a medical disorder or condition is used herein to generally describe regression, suppression, or mitigation of symptoms of the medical disorder or condition so as to make the subject more comfortable as determined by subjective criteria, objective criteria, or both.

The term "diversion" is used here to generally describe the act or an instance of diverting the use of a dispensing device and/or drug dosage forms therein from the intended patient to any other unauthorized or unintended individual, whether it is accidental or intentional diversion.

The term "Therapeutic Time Ratio" or "TTR" presents the average time that the drug is present at therapeutic levels, defined as time within which the drug plasma concentration is maintained above 50% of $C_{max}$ normalized by the drug's elimination half-life and it is calculated by the formula: TTR=(Time above 50% of $C_{max}$)/(Terminal intravenous elimination half-life of the drug). The last term is obtained from literature data for the drug of interest in the appropriate species.

The term "$T_{max}$" as used herein means the time point of maximum observed plasma concentration.

The term "$T_{onset}$" as used herein means the observed "time of onset" and represents the time required for the plasma drug concentration to reach 50% of the maximum observed plasma concentration, $C_{max}$.

The term "therapeutically effective amount" means an amount of a therapeutic agent, or a rate of delivery of a therapeutic agent (e.g., amount over time), effective to facilitate a desired therapeutic effect, such as pain relief. The precise desired therapeutic effect (e.g., the degree of pain relief, and source of the pain relieved, etc.) will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

The term "transmucosal" delivery of a drug and the like is meant to encompass all forms of delivery across or through a mucosal membrane. In particular, "oral transmucosal" delivery of a drug includes delivery across any tissue of the mouth, pharynx, larynx, trachea, or upper gastrointestinal tract, particularly including the sublingual, gingival and palatal mucosal tissues.

III. Drug Dosage Forms

The claimed small volume oral transmucosal drug dosage forms produce a reduced saliva response as compared with conventional, larger dosage forms that are intended to deliver a drug in the oral cavity. The dosage forms contain a pharmaceutically active substance and provide for high absorption rates of the pharmaceutically active substance across the oral mucosa and reduced uptake via the gastrointestinal tract, thereby offering a more consistent and reproducible pharmacokinetic and corresponding pharmacodynamic profile.

The dosage forms are typically a "sublingual dosage form", but in some cases other oral transmucosal routes may be employed. The dosage form is a substantially homogeneous composition which comprises one or more active drugs together with pharmaceutically acceptable excipients.

The preferred site for oral transmucosal drug delivery is the sublingual area, although in certain embodiments it may be advantageous for the dosage form to be placed inside the cheek, or to adhere to the roof of the mouth or the gum.

Sublingual delivery is preferred as the sublingual mucosa is more readily permeable to medications than other mucosal areas, such as the buccal mucosa, resulting in more rapid uptake.

The dosage forms provide for the delivery of a greater percentage (and amount) of the drug via the oral mucosa and a corresponding decrease in delivery via the gastrointestinal (GI) tract as compared to traditional oral dosage forms and other oral transmucosal dosage forms.

Typically, the dosage forms are generally adapted to adhere to the oral mucosa (i.e. are bioadhesive) during the period of drug delivery, and until most or all of the drug has been delivered from the dosage form to the oral mucosa.

The claimed dosage forms have a mass of less than 100 mg and a volume of less than 100 µl. More specifically, the dosage forms have a mass of less than 100 mg, 90 mg, 80 mg, 170 mg, 60 mg, 50 mg, 40 mg, 30 mg, 29 mg, 28 mg, 27 mg, 26 mg, 25 mg, 24 mg, 23 mg, 22 mg, 21 mg, 20 mg, 19 mg, 18 mg, 17 mg, 16 mg, 15 mg, 14 mg, 13 mg, 12 mg, 11 mg, 10 mg, 9 mg, 8 mg, 7 mg, 6 mg or 5 mg or a volume of less than 100 µl, 90 µl, 80 µl, 70 µl, 60 µl, 50 µl, 40 µl, 30 µl, 29 mg, 28 mg, 27 µl, 26 µl, 25 µl, 24 µl, 23 µl, 22 µl, 21 µl, 20 µl, 19 µl, 18 µl, 17 µl, 16 µl, 15 µl, 14 µl, 13 µl, 12 µl, 11 µl, 10 µl, 9 µl, 8 µl, 7 µl, 6 µl or 5 µl. The dosage forms typically have bioadhesive characteristics and may form a hydrogel upon contact with an aqueous solution.

The dosage forms typically have an erosion time of from 30 seconds up to 5 minutes, up to 10 minutes, up to 15 minutes or up to 30 minutes.

In general, at least 55%, at least 60%, at least 65%, at least 70%, at least 75%, at least 80%, at least 85%, at least 90%, at least 95%, at least 98% or at least 99% of the total amount of pharmaceutically active substance in a dosage form administered to the oral mucosa of a subject is absorbed via the oral transmucosal route.

The dosage forms may have essentially any shape, examples of which include a round disc with a flat, concave, or convex face, an ellipsoid shape, a spherical shape, a polygon with three or more edges and flat, concave, or convex faces. The dosage forms may be symmetrical or asymmetrical, and may have features or geometries that allow for controlled, convenient, and easy storage, handling, packaging or dosing.

Oral transmucosal drug delivery is simple, non-invasive, and can be administered by a caregiver or patient with minimal discomfort. A dosage form for oral transmucosal delivery may be solid or non-solid. In one preferred embodiment, the dosage from is a solid that turns into a hydrogel following contact with saliva. In another preferred embodiment, the dosage from is a solid that erodes without forming a hydrogel following contact with saliva.

Generally, oral transmucosal delivery of pharmaceutically active substances is achieved using solid dosage forms such as lozenges or tablets, however, liquids, sprays, gels, gums, powders, and films and the like may also be used.

For certain drugs, such as those with poor bioavailability via the GI tract, e.g., lipophilic opioids such as sufentanil and alfentanil, oral transmucosal delivery is a more effective delivery route than GI delivery. For such lipophilic drugs, oral transmucosal delivery has a shorter onset time (i.e., the time from administration to therapeutic effect) than does oral GI delivery and provides better bioavailability and more consistent pharmacokinetics.

The claimed drug dosage forms are designed and adapted to reduce the saliva response, thus reducing the amount of drug swallowed, and thereby delivering a substantial amount of drug to a subject via the oral mucosa. The claimed drug dosage forms also provide efficacious delivery of drug via the oral mucosa and a consistent plasma level within the therapeutic window.

The claimed dosage forms comprise substantially homogeneous formulations which include at least 0.001% percent by weight of the pharmaceutically active substance in combination with pharmaceutically acceptable excipients. Typically the claimed dosage forms comprise from 0.01-99% or from about 0.25 µg to 99.9 mg, from about 1 µg to 50 mg or from about 1 µg to 10 mg w/w of the pharmaceutically active substance.

Formulations for preparation of the claimed dosage forms and methods of making them are described in U.S. application Ser. Nos. 11/825,251 and 11/650,227, expressly incorporated by reference herein. An exemplary formulation is bioadhesive and comprises from about 0.0004% to about 0.04% sufentanil, e.g., 0.0005%, 0.001%, 0.002%, 0.003%, 0.004%, 0.006%, 0.008%, 0.01%, 0.012%, 0.014% or 0.016% sufentanil. In general, the formulation comprises (a) a non-ordered mixture of a pharmaceutically active amount of a drug; (b) a bioadhesive material which provides for adherence to the oral mucosa of the subject; and (c) stearic acid, wherein dissolution of a dosage form comprising the formulation is independent of pH, e.g., over a pH range of about 4 to 8.

Numerous suitable nontoxic pharmaceutically acceptable carriers for use in oral dosage forms can be found in Remington's Pharmaceutical Sciences, 17th Edition, 1985.

It will be understood that the formulation is converted into a dosage form for delivery to a subject using procedures routinely employed by those of skill in the art, such as direct compression, wet granulation, etc. The process for preparation of the dosage form is optimized for each formulation in order to achieve high dose content uniformity.

While not wishing to be bound by theory, when a claimed dosage form is placed in the sublingual cavity, preferably under the tongue on either side of the frenulum linguae, it adheres upon contact. As the dosage form is exposed to the moisture of the sublingual space the dosage form absorbs water, resulting in erosion of the dosage form and release of the active drug to the circulation of the subject.

IV. Sufentanil

Opioids are widely used for the treatment of pain, and are generally delivered intravenously, orally, epidurally, transdermally, rectally and intramuscularly. Morphine and its analogues are commonly delivered intravenously and are effective against severe, chronic and acute pain. However, they can also have severe respiratory depressive effects if not used appropriately and also suffer from a high abuse potential. The predominant cause of morbidity and mortality from pure opioid overdoses is due to respiratory complications.

One exemplary use of the claimed drug dosage forms is with application to pain-relief. When the claimed drug dosage forms are used for treatment of pain, they comprise a drug such as an opioid or opioid agonist and are utilized to treat both acute and chronic pain of moderate to severe intensity.

The active agent in such drug dosage forms is sufentanil or a sufentanil congener such as alfentanil, fentanyl, lofentanil, carfentanil, remifentanil, trefentanil, or mirfentanil. In a preferred embodiment, sufentanil is the active agent. Sufentanil may be provided in the claimed dosage forms in any of a number of formulations, e.g., as sufentanil citrate or as sufentanil base.

Another preferred embodiment relies on a sufentanil congener as the active agent. Yet another preferred embodiment relies on a combination of sufentanil and at least one additional agent for treatment of analgesia as the active agent, e.g., a combination of sufentanil and alfentanil. Various opioid drugs have different pharmacokinetic profiles and different interactions with mu opioid receptor splice variants and, therefore, may be used in combination to enhance the therapeutic effect.

Sufentanil (N-[(4-(Methoxymethyl-1-(2-(2-thienyl) ethyl)-4-piperidinyl)]-N-phenylprop-anamide), is used as a primary anesthetic, to produce balanced general anesthesia in cardiac surgery, for epidural administration during labor and delivery and has been administered experimentally in both intranasal and liquid oral formulations. A commercial form of sufentanil used for IV delivery is the SUFENTA FORTE® formulation. This liquid formulation contains 0.075 mg/ml sufentanil citrate (equivalent to 0.05 mg of sufentanil base) and 9.0 mg/ml sodium chloride in water. It has a plasma elimination half-life of 148 minutes, and 80% of the administered dose is excreted in 24 hours.

Following transbuccal administration of fentanyl using a lozenge (e.g., Actiq®), the bioavailability is 50%, although the $T_{max}$ for the 200 mcg dosage of Actiq® ranges from 20-120 minutes resulting from erratic GI uptake due to the fact that 75% of the fentanyl is swallowed (Actiq® package insert). More recent publications on the $T_{max}$ of Actiq indicate that these original times were skewed towards more rapid onset (Fentora package insert indicates a range of $T_{max}$ for Actiq extending up to 240 minutes). Fentora (a fentanyl buccal tablet) exhibits a bioavailability of 65%, with reported swallowing of 50% of the drug. In contrast to the claimed dosage forms, both Actiq® and Fentora suffer from the disadvantage that substantial amounts of lozenge-administered fentanyl are swallowed by the patient.

Although sufentanil and fentanyl have many similarities as potent mu-opioid receptor agonists, they have been shown to differ in many key ways. Multiple studies have demonstrated sufentanil to be in the range of 7-24 times more potent than fentanyl (SUFENTA® package insert; Paix A, et al. Pain, 63:263-69, 1995; Reynolds L, et al., Pain, 110:182-188, 2004). Therefore, sufentanil may be administered using a smaller dosage form, avoiding the increased saliva response of a larger dosage form and thereby minimizing the amount of drug that is swallowed. This leads to minimal GI uptake.

In addition, fentanyl and other opiate agonists, have the potential for deleterious side effects including respiratory depression, nausea, vomiting and constipation. Since fentanyl has a 30% bioavailability from the GI route, this swallowed drug can contribute to the $C_{max}$ plasma levels to a significant degree and results in the erratic $C_{max}$ and $T_{max}$ observed with these products.

Further, the lipid solubility (octanol-water partition coefficient) of sufentanil (1778:1) is greater than fentanyl (816:1). Sufentanil also displays increased protein binding (91-93%) compared with fentanyl (80-85%) (SUFENTA® and Actiq® package inserts, respectively). Sufentanil has a pKa of 8.01, whereas the pKa of fentanyl is 8.43 (Paradis et al., Therapeutic Drug Monitoring, 24:768-74, 2002). These differences can affect various pharmacokinetic parameters, for example, sufentanil has been shown to have a faster onset of action and faster recovery times than fentanyl (Sanford et al., Anesthesia and Analgesia, 65:259-66, 1986). As compared to fentanyl, use of sufentanil can result in more rapid pain relief with the ability to titrate the effect and avoid overdosing.

Importantly, sufentanil has been shown to produce endocytosis of the mu-opioid receptor 80,000 times more potently than fentanyl (Koch et al., Molecular Pharmacology, 67:280-87, 2005). The result of this receptor internalization is that neurons continue to respond to sufentanil more robustly over time than with fentanyl, suggesting that clinically less tolerance would develop to sufentanil compared to fentanyl with repeated dosing.

The use of sufentanil clinically has predominantly been limited to IV administration in operating rooms or intensive care units. There have been a few studies on the use of liquid sufentanil preparations for low-dose intranasal administration (Helmers et al., 1989; Jackson K, et al., J Pain Symptom Management 2002: 23(6): 450-452) and case reports of sublingual delivery of a liquid sufentanil preparation (Gardner-Nix J., J Pain Symptom Management. 2001 August; 22(2):627-30; Kunz K M, Theisen J A, Schroeder M E, Journal of Pain and Symptom Management, 8:189-190, 1993). In most of these studies, the smallest dosing of sufentanil in adults was 5 mcg in opioid naive patients. Liquid administered to the oral or nasal mucosa suffers from lower bioavailability and possibly a shorter duration of action as demonstrated by the animal studies (sublingual liquid) described herein, as well as the literature (nasal liquid drops—Helmers et al., 1989). Gardner-Nix provides analgesic data (not pharmacokinetic data) produced by liquid sublingual sufentanil and describes the analgesic onset of liquid sublingual sufentanil occurring within 6 minutes but the duration of pain relief lasted only approximately 30 minutes.

Prior to the work of the current inventors, no pharmacokinetic data had been published on sublingual sufentanil in any form.

The claimed drug dosage forms contain from about 0.25 to about 200 mcg of sufentanil per dosage form for oral transmucosal delivery. In one exemplary embodiment, each dosage form contains from about 0.25 to about 200 mcg of sufentanil, alone or combination with one or more other therapeutic agents or drugs.

Exemplary drug dosage forms for administration to children (pediatric patients) contain from about 0.25 to about 120 mcg of sufentanil per dosage form. For example, a drug dosage form for administration to children may contain about 0.25, 0.5, 1, 2.5, 4, 5, 6, 8, 10, 15, 20, 40, 60 or 120 mcg of sufentanil for oral transmucosal delivery. It follows that for pediatric patients, an exemplary dose range is from at least about 0.02 mcg/kg to about 0.5 mcg/kg with a preferable range of from about 0.05 to about 0.3 mcg/kg.

Exemplary drug dosage forms for administration to adults contain from about 2.5 to about 200 mcg of sufentanil per dosage form. For example, a drug dosage form for administration to adults may contain about 2.5, 3, 5, 7.5, 10, 15, 20, 40, 60, 80, 100, 120, 140, 180 or 200 mcg or more of sufentanil for oral transmucosal delivery.

Preferably, a sufentanil-containing dosage form comprises from about 2 to about 200 micrograms (mcg) of sufentanil, e.g., 5 mcg, 10 mcg, 15 mcg, 20 mcg, 30 mcg, 40 mcg, 50 mcg, 60 mcg, 70 mcg or 80 mcg of sufentanil.

As will be understood by those of skill in the art, the dose will be on the low end of the range for children and the high end of the range for adults dependent upon body mass, in particular when administered long term to opioid-tolerant adults. Prior to the work of the current inventors, small-volume oral transmucosal drug delivery dosage forms of sufentanil have not been described.

In various embodiments, the claimed dosage forms provide effective pain relief in all types of patients including children, adults of all ages who are opioid tolerant or naive and non-human mammals. The invention finds utility in both the inpatient and outpatient setting and in the field.

V. Congeners of Sufentanil

Congeners of sufentanil find use in the compositions, methods and systems described herein, examples of which include remifentanil and alfentanil.

In certain embodiments, the dosage form comprises at least 0.005% to as much as 99.9% by weight of alfentanil, lofentanil, carfentanil, remifentanil, trefentanil or mirfentanil. The percentage of active ingredient(s) will vary dependent upon the size of the dosage form and nature of the active ingredient(s), optimized to obtain maximal delivery via the oral mucosal route. In some aspects more than one active ingredient may be included in a single dosage form.

Remifentanil is a potent sufentanil congener that is metabolized much more rapidly than fentanyl or sufentanil, but may be suitable for treatment of acute pain when delivered via a sustained-release formulation. A remifentanil-containing dosage form typically comprises from about 0.25 mcg to 99.9 mg of remifentanil. The dose ranges for the remifentanil formulation may include 0.1 mcg/kg-50 mcg/kg over a time period of 20 minutes, for example, for both adult and pediatric patients. These dosages may be repeated at appropriate time intervals, which may be shorter than the time intervals for fentanyl or sufentanil.

Alfentanil is also a potent sufentanil congener that is rapidly metabolized but may be suitable for use in a sustained-release formulation. The dosage forms may contain from about 10 to about 10000 mcg of alfentanil per dosage form for oral transmucosal delivery. As will be understood by those of skill in the art, the dose will be on the low end of the range for children and the high end of the range for adults dependent upon body mass, in particular when administered long term to opioid-tolerant adults.

Exemplary dosage forms for administration to children (pediatric patients) contain from about 10 to about 6300 mcg of alfentanil per dosage form. For example, a dosage form for administration to children may contain about 10, 25, 50, 130, 210, 280, 310, 420, 600, 780, 1050, 2100, 3000 or 6300 mcg of alfentanil for oral transmucosal delivery.

Exemplary dosage forms for administration to adults contain from about 70 to about 10000 mcg of alfentanil per dosage form. For example, a dosage form for administration to adults may contain about 70, 140, 160, 210, 280, 310, 420, 600, 780, 1050, 2100, 3000, 6300 or 10000 mcg or more of alfentanil for oral transmucosal delivery.

Following delivery of a single dose of a sufentanil-, alfentanil-, or remifentanil-containing dosage form to a human subject, the plasma level of sufentanil, alfentanil or remifentanil may reach a maximum level within 60 minutes, e.g., between 5 and 50 minutes or between 10 and 40 minutes following administration.

VI. Treatment of Pain

Patients suffering from chronic painful conditions can also have intermittent exacerbations of their pain, requiring acute use of fast-acting breakthrough opioids in addition to their use of slow-onset time-release opioids for their baseline chronic pain.

Breakthrough pain or procedural pain can be intense for short periods of time, as short as 1 or 2 minutes or as long as 30 minutes or more, therefore there would be a significant advantage in providing an opioid formulation that produced more rapid clinically effective plasma levels with a more consistent and predictable period of effect, but also had a limited half-life to avoid excessive opioid dosing for short duration pain events.

Opioids remain the most powerful from of analgesics, however, improved forms are needed that have minimal side effects, and can be provided in a manner in which patient use can be easily tracked by the physician.

Using current treatment methods, pain control is attempted using a number of interventions, which generally include: patient-controlled analgesia (PCA), continuous epidural infusion (CEI), other types of acute pain control, palliative care pain control, and home health patient pain control. These methods meet with varying degrees of success with respect to duration of control, ease of treatment and safety versus side effects.

The need for rapid treatment of acute pain occurs in many different clinical situations, including post-operative recuperation, rheumatoid arthritis, failed back, end-stage cancer (i.e., breakthrough pain), etc. Post-operatively, for example, patients suffer from severe pain for the first few days followed by days of mild to moderate levels of pain.

The most common analgesic used to treat moderate to severe post-operative pain is IV morphine. This is either delivered on an "as needed" basis by a nurse to the patient by an IV injection or commonly a morphine syringe is placed in a PCA pump and the patient self-administers the opioid by pressing a button which has a lock-out feature. Other opioids, such as hydromorphone and fentanyl may also be used in this manner.

Treatment of acute pain is also necessary for patients in an outpatient setting. For example, many patients suffer from chronic pain and require the use of opioids on a weekly or daily basis to treat their pain. While they may have a long-acting oral or transdermal opioid preparations to treat their chronic underlying pain levels, they often need short-acting potent opioids to treat their severe breakthrough pain levels.

Treatment of acute pain is also necessary "in the field" under highly sub-optimal conditions. Paramedics or military medics often are required to treat severe acute pain in un-sterile situations, where needles used for IV or IM administration can result in unintended needle sticks, risk of infection, etc. Oral opioid tablets often take 60 minutes to provide relief which is too long for someone in severe pain.

In a number of clinical settings, there is clearly a need for improved means to administer a drug that produces effective pain relief in a manner that is titratable, safe and convenient, and non-invasive that provides relief from acute, severe breakthrough or intermittent pain over an appropriate period of time.

The claimed methods and systems rely on administration of dosage forms comprising a pharmaceutically active substance such as sufentanil which is effective for the treatment of pain (acute, intermittent or breakthrough pain) using a dispensing device that includes features such as lock-out, a means for patient identification prior to drug administration and a means to protect the dosage forms stored therein. The claimed methods and systems thereby provide significant advantages over currently available treatment modalities in terms of both safety and efficacy.

Oral Transmucosal Administration

In practicing the invention, dosage forms are administered to the oral mucosa of a subject with or without a device, for example using a single or multiple dose applicator.

In one exemplary embodiment, a dispensing device of the invention is used for oral transmucosal administration of a dosage form directly to the patient in the inpatient (hospital, clinic, etc.) or outpatient setting.

In other exemplary embodiments, a dosage is administered to the patient in the inpatient (hospital, clinic, etc.) or outpatient setting using a disposable single or multiple dose applicator.

Outpatient Acute Setting

One exemplary use of a dispensing device is to provide a rapid-acting dosage form that produces a therapeutic effect rapidly, may be used safely and conveniently, and provides a therapeutic effect for an appropriate period of time. The dispensing device of the invention may be used in the outpatient setting. In the outpatient setting, one embodiment of the dispensing device of the invention may exhibit the following structural and functional features: the dispensing device may be a standalone portable model; the dispensing device may be capable of up to several weeks of treatment; the dispensing device may be disposable, and/or non-refillable; the dispensing device may be child proof; the dispensing device may have a fixed lockout between doses; the dispensing device may exhibit a shutdown after a fixed period of time; the dispensing device may have an interface limited to a dispense button, sounds or tones, and LEDs; the dispensing device may monitor the temperature and shutdown if the drug dosage exceeds safe limits; a display; and the dispensing device may have a dose counter.

When used in the outpatient acute (home, office, field, etc.) setting, the dispensing device of the invention offers several features and advantages over the state of the art in outpatient drug administration. The dispensing device allows individuals to self administer drugs in accordance with physician, healthcare provider, or drug label guidelines. Some exemplary acute outpatient indications are post-operative pain, pain associated with physical trauma, anxiety, insomnia, hypertension, angina, coronary artery disease, depression, psychosis, constipation, nausea, addiction, ADHD, and others. See, e.g., U.S. application Ser. No. 11/429,904, expressly incorporated by reference herein. To effectively assist in the dispensing of drugs in the acute outpatient setting, the dispensing device may provide some or all of the following features: allow the patient to self administer the medication; record a dosing history; allow the dosing history to be read or transferred to a computer, network or other electronic device; deter tampering or diversion; deliver the drug dosage form to the appropriate location (e.g. sublingual, buccal, oral gastro-intestinal, rectal, ocular, nasal, inhalation, aural, transdermal or any other route of administration); and notify a pre-determined individual or individuals (by alert, alarm, cell phone message, text message, email, or other wired or wireless communication means) of an event like a dosing administration, a need for a refill of a prescription, a tamper attempt, a misuse of the device, a GPS location, an expiration of the drug contained in the device, a temperature or humidity event. The dispensing device of the invention may be used to dispense any medication in the outpatient acute setting, in any drug dosage form, affording any combination of the features set forth above. Some examples of uses for a device of the invention are in acute field care for first responders, military field medics, emergency rescue, etc.

For example, treatment of acute pain is often necessary "in the field" under highly sub-optimal conditions. First responders, such as paramedics or military field medics, often are required to treat severe acute pain in non-sterile situations, where needles used for IV or IM administration can result in unintended risk, such as infection, and so on. The dispensing devices, systems and methods of the present invention find utility in this setting as well as in circumstances such as when a subject is suffering from angina, which may be treated with nitroglycerine using a dispensing device of the invention.

Chronic Outpatient Setting

Yet another embodiment of a dispensing device of the invention is in the outpatient setting where chronic administration is needed for patients suffering from chronic conditions.

One embodiment of the dispensing device for delivering drug dosage forms in dispensing device may be capable of 1-2 years of treatment; the dispensing device may be rechargeable and may be part of a system which includes a recharging station/dock/portable docking fob; the dispensing device may have a graphic display and indicator lights on the dispensing device; the dispensing device may be part of a system which includes a dock, or fob; the dispensing device may include a keypad on the device; the dispensing device may include a dock, or fob; the dispensing device may record a dosing history; the dispensing device may allow the dosing history to be queried; the device may store one or more patient or user identifications; the dispensing device is typically theft deterrent, child proof and has controlled access, the dispensing device may have a resetable counter; the dispensing device may have fixed or variable lockout times; the dispensing device may be refillable; the dispensing device may be networked; and the dispensing device may have an alert function.

When used in the outpatient chronic (home, office, field, etc.) setting, the dispensing device offers several features and advantages over the state of the art in outpatient drug administration. The dispensing device allows individuals to self administer drugs in accordance with physician, healthcare professional, or drug label guidelines. Examples of chronic outpatient indications where a dispensing device of the invention finds utility include chronic pain, chronic breakthrough pain, anxiety, insomnia, hypertension, coronary artery disease, depression, psychosis, addiction, ADHD, high blood pressure, diabetes, and others. To effectively assist in the dispensing of drugs in the chronic outpatient setting the dispensing device may provide some or all of the following features: the dispensing device may allow the patient to self administer the medication; record a patients' dosing history; allow the dosing history to be read or transferred to a computer network or other electronic device; allow a physician or healthcare provider to modify the settings and programming either in person or remotely; automatically upload or transfer information at a pre-determined time, on a pre-determined schedule or upon a specific event taking place; deter tampering or diversion; deliver the drug dosage form to the appropriate location (e.g. sublingual, buccal, oral gastro-intestinal, rectal, ocular, nasal, inhalation, aural, transdermal or by any other route of administration); and notify a pre-determined individual or individuals (by alert, alarm, cell phone message, text message, email, or other wired or wireless communication means) of an event like a dosing administration, a need for a refill of a prescription, a tamper attempt, a misuse of the device, a GPS location, an expiration of the drug contained in the device, a temperature or humidity event. A dispensing device of the invention may be used to dispense any medication in the outpatient setting, in any drug dosage form, affording any combination of the features set forth above.

In some embodiments, the dispensing device includes a docking connector or wireless docking means and is capable of communicating with a system which includes software and access to a computer network. A system comprising this device has a stationary or portable docking station which bidirectionally transmits information from the device to a network by wired or wireless mode or the hook-up may be by way of a docking connector or a wireless docking means, together with a means of connecting to a phone line, a computer, or a network.

In one exemplary embodiment the dispensing device would have two interface modes: a patient mode and a medical personnel mode, e.g., a nurse mode. In a patient mode, only the dispensing button would work, and the display and keypad would be non-functional. In the medical personnel mode, the display and keypad would be functional and a nurse would be able to access the dosing history, the dosage strength, the patient ID, the remaining doses in the device, and any other information that the dispensing device would have for nurse access. A nurse may have an RFID tag that the dispensing device would recognize as a medical personnel access tag, shifting to the medical personnel interface mode when it is present and switching back to the patient interface mode when it is not present.

In another exemplary embodiment, the dispensing device of the invention is used for administration of a sublingual tablet in the outpatient (home, office, etc.) setting. The dispensing device includes a microprocessor, a memory means, a dispensing button for dispensing a sublingual tablet, a small electronic speaker, and a docking connector or wireless docking means. Additionally there would be a stationary docking station that would contain a microprocessor, a memory means, a docking connector or a wireless docking means, and means of connecting to a phone line, a computer, or a network. In the patient dosing mode, the patient would depress the dispensing button when a dose was required. If the patient presses the dispensing button during the timed lockout period between doses, a tone would sound, informing the patient that he must wait before re-dosing and the dispensing device would not dispense a tablet. If the patient presses the dispensing button after the timed lockout period between dosing has expired, then the dispensing device would dispense a tablet and a confirmatory tone would sound, informing the patient that a dose had been dispensed. When the dispensing device is docked, either physically or wirelessly, to the stationary dock, the dispensing device would communicate with the patient's physician by means of a dock or other communication means to the physician's computer or other device, and exchange information, allowing the physician to view the patient's history, download information, reset a counter on the dispensing device, or enable or disable any other features on the device in a remote fashion. When the dispensing device is removed from the dock, the dispensing device would return to the patient interface mode, unless the physician had instructed the dispensing device to do otherwise.

In yet another embodiment of the invention, a dispensing device of the invention comprises some or all of the following features: the device has a patient identification feature, e.g., RFID; the device may monitor the temperature and shutdown if the drug dosage exceeds safe limits; the device has a display; the device has a means for connection and communication with a docking station or other docking or communication means such that the device is capable of connectivity for two-way data transfer, e.g., automatic data upload and down load via a local or remote computer system.

To effectively assist in the dispensing of drugs in the acute outpatient setting, the dispensing device may provide some or all of the following features: allow the patient to self administer the medication; record a dosing history; allow the dosing history to be read or transferred to a computer, network or other electronic device; deter tampering or diversion; deliver the drug dosage form to the appropriate location (e.g. sublingual, or buccal); record a dosing administration or a temperature or humidity event.

When used in the outpatient acute (home, office, field, etc.) setting, the dispensing device of the invention offers several features and advantages over the state of the art in outpatient drug administration. The dispensing device allows individuals to self administer drugs in accordance with physician, healthcare provider, or drug label guidelines. Some exemplary acute outpatient indications are post-operative pain, pain associated with physical trauma, anxiety, insomnia, hypertension, angina, coronary artery disease, depression, psychosis, constipation, nausea, addiction, ADHD, vertigo and others. See, e.g., U.S. application Ser. No. 11/429,904, expressly incorporated by reference herein.

The dispensing device of the invention may be used to dispense any medication in the outpatient acute setting, in any drug dosage form, affording any combination of the features set forth above. Some examples of uses for a device of the invention are in acute field care for first responders, military field medics, emergency rescue, etc.

Inpatient Setting

Another use for the dispensing device of the invention arises in the inpatient setting. For example, the need for rapid treatment of acute pain occurs in many different clinical situations, including post-operative recuperation, rheumatoid arthritis, failed back, end-stage cancer, etc. in the hospital settings. Post-operatively, for example, patients suffer from severe pain for the first few days followed by days of mild to moderate levels of pain.

In another embodiment the drug dispensing device is comprised of a disposable drug cartridge, a disposable dispensing end, a reusable controller end, a patient identification means like an RFID tag, a portable docking fob for controlling and accessing the drug dispensing device, and a base station for recharging the reusable dispensing end and the portable docking fob. In this embodiment the drug cartridge is loaded into the disposable dispensing end, which, in turn, is connected to the reusable controller end and affixed together. This assembly completes the drug dispensing device which is capable of dispensing dosage forms to the patient upon request, providing a lockout period between dosing, recording dosing and usage history, and allowing this history and the drug dispensing device settings to be reviewed or electronically downloaded. An RFID tag would be affixed to a patient so as to provide a wireless identification means that would enable the drug dispensing device to operate properly when in proximity to the correct RFID tag. A healthcare provider could use the portable docking fob to dock with the drug dispensing device, allowing access to settings, controls, history, and other features. When not in use, the reusable controller end and the portable docking fob could be placed in the base station to recharge the batteries or power supply.

When used in the inpatient (hospital, clinic, etc.) setting, a dispensing device of the invention offers several features and advantages over the state of the art in patient drug administration. The dispensing device allows healthcare providers to provide drug dosage forms to a patient for self administration of PRN ("Pro Re Nata") medications. PRN refers to drugs that are taken as needed, such as for pain, nausea, constipation, anxiety, etc. To effectively operate in the inpatient setting, a PRN patient controlled dispensing device should allow the patient to self dose as needed, prevent the patient from over dosing, record the dosing history, allow for the dosing history to be read, downloaded, or otherwise transferred to a patient's records, deliver the drug dosage form to the appropriate location (e.g. sublingual, buccal, oral gastrointestinal, rectal, ocular, nasal, pulmonary, vaginal, aural, transdermal or any other route of administration) and prevent or deter unauthorized individuals from gaining access to the drugs. The dispensing device of the invention may be used to dispense any PRN medication in any drug dosage form in the inpatient setting affording any combination of the features set forth above, as described in U.S. application Ser. No. 11/473,551, which is expressly incorporated by reference herein.

A system comprising the dispensing device of the invention may have a portable dock which bidirectionally transmits information from the device to a network in a wired or wireless mode. Software for downloading or uploading data, such as dosing histories, to a computer system is also part of this embodiment of the invention.

In other embodiments, the dispensing device can be adapted to attach to a cord so as to allow the device to hang from the neck of the patient or to be affixed to the hospital bed, for example. This would help avoid misplacing the device or theft of the device, such as in the hospital setting. The dispensing device may also have a clip so that it can be attached to an article of clothing or to a hospital bed.

The dispensing device may employ one or more theft deterrent features to prevent or deter unauthorized theft of, or tampering with the device or the drug dosage forms therein. Such deterrents may be employed to prevent theft of, or tampering with the device within the hospital, clinic, or healthcare setting, within the home, office, or any other location where the device is intended or not intended to reside or function, whether temporarily or permanently. Exemplary deterrents include physical locks, tethers, cables, clamps, or other physical attachments, whether permanent or temporary, to another object or to a person.

An exemplary embodiment of a physical theft deterrent means is a flexible cable that locks to the dispensing device on one end and locks, by means of a loop, locking mechanism, or other attachment, to a hospital bed on the other end. In this embodiment the cable tether may be unlocked from either the drug dispensing device or from the hospital bed to enable patient ambulation or to enable disposal or reuse of the device by means of a key, combination, or other locking mechanism that affords controlled access.

The deterrent means may include alarms or notifications that may trigger an alert on the dispensing device, on a dock or other peripheral device; on a computer or by means of a wired or wireless network, or may alert other remote devices. The alarm or notification may be audible, tactile, visual, or may employ other means of notifying one or more individuals. In one embodiment such an alarm or notification may indicate that the dispensing device has been stolen or is in the process of being stolen. In addition to an alarm, information about the theft event may be transferred to or from the device, including the time, date, audio data, visual data, GPS or other location information, or any other information that aids in the prevention of or tampering with the dispensing device or tablets therein. Such deterrents may involve an activation of a feature of the dispensing device, including a loud siren alarm, an electric shock, a shutting down or destruction of one or more aspects of the device, the dispensing of an ink or other marker, or an action that renders the internal drug unusable or undesirable. The dispensing device of this invention may use one or more means to deter theft or tampering.

In some embodiments, One exemplary embodiment of such a deterrent means can be exemplified by the case of the delivery of a sublingual opiate tablet in the inpatient (e.g. hospital or clinic, etc.) setting. In such a case the dispensing device includes a wireless proximity detection, like RFID or a detector for a wireless network, to detect when the dispensing device is removed from a predetermined proximity to a person, object, or physical location. Upon detecting that the dispensing device has been removed from a predetermined location or proximity, the dispensing device would shut down normal functionality, sound an audible alarm, send a wireless alert message to a remote device or network, and trigger the internal release of a liquid into the tablet cartridge in such a manner as to wet and/or inactivate all tablets, rendering them unusable.

In another exemplary embodiment, the dispensing device of the invention is used for delivery of a sublingual opiate dosage from in the outpatient (e.g. home, office, etc.) setting, an internal sensor or switch would detect when the dispensing device was opened, disassembled, damaged or lost power in an unauthorized or unintended fashion. The detection of this event would cause the internal micro processor to log an event record, if the system were able to, and trigger the internal release of a liquid opiate antagonist, like naloxone, into the tablet cartridge in such a manner as to wet all tablets, rendering them unusable as a opiate drug and unusable as a sublingual tablet dosage from.

The dispensing device may employ one or more levels of interface for different types of authorized users, for example the patient, the nurse, the physician, pharmacist or other authorized medical or healthcare personnel. These different interfaces may include components such as keypads, buttons, graphical icons and instructions, lights, LED's, monochrome or color graphical or text displays, touch-screens, LCD's, sounds, tactile feedback, voice recognition interfaces, and other input and output devices and means. The activity, or mode, of the user interface may be determined by the mode of operation of the dispensing device, by a login or access activity by a user such as a password or code entry, by the connection or disconnection of the dispensing device from a dock, computer, or network, or by the detection of an authorized access key, such as a key, and/or RFID tag, or similar combination. Upon changing the interface mode, the functionality of the device may be changed, either activating, inactivating or changing the functionality of the various interface components described above. By allowing the device to have one or more interface modes, with differing functionality associated with each one, the device can be optimized for various uses.

In one exemplary embodiment, a dispensing device of the invention is used for administration of a sublingual tablet in the inpatient (hospital, clinic, etc.) setting. Such a device would contain a microprocessor, a memory means, an LCD text and graphical display, a keypad with several buttons for navigating a graphical menu and selecting functions, and a dispensing mechanism for dispensing a sublingual tablet.

The dispensing device can include a microprocessor, a memory means, a multi-color LED light, a dispensing button for dispensing a sublingual tablet, and a docking connector or wireless docking means. Additionally, there would be a portable handheld dock that contains a microprocessor, a memory means, a graphical and text display, a keypad, and a docking connector or a wireless docking means. When this dispensing device is used in the patient mode, the LED would display a one color, e.g., green, when patient dosing was allowed, and it would display another color, e.g., an amber color when patient dosing was not allowed because the dispensing device was in a timed lockout period, and the dispensing device would display a third color, e.g., a red color when the dispensing device malfunctioned. The patient would be able to self administer a sublingual tablet when the LED was green. In one scenario, a nurse or other authorized medical personnel would bring a portable dock into the patient's room and physically or wirelessly dock to the dispensing device, allowing the medical personnel interface mode to be operable. In the medical personnel interface mode, a nurse would be able to view the patient dosing history, the dosage strength, the patient ID, the remaining doses in the device, and any other information that the device would have for the nurse to access. Furthermore, a nurse could reset dosing counters on the device, query error conditions, deliver bolus doses if needed, etc. When the portable dock was disconnected from the dispensing device, the dispensing device would return to the patient interface mode.

VII. Dispensing Devices

Dispensing devices and systems for oral transmucosal administration of small volume drug dosage forms are provided. The dispensing devices are handheld and portable and comprise a housing having a dispensing end which typically has a proboscis with a shroud that provide a means for blocking or retarding saliva ingress and/or moisture control. The dispensing devices further provide safety features such as a means for lock-out and a means for patient identification.

Single and Multiple Dose Applicators

The invention provides disposable applicators for delivering dosage forms to the oral mucosa such that application to a pre-determined location for drug delivery (e.g. the mouth, sublingual space, etc.) is effected.

In one approach to the invention, a dosage form, for example, a NanoTab™ may be delivered to the oral mucosa, using a single dose applicator. The dosage form is provided in a child-resistant drug dispensing device or packaging and delivered to the oral mucosa, for example, the sublingual cavity, with supervision/assistance. Alternatively, the dosage form is administered with supervision/assistance with or without a device.

In one embodiment, the invention provides dispensing device which can provide for a pre-determined delay between doses in a liquid or gel dispensing device. The mechanism includes a liquid or gel reservoir that is slightly pressurized, for example by a propellant or a spring loaded plunger, a thin exit tube leading from the reservoir to a second cylinder chamber. The cylinder chamber may contain a dispensing piston attached to a rod, and a dispensing port that is much larger than the thin exit tube connecting to the reservoir. The dispensing port may include a valve to prevent unintended dispensing of the drug. The viscosity of the drug formulation, the pressure in the reservoir, and size of the thin exit tube may be designed such that the viscous drug formulation slowly flows from the pressurized reservoir to the cylinder chamber, driving the piston backward until the chamber is full. This process takes a period of time that may be pre-determined and coordinated with an appropriate lockout time between drug doses. When the cylinder chamber is full, the dispensing valve may prevent drug from escaping. To dispense drug from the cylinder, the rod is pressed. The actuation of the rod also opens the dispensing valve allowing the liquid or gel to be dispensed. In one approach, the dispensing port is much larger than the exit tube, such that the drug is preferentially driven out the dispensing port. Also, it is possible to dispense a drug using this system prior to the cylinder chamber being completely full. If the chamber fills at a constant rate, the amount of drug dispensed is proportional to the time that the chamber has been filled, up to the point that the chamber is completely filled. For this reason, if the dispensing device is actuated prematurely, the dispensing device will only dispense a partial bolus of liquid or gel.

In one embodiment, a single dose applicator (SDA) is used to administer variety of drug dosage forms, including a solid tablet, a liquid capsule, a gel capsule, a liquid, a gel, a powder, a film, a strip, a ribbon, a spray, a mist, a patch, or any other suitable drug dosage form.

The single dose applicator (SDA) may contain the dosage form within, may have the drug dosage form attached or affixed to it, may have the dosage form dissolved in it, and may afford a seal against moisture, humidity, and light. The single dose applicator may be manually manipulated by a patient, healthcare provider, or other user to place the dosage form in the proper location for drug delivery.

In practicing the invention, a single- or multiple-dose applicator or drug dispensing device may be used to deliver tablets or other dosage forms into the hand, the mouth, under the tongue, or to other locations appropriate for specific drug delivery needs.

In one embodiment, a single- or multiple-dose applicator or drug dispensing device is used to deliver a dosage form to the oral mucosa, e.g., the sublingual space.

The dosage forms inside the dispensing device remain dry prior to dispensing, at which point a single dosage form is dispensed from the device into the mouth, e.g., the sublingual space, wherein a patient's saliva will wet the tablet and allow for tablet disintegration/erosion and drug dissolution.

The SDA may be provided as a pair of forceps, a syringe, a stick or rod, a straw, a pad, a dropper, a sprayer or atomizer, or any other form suitable for the application of a single drug dosage form. After use, the SDA may be disposed of, so as to eliminate the risk of contaminating the drug dispensing device with saliva, or other contaminants.

In one aspect of the invention, a small volume dosage form according to the present invention is placed in the sublingual cavity, preferably under the tongue on either side of the frenulum linguae, such that it adheres upon contact.

For sublingual administration, a small volume dosage form may be administered sublingually by placement under the tongue, adjacent to the frenulum using forceps. Alternatively, a small volume dosage form may be administered sublingually by placement under the tongue, adjacent to the frenulum using a syringe, a stick or rod, a straw, a dropper, or any other form suitable for the application of a single drug dosage form, including but not limited to a SDA, as further described herein.

The dosage forms may be provided in a package that consists of molded plastic or laminate that has indentations ("blisters") into which a dosage form, is placed, referred to herein as a "blister pack". A cover, typically a laminated material or foil, is used to seal to the molded part. A blister pack may or may not have pre-formed or molded parts.

In one embodiment, the blister pack has two flexible layers that are sealed with the dosage form in between and the primary unit dose blister pack also serves as an applicator for delivering a single dosage form to the sublingual space, once the child-resistant foil is peeled back.

In yet another embodiment of the invention, a long tape or array of dosage forms sealed between a flexible blister layer and a foil or otherwise breakable layer is provided. A push rod is positioned above a dosage form, and upon actuation pushes against the blister, forcing the dosage form through the foil or breakable layer, dispensing the dosage form.

Such blister packs may be provided in a child resistant multiple dosage drug dispensing device.

The claimed dispensing devices, methods and systems comprise delivery of small volume dosage forms to the oral mucosa. The invention is not limited to the specific devices, systems, methodology and dosage forms detailed herein, as these may, of course, vary. It is also to be understood that the terminology used herein is for the purpose of describing particular embodiments only, and is not intended to limit the scope of the present invention.

There is a continuing, unfilled need for a drug dispensing device that can accurately dispense a given medication to the correct patient in a manner that is cost-effective, minimizes the risk of error, is resistant to accidental and intentional abuse and diversion, eliminates the need to handle the medication and is not labor-intensive.

In another embodiment, the present invention provides a drug dispensing device that greatly simplifies the logistics of dispensing single and multiple doses of a given medication under controlled conditions. One exemplary use of a drug dispensing device of the invention is in the administration of controlled substances such as opioids. In such cases, the dosage form contains a highly potent and controlled narcotic drug that must be contained and administered under controlled conditions. Storage and delivery of such a formulation requires a specially designed device. The device must safely store the dosage form, prevent or deter abuse or accidental or inadvertent misuse, readily and accurately allow dispensing of individual dosages only to the patient for whom the drug was prescribed in an efficacious and safe manner as well as provide a means for monitoring and reporting of the history of use. The drug dispensing devices of the present invention meets these needs.

In another embodiment, the dispensing device comprises a package that holds a single or multiple drug dosage forms, a distal orifice for delivery of the drug dosage form, an internal mechanism that segregates and releases the dosage forms, internal electronics that control the number of dosage forms that can be delivered in a given time period (lockout time), a security feature that limits access to the device to the patient and/or one or more healthcare professionals, a security feature that reduces likelihood of dispensing device theft, a queriable interface that allows for dispensing device use history information to be stored and retrieved, a means of preventing saliva from penetrating the device, and an external switch for the user to actuate the dispensing device. The dispensing device is typically handheld and may be capable of data communication by way of a docking station ("dock"). A fixed or portable dock may be incorporated to aid in charging the dispensing device and for data access by authorized healthcare professionals. The dispensing device is capable of shutting down if a user does not match patient ID, lockout period has not expired when a dosing attempt is made, or sensors indicate that the drug form is no longer good (due to humidity, heat or expiration). The dispensing device is capable of issuing alarms when functional issues arise. In one aspect of this embodiment, the drug dosage form and drug dispensing device are designed for oral transmucosal drug delivery, e.g., into the sublingual space.

In another embodiment, the dispensing device of the invention includes a detecting means for patient identification such as a fingerprint reader, an optical retinal reader, a voice recognition system, a face recognition system, a dental imprint recognition system, a visual recognition system, or a DNA reader. The dispensing device may employ one or more means to identify the user, enabling the system to determine if a dispensing request is being made in an authorized or unauthorized manner. It is important for effective delivery of many potential drugs and drug dosage forms to ensure that the dispensing device is not accidentally or intentionally used by an unauthorized individual to prevent accidental or intentional diversion of the drug. Such patient identification systems may recognize one or more users, for example, in an inpatient hospital setting the dispensing device could be programmed to recognize the patient to whom it is prescribed, as well as authorized healthcare providers such as nurses and physicians. In an outpatient home setting, for example, the dispensing device may only respond to the patient to whom it is prescribed. The dispensing device may employ any means of user identification, including fingerprint identification, RFID detection with the use of an active or passive RFID tag on bracelet, necklace, clip, belt, strap, adhesive patch, implant, or means of locating and affixing a tag, retina identification, DNA identification, voice recognition, password or code entry, physical key, electronic or magnetic key, personal area network identification using the human body or clothing as a data or signal conduit, optical scanner or face recognition, sonic, subsonic or ultrasonic identification, or any other means of identifying an individual and verifying their identity.

One method of patient identification is the use of a short distance ("near field") passive RFID tag attached to a bracelet, necklace, adhesive patch, clothing tag, orally mounted device, like an orthodontic retainer, belt, strap, some combination of these, or another location. When an RFID tag is used in the "near field", roughly defined as about 16% of the wavelength of the received signal, the tag behaves in the inductive mode of operation, coupling between the reader and tag antenna magnetically. The near field is characterized by at least two features: first is a rapid decline in field strength with distance, and second is a strong directionality of the signal. In the near field, the signal strength falls off very rapidly, with a signal strength loss of approximately 60 dB per decade in distance. For good inductive coupling between the transmitter antenna and the RFID tag antenna, the two antennas are oriented in parallel planes with the axes through the center of each antenna in close proximity. Strong signal strength (robust patient identification) is provided when the device is very close to the RFID tag. At the same time, a very poor signal is provided when the device is further away from the tag, which helps prevent unauthorized use by someone other than the patient who attempts to use the device. It is preferable to operate in this near field region with good antenna alignment. Furthermore, it is preferable to operate with a very short distance of adequate signal strength for a positive identification, so that it is very difficult to receive a signal if the device is not in the proper orientation and proximity to the RFID tag. To attain a short distance and a proper alignment between antennas, the dispensing device may be designed so as to properly locate the RFID reader antenna, mounted in the dispensing device, adjacent to an RFID tag antenna, mounted, for example, on a wrist band or bracelet, or a clothing tag on the collar, or an adhesive patch on the hand, arm, cheek, neck, or elsewhere. Furthermore, an RFID tag antenna on a wrist band or bracelet may be held in proper alignment and location by means of a small adhesive patch that prevents the bracelet from moving or rotation on the wrist.

In another embodiment, the dispensing device employs a high frequency RFID reader for use in the inpatient (hospital, clinic, etc.) setting, operating on or near the 13.56 MHz frequency band, and the patient is be fitted with a matching RFID tag and antenna on a disposable bracelet or wrist band, designed in such a way that if the bracelet or wrist band is removed the RFID tag, the antenna, or another component of the associated circuit will be damaged or destroyed, rendering the bracelet or wrist band non-functional. In one example, the range of the RFID communication is short, between 0 inches and 10 inches preferably, more preferably between 0 and 5 inches, and most preferably between 0 and 3 inches, and may additionally be directional, allowing proper use by the intended patient to be easy and reliable, while at the same time making unauthorized use by another individual difficult, very difficult, or impossible.

In another embodiment, the dispensing device of the invention for use in the outpatient setting (e.g. home, office, etc.) would include an electronic fingerprint sensor system and would be trained to identify the patient's fingerprint at the time of prescription or first use. When the intended patient doses herself, she would first use the fingerprint identification sensor to attempt identification. Once the dispensing device has successfully identified the patient as the authorized user of the device, the dispensing device would allow a single dosing, effectively unlocking itself for a brief period of time, for example 5 seconds. Once the dose has been delivered or the 5 seconds have elapsed the dispensing device would effectively re-lock itself, requiring another fingerprint identification prior to another dosing.

In another embodiment, the dispensing device of the invention allows for a heart rate measurement, and does not dispense a dose unless the patient's heart rate is within a pre-specified range. The dispensing device may have any of a number of a number of types of sensors for measurement of internal and external parameters including biometric parameters such as body temperature, respiratory rate, blood pressure, blood chemistry, saliva chemistry, breath chemistry, or any other biological state or detectable input, or include external parameters such as time, date, temperature, humidity, global position, etc.

In another embodiment, the dispensing device of the invention may have a dose counting feature that monitors and stores the history of drug usage, including a global dosing counter that counts all doses taken since the device was set up, and a resettable dosing counter that may be reset by authorized medical personnel, e.g., a nurse and tracks doses taken since the last reset. The dispensing device of the invention can count and display the number of doses which have been dispensed and the number of doses that are remaining to be dispensed.

In addition, in another embodiment, the dispensing device of the invention may have a memory means for retaining information about the dose delivered over time. The memory means may include RAM and/or ROM. A central processing unit (CPU) for processing information and controlling various functional elements of the device is also provided.

In another embodiment, the dispensing device of the invention may also have a convenience feature that can provide for ease of use. Exemplary convenience features include disposability, reusability, ease of refill, remote wired or wireless activation, rechargeable batteries, and multiple dose capability.

In another embodiment, the dispensing device of the invention may also have a drug expiration alert feature that can prevent inappropriate dosing of an expired drug; drug expiration information; an interface for exchanging information with another device such as a computer; a clock feature to track date and time for drug access control; and/or other communication capabilities that may be time dependent.

In another embodiment, the dispensing device of the present invention provides a drug delivery device that is capable of controlled delivery that is electrically monitored and controlled such that the patient receives a dose that is both safe and efficacious.

In another embodiment, the drug dispensing device of the present invention is an easily handled, portable, self powered, relatively inexpensive device that allows for timed lock-out periods to avoid overdosing, is child-proof and tamper proof, and is capable of multi-unit dosing, such that days, weeks or months of medication can be housed in the device.

In another embodiment, the drug dispensing device of the present invention may include the following structural components which are functionally connected: a drug reservoir, a dispensing tip, a manual or powered activation trigger or button, one or more communication port(s), an internal power supply, a user interface with input and output functions, a microprocessor, wireless communication capability, patient and user identification (e.g. fingerprint reader, RFID) capability, saliva ingress prevention, internal humidity and moisture control, an opioid antagonist reservoir, a refilling or other access port, one or more sensors to detect internal and external states, and biometric or access code input.

In another embodiment, the drug dispensing device of the invention may employ one or more sensors inside or outside of the dispensing device to monitor various inputs. Some inputs may be indicators of internal system states, such as the number of tablets in the device, the location of tablets within the device, the successful dispensing of a tablet, an unsuccessful dispensing attempt, the presence of a tablet at a specific location, the presence of a tablet cartridge, the identity of the cartridge, the position of the dispensing mechanism, the temperature or humidity within the device, or the sensing of any other internal configuration or state. Other inputs may be indicators of conditions external to the device, including temperature, humidity, acceleration, light, or proximity to a user, another person, or an object, among others. These inputs may be specific to a user or other person and may include direct or indirect interactions with the device, actuation or activation of a switch, button, or other input, body temperature, heart rate, respiratory rate, blood pressure, blood chemistry, saliva chemistry, breath chemistry, pupil dilation, or any other biologic state or detectable input. The sensors may employ any means of detecting an input. A range of sensors for detecting temperature, humidity, acceleration, saliva ingress, or other biometric input may serve as a means to allow the device to activate or shut down under predetermined or programmable conditions.

In another embodiment, the drug dispensing device may be powered by a battery, capacitor, fuel cell, or other power supply source, or may require no electrical power, but be manually activated.

In some embodiments, the drug dispensing device of the invention includes a battery that can be charged by a photovoltaic cell or manually by a hand-actuated crank or lever. A rechargeable battery or other power source may be recharged in a dock, with a recharging cable, or by other means.

Blocking/Retarding Saliva and Moisture Ingress

The claimed dispensing devices comprise a means for minimizing or eliminating saliva ingress and moisture ingress into the dispensing device: (1) to avoid wetting the dosage forms therein; (2) to isolate any saliva that enters the dispensing device in such a manner that the dosage forms therein remain dry; (3) to absorb or adsorb any saliva that enters the dispensing device in such a manner that the dosage forms remain dry; (4) to block saliva and moisture from entering the device to protect the dosage forms from vapor and liquid phase moisture, or (5) any combination thereof.

The dispensing device has a means for preventing and/or controlling humidity ingress due to ambient conditions outside of the device.

The means for minimizing or eliminating saliva ingress or preventing other moisture from entering the dispensing device includes, but is not limited to, one or more flexible or rigid seals, one or more flexible or rigid wipers, use of one or more absorbent material components such as a desiccant or pad, a door or latch that is manually or automatically opened and closed, multiple stage delivery systems, a positive air pressure and airflow, or an air gap or prescribed distance or barrier/shroud maintained between the tablet delivery orifice and the mucus membrane tissues within the mouth that may transport the saliva. The shroud limits the ability of the tongue or sublingual mucosa to contact the dosage form dispensing area, thereby controlling saliva contact and ingress. By inhibiting or eliminating the "wetness" inside the shroud and on the surface of the valve/seal, the dosage form is dispensed without adhesion occurring between the dosage form and the shroud or valve/seal. The drug dispensing devices of the invention provide a means for minimizing or eliminating saliva ingress into the dispensing device during administration of the drug to the oral mucosa of the patient.

To protect the drug dosage forms from exposure to moisture either from humidity, saliva ingress, or accidental exposure to other water based liquids, the dispensing device and the container or cartridge which houses the dosage form within the device contains a desiccant. Mechanisms to prevent drug dosage forms inside a device of the inventions from exposure to moisture include but are not limited to use of desiccants, seals, absorbents, adsorbents, wipers, and sensors.

Means for trapping or otherwise isolating saliva or moisture if it enters the device include, but are not limited to, a hydrophilic wicking material or component, an absorbent or adsorbent material or component, a desiccant material or component, a separate track or channel for moisture to collect, a separate channel to communicate moisture to the absorbents or adsorbents, or any combination of these materials or components.

A desiccant is a sorbant, in the form of a solid, liquid, or gel that has an affinity for water, and absorbs or adsorbs moisture from it's surrounding, thus controlling the moisture in the immediate environment. Any commercial desiccant may be used. Commercial desiccants typically take the form of pellets, canisters, packets, capsules, powders, solid materials, papers, boards, tablets, adhesive patches, and films, and can be formed for specific applications, including injection moldable plastics. There are many types of solid desiccants, including silica gel (sodium silicate, which is a solid, not a gel), alumino-silicate, activated alumina, zeolite, molecular sieves, montmorillonite clay, calcium oxide and calcium sulfate, or others, any of which may be used in the claimed dispensing devices. Different desiccants have different affinities to moisture or other substances, as well as different capacities, and rates of absorption or adsorption. Also, different types of desiccants will come to equilibrium at different relative humidities in their immediate surroundings. As a means for protecting the dosage forms and the internal portions of the dispensing device from moisture, one or more desiccants may be employed at the proboscis; in or adjacent to the dosage form; in or adjacent the delivery pathway; in or adjacent the dosage form, tablet magazine or cartridge; in or adjacent to other components of the dispensing device; formed as an injection molded component of the dispensing device; a compressed desiccant that is pressed into location; or desiccant in any other location within or without the device.

In one preferred embodiment, the desiccant snaps into a cavity in the side of the cartridge. There are holes in the desiccant cavity that connect it to the dosage form stack, exposing the dosage forms to desiccant and keeping them dry.

The claimed dispensing devices rely on valves, pads, seals, the rest position of the push rod, proboscis design and a shroud to minimize or eliminate saliva ingress or moisture into the dispensing device during administration of the dosage form.

Valves for use in the claimed devices are typically dome/trocar type valves that provide enough sealing force to keep saliva and/or moisture from entering the device and serve to minimize or eliminate saliva ingress or moisture by closing the distal orifice during dispensing and after a dosage form has been dispensed.

Pads for use in the claimed devices have various geometries that aid in contacting or communicating with the pushrod in order to removed liquid from the push rod surface. Such pads typically contain hydrophilic properties and serve to minimize or eliminate saliva ingress or moisture ingress by transporting the liquid away from the track and push rod.

Seals and wipers for use in the claimed devices are designed to maintain a uniform seal around a drug dosage form and a pushrod during delivery and are characterized by flexible materials that impart a seal around the dosage form and pushrod and serve to minimize or eliminate saliva ingress or moisture by sealing and wiping the orifice and pushrod before, during, and after dispensing.

The rest position of the push rod in the claimed devices is characterized by positioning the pushrod in an intermediate location distal to the cartridge exit, and proximal to the distal dispensing orifice and serves to minimize or eliminate saliva ingress and moisture by allowing the pushrod to reside in a location that contains a desiccant, absorbents, or channel that dries the pushrod while at rest between dosage dispenses.

The proboscis design for use in the claimed devices is characterized by a distal device shape, typically an S-shape, that aids in use of the device and/or placement of the tip on the oral mucosa of the subject. The shape typically has curves, angles, and geometries such that it enables proper use of the device and placement of the dosage form on the oral mucosa of the subject, e.g., in the sublingual space.

The shroud of the claimed devices has a geometry that forms a barrier between the device and the oral mucosa and tongue, a relief for dosage form delivery, and an interior that is hydrophobic or hydrophilic and serves to minimize or eliminate saliva ingress or moisture ingress by creating a barrier from the oral mucosa contacting the valve area and dosage form, aiding in dosage form dispensing and discouraging dosage form adherence to the shroud. The shroud may have a rounded interior surface or other geometries to mitigate the dosage form adhering to the shroud. The shroud limits the ability of the tongue or sublingual mucosa to contact the dosage form dispensing area, thereby controlling saliva contact and ingress.

Figure 1A:
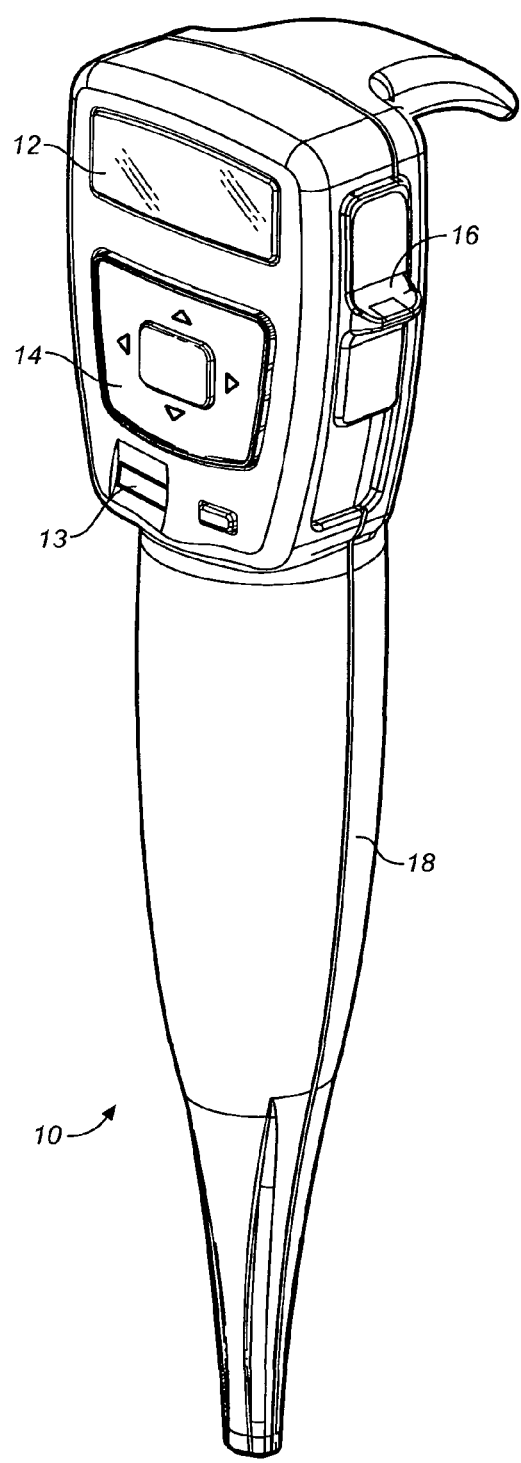
FIG. 1A is a schematic depiction of an exemplary dispensing device of the invention wherein the device is designed to deliver drug dosage forms to the sublingual space of a patient under treatment, wherein a graphic display, a biometric patient identification reader, a dispensing button, a user interface, and a housing in which a dispensing cartridge is located are illustrated.

FIG. 1A is a schematic depiction of one embodiment of a dispensing device 10 for delivering drug dosage forms to a patient. The dispensing device 10 includes a graphic display 12, a biometric patient identification reader 13, a user interface 14, a dispensing button 16, and a housing 18 in which a dispensing cartridge is located. The dispensing device 10 is constructed to hold a plurality of dosage forms. The graphic display 12 includes an LCD display that enables the dispensing device 10, for instance, to monitor and display dosing frequency, patient information, and/or schedule information. The user interface 14 may used for navigating and selecting menu items displayed on the graphic display 12. The dispensing button 16 may dispense single doses when pushed by a user, such as a patient. This allows post operative or otherwise incapacitated patients to operate the device without undue physical exertion. It also allows an attending nurse or physician to dispense a dose to the patent and monitor their dosing history. The dispensing button 16 may either actively dispense a dosage form or trigger a logic switch that will inform a processor within the device that a dispense request has been made. The patient identification reader 13 requires input of identification (e.g. fingerprint reader, optical retinal reader, voice recognition, dental recognition, face recognition system, or DNA reader, RFID) or an access code to prevent accidental or intentional diversion or abuse from unauthorized individuals.

In one exemplary embodiment, the dispensing device 10 may employ a high frequency RFID reader for use in the inpatient (hospital, clinic, etc.) setting, operating on or near the 13.56 MHz frequency band, wherein the patient is fitted with a matching RFID tag and antenna on a disposable bracelet or wrist band, designed in such a way that once the bracelet or wrist band is removed the RFID tag, the antenna, or another component of the associated circuit is damaged or destroyed, rendering the bracelet or wrist band non-functional. In one example, the range of the RFID communication is short, between 0 inches and 5 inches, and may additionally be directional, allowing proper use by the intended patient to be easy and reliable, but at the same time making unauthorized use by another individual difficult, very difficult, or impossible.

In another exemplary embodiment, the dispensing device 10 for use in the outpatient setting (e.g. home, office, etc.), the biometric patient identification reader 13 is an electronic fingerprint sensor system and would be trained to identify the patients' fingerprint at the time of prescription or first use. When the intended patient doses herself, she would first use the fingerprint identification sensor to attempt identification. Once the dispensing device 10 has successfully identified the patient, the patient identification reader 13 prevents the possibility of accidentally or intentionally switching devices with another patient and an accidental or inadvertent misuse of the device 10.

Figure 1B:
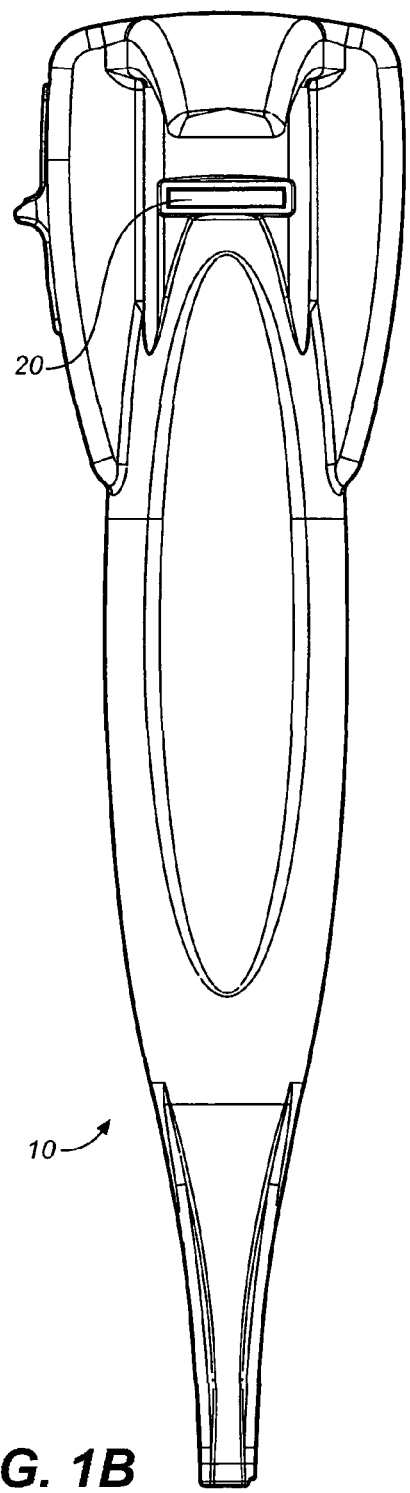
FIG. 1B is a schematic depiction of an exemplary dispensing device of the invention wherein the device is designed to deliver drug dosage forms to the sublingual space of a patient under treatment, wherein a docking connector is illustrated.

FIG. 1B is a schematic depiction of the dispensing device 10 for delivering drug dosage forms to a patient. In this embodiment, the dispensing device 10 includes a docking connector 20. The docking connector 20 can allow the dispensing device 10 to connect to another device, peripheral, or computer to retrieve, store, communicate data to the other device, peripheral, or computer.

FIG. 1C is a schematic depiction of one embodiment of a dispensing tip 22 of a dispensing device for delivering drug dosage forms to a patient. The dispensing tip includes a dispensing shuttle mechanism 24 near a dispensing end 26.

FIG. 1D is a cross-sectional schematic depiction of another embodiment of the dispensing device 10 for delivering drug dosage forms to a patient. The dispensing device 10 includes a cartridge assembly 30; one or more batteries 32; a processor and pc board 34; an antenna 36; and an antagonist reservoir 38. The dispensing device 10 may contain a shuttle mechanism, such as shuttle mechanism 24, to remove a drug dosage form from a stack and the dispensing end may have a slider mechanism to dispense single doses when the dispensing button is pushed.

The dispensing device of the present invention may comprise one or more of the following features: be hand held or portable; comprise a graphic display, interface buttons, scroll buttons and a dispensing button; comprise a biometric finger print reader or other means to identify and confirm that the correct patient is using the device; comprise an RFID reader; comprise a dose counting feature; comprise a memory means for retaining information about dosing history; comprise an interface for bidirectional exchange of information with another device such as a computer; comprise an LED, light, sound or tactile indicator that is activated when a dosage form is dispensed; be capable of dispensing a single dosage form at a time; not require the opening and closing of a lid or other hinged aperture in order to dispense a dosage form; comprise an antagonist reservoir; comprise an indicator, wherein the indicator notifies a patient when it is time to take a dose or comprise an indicator, wherein the indicator provides notification in the event of a potentially dangerous or non-efficacious dosing situation or comprise an indicator, wherein the indicator notifies the patient of the remaining time to the end of the lockout period.

In some embodiments, the dispensing device of the invention has the visual look of a pipette (as shown, for instance, in FIG. 1A) and therefore is not enticing to a child (as opposed to the ACTIQ lozenge which has the look of a lollipop).

In one exemplary embodiment, the dispensing device is a handheld device, with a control interface on one end and a dispensing device tip on the other. The control interface has a number of features, selected from an LCD monitor screen (for example, the graphic display 12 shown in FIG. 1A), a speaker for user feedback, various interface and/or scroll buttons (for example, the user interface 14 shown in FIG. 1A), a dispensing button (for example, the dispensing button 16 shown in FIG. 1A), and a biometric thumbprint reader (for example, the biometric patient identification reader 13 shown in FIG. 1A). The dispensing end may have a slider mechanism (for example, the user interface 14 shown in FIG. 1A) to dispense single doses when the dispensing button is pushed.

FIG. 2 is a schematic depiction of a cartridge assembly 40 for use in a dispensing device for delivering drug dosage forms. The cartridge assembly 40 includes a cap 42, a spring 44, a plunger 46, dosage forms 48, and a cartridge tube 50. To assembly, the drug dosage forms 48 are loaded into the cartridge tube 50, followed by the plunger 46, the spring 44 and the cap 42. Once this cartridge is assembled it is inserted into a drug dispensing device, such as dispensing device 10.

FIGS. 3A-E provide schematic depictions of a variety of aspects of one embodiment of a drug dispensing device constructed to hold a plurality of dosage forms for oral transmucosal delivery. FIG. 3A is a schematic depiction of a fully assembled or single piece dispensing device 5011 of the invention. In FIG. 3B, the dispensing device 5011 includes a reusable head 5013 and a disposable body 5015; in FIG. 3C the dispensing device 5011 further includes a cartridge 5017 in FIG. 3D the dispensing device 5011 includes a valve 5033, a proboscis 5031, a latch button 5019, a power train coupling 5025, a hub lock 5021 and a dispense button 5023; and FIG. 3E is a schematic depiction of a reassembled and complete dispensing device 5011.

Figure 4:
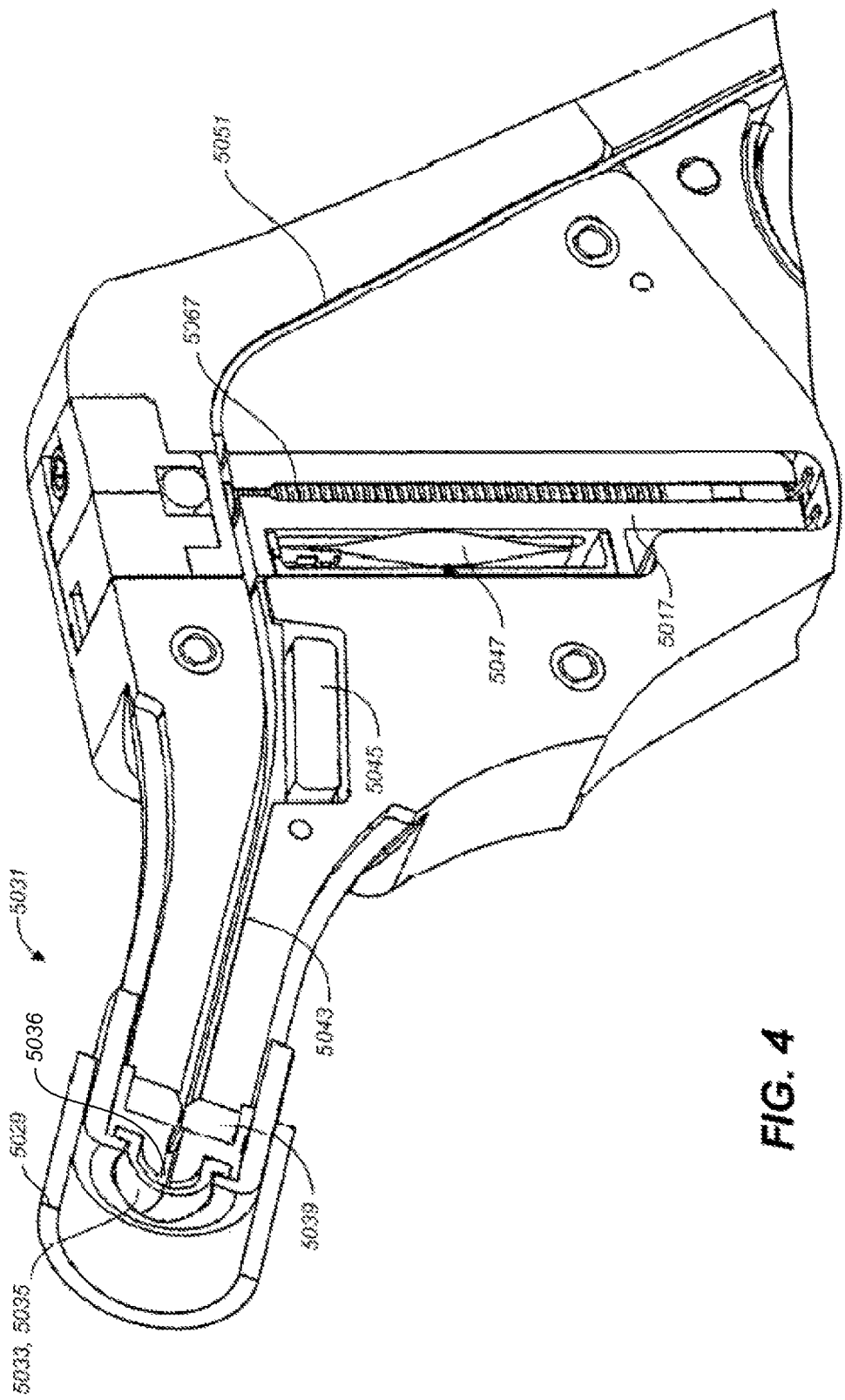
FIG. 4 is a schematic depiction of an exemplary dispensing device showing features designed to block or retard saliva and moisture ingress. The preferred embodiment includes a dispensing tip defining an exit port 5036, having a shroud 5029, and having one or more of: a wiping seal/valve 5033, 5035, an absorbent pad 5039, a pushrod 5051, a drying chamber/moisture communication channel 5043, desiccant 5045 in the channel 5043, a cartridge 5017 containing dosage forms 5067 and desiccant 5047 in the cartridge 5017.

FIG. 4 provides a schematic depiction of an exemplary dispensing device wherein the dispensing tip includes a proboscis 5031 comprising a shroud 5029 having a one or more of: a wiping/sealing valve 5033, 5035, an absorbent pad 5039, a drug drying chamber/moisture communication channel 5043, desiccant 5045 in the channel 5043, a cartridge 5017 containing dosage forms 5067 and desiccant 5047 in the cartridge 5017. A pushrod 5051 is configured to push the dosage form 5067 through the channel 5043.

Figure 5A:
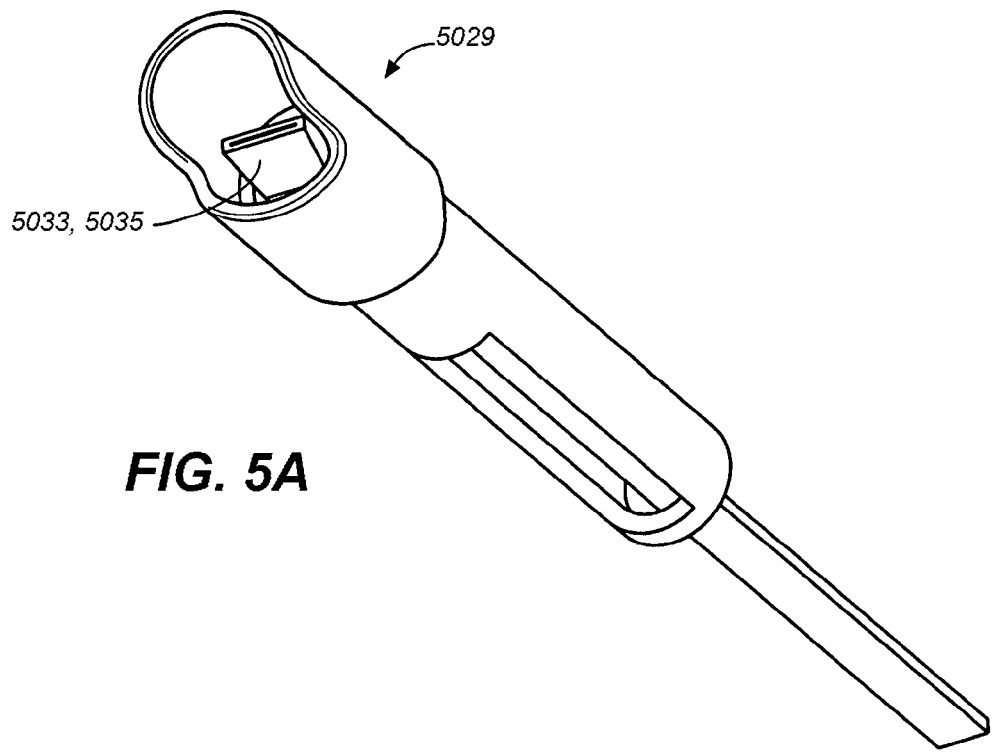
FIGS. 5A and 5B are schematic depictions of an exemplary geometry for a dispensing tip.
Figure 5B:
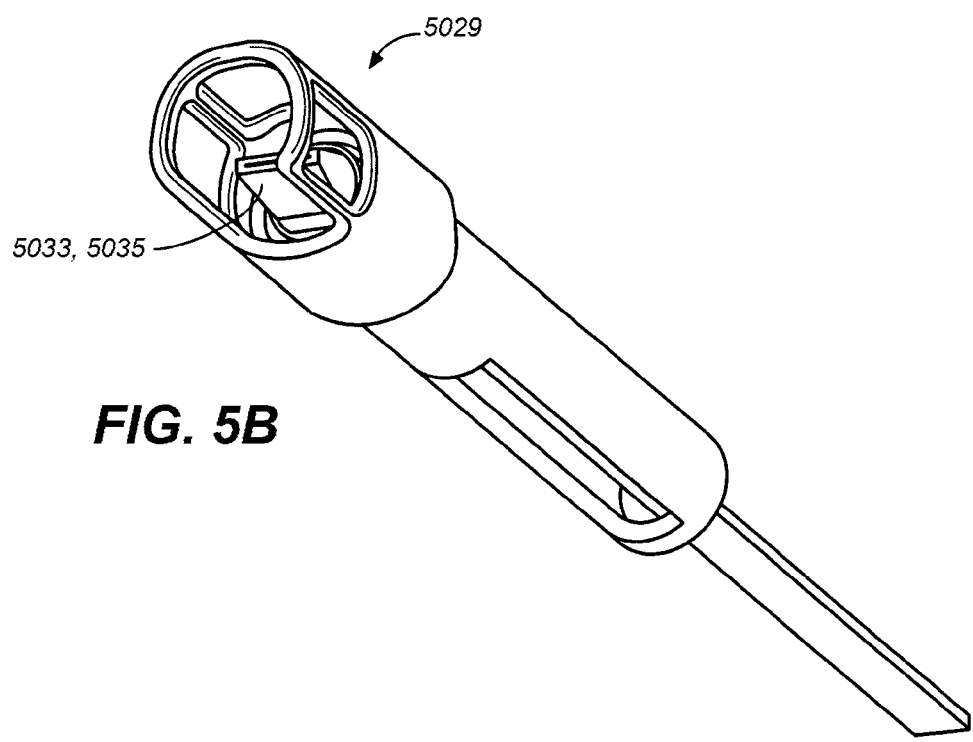
Figure 6A:
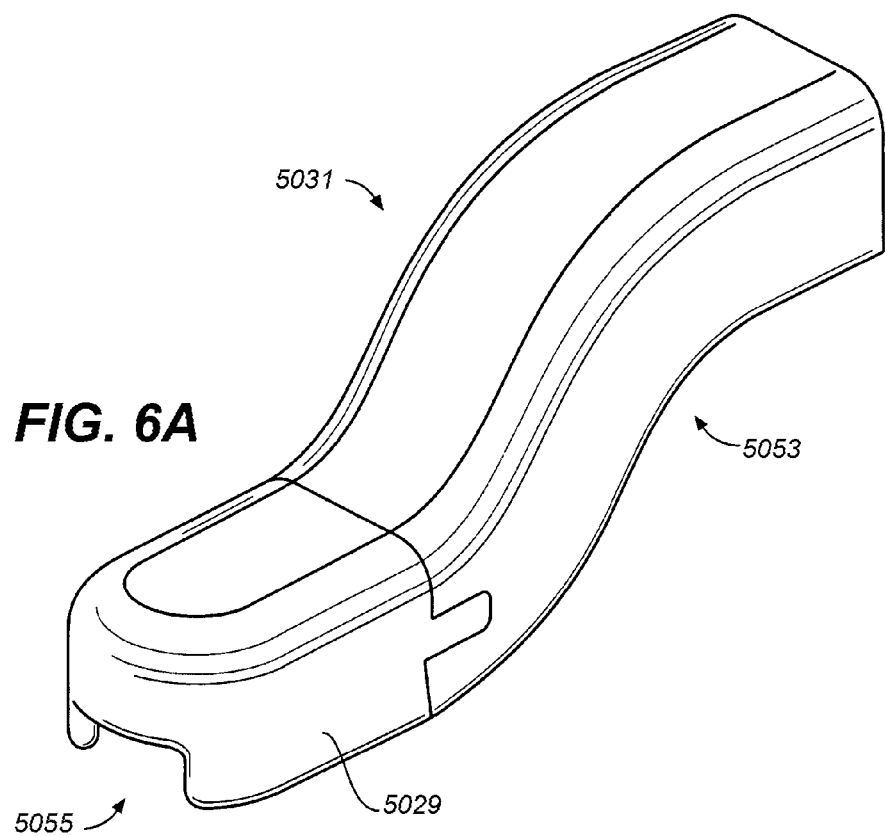
FIGS. 6A-D are a schematic depiction of an exemplary proboscis 5031 of a dispensing device wherein the proboscis 5031 has an S-shape 5053 and comprises a shroud 5029 and a valve.
Figure 6B:
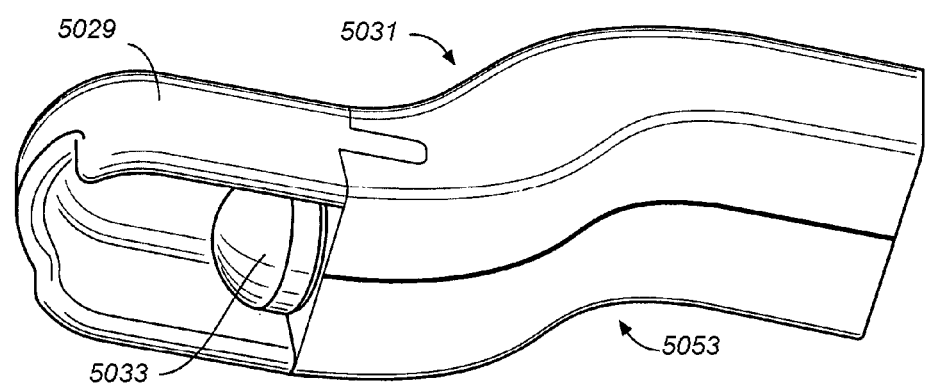
Figure 6C:
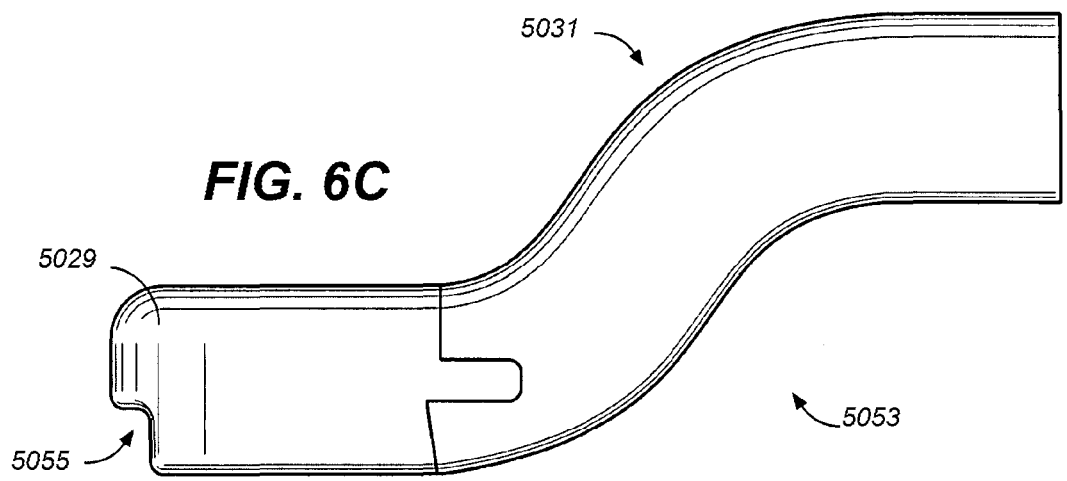
Figure 6D:
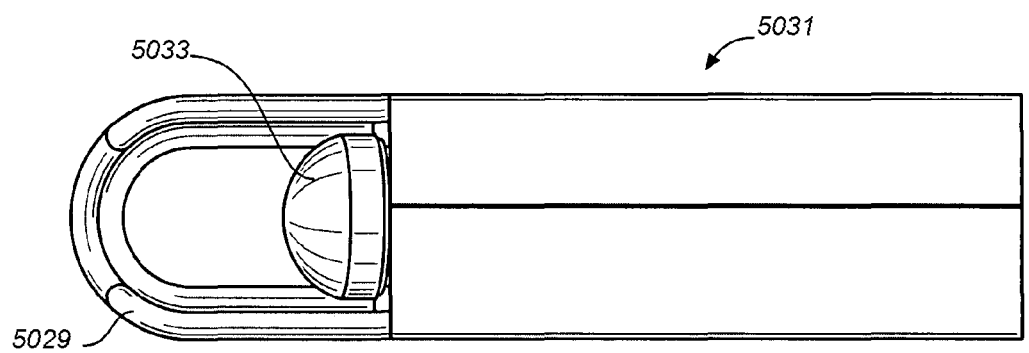

FIGS. 5A and 5B are schematic depictions of an exemplary geometry for the dispensing tip that prevents contact of one or more seals 5033, with the moist or wet surface of the oral mucosa via a shroud 5029.

FIGS. 6A-D are a schematic depiction of an exemplary proboscis 5031 has an S-shape 5053 of a dispensing device, for example the dispensing device 5011, as shown and described above with reference to FIGS. 3A-3D, wherein the proboscis 5031 comprises a shroud 5029, a valve 5033 for dispensing a dosage form and a cut-out/relief 5055 for the dosage form to be placed against the oral mucosa and not moved when the device 5011 is withdrawn following dispensing.

FIGS. 7A and 7B are schematic depictions of a drug dosage form being pushed through a seal by a pushrod, wherein the geometry of the seal is tailored to the shape of the dosage form and pushrod. FIG. 7A depicts a dispenser 254 comprising drug dosage forms 48, a cartridge 255, septum or seal 256, and a pushrod 257, wherein the drug dosage forms are stacked for dispensing. In the dispenser 254 in FIG. 7B 256, drug dosage forms 48 are being pushed through the septum 256 by the pushrod 257, wherein the geometry of the septum 256 is tailored to the shape of the dosage form 48 and the pushrod 257.

FIG. 8 is a schematic depiction of geometry 258 of an exemplary pushrod 260, drug dosage forms 48, and septum-type seal 264. The exemplary slit type septum seal 264 is designed to maintain a uniform seal around the drug dosage form 48 and the pushrod 260 during delivery. Additionally, the means for transporting the drug dosage forms through the seals, wipers, doors, absorbents, etc. may include the use of a push rod or shuttle that is specifically designed to limit saliva ingress and manipulate the tablet through the components.

FIGS. 9A-9F are schematic depictions of the geometry 266, 268, 270, 272, 274 and 276 respectively, of other exemplary slit type septum seals designed to maintain a uniform seal around a drug dosage form and a pushrod during delivery of the drug dosage form. The exemplary slit type septum seal is designed to maintain a uniform seal around a drug dosage form and a pushrod during delivery. Additionally, the means for transporting the drug dosage forms through seals, wipers, doors, absorbents, etc. may include the use of a push rod or shuttle that is specifically designed to limit saliva ingress and manipulate the tablet through the components.

A means for minimizing saliva ingress and moisture into the claimed devices is important for preservation of the integrity of dosage forms during storage, e.g., prior to and between oral transmucosal administrations.

The claimed dispensing devices may be used to administer a drug dosage form that is sensitive to moisture and/or humidity. In such cases, a drug dosage form cartridge serves to protect the drug dosage form from liquid and vapor phase moisture, including humidity, liquid moisture, saliva, mucus, etc. The cartridge may be cylindrical, disk-shaped, helical, rectilinear, non-ordered, or may take the form of any assemblage of drug dosage forms that allows the drug dispensing device to dispense them in a controlled manner. To prevent the unused drug dosage forms from absorbing moisture or otherwise becoming exposed to moisture prior to use, the cartridge may provide a means of sealing the drug dosage forms from exposure to moisture. This may accomplished by use of a cartridge that contains individually packaged drug dosage forms separated by a thin impermeable foil or impermeable material such that when one drug dosage form is dispensed from the cartridge, the seal protecting the remaining dosage forms remains unbroken. Alternatively, the dosage forms may be packaged in such a manner within the cartridge that two or more dosage forms are packaged together in each separate sealed compartment. In some embodiments, all of the dosage forms in a cartridge may be packaged together in a foil sealed compartment.

A drug cartridge that houses small volume drug dosage forms within the dispensing device may afford a seal against moisture by means of a septum, an elastomeric seal or valve, a sliding, translating, hinged door or valve, or by means of sealing against another component of the drug dispensing device when loaded. In this manner, a single re-sealable seal may be opened either independently or by means of the passage of a dosage out of the cartridge. Once the dosage form is delivered from the cartridge, the re-sealable seal on the cartridge may be re-sealed to prevent moisture or other contaminants from damaging the remaining drug dosage forms within the cartridge. The cartridge may further have a non-re-sealable seal that is broken when it is loaded into the drug dispensing device or upon delivery of the first dosage form from the cartridge.

In other embodiments, the cartridge contains a desiccant or other absorbent or adsorbent material to absorb or adsorb moisture that penetrates the cartridge either prior to use or during normal use. A cartridge for use in a claimed dispensing device may contain any combination of individually sealed dosage forms, multiply sealed dosage forms, re-sealable seals, non-re-sealable seals, desiccants, absorbents, or adsorbents. In one embodiment, a cartridge for use in the dispensing device in holds sufficient drug dosage forms for 1-5 days of treatment, e.g. 40 dosage forms or sufficient drug dosage forms to provide 48 to 72 hours of treatment.

Dispensing Mechanism

Figure 10A:
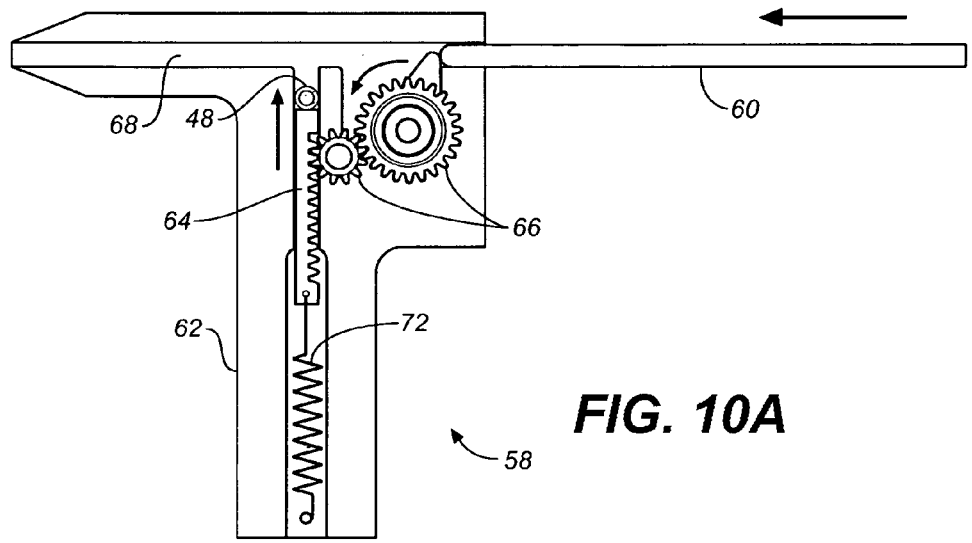
Figure 10B:
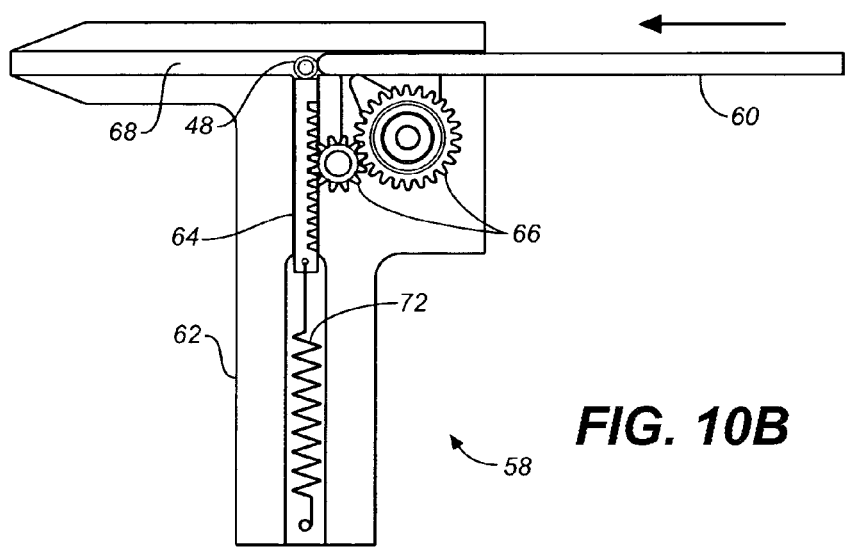
Figure 10C:
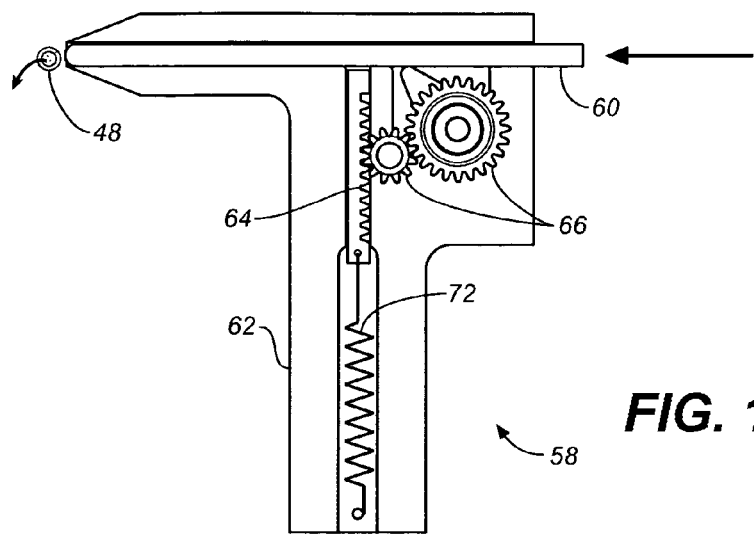
Figure 10D:
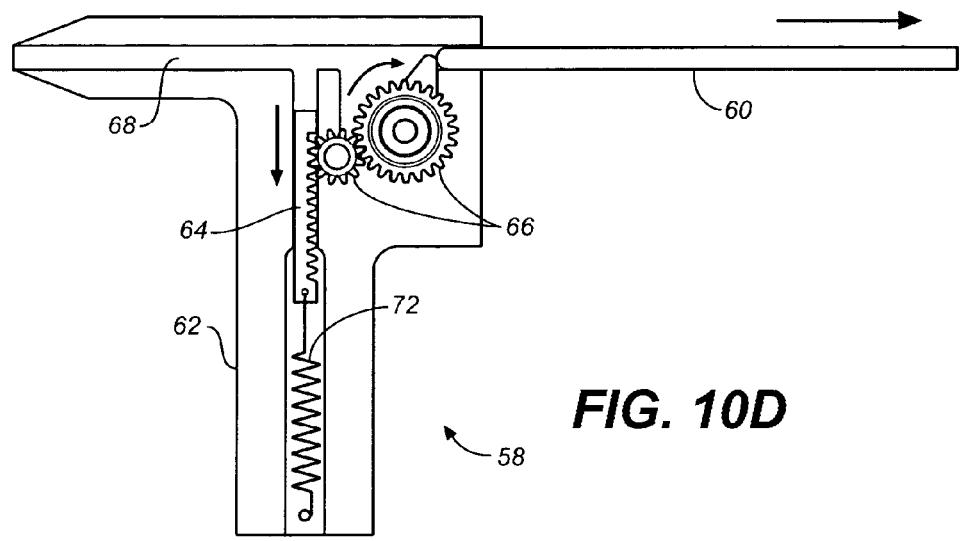

FIGS. 10A-10D are schematic depictions of an exemplary dispensing device 58 for delivering drug dosage forms 48, wherein a means for minimizing saliva influx into the dispensing device 58 during the administration of the dosage forms 48 to the patient is provided. The dispensing device 58 includes a pusher/slider 60, a housing 62, a push rack 64, pinions 66, and a channel 68 in the housing and a spring 72. FIGS. 10A-10D depict a multiple stage dispensing of drug dosage forms 48 as a means to reduce saliva ingress into the dispensing device 58. In FIG. 10A, the pusher/slider 60 is ready to push rack 64 and pinions 66 housed in the housing 62 of the device 58. The channel 68 provides space for the pusher 60 to freely move within the channel 68. The drug dosage form 48 is sitting on top of the rack 64 and spring 72 provides necessary tension in moving and returning the rack 64 and mechanism. In the dispensing device 58 shown in FIG. 10B, the pusher/slider 60 is moving the rack 64 and pinions 66 housed in the housing 62 of the device 58. The drug dosage form 48 is pushed upward within the channel 68 by the force provided by the spring 72 on the rack 64. In the dispensing device 58 shown in FIG. 10C, the dosage form 48 is being dispensed from the end of the channel 68 and into a subject, such as human. Then the steps are repeated for successive dispensing of the dosage form 48 minimizing saliva ingress into the device 58 as shown in FIG. 10D. Saliva influx/ingress into the dispensing device 58 may be minimized by inclusion of seals, wipers, absorbents, desiccants, ejection type devices, air gaps, or combinations thereof, or any other means of minimizing saliva ingress in the device design. A means of allowing saliva to enter the device while preventing saliva from reaching the remaining tablets within the device may include one or more flexible or rigid internal wipers or seals, a drug dosage cartridge that contains a plurality of individually packaged or isolated drug dosage forms, a delivery pathway for the tablet from a drug dosage cartridge to the exit port that is tortuous or multi-staged in such a manner that saliva or moisture not capable of wicking up the delivery pathway.

FIG. 11A is a schematic depiction of an exemplary dispensing mechanism for a dispensing device 100 for delivering small-volume oral transmucosal drug dosage forms, wherein a column type dispensing mechanism at a rest position. The dispensing mechanism includes one or more cartridge assembly 102, an activation button 104, a motor 106, a cam 108, desiccant 110, one or more seals 112, a delivery sensor 114, a spring clip 116, and a spring 118. The dispensing device 100 of the invention provides for dispensing of dosage forms based on a stack or plurality of dosage forms 48 contained in the tubular cartridge or magazine 102, with a spring 120 at one end wherein a loading force is applied to the stack of dosage forms. FIG. 11B is a schematic depiction of the dispensing device of FIG. 11A wherein the positions of the dispensing mechanism, motor and cam are at a rest position. The assemblies 102 and dosage form stack 48 rest upon the slider 124 which is perpendicularly movable to the axis of the dosage form stack 48. The slider 124 is a thin blade, with a thickness equal to or less than that of a single dosage form, on axis with the dosage form stack. The slider 124 slides between the end of the dosage form cartridge 102 and a solid face such that the spring 120 pushes the stack so as to place the first dosage 48 against the solid face on the other side of the slider 124. The slider 124 includes a receiving portion 128 sized to accept the first dosage 48 opposite the cam. Exemplary cartridge dispensing mechanisms include column type, ribbon/tape type, disc type, helical type, barrel type, index/spring-load type, hopper type, conveyor type, continuous tablets type, shrink wrap type, snap-out type, track type, barrel lock type, adhesive tape, pocket tape type, a single dose applicator, and foil on stack type.

A dispensing device of the present invention may dispense a dosage form by manual actuation of a button, lever, slider, wheel, or other actuator or by a mechanism selected from the group consisting of mechanical actuation, electro-mechanical actuation, spring loaded actuation, pneumatic actuation, hydraulic actuation, magnetic actuation, gravitational force activation, thermal actuation, combustive actuation, phase change expansion or contraction actuation, sonic actuation, and absorbent actuation. The device may dispense a dosage form by means of a microprocessor controlled actuator.

The dispensing mechanism for dispensing a drug dosage form may comprise a mechanical or electromechanical means for dispensing the drug dosage form.

FIGS. 11C and 11D are a schematic depiction of the dispensing device 100 with the dispensing mechanism at a retrieval position. In the retrieval position, the motor 106 turns the cam 108, retracting the slider 124, and allowing placement of the first dosage 48 in the receiving portion 128. FIG. 11C shows the slider 124 retracted by means of a rotation of the cam 108, and displacement by the spring 118. In this position a dosage form 48 is pushed by the spring 120 into the receiving cup 126 portion of the slider 124.

FIGS. 11E and 11F are a schematic depiction of the dispensing device 100 with the dispensing mechanism at a dispensing position for delivering drug dosage forms. In the dispensing position, the motor 106 turns the cam 108, extending the slider 124 with the first dosage form 48, and allowing dispensing of the first dosage 48. FIG. 11E shows the cam 108 rotated so as to drive the slider 124 forward and dispense a dosage form 48 past the sensor 114 and through the seal 112. The slider 124 continues to move until such a point as the dosage form that has been removed from the stack is free to fall from the cup 126 or is forcibly pushed from the cup 126 by the spring clip 116 and dispensed.

FIGS. 11G and 11H are depictions of the optical sensing mechanism for detecting delivery of drug dosage forms of the dispensing device 100, wherein the position of a slider 124 and a drug dosage form 48 are illustrated. In this embodiment, the slider 124 includes a slot 130 for the delivery sensors 114, so that the delivery sensors 114 will detect the passing and delivery of drug dosage forms 48. When the slider 124 pushes a dosage form 48 past the optical sensors 114, the optical sensors 114 record an interrupted signal, indicating that a dosage form is present in the cup of the slider 124. If a dosage form 48 were not present in the cup of the slider 124 then the optical sensors 114 would not record an interrupted signal, indicating that a dosage form 48 was not present.

FIGS. 12B-E provide a schematic depiction of push rod embodiments for use in a dispensing device of the invention. The pushrod 3051 can be operable to dispense a dosage form 3067. The push rod 3051 may be transparent 3107 (FIG. 12B); the push rod may have a opaque portion 3109 with or without a window 3105 and with or without a reflector 3106 (FIG. 12C); the push rod may have a transparent 3107 tip and an opaque push rod portion 3109 (FIG. 12D); or have a transparent push rod portion 3107 and an opaque tip portion 3109 (FIG. 12E). These approaches provide for various schemes for optical tablet and push rod position detection.

In yet another embodiment of the invention, a long tape or array of dosage forms sealed between a flexible blister layer and a foil or otherwise breakable layer is provided. A pusher is positioned above a dosage form, and upon actuation pushes against the blister, forcing the dosage form through the foil or breakable layer, dispensing the dosage form.

FIGS. 13A, 13B and 13C depict an additional embodiment of the dispensing devices of the invention, wherein a ribbon type dispensing mechanism 134 is illustrated. FIG. 13A depicts the dispensing mechanism at the rest position, FIG. 13B depicts the dispensing mechanism at retrieval position, and 9C depicts the dispensing mechanism at dispensing position. The mechanism includes a long tape or array of dosage forms adhered to one face with an adhesive. To dispense a dosage form 48, the tape 136 is rolled rollers 140 such that the surface with the dosage forms 48 adhered to it forms a convex shape, causing the dosage forms 48 to peel off of the adhesive. In the embodiment shown, a peeler blade 142 may be incorporated to assist in removing the dosage form 48 from the adhesive.

FIG. 14 depicts an additional embodiment of the dispensing mechanism 134, wherein a different shape of a peeler blade 150 is shown. In another embodiment, gas pressure may be used to assist in removing the dosage form 48 or force a single dosage form 48 from the dispensing mechanism 134. To dispense a dosage form 48 the tape 136 is rolled on a roller 140 such that the surface with the dosage forms adhered to it forms a convex shape, causing the dosage forms 48 to peel off of the adhesive. A peeler blade may be incorporated to assist in removing the dosage form from the adhesive tape 136. A peeler blade 150 may be incorporated to assist in removing the dosage form 48 from the adhesive.

FIGS. 15A and 15B depict yet another embodiment of the dispensing devices of the invention, wherein a disc type dispensing mechanism 152 utilizing a disk cartridge 146 is shown at a rest position (FIG. 15A) and at a dispensing position (FIG. 15B). The dispensing mechanism 152 includes a lever handle 150 with teeth that engage a gear 151, a rack/pusher 153, and a channel 154 in a housing, and a spring 156. The channel 154 provides space for the rack/pusher 153 to freely move within the channel 154. In FIG. 15A, the rack/pusher 153 is ready to push a dosage form 48. As the lever handle 150 is pushed, the spring 156 is compressed and the gear 151 rotates and the rack/pusher 153 engages the drug dosage form 48. The drug dosage form 48 is pushed within the channel 154. FIG. 15B shows the dosage form 48 being dispensed from the end of the channel 154 and into a subject, such as human. Then the steps are repeated for successive dispensing of the dosage form 48.

The dispensing mechanism 152 consists of the following: a dispensing trigger 150, a return spring 156, a gearing reduction 151, a pusher 153, a disk cartridge 146, a circular cam/ratchet 145, a dosage form 48, a housing 144, and a seal 143. When the trigger 150 is depressed, driving the gearing reduction 151, the pusher 153 is driven through a disk cartridge 146 in such a manner that the pusher 153 drives a single dosage 48 from the disk cartridge 146. The disk cartridge 146 is fabricated with individual dosage compartments arrayed around the perimeter of the disk, and sealed with foil on both faces so as to individually seal and package the dosage forms 48. As the pusher 153 is driven through the disk cartridge 146, it breaks the foil seals on each face, pushing the dosage form 48 out of the disk cartridge 146, through a seal 143, and delivering it from the dispenser housing 144.

FIG. 15B depicts an additional means of dispensing drug dosage forms, wherein a disc type dispensing mechanism in a dispensing position 154 is illustrated. This figure depicts the pusher 153 in a dispense position after it has pushed a dosage form 48 out of the disk cartridge 146 and through the seal 143. After the dosage form is delivered from the housing 144, the return spring 156 returns the mechanism and a circular cam/ratchet 145 indexes the disk cartridge 146 by rotating it so that the next dosage form 48 is in position for the next delivery.

A disk delivery and indexing mechanism may be employed to deliver a drug dosage form from a dispenser of the invention. A disk delivery mechanism may be manually or electro-mechanically actuated, and my use lead screws, gears, mechanisms, linkages, rotary drives or any other means of advancing that enables the delivery mechanism to deliver a dosage form. The indexing ratchet may be achieved by means of a circular cam, an escapement, a lead screw, a gear train, a linkage, a stepper motor or other motor drive or any other means of indexing a disk.

A dispensing device may be pre-filled with a number of drug dosage forms in such a manner that the device is purchased and stored with the dosages in the device, or it may be filled on site at a pharmacy, or it may be filled on the hospital floor by a nurse or other healthcare professional. The dosage forms may be packaged as a group of tablets in a bottle, vial, or other container, or they may be packaged in a controlled orientation in a drug cartridge. The drug cartridge may contain the doses in any configuration, including a stack, a row, a circular disk, a circular-arc disk, a strip, ribbon, tape, helix, or an array or combination of any of the above, for example a multitude of stacks of doses arranged in a geometric array. The invention further provides additional methods of dispensing drug dosage forms which may include combinations of these or other mechanisms. For example, a system may contain a shuttle to remove a dosage form from a stack, and a pusher to forcibly push the dosage form out of the system.

FIGS. 16A-16C depict an exemplary pushrod 158 designed for dispensing a drug dosage form 48. The pushrod may be made from any suitable material, for example, stainless steel.

FIGS. 17 and 18 depict other exemplary dispensing mechanisms with pushrods for dispensing drug dosage forms, wherein the pushrods are designed to be flexible. FIG. 17 shows dispensing mechanism 174 for singulating and advancing a drug dosage form 48 through a nonlinear or linear pathway by means of a flexible shaft 176 attached to an advancing mechanism, such as a rotation hub, such that advancing or retracting the flexible shaft within the nonlinear or linear pathway allows for the dispensing of a tablet or other dosage form 48 through the nonlinear pathway. FIG. 18 shows dispensing mechanism 180 for singulating and advancing a drug dosage form 48 through a nonlinear or linear pathway by means of a flexible shaft 182 attached to an advancing mechanism, such as a rotation hub, such that advancing or retracting the flexible shaft within the nonlinear or linear pathway allows for the dispensing of a tablet or other dosage form 48 through the nonlinear pathway.

In a related approach, the drug delivery device of the invention comprises a tubular cartridge containing the stack, a spring pushing the stack, a solid face, and a slider or pusher, similar to the embodiment described above. In this embodiment, the slider or pusher lacks a hole, but rather retracts from beneath the dosage form stack such that the spring can push the dosage forms up against the solid face. During actuation the pusher, which has a thickness equal to, larger than, or less than that of a single dosage form, pushes the first dosage form in the stack perpendicular to the cartridge and dispenses it out of the side slot.

In another embodiment of the invention, dosage forms are dispensed by moving a dosage form stack which is mounted with a pusher at one end and an elastomeric diaphragm retaining the opposite end of the dosage form stack. The diaphragm contains an orifice or hole or slot at the location of the first dosage form. Upon actuation, the pusher pushes the stack and a single dosage form emerges from the diaphragm hole, at which point the pusher retracts slightly to allow the elastomeric diaphragm to re-seal and close again. The elastomeric diaphragm may be a seal or wiper type seal.

FIGS. 19A-19D provide schematic depictions of exemplary drug cartridges including barrel type cartridge 224, index/springload type cartridge 230, snap-out type cartridge 244, and track type cartridge 250. FIG. 19A depicts a barrel type cartridge 224 which dispenses drug dosage forms 48 stacked in each barrel 228 and rotates upon each actuation. FIG. 19B depicts an index/springload type cartridge 230. When a pusher 234 is pressed upon a rack 232, a spring 240 is used to minimize compression exerted on the drug dosage forms 48 stacked in the cartridge 242 and a pushrod 238 pushes the dosage forms 48 to dispense. FIG. 19C depicts a snap-out type cartridge 244. In the cartridge 244, a stick holding drug dosage forms 48 is moved toward a pushrod 248 and the pushrod 248 pushes the drug dosage form 48 and snaps on the stick when dispensing is completed. FIG. 19D depicts a track type cartridge 250. Drug dosage forms 48 stacked in the track are dispensed.

Calibration

The dispensing device may be capable of self-calibration of the dispense mechanism, or the device may be calibrated manually. This process may employ a shipping tablet with a feature or features that physically differentiate it from a drug dosage form or the push rod. These features may be designed so that device calibration precision is higher that that attainable using a dosage form or push rod. The differentiating feature may be physical, optical, radio frequency (RF), electronic or magnetic.

FIG. 20 is a schematic depiction of an exemplary dispensing device showing the stages of push rod/dosage form interaction during device use. In FIG. 20, the push rod 5051, dosage forms 5067, shipping tablet 5069, spring 5073 and position sensor 5071 are shown. During use, the push rod 5051 moves between positions 5057, 5059, 5061, 5063 and 5065, also shown in FIG. 20 and further detailed in FIGS. 21A-D.

FIGS. 21A-D provide a series of flow diagrams for use of an exemplary device of the invention showing pusher logic, wherein FIG. 21A shows the LOAD feature; FIG. 21B shows the device calibration logic flow. Referring to FIG. 20, the pushrod 5051 is advanced from position 5065, picks up the shipping tablet 5069 at position 63, and is further advanced to position 5061. At position 5061, the device senses the presence of the shipping tablet 5069 and/or push rod 5051. In doing so, the device is calibrated and knows the location of the shipping tablet 5069 and/or end of the push rod 51 regardless of assembly tolerances, variations in push rod length and push rod end conditions. Following this calibration, the push rod 5051 advances the shipping tablet 5069 from position 5061 to position 5057 where the shipping tablet 5069 is dispensed from the device. During this operation, the device is able to distinguish between a shipping tablet 5069, a push rod 5051, and a drug tablet 5067. This differentiation enables the device to confirm that a cartridge is unused because a shipping tablets is the first thing dispensed from a new cartridge during device setup. The feature that provides the means for differentiating between the shipping tablet, push rod, and tablet 5067 may be optical, physical, RF, electronic (resistive, capacitive, or other) or magnetic. In addition, this feature may be designed to provide a means for greater device calibration precision than that attainable using a tablet or push rod. The push rod 5051 advance from position 5065 and position 5057 described above, could be continuous or intermittent and a physical stop at position 5061 is not required. The push rod 5051 then retracts from position 5057 to position 5059, placing the device 11 in the ready position with the push rod 5051 under the remaining dosage forms 5067. In this position, the push rod 5051 keeps dosage forms 5067 from inadvertently falling out of the device.

FIG. 21C shows the device dispense logic flow. Referencing FIG. 20, following a dose command, the push rod 5051 retracts from position 5059 to position 65, allowing the dosage forms 5067 to advance into the push rod track. The push rod 5051 then advances from position 65, picks up a dosage form at position 5063, and then dispenses the dosage forms 5067 from the device at position 5057. Between positions 5063 and 5057, the presence of a dosage form 5067 is sensed/confirmed at position 5061 by the position sensor. The push rod then retracts from position 5057 to position 5059, placing it in the ready position with the push rod 5051 is under the remaining dosage forms 5067. In this position, the push rod 5051 is allowed to dry before the next dosage form 5067 dispense, as well as keeps dosage forms 5067 from inadvertently falling out of the device.

FIG. 21D shows the device disassemble logic flow. Following a "disassemble" command, the push rod 5051 is moved to position 5065. This allows for the removal of any remaining dosage forms 5067 without push rod interference.

Dosage Forms Delivered with the Dispensing Device of the Invention

Oral transmucosal drug delivery is effective, easy to deliver, non-invasive, and can be administered by the caregiver or the patient with minimal discomfort. Generally, oral transmucosal delivery of pharmaceuticals is achieved using solid dosage forms such as lozenges or dosage forms, however, liquids, sprays, gels, powders, gums, foams, patches, and films may also be used. A drug dispensing device of the present invention provides a means to deliver a small-volume drug dosage form that is adapted for delivery of the drug via the oral mucosa.

In one embodiment, a drug dispensing device of the invention provides a means to deliver dosage forms for oral transmucosal delivery of pharmaceutically active substances. The dosage forms may be solid or non-solid and may serve as a delivery vehicle for any medication, e.g., a pain-relieving drug such as an opioid or an opioid agonists, or drugs for treating angina, anxiety, insomnia, ADHD, addiction, nausea, and so on. Solid dosage forms, such as sublingual dosage forms, troches, lozenges, powders, and films that can be used to deliver drugs via the oral mucosal tissue are considered to be within the scope of the invention.

The invention also encompasses drug dispensing devices for delivery of other non-solid dosage forms such as gels, salves, pastes, mists, liquids, aerosols, gases, vapors, foams, emulsions, sprays, suspensions and the like.

In one embodiment, a drug dispensing device of the invention provides a means to deliver small-volume drug delivery dosage forms, exemplified herein for the treatment of pain. In this embodiment, the dosage form is designed to remain in the sublingual area, adhering to the oral mucosa, and is small enough to elicit little or no saliva response from the patient. Although the dosage form is intended to remain in the sublingual space, it will be effective when absorbed through any oral transmucosal route.

In one embodiment, a drug dispensing device of the invention is used for administration of a small-volume drug delivery dosage form for oral transmucosal delivery of drugs, wherein the dosage form is prepackaged and is self-administered. The invention also encompasses use of the device to deliver a small-volume drug delivery dosage form for oral transmucosal delivery of drugs that are not prepackaged.

A means for minimizing saliva influx into a dispensing device for oral transmucosal administration of a drug dosage form comprises seals, wipers, absorbants, air gaps, desiccants, and multiple stage delivery systems. The dispensing device dispenses the drug dosage form one at a time without adversely affecting other drug dosage forms contained in a cartridge filled with the drug dosage form.

In one preferred embodiment, a drug dispensing device of the invention provides a means to deliver a drug dosage form that is generally very small, e.g., a NanoTab®. The NanoTabs® may be used to deliver any drug that may be administered by the oral transmucosal route in an amount amenable to administration via the small size of the NanoTabs®, i.e. about 0.1 mg to about 99.9 mg. In one preferred embodiment, the NanoTab® is adhered sublingually.

The dosage form will typically comprise 0.01%-99% w/w of the active ingredient(s) percent by weight of the active ingredient or "drug". The term "drug" as used herein means any "drug", "active agent", "active", "medication" or "therapeutically active agent". In some embodiments, the dosage form is a NanoTab®, which may be used to deliver any drug that may be administered by the oral transmucosal route in an amount amenable to administration via the small size of the dosage form, e.g., up to 99.9 mg of drug, for example, 0.25 μg to 99.9 mg, 1 μg to 50 mg or 1 μg to 10 mg of drug.

The shape of a drug dosage form for use in practicing the invention is preferably approximately disc-shaped, but may be rectangular, square, polygonal, oval or spherical, any combination of these, or may be non-symmetric. When disc-shaped, the flattened surface provides an increased surface area for adhesion and drug elution. The drug dosage form may be formed in any geometry that may be delivered using a drug dispensing device of the invention. Optimally the drug dosage forms are formed as round discs with flat, concave, or convex faces. Alternately, they may be ellipsoids with flat, concave, or convex faces, or polygons with 3 or more edges and flat, concave, or convex faces. The drug dosage forms may also be spherical, ellipsoidal, or have the shape of any other curved solid body. The drug dosage forms may also be any non-symmetrical shape and may enable specific handling and orientation in the dispenser device and during placement.

FIGS. 22A and 22B provide depictions of exemplary drug shapes. FIG. 22A is a schematic depiction of symmetric drug dosage forms 368 including round discs with flat, concave, or convex faces, ellipsoids with flat, concave, or convex faces, spherical, polygons with 3 or more edges and flat, concave, or convex faces, or any other curved solid body. FIG. 22B is a schematic depiction of other drug shapes 370 in asymmetric dosage forms.

In one exemplary formulation, the dosage form is approximately disc-shaped, the volume of the drug dosage form is about 5 microliters, and the dimensions of the drug dosage form are approximately 0.85 mm in thickness, and 3.0 mm in diameter.

A drug dispensing device of the invention will provide a number of dosage forms that will vary according the nature and amount of active ingredients while maintaining the size and features appropriate for efficacious delivery.

A device of the invention can be loaded with many days worth of medication (e.g., 30 days or more) at one time, and may require no special packaging for the medication. Alternatively, the medication may be provided in the form of a pre-filled cartridge.

The present invention provides the advantage that the drug is delivered via a dispensing device which provides for the dispensing of multiple dosages of a small-volume oral transmucosal drug delivery dosage form such that the appropriate dose and frequency for therapeutic efficacy may be obtained, while simultaneously providing a timed lock-out feature to prevent accidental overdosing. The dose and corresponding lock-out time may be adjusted dependent upon the size of the subject and the intended therapeutic goal.

As set forth above, a drug dispensing device of the invention comprises a means for minimizing saliva influx into the device when used for oral administration. In this embodiment, the dispensing device dispenses the drug dosage form one at a time without adversely affecting other drug dosage forms contained in a cartridge filled with additional drug dosage forms. A means for trapping or otherwise isolating saliva or moisture once it has entered the device may include but is not limited to a hydrophilic wicking material or component, an absorbent or adsorbent material or component, or a desiccant material or component, or any combination of these materials or components.

The drug dosage form dispenser of the invention may dispense drug dosage forms or it may dispense drug dosage forms attached to or contained within a disposable applicator with means of allowing manual application of said dosage form to a pre-determined location for drug delivery (e.g. the mouth, sublingual space, the eye, etc.). In one embodiment, a single dose applicator may be used for a variety of drug dosage forms, including a solid tablet, a liquid capsule, a gel capsule, a liquid, a gel, a powder, a film, a strip, a ribbon, a spray, a mist, a patch, or any other suitable drug dosage form. The single dose applicator (SDA) may contain the dosage form within, may have the drug dosage form attached or affixed to it, may afford a seal against moisture, humidity, and light, and may be manually manipulated by a patient, healthcare provider, or other user to place said dosage form in the proper location for drug delivery. The SDA may be of the form of a pair of forceps, a syringe, a stick or rod, a straw, a dropper, a sprayer or atomizer, or any other form suitable for the application of a single drug dosage form. After use, said SDA may be disposed of, so as to eliminate the risk of contaminating the dispenser with saliva, or other contaminants.

Figure 23A:
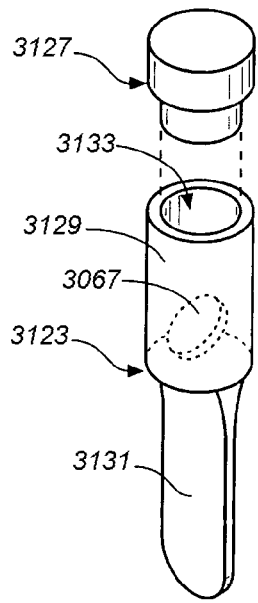
Figure 23B:
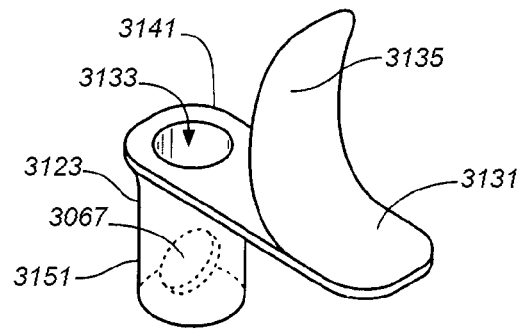
Figure 23C:
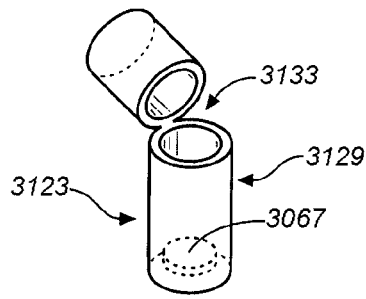
Figure 23D:
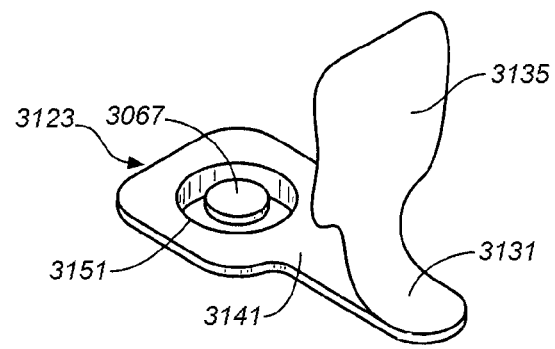

The present invention provides disposable single dose applicators comprising a blister pack 3151, which contains drug dosage forms 3067 inside a housing and a handle 3131, wherein a backing, such as a foil seal 3135 covers the dosage form 3067 and the handle 3131, as shown for example in FIGS. 23B and 23D.

FIG. 23A shows an embodiment of a single dose applicator 3123 that is comprised of a applicator shaped as a tube 3129, a stopper seal 3127, a handle 3131 (e.g., an ergonomic handle), and a single dosage form 3067. The tube 3129 defines an opening 3133; the stopper seal 3127 can be removeably coupled to the tube 3129 obstructing the opening 3133.

In one embodiment, the disposable single dose applicator, the combination of housing or tube 3129 and handle 3131 has the shape of a spoon.

The housing or tube 3129 for the dosage form 3067 is a blister pack 3151 that accommodates a unit dose of a dosage form 3067 for administration to a subject. The dosage form 3067 is sealed in the blister pack 3151 by a foil or other type of seal 3135 backing.

In some embodiments, the foil or other type of seal 3135 is removed prior to administration of the dosage form 3067 and the handle 3131 is used to place the dosage form 3067 in the appropriate location against the oral mucosa of the subject such that the dosage form 3067 adheres to the oral mucosa. See, e.g., FIGS. 23B, 23D, 23E and 23F. In other embodiments, the foil or other type of seal 3135 is perforated and removed prior to administration of the dosage form 3067 by folding the applicator 3123 at the perforation 3149 prior to administration where the handle 3131 is used to place the dosage form 3067 in the appropriate location against the oral mucosa of a subject. See, e.g., FIGS. 26A and B. This permits the handling of only a single drug dosage form 3067 at a time and prevents the other individually sealed drug dosage forms 3067 from becoming exposed to saliva, humidity and the like.

The foil or other type of seal 3135 of a disposable applicator 3123 including handle 3131 is typically made of a single piece of foil laminate, paper, plastic or other covering, i.e. an applicator tab 3147 that spans the back of the housing or tube 3129 alone or both the housing or tube 3129 and the handle 3131, effectively seals the dosage form 3067 in a blister pack 3151 or other container.

The handle 3131 enables proper placement of the dosage form 3067 without touching the dosage form 3067.

A plurality of single dose applicators may be provided as a series of individual single dose applicators attached by the backing or housed in multiple dose dispenser 3137.

In another embodiment, a dispensing device 3011 comprises a package 3141 that holds a single or multiple drug dosage forms, a distal orifice for delivery of the drug dosage form, and an internal mechanism that segregates and releases the dosage forms. See, e.g., FIG. 24. The dispensing device is typically handheld and may comprise some or all of the features set forth above for a device used to dispense non-packaged dosage forms.

FIGS. 27A-B are schematic depictions of exemplary single dose applicators 3123 for delivering dispensing drug dosage forms 3067, wherein exemplary single dose applicators are shown. When the applicator 3123 is positioned for delivery and is squeezed 3125, as shown in FIG. 27B, a flexible hinged section deforms, allowing the dosage from 3067 to be released on an oral mucosal membrane, e.g., into the sublingual space. After applying the dosage form 3067, the drug dispensing device may be disposed.

FIGS. 27A and 27B show one embodiment of a single dose applicator 3123 a dispensing device for delivering drug dosage forms. The dispensing device shown in FIG. 27A depicts the single dose applicator 3123 that is ready to dispense a drug dosage form 3067. In one aspect of this embodiment, a user pinches the single dose applicator 3125 which opens the applicator and a drug dosage form 3067 is dispensed as shown in FIG. 27B.

FIGS. 23A-F, FIGS. 25A-C, FIGS. 26A, and B FIGS. 28A-C are schematic depictions of exemplary embodiments of a SDA of the invention.

Figure 23E:
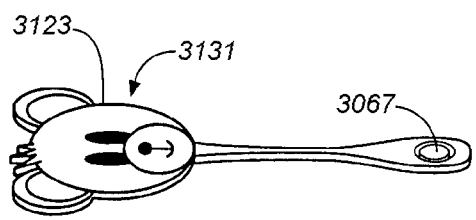
Figure 23F:
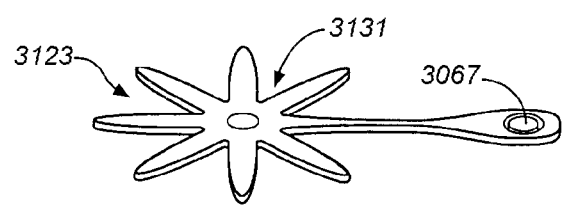

FIGS. 23A-F show several alternate embodiments of the single dose applicator 3123. In all of these figures the applicator seal 3127 is broken and the applicator is tilted so as to drop the drug dosage form 3067 on an oral mucosal membrane in the mouth of a subject, e.g., under the tongue for sublingual dosage form placement. FIG. 23A shows a tube like applicator 3129 with a handle 3131 located axially under the tube 3129. FIG. 23B shows an applicator formed as a thermoform or blister package 3151 with a foil seal 3135 that is peeled so as to open the applicator package 3141 prior to placing the dosage form 3067. FIG. 23C shows an applicator that is a tube 3129 which is broken to break the seal prior to dosage form 3067 placement. FIG. 26D shows a blister pack tube 3151 type dosage form package 3141 with a handle 3131 such that after the seal 3135 is peeled back the blister pack 3151 can be held and tilted to place the drug dosage form 3067, on an oral mucosal membrane. FIGS. 23E and 23F show blister pack 3151 type packaging with a handle 3131 shaped like a flower or an animal, respectively, to be used for single dose applicator 3123 designed for pediatric use. Other single dose applicator shapes could include cartoon characters, animals, superheroes or other appropriate shapes for pediatric applications.

FIG. 25A shows a flat rigid applicator 3123 with a dosage form 3067 adhered to one end, for example, by means of a rapidly dissolving ingestible adhesive material 3139 such that when the applicator end with the dosage form is placed under the tongue, the adhesive dissolves, the dosage form 3067 is placed on an oral mucosal membrane, such as in the sublingual space, and the applicator can be removed. FIG. 25B shows an applicator 3123 made from a water permeable material, impregnated with drug, forming a material and dosage form matrix. When the impregnated end of this applicator is placed under in the mouth on the oral mucosa, the moisture in the saliva dissolves the drug and delivers it transmucosally. FIG. 25C shows a dissolving film dosage form 3145 and a dosage form package with a plurality of dissolving film dosage forms 3143 within it. The dissolving film dosage form 3143 is removed from the package 3141 and placed on an oral mucosal membrane, e.g., in the sublingual space where it dissolves and delivers the drug transmucosally.

FIGS. 26A-B provide illustrations of two stages of use of one embodiment of a single dose applicator 3123. FIG. 26A shows the applicator 3123 in its configuration prior to use, with the following features: applicator tab 3147, perforation 3149, and blister pack 3151 containing a dosage form 3067. In order to administer the dosage form 3067, the applicator tabs 3147 are bent downward at the perforations 3149, and the seal 3135 is peeled back to reveal the blister pack 3151 and allow the dosage form 3067 to be dropped on an oral mucosal membrane, e.g., in the sublingual space.

FIGS. 28A-C show an embodiment of a single dose applicator 3123 that is comprised of a applicator shaped as a tube 3129, a stopper seal 3127, a handle 3131 (e.g., an ergonomic handle), and a single dosage form 3067. FIG.

28A shows the single dose applicator 3123 in its sealed configuration, prior to use. FIG. 28B shows the single dose applicator 3123 with its stopper seal 3127 removed, forming an opening 3133, and ready for use. FIG. 28C shows the single dose applicator 3123 tilted so as to dispense the dosage form 3067 on the oral mucosa, e.g., in the sublingual space.

The invention provides exemplary dispensing devices with a singulator dispensing mechanism including a reusable single dose applicator. The singulator dispensing mechanisms may include the following; a reusable single dose applicator; a foil blister; rotating stations; a disk with ejectors; a ribbon peeler; a ribbon picker; disk singulators; a flexible disk; an arc or helical type single dose applicator; a pushrod stack ejector; and a rotating stack ejector.

In another embodiment, a drug dispensing device of the invention may contain a plurality of SDA's, in a cartridge or individually packaged, and may dispense a single SDA containing a single drug dosage form for use by the patient, healthcare provider, or user. The drug dispensing device may dispense single SDA's in the same way and with the same features as would be advantageous for the dispensing of single drug dosage forms described in the invention.

In yet another embodiment the multiple dose applicator 137 comprises one or more drug dosage forms 67 or single dose applicators 123, a portable power means, like a battery, a printed circuit board, a data connectivity means, and a user interface. In this embodiment the drug dispensing device may include the ability to perform one or more of the following functions: record drug dosage dispensing history, check user identification by means of fingerprint identification, RFID, voice recognition, etc., allow the dosage history to be transferred to another device, computer or network, and/or provide a lockout period between dose dispenses.

FIG. 24 is a schematic depiction of an exemplary multiple dose applicator 3137 for delivering dispensing drug dosage forms 67, each individually packaged in a single dose applicator 3123.

Dosing History/Feedback

Further embodiments of the device include the ability to store historical use information and the ability to transmit such information. The device may be capable of unidirectional (downloading) or bidirectional information transfer. For example, an exchange of information may be accomplished by downloading stored information to a computer through a physically wired interface, such as a USB or any other communication connection. Alternatively, information may be communicated via a wireless system.

In another embodiment, the dispensing device has a dose counting feature that monitors and stores the history of drug usage. Such information may include historical use information, for example the number of dosages stored and dispensed, and the times of dispensing.

Lock Out

The dispensing device provides for lock out, requiring the patient to communicate with the physician or other authorized care giver to unlock the device for the next fixed period. In this way the device and dock provide for safe drug administration due to greater physician oversight and care management.

The dispensing device provides a means for adjusting both the initial dose and subsequent doses, as well as the lock-out time. The initial dose and lock out time may subsequently be adjusted dependent upon patient response, duration of treatment and the like.

The initial timed lock-out period for a claimed dispensing device is typically from about 1 minute to about 60 minutes, from 3 minutes to 40 minutes or from 5 minutes to 30 minutes, and in particular cases is set at any one minute interval from 1 to 60 minutes, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

In some cases, a dispensing device has a fixed lockout between doses and may exhibit a shutdown after a fixed period of time. In other cases, the lock-out time is a programmable lock-out time. The lock-out time may also be a fixed time lock-out interval, a predetermined lock-out interval, a predetermined variable lock-out interval, a lock-out interval determined by an algorithm or a variable lock-out interval communicated to the device from a remote computer or docking station.

The dispensing device may include a lockout feature that prevents dosing the drug in an unsafe or non-prescribed manner. This lockout feature may mechanically prevent the device from dispensing a dose by either locking the mechanism, disengaging a component of the mechanism, or by controlling the dispensing mechanism by means of a microprocessor and an algorithm during the lockout period. The lockout may be of a fixed period (10 minutes, for example), of a predetermined variable period, a "smart" variable period, or a "triggered" lockout based on an internal or external event or state. The fixed lockout would afford a fixed lockout period after each dose, wherein the device will not allow a subsequent dose to be delivered. The predetermined variable lockout would afford a variable lockout period after dosing, following a pre-determined lockout schedule (for example, the lockout period may increase by one minute following each subsequent dose). The "smart" lockout would afford a variable lockout period based on an internal algorithm taking into account the dosing history, dosing requests, or any other data or inputs that the algorithm may use for determination. For example, the smart lockout may base the lockout period on the dosing history, taking into account the pharmacokinetics of the specific drug molecule, and how the body naturally clears or metabolizes the drug over time. The triggered lockout would respond to internal or external triggers, such as data from sensors (e.g. temperature, humidity, heart rate, respiratory rate, blood pressure), internal signals (date, time, or location from GPS), signals from external computers, networks, or other electronic devices, the presence of a physical, magnetic or electronic key, the receipt of a mechanical or electronic access signal such as a password, code, RFID signal, or any other wired or wireless signal. The dispensing device of the invention may employ one or more of the lockout described herein.

In one exemplary embodiment, the dispensing device has a smart lockout preventing dosing of a tablet for a period of time following an initial dose, based on the dosing history and an internal algorithm. In this embodiment the lockout time is calculated to predict the safe dosing interval knowing the history of drug doses the patient has already taken and the pharmacokinetics of the drug.

In another exemplary embodiment, the dispensing device is programmed to allow dosing for the 72 hour recovery period following a minor outpatient orthopedic surgery procedure. When the device is first prescribed to the patient, the internal clock in the device begins to track the elapsed time. When the elapsed time reaches 72 hours the device locks down, notifying the patient that the dispensing device has expired and will no longer allow dosed to be delivered.

In another exemplary embodiment, the dispensing device is programmed to allow dosing for the 72 hour recovery period following a minor outpatient orthopedic surgery procedure. When the device is first prescribed to the patient, the internal clock in the device begins to track the elapsed time. When the elapsed time reaches 72 hours the device locks down, notifying the patient that the dispensing device has expired and will no longer allow dosed to be delivered.

The present invention may also provide a means for adjusting both the initial dose and subsequent doses, as well as the lock-out time. Patients can be evaluated to determine the appropriate dosing schedule and lock-out time following an evaluation of drug plasma concentration.

The dispensing device allows for a variable, pre-determined lockout schedule that may vary with length of the prescription, time of day, progression of ailment or symptoms, etc. and may utilize an algorithm to determine the lockout schedule and duration, based on prescription, medication, dosing history, and other patient specific information such as vital signs (e.g., respiratory rate or blood pressure determined by a non-invasive means), taken together with pharmacokinetics of the active drug agent.

If the patient does not achieve sufficient therapeutic benefit from a single administration, the advantage of the repetitive dosing feature with lock-out is that the patient can re-dose, thereby titrating their plasma levels of drug in a safe manner. This can be repeated until a therapeutic plasma level is achieved.

An initial dose and lock out time for a dispensing device of the invention is set upon initiation of treatment depending upon the age and weight of the patient and medical history. However, the initial dose and lock out time may subsequently be adjusted dependent upon patient response, duration of treatment and the like.

The present invention provides a dispensing device with a programmable lock-out feature for locking the dispensing device when the device is locked. This prevents or deters abuse or accidental or inadvertent misuse. The lock-out feature operates by a means selected from the group consisting of a movable pushrod, a non-returning pushrod, an electromechanical regulator, an optical sensor pair, a magnetic clutch, a lockout on actuator, a rack and pinion, a safety button latch, a solenoid, a collect on shaft, a keyed hubs, lead screw, rotary actuator or mechanism, a movable coupling, and cams.

The present invention provides a dispensing device with an access control means for controlling abuse or accidental or inadvertent misuse other than by a healthcare professional. The dispensing device will not function if the cartridge is not loaded, locked-in, and activated by the healthcare professional.

The dispensing device of the invention may be used multiple times or be disposable such that it is discarded when all of the medication initially loaded into the device has been dispensed.

Figure 29A:
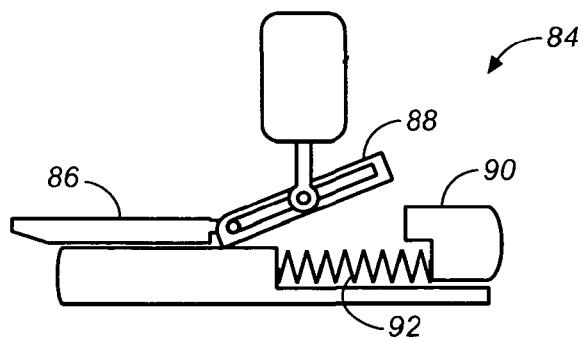
Figure 29B:
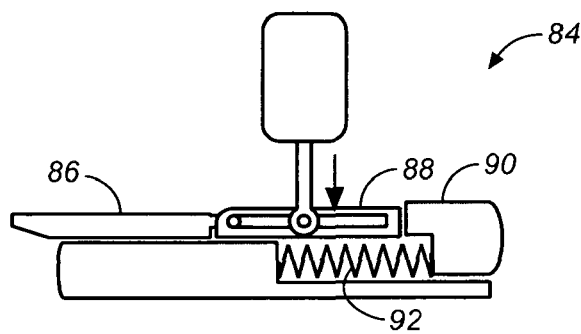
Figure 29C:
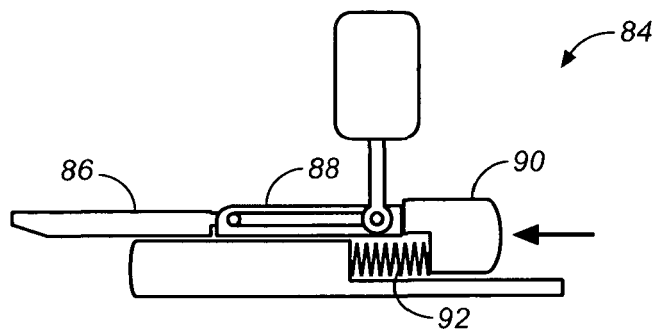
Figure 29D:
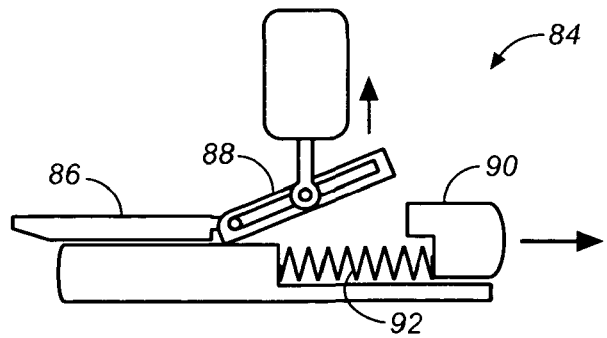

FIGS. 29A-29D are schematic depictions of one embodiment of a drug dispensing mechanism 84 which includes a lockout feature. The drug dispensing mechanism 84 includes a pushrod 86, a lock 88, a button/pusher 90, and a wedge 92. In use, the button/pusher 90 pushes the lock 88 into the pushrod 86. When the lock 88 is raised, the button/pusher 90 is unable to push it and the mechanism is locked. FIGS. 29A through 29D illustrate various stages of a lockout mechanism related to dispensing drug dosage forms. FIG. 29A depicts a situation where a predetermined lockout period has not passed and the dispensing mechanism 84 is still in locked position, with the lock 88 raised. In FIG. 29B, a predetermined lockout period has passed and the lock 88 is in the lowered position and the lockout mechanism allows the dispensing mechanism in dispensing position. FIG. 29C depicts a further step where the dispensing mechanism 84 operates with the button/pusher 90 pushing the lock 88 into the pushrod 86 to dispense drug dosage forms (not shown). FIG. 29D depicts a locked position for a predetermined lookout period for a next dispensing. The locking device may be attached to the drug dispensing device to prevent unauthorized dispensing of the medication. Sensors may be located on the exit port to detect the successful dispensing of a dosage form, which is recorded internally by the dispensing device, or by a wired or wirelessly attached dock or computer. The types of the locking devices may include the following: a movable push rod; a non-returning push rod; an electromechanical regulator; an optical sensor pair; a magnetic clutch; a lockout on actuator; a rack and pinion; a safety button latch; a solenoid; a collet on shaft; a keyed hub; a movable coupling; and a cam.

FIGS. 30A-30F are schematic depictions of exemplary lockout mechanisms. FIG. 30A depicts a pushrod type lockout mechanism 186. When a pushrod 188 is pressed, a solenoid 190 reacts to a signal to move a return lock 192 in a locking position, to prevent a dispensing device from dispensing drug dosage forms 48 during a lockout period. FIG. 30B depicts an actuator type lockout mechanism 196. When a pushrod 200 is pressed in a lockout mechanism 196, a lock 198 moves in response to the pushrod's 200 movement with the help of solenoid 202 to lockout on actuator. FIGS. 30C and 30D depicts a safety button/latch type lockout mechanisms 204 and 214, respectively. In the figures, a latch 206 locks a pushrod 210 in a locked position. A patient pushes the dispenser 212 to reveal button 208 to unlock the latch 206. FIG. 30E depicts a solenoid type I lockout mechanism 216, wherein solenoid 217 moves to lock the device. Another solenoid type lockout mechanism 218 is shown in FIG. 30F. Solenoid 220 moves upon a button 222 being pressed and locks the device.

Patient Identification Feature

In one aspect, the dispensing device comprises a detecting means for patient identification such as a fingerprint reader, an optical retinal reader, a voice recognition system, a face recognition system, a dental imprint recognition system, a visual recognition system, or a DNA reader. The dispensing device may employ one or more means to identify the user, enabling the system to determine if a dispensing request is being made in an authorized or unauthorized manner. It is important for effective delivery of many potential drugs and drug dosage forms to ensure that the dispensing device is not accidentally or intentionally used by an unauthorized individual to prevent accidental or intentional diversion of the drug. Such patient identification systems may recognize one or more users, for example, in an inpatient hospital setting the dispensing device could be programmed to recognize the patient to whom it is prescribed, as well as authorized healthcare providers such as nurses and physicians. In an outpatient home setting, for example, the dispensing device may only respond to the patient to whom it is prescribed.

The dispensing device may employ any means of user identification, including fingerprint identification, RFID detection with the use of an active or passive RFID tag on bracelet, necklace, clip, belt, strap, adhesive patch, implant, or means of locating and affixing a tag, retina identification, DNA identification, voice recognition, password or code entry, physical key, electronic or magnetic key, personal area network identification using the human body or clothing as a data or signal conduit, optical scanner or face recognition, sonic, subsonic or ultrasonic identification, or any other means of identifying an individual and verifying their identity.

One method of patient identification is the use of a short distance ("near field") passive RFID tag attached to a bracelet, necklace, adhesive patch, clothing tag, orally mounted device, like an orthodontic retainer, belt, strap, some combination of these, or another location. When an RFID tag is used in the "near field", roughly defined as about 16% of the wavelength of the received signal, the tag behaves in the inductive mode of operation, coupling between the reader and tag antenna magnetically. The near field is characterized by at least two features: first is a rapid decline in field strength with distance, and second is a strong directionality of the signal. In the near field, the signal strength falls off very rapidly, with a signal strength loss of approximately 60 dB per decade in distance. For good inductive coupling between the transmitter antenna and the RFID tag antenna, the two antennas are oriented in parallel planes with the axes through the center of each antenna in close proximity. Strong signal strength (robust patient identification) is provided when the device is very close to the RFID tag. At the same time, a very poor signal is provided when the device is further away from the tag, which helps prevent unauthorized use by someone other than the patient who attempts to use the device. It is preferable to operate in this near field region with good antenna alignment. Furthermore, it is preferable to operate with a very short distance of adequate signal strength for a positive identification, so that it is very difficult to receive a signal if the device is not in the proper orientation and proximity to the RFID tag. To attain a short distance and a proper alignment between antennas, the dispensing device may be designed so as to properly locate the RFID reader antenna, mounted in the dispensing device, adjacent to an RFID tag antenna, mounted, for example, on a wrist band or bracelet, or a clothing tag on the collar, or an adhesive patch on the hand, arm, cheek, neck, or elsewhere. Furthermore, an RFID tag antenna on a wrist band or bracelet may be held in proper alignment and location by means of a small adhesive patch that prevents the bracelet from moving or rotation on the wrist.

In another embodiment, the dispensing device employs a high frequency RFID reader for use in the inpatient (hospital, clinic, etc.) setting, operating on or near the 13.56 MHz frequency band, and the patient is be fitted with a matching RFID tag and antenna on a disposable bracelet or wrist band, designed in such a way that if the bracelet or wrist band is removed the RFID tag, the antenna, or another component of the associated circuit will be damaged or destroyed, rendering the bracelet or wrist band non-functional. In one example, the range of the RFID communication is short, between 0 inches and 10 inches preferably, more preferably between 0 and 5 inches, and most preferably between 0 and 3 inches, and may additionally be directional, allowing proper use by the intended patient to be easy and reliable, while at the same time making unauthorized use by another individual difficult, very difficult, or impossible.

In another embodiment, a dispensing device of the invention for use in the outpatient setting (e.g. home, office, etc.) includes an electronic fingerprint sensor system and would be trained to identify the patient's fingerprint at the time of prescription or first use.

Additional Features

A dispensing device may provide the ability to recognize a specific cartridge by a mechanical, optical (e.g. bar code), electronic (e.g. microchip), magnetic, radio frequency, chemical, or other means of detecting and identifying the cartridge. In one exemplary embodiment, the drug-containing cartridge contains a physical keying detail on the cartridge that is physically detected by a sensor or switch or a series of sensors or switches in the dispensing device. Furthermore, the dispensing device may communicate unidirectionally or bi-directionally with the cartridge to exchange information. Such information may include drug name, dosage strength, usage information, lockout period, manufacturing lot number, indications for use, side effects, drug interactions, date of manufacture, date of expiration, serial number, number of doses in the cartridge, or any other relevant information. The dispensing device may be able to write, in addition to read, information to the cartridge, like date used, nurse or patient identification, number of doses used, etc.

The dispensing device may provide mechanical protection for the dosage forms contained therein, preventing breakage, chipping, hydration etc., thereby allowing for dispensing of the undamaged dosage forms contained therein. This is of particular importance for small fragile and friable dosage forms.

The drug dispensing device may be powered by a battery, capacitor, fuel cell, or other power supply source, or may require no electrical power, but be manually activated.

In one embodiment, the dispensing device of the invention includes a means to produce an audible, visual, or tactile signal when the drug is administered (such as a click, beep or visual indication such as a light) to provide feedback to the patient that a dosage has been dispensed. In the example of a small sized dosage from such as a NanoTab® dosed sublingually, the patient may not be aware of the drug in their sublingual cavity, therefore another means of feedback may be necessary. The present invention provides a solution to meet this need.

A dispensing device of the invention may be manufactured in an array of colors that correlate to the array of unit doses to allow for easy identification of drug dose. The device may have other visual, audible, or tactile identifiers to communicate the dosage contained therein.

The dispensing device of the invention finds utility in the dispensing of one or more medications, and in some embodiments provides a plurality of dispensing devices which comprise more than one drug, drug dosage, drug form, etc. In a similar fashion the dispensing device may contain a plurality of dosage forms, in a plurality of cartridges, dispensed by means of multiple mechanisms and delivery channels, etc.

The dispensing device of the invention includes an architecture that allows refilling of the drug dosage form by an approved or authorized user (such as a doctor, nurse, pharmacist or other medical personnel), while denying access to unapproved individuals.

In other embodiments, the dispensing device of the invention includes a disposable tip that contacts the patient's body or mouth, so that the device may be used with multiple patients without the risk of cross contamination.

In some embodiments, the dispensing device is capable of issuing alarms or other notifications when functional or safety issues arise. The alarm or other notification may trigger an alert on the dispensing device, on a dock or other peripheral device; on a computer or by means of a wired or wireless network, or may alert other remote devices. The alarm or notification may be audible, tactile, visual, or may employ other means of notifying one or more individuals.

Docking Station

In certain embodiments, the device includes a portable or fixed docking station that may query the device, reset it between dosing, lock it when not properly accessed, and control the dosing regimen. The drug dispensing device may communicate with a physician or care giver, via the dock; or by a wired or wireless communication means.

In yet another embodiment, the dispensing device is adapted to have the ability to track and communicate the total number of doses remaining in the device to allow anticipation and scheduling of refilling. The dispensing device also may include the ability to record and track drug usage and communicate this, optionally via wireless protocols or by electronic docking, to a healthcare provider to monitor the patient's drug use.

In some embodiments, the dispensing device may be remotely programmed to allow physician oversight and care management. It may include a radio frequency identification (RFID) system, WiFi communication, or other remote operation system that provides a means of communication and control of the device to allow remote monitoring of error codes, dosing histories, patient use histories, remaining doses, battery levels, etc. Such a system may include a unique key for each device that must be proximal to the device for operation, so as to prevent accidental or intentional tampering, abuse, or access to the drug by an unauthorized individual. Such a remote operation system may also provide a unique key located at the patient's bedside, possibly in a stand or dock, or attached to the patient or his or her clothes, possibly on a bracelet, necklace, adhesive patch, or clip, to avoid accidental or intentional swapping of devices between patients or other accidental or intentional diversion.

In embodiments where a dispensing device of the invention is used to dispense a controlled substance such as an opioid, the dispensing device may be designed in such a way as to provide containment of an opioid antagonist in a configuration that prevents intentional diversion. The dispensing device may be equipped with a small liquid opiate antagonist reservoir that is held at slight pressure, and biased to dump the antagonist into the dosage form cartridge. The powered up system actively prevents the antagonist reservoir from flooding the cartridge by means of a valve or other controllable conduit. In the event of a power failure, major physical damage, or malicious tampering, the antagonist reservoir will dispense the opiate antagonist into the cartridge, rendering the dosage forms unsuitable for use. In this embodiment, the dispensing device provides, for example, in a liquid form, in a separate reservoir that will mix with the drug formulation in the event of a power or system failure, device damage or tampering.

In some embodiments, a spoiling agent is used in place of the antagonist. If the dispensing device is forced open, the spoiling agent will contact and contaminate the drug formulation, making it unsuitable for any non-approved use.

To protect the drug dosage forms from exposure to moisture either from humidity, saliva ingress, or accidental exposure to other water based liquids, the dispensing device and the container or cartridge which houses the dosage form within the device may contain a desiccant. A mechanism to prevent saliva ingress includes inclusion of a desiccant, seals, absorbents, adsorbents wipers, and sensors. A desiccant is a sorbent, in the form of a solid, liquid, or gel that has an affinity for water, and absorbs or adsorbs moisture from the surrounding, thus controlling the moisture in the immediate environment. Any commercial desiccant which typically, take the form of pellets, canisters, packets, capsules, powders, solid materials, papers, boards, tablets, adhesive patches, and films, and can be formed for specific applications, including injection moldable plastics find application in practicing the present invention. There are many types of solid desiccants, including silica gel (sodium silicate, which is a solid, not a gel), alumino-silicate, activated alumina, zeolite, molecular sieves, montmorillonite clay, calcium oxide and calcium sulfate, any of which may be used in practicing the present invention. Different desiccants will have different affinities to moisture or other substances, as well as different capacities, and rates of absorption or adsorption. Also, different types of desiccants will come to equilibrium at different relative humidities in their immediate surroundings. As a means for protecting the dosage forms and the internal portions of a dispensing device of the invention from moisture, one or more desiccants may be employed at the dispensing tip, in or adjacent to the dosage form, e.g., tablet, delivery pathway, in or adjacent to the dosage form, tablet container or cartridge, in or adjacent to other components of the dispensing device, formed as an injection molded component of the dispensing device, or in any other location within or without the device.

The dispensing device may employ one or more levels of interface for different types of authorized users, for example the patient, the nurse, the physician, pharmacist or other authorized medical or healthcare personnel. These different interfaces may include components such as keypads, buttons, graphical icons and instructions, lights, LED's, monochrome or color graphical or text displays, touch-screens, LCD's, sounds, tactile feedback, voice recognition interfaces, and other input and output devices and means. The activity, or mode, of the user interface may be determined by the mode of operation of the dispensing device, by a login or access activity by a user such as a password or code entry, by the connection or disconnection of the dispensing device from a dock, computer, or network, or by the detection of an authorized access key, such as a key, and/or RFID tag, or similar combination. Upon changing the interface mode, the functionality of the device may be changed, either activating, inactivating or changing the functionality of the various interface components described above. By allowing the device to have one or more interface modes, with differing functionality associated with each one, the device can be optimized for various uses.

Base Station

In some embodiments the drug dispensing system includes a base station for recharging the drug dispensing device and the portable docking FOB between uses. This base station allows for recharging the batteries or fuel cells in multiple dispensing devices and/or FOBs simultaneously. In addition to recharging the drug dispensing devices and FOBs, the base station may provide one or more of the following functionality: wireless or wired connectivity to a peripheral device, computer or network; feedback on the charging state for the devices being recharges; an interface for viewing, adding, deleting, or modifying the data on a drug dispensing device or FOB; a means for synchronizing data between multiple drug dispensing devices and/or FOBs; and a means for conducting a diagnostic test on drug dispensing devices and/or FOBs.

VIII. Methods and Systems for Delivering Small Volume Dosage Forms Using a Device Exemplary features of the dispensing device include the following:

In one embodiment, the head, body, and cartridge comprise the handheld portion of the device. This device assembly has a latch to disconnect the head and body, and a dispense button for patient use. The device also has lights to show lock-out status, errors, and power. In this embodiment, the cartridge which contains the drug dosage forms and the body are used a single time only.

The system may comprise a portable dock which is handheld, independent of the patient device and solely for healthcare professional use. The dock enables higher level feature use such as deeper queries into patient device use, the ability to upload device data, unlocking of the head/body and the tether, lockout override for dosing the patient, and a larger reading display. The dock is also used to setup and take down the patient device.

The system may also comprise an RFID bracelet that is activated via the dock and is worn by the patient to establish and control dosing to correct patient and to that patient alone. This feature prohibits use of the device by others.

The system may further comprise a recharging base used to charge the dock and heads and is also used to update the heads and docks when new software becomes available or when new users are programmed into the system.

The drug dosage forms are typically provided in single use disposable cartridges which are loaded into the device prior to administration.

Exemplary set-up instructions for the device include the following steps:

The device head and dock are charged on the recharging station.

The device body and wristband are removed from the packaging.

The device head and dock are removed from the charging station.

The cartridge is loaded into the body by inserting a cartridge into the device body as indicated ensuring that the cartridge "clicks" and is locked in place.

The device body (with cartridge) is assembled onto the head.

The power button on the assembled device is pushed to power-up the system.

The power button on the dock is pushed to power-up the dock.

The assembled device is plugged into the dock.

A healthcare professional scans their fingerprint or inputs a unique password in order to unlock the dock.

The device reads the label on the cartridge and the dock displays setup information, for example, the drug name, the quantity of tablets, the drug concentration, the preset lockout time, the duration of use (72 hours), and the battery status of the head.

After the information is read from the cartridge and displayed on the dock, the healthcare professional will be requested to confirm that all information is correct and will require a witness to verify the information.

The dock will require that the patient wristband be paired to the device by bringing the wristband close to the device. The device will read the band and request confirmation of the band number; selection and confirmation of the number.

The patient ID is entered into the dock. i.e. patient medical record number.

The wristband is placed on the patient's hand that will be used to operate device.

Then, the dock will indicate that it is ready to dispense a plastic initialization tablet or "shipping tablet".

Upon confirmation, the device will dispense a plastic initialization tablet or "shipping tablet". This step is used by the device to calibrate the dispensing mechanism, initiate the cartridge for use, and allows the healthcare professional to verify proper use and to train the patient with a "shipping" or placebo-type tablet.

Once the plastic initialization tablet or "shipping tablet" is dispensed, the dock will require the healthcare professional to confirm that the plastic tablet was dispensed.

After confirmation, the display will indicate that the device is ready for use.

In some cases, a tether can be connected to the device via the dock. The dock will allow the healthcare professional to lock and unlock the tether as required.

If a patient will self administer a drug dosage form using the device, the patient will be trained prior to use.

Exemplary use of the claimed devices and systems is provided in Examples 6-8.

In one exemplary embodiment, the present invention provides a system, comprising: (1) a dispensing device for administration of a drug dosage form to the oral mucosa of a subject, for example, a small-volume dosage form or NanoTab®; (2) a dosage form for oral transmucosal administration, such as a small-volume dosage form or NanoTab®; and (3) a subject.

In another exemplary embodiment, the system for administration of dosage forms to a patient using a drug dispensing device of the invention includes a drug dispensing device wherein the dispensing device includes a means for reducing or eliminating moisture and saliva ingress such that the drug dosage forms remain dry inside the device prior to and during use.

Additional features which may be included in a system of the invention include a docking station or other docking means, a means of communication with a computer network such as a bidirectional communication link with a local or remote computer system (wired or wireless), a pharmaceutical network monitoring and control apparatus, a computer network that stores, records and transits information about drug delivery from the device and one or more user interfaces.

In one approach, the computer network of the dosage form dispensing system of the present invention may comprise one or more of: a means to store, record, receive, and transit information about drug delivery from the drug delivery device; an internal clock to track time and date, a means to reset or modify memory, a non-invasive means to measure respiratory rate, temperature, pulse rate, or blood pressure wherein the results are stored and transmitted via the computer network; a means to change the lock-out time of the drug delivery device or dispenser. A docking station that finds utility in practicing the present invention may function to retrieve, store, communicate data to another device, peripheral, or computer, and/or recharge a battery. The system further comprises one or more user interfaces and a graphic display such as an LCD display.

Disposable and Reusable Drug Dispensing Devices of the Invention

When the desired use of the dispensing device of the invention has been completed, and the dispensing device is no longer needed, it may be either fully disposable, partially disposable and partially reusable, or it may be fully reusable.

In one exemplary application, the dispensing device may be used to place a sublingual tablet under the tongue of a patient, and then afford a means of locking the patient out from self-administering another sublingual tablet until a safe lockout time has elapsed between dosing, a means for recording the dosing history, and a means for communicating this history to a user, a computer, another electronic device, or a network.

Because many of the components of the dispensing device of the invention are of high value, and the dispensing end may pose a contagious disease hazard, it may be advantageous to dispose of the dispensing end and reuse the end containing the microprocessor, the memory means, battery, etc. A reusable dispensing device dispenser would require a replenishable power source, such as a rechargeable battery, replaceable battery, refillable fuel cell, or other means of replenishing the system power. The dispensing device may consist of any combination of the following: fully disposable or reusable tip portion, fully disposable or reusable cartridge portion, fully disposable or reusable head portion, fully disposable or reusable head and tip combination, a fixed or portable dock for access and data transfer, a recharge station, a diagnostic station, and a keyed assembly and disassembly station.

In one exemplary embodiment the dispensing device for inpatient (hospital, clinic, etc.) use consists of a disposable tip portion, a disposable drug cartridge portion, and a reusable head portion. The disposable tip portion would contain the delivery tip, a dispensing mechanism, a means to connect and lock to a reusable head, and means to prevent saliva from entering beyond the tip. The disposable drug cartridge would contain a plurality of drug dosage forms, a means for being inserted into a reusable head or a disposable tip, and a means for ordering and containing the dosage forms. The reusable head would contain a microprocessor, a memory means, a power supply such as a battery, a user interface including buttons, a keypad, a display, and LED lights, a means to be recharged between uses and a means for allowing a disposable cartridge to be inserted into the head, a means for attaching and locking to a disposable tip. During setup when an authorized user, e.g., a nurse, is preparing the dispensing device for use by a patient, the nurse would open a new disposable tip from a package, would obtain a new drug filled cartridge from the hospital drug dispensing system, and would obtain a recharged reusable head from a recharging station. The nurse would insert the drug cartridge into the reusable head or disposable tip, then would assemble and lock the disposable tip to the reusable head, thus enclosing the disposable drug cartridge inside the assembled device. The nurse would then show the patient how to use the device and give the device to the patient for self dosing. During disassembly, when the patient had completed his therapy with the dispensing device, the nurse would unlock the reusable head from the disposable body, revealing the drug cartridge (container) within. The nurse would dispose of the drug cartridge and any remaining drug in accordance with hospital protocols, dispose of the disposable tip in a sharps or biohazard container, and would wipe down the reusable head with an antiseptic wipe, then place the head on a recharging station for recharging the battery and future reuse.

The present invention provides exemplary dispensing devices with a singulator dispensing mechanisms including a reusable single dose applicator. The singulator dispensing mechanisms may include the following; a reusable single dose applicator; a foil blister; rotating stations; a disk with ejectors; a ribbon peeler; a ribbon picker; disk singulators; a flexible disk; an arc or helical type single dose applicator; a pushrod stack ejector; and a rotating stack ejector.

The ability of the dispensing device to recognize a specific cartridge may include mechanical, optical (e.g. bar code), electronic (e.g. microchip), magnetic, radio frequency, chemical, or other means of detecting and identifying the cartridge. In one exemplary embodiment of the invention, the cartridge may contain a physical keying detail on the cartridge that is physically detected by a sensor or switch or a series of sensors or switches in the dispensing device. When the cartridge is loaded into the dispensing device, the sensor or switch array can read a mechanical key and identify the cartridge and its contents and/or other information.

In another exemplary embodiment, the cartridge is manufactured with a unique electronic microchip and the dispensing device is equipped with a microchip reader, such that upon loading of the cartridge into the dispensing device the dispensing device reads the information on the microchip identifying the cartridge and its contents and/or other information.

In some embodiments, the cartridge may be modified such that upon a successful or unsuccessful loading attempt into a dispensing device, the dispensing device passes information to the cartridge that it has been loaded or a loading attempt was made. Such a system may include a cartridge with a physical, electronic, optical, magnetic, chemical, or other means of recording information from the dispensing device to the cartridge.

Once the dispensing device has identified the cartridge, or attempted to identify the cartridge, the dispensing device may alter its functionality or cease its functionality based on this information. For example, if the device detects and identifies a cartridge that contains a sublingual opioid dosage form, of a specific strength and duration of action for the treatment of post operative pain, the dispensing device may institute a specific lockout protocol between doses, a specific patient identification protocol, a dosage history recording protocol, and it may alter its user interface appropriately, among other things.

Furthermore, an identification or keying feature on a cartridge may be modified in the event of drug access inside or outside of the dispensing device such that the dispensing device may identify that the cartridge has been opened prior to loading into the dispensing device. In this fashion the dispensing device may detect if a cartridge that is being loaded has been tampered with or previously used.

The present invention provides exemplary architectures including reusable options. The present invention provides exemplary architectures including reusable options. The reusable device may be cleaned, recharged, reloaded, or have its memory cleared after treatment and be used again. The drug dosage dispenser of the invention may contain a plurality of components that are assembled such that one or more components are reusable, to allow for reuse of expensive or high value components and reduce waste, and one or more components are disposable, to allow easy disposal of dirty or contaminated components, components that pose a contagious disease hazard, or components that contain unused or contaminated drug. In one such exemplary embodiment, a dispenser system, a disposable drug dosage form cartridge would be loaded into a disposable delivery portion of a dispenser. A reusable portion of the dispenser would then be joined to the disposable portion in such a manner as to afford a tamper deterrent lock between the components. The reusable portion of the dispenser would detect the proper assembly of the cartridge and disposable portion of the dispenser, confirming proper assembly and allowing normal use of the dispenser to ensue. Improper or incomplete assembly would result in the reusable portion of the dispenser locking and displaying an error code or indication for error diagnosis.

The assembly of two or more components of the dispenser may contain a locking mechanism to prevent or deter tampering or diversion of the drug within. The locking mechanism may be afforded by means of a solenoid, a motor, a piezo-electric actuator, a pneumatic or hydraulic actuator, a shape-memory actuator, a latch, a pin, a snap, a cam, a slider, a linkage, or any other mechanical or electromechanical means. Furthermore, the locking means may be locked or unlocked by means of a physical key, a combination, an electronic key, a magnetic key, pass code, PIN, encrypted or unencrypted logic signal, a wireless signal, RFID, finger print identification, or other means of mechanical or electromechanical unlocking of a lock.

After use of the dispenser, and upon disassembly, the reusable portion or portions, may be retained for future use, while the disposable portion or portions may be disposed of.

Methods and systems for delivering small volume dosage forms, e.g. sufentanil-containing dosage forms using a device are provided. FIG. 31 provides a schematic architecture connection diagram illustrating the various components that may be included in a dispensing device or system for dispensing small volume drug dosage forms, including a device with a separate head 280, body 282 and disposable drug dosage cartridge 48, a portable docking fob 296, Patient RFID 281 and a base station 292.

FIG. 32A is a schematic depiction of an exemplary architecture 278 having a reusable head. The reusable option includes the following: a reusable head 280, a body 282, and a recharge station 284. This embodiment 278 is comprised of the following: a reusable head 280 containing a power supply 277, a microprocessor and printed circuit board (PCB) 275, an actuator 273, a user interface 279, a user identification means 281; a disposable body 282 containing a disposable drug dosage cartridge 48; and a recharging station 284. In this embodiment the reusable head 280 is lockably connected and disconnected from a disposable body 284. After use, the disposable body 282, the drug dosage form, and the cartridge 48 are disposed of, while the reusable head 280 is cleaned and docked in the recharge station 284 to recharge the power supply. The power supply 277 may be a rechargeable or replaceable battery, a fuel cell, or any other means of powering the device. The actuator 273 may be a motor, solenoid, linear actuator, piezo-electric actuator, shape memory actuator, hydraulic or pneumatic actuator or any other means of actuating a mechanism. The user interface 279 may be include a graphical or numeric display, a keypad, buttons, switches, dials, sliders, lights, LED's, LCD's, speakers, microphones, buzzers, or any other means of communication to or from a user. The user identification means 281 may be an RFID tag reader, a Wi-Fi system, a fingerprint reader, a voice recognition system, an image or facial recognition system, a local area network that communicates by way of the human body, a DNA recognition system, a retinal scanner, or any other means of identifying an individual user or patient. The drug dosage cartridge 48 may be a stack, disk, tape, single dose applicator, an may contain a single dose or a plurality of doses. The PCB 275 may include a processor, a memory means, a power regulator, a recharge cycle, a patient identification means, graphic drivers, and any other components or systems to affect the performance of the dispenser device 278.

The dispensing mechanism may be contained in the disposable body 282 or in the reusable head 280 or partially in both locations. The recharge station 284 may recharge the power supply, may perform a diagnostic on the reusable head 280, or may serve as an informational dock, either wired or wireless, to communicate between the dispenser device and another device, computer or network.

FIG. 32B is a schematic depiction of an exemplary architecture 286 having a reusable head 280 containing an actuator 273, a PCB 275, a power supply 277, and a user identification means 281, a disposable body 290, containing a drug dosage cartridge and drug dosage forms 48, a docking station 292 containing a communication means and user interface 279, and a recharge station 284. The reusable option includes the following: the reusable head 280, a disposable body 282, docking station 284, and the docking station 292.

FIG. 32C is a schematic depiction of an exemplary architecture 294 having a disposable body containing an actuator 273, a PCB 275, a power supply 277, a user identification means 281, and a drug dosage cartridge containing drug dosage forms 48, a portable docking fob 296 containing a user interface 279, and a recharge station 284. The reusable option includes the following: a disposable body 282 with the portable docking fob 296, and a recharge station 284 for recharging the fob.

FIG. 32D is a schematic depiction of an exemplary architecture 302 having a disposable body 282 with dockability. The reusable option includes the following: a disposable body 282 containing an actuator 273, a PCB 275, a power supply 277, a user identification means 281, and a drug dosage cartridge with drug dosage forms 48, and a docking station 292 containing a user interface 279. The reusable option includes the following: disposable body with a docking station.

FIG. 32E is a schematic depiction of an exemplary architecture 308 having a reusable head 280 containing a power supply 277, a microprocessor and printed circuit board (PCB) 275, an actuator 273, and a user identification means 281, a disposable body containing a drug dosage cartridge with drug dosage forms 48, a portable docking fob 296 containing a user interface 279, and a recharge station for the head and fob. The reusable option includes the following: the reusable head 280 with the fob 296, a disposable body 282, and a recharge station 284.

In one embodiment, the present invention further provides a fully disposable device. The device is one-piece incorporating all components necessary for drug dispensing and disposable after use, including a power supply 277, a microprocessor and printed circuit board (PCB) 275, an actuator 273, and a user identification means 281, a drug dosage cartridge with drug dosage forms 48, and a user interface 279. FIG. 32F is a schematic depiction of an exemplary architecture 318, wherein a fully disposable body 282 is shown.

The present invention further provides a dispensing device with a locking feature including movable push rod; non-returning push rod; electromechanical regulator; optical sensor pair; magnetic clutch; lockout on actuator; rack and pinion; safety button latch; solenoid; collet on shaft; keyed hubs; coupling; and cams.

FIG. 33 is a schematic depiction of the functional elements of the drug dispensing system 326, including a drug dispensing device and pharmaceutical network with a monitoring and control apparatus coupled via a wireless or other bi-directional communication network. The system 326 includes a battery 342 controlled microprocessor 352 which comprises RAM 330 and ROM 332, is operably connected to a docking connector 344, and communicates in a bi-directional manner with an RFID antenna 336, a WI/FI antenna 338, wherein the drug dispensing device and pharmaceutical network further comprises, a user interface 328, an audible alarm 350, a graphic display 348, a dispensing button 346, dispensing sensor 340, and a dispensing button lockout 344. The device or dispensing device of the present invention may have a bidirectional communication link with a local or remote computer system, wherein the computer system provides a signal that allows the device to dispense a small-volume drug delivery dosage form. The drug delivery device can store and dispense many doses of a small, oral transmucosal drug formulation. The device/system 326 includes a memory means such as RAM 330 and/or ROM 332, the micro processor 352 or a central processing unit (CPU) for processing information and controlling various functional elements of the device 326 and a battery 342, the docking connector 334 that can allow the device 326 to connect to another device, peripheral, or computer to retrieve, store, communicate data to the another device, peripheral, or computer, and recharge the battery 342, the RFID Antenna 336 or other unique tag that allows easy identification of each individual device 326, the Wi/Fi Antenna 338 that allows information be communicated bi-directionally via a wireless system, a dispensing sensor 340 located on the exit port to detect the successful dispensing of a dosage form. In some embodiments, the drug dispensing system 326 can include a tether sensor, and/or a head/body assembly sensor.

FIG. 34A is a block diagram illustrating a system communication diagram 354, comprising an RFID tag 356, a dispensing device 358, a base station/dock 360 and a healthcare provider personal computer 362. The drug dispensing device 358 may communicate with the physician or care giver, via the dock 360, by means of a wired or wireless communication method to provide usage information and information regarding the respiratory status or blood pressure of the patient to the physician at regular intervals.

FIG. 34B is a block diagram illustrating a system communication diagram 364, comprising an RFID tag 356, a dispensing device 358, a fob 366 and a healthcare provider personal computer 362. The drug dispensing device 358 may communicate with the physician or care giver, via the fob 366, by means of a wired or wireless communication method to provide usage information and information regarding the respiratory status or blood pressure of the patient to the physician at regular intervals. The fob 366 can be adapted to attach to a cord so as to allow the fob 366 to hang from the neck of the physician or caregiver. This would help avoid misplacing the fob 366 or theft of the fob 366, such as in the hospital setting.

The present invention provides a drug dispensing system including a drug dispensing device and a detecting means for detecting the identity of a patient. The dispensing system may further include a computer, a docking station, an access control means, and small volume drug dosage forms. The system further comprises a docking station, wherein the docking station is electrically connected to a computer network and information is transmitted from the drug delivery device or dispensing device to the computer network. The computer network is wireless and information is transmitted from the drug delivery device or dispensing device to the computer network via the wireless network. The computer network stores, records and transits information about drug delivery from the drug delivery device. The system may further comprise a non-invasive means to measure respiratory rate, pulse rate, temperature or blood pressure wherein the results of the measurements are stored and transmitted via the computer network. In one embodiment, the system further comprises a means to change the lock-out time of the drug delivery device. In another embodiment, the system may comprise a drug delivery device with an antagonist reservoir that allows the antagonist and drug to combine in the event of a system or power failure, device damage or tampering. In addition, a means that uses a sensor to detect blood chemistry, breath chemistry, saliva chemistry and on the like is also provided.

Further embodiments of the device include the ability to store historical use information and the ability of the device to communicate with another device or computer to transmit such information. For example, such a bidirectional exchange of information may be accomplished by downloading stored information to a computer through a physically wired interface, such as a USB or any other communication connection. Alternatively, information may be communicated via a wireless system. Such information may include historical use information, for example the number of dosages stored and dispensed, and the times of dispensing.

In certain embodiments, the device includes a docking station that may query the device, reset it between dosing, lock it when not properly accessed, and control the dosing regimen. The drug dispensing device may communicate with a physician or care giver, via the dock, by means of a wired or wireless communication method to provide usage information and information regarding the respiratory status, blood pressure or other biometric measurement of the patient's status to the physician at regular intervals. The dispensing device may lock out at regular intervals or time periods, e.g., each day or week or two weeks, requiring the patient to dock the dispensing device and communicate with the physician or care giver to unlock the device for the next fixed period. In this way the device and dock enable greater physician oversight and care management.

In other embodiments, the docking station may load single or multiple doses into the device each time it is docked and properly accessed.

In certain embodiments, the device may be adapted to receive a cartridge of individually packaged single dose applicators each containing a single dose of the drug.

A drug dosage dispenser of the invention may be used to administer a drug dosage forms that is sensitive to moisture and/or humidity. In such cases, there is a need for a drug dosage form cartridge that protects the drug dosage form from humidity, moisture, saliva, mucus, etc. The cartridge may be cylindrical, disk-shaped, helical, rectilinear, non-ordered, or may take the form of any assemblage of drug dosage forms that allows the dispenser to dispense them in a controlled manner. To prevent the unused drug dosage forms from absorbing moisture or otherwise becoming exposed to moisture prior to use, the cartridge may provide a means of sealing the drug dosage forms from exposure to moisture. This may accomplished by use of a cartridge that contains individually packaged drug dosage forms separated by a thin impermeable foil or impermeable material such that when one drug dosage form is dispensed from the cartridge, the seal protecting the remaining dosage forms remains unbroken. Alternatively, the dosage forms may be packaged in such a manner within the cartridge that two or more dosage forms are packaged together in each separate sealed compartment. In some embodiments, all of the dosage forms in a cartridge may be packaged together in a foil sealed compartment.

The drug dosage form cartridge may afford a seal against moisture by means of a septum, an elastomeric seal or valve, a sliding, translating, hinged door or valve, or by means of sealing against another component of the dispenser when loaded. In this manner, a single re-sealable seal may be opened either independently or by means of the passage of a dosage out of the cartridge. Once the dosage form is delivered from the cartridge, the re-sealable seal on the cartridge may be re-sealed to prevent moisture or other contaminants from damaging the remaining drug dosage forms within the cartridge. The cartridge may further have a non-re-sealable seal that is broken when it is loaded into the dispenser or upon delivery of the first dosage form from the cartridge.

In other embodiments, the cartridge contains a desiccant or other absorbent or adsorbent material to absorb or adsorb moisture that penetrates the cartridge either prior to use or during normal use. A cartridge for use in a dispensing device of the invention may contain any combination of individually sealed dosage forms, multiply sealed dosage forms, re-sealable seals, non-re-sealable seals, desiccants, absorbents, or adsorbents.

In one exemplary embodiment a stack of solid tablet dosage forms is packaged in a cylindrical cartridge with a sliding seal at the distal end and a spring pre-loading the tablets toward this distal end. When the drug cartridge is loaded into the dispenser, the sliding seal remains in place, protecting the drugs within the cartridge from moisture and humidity. Upon dispensing of a dosage form, the sliding seal slides out of the way, allowing the spring to advance the stack so that a single tablet dosage form is dispensed. Once this tablet is dispensed, the sliding seal moves back into place to continue to seal the remaining tablets from moisture and humidity.

In a second exemplary embodiment, a stack of solid tablet dosage forms is packaged in a cylindrical cartridge with a foil seal at the distal end, a spring pre-loading the tablets toward this distal end, and a sealing surface that will seal against a component internal to the dispenser once it is loaded into the dispenser. When the cartridge is loaded into the dispenser, the foil seal is broken, and the distal end of the cartridge seals against a component of the dispenser so as to protect the tablet dosage forms from humidity and moisture. When a tablet is dispensed, a component of the dispenser that provides a seal to the cartridge is moved out of the way, allowing a single dosage form to be dispensed. Once the dosage form is dispensed, the dispenser re-seals the cartridge, protecting the remaining dosage forms from moisture and humidity.

In a third exemplary embodiment, a disk shaped cartridge with individual spaces for individual solid tablet dosage forms arranged around the periphery of the disk is loaded with solid tablet dosage forms and sealed on both faces with a metal foil to protect the tablets from moisture and humidity. When loaded into the dispenser and when a dosage form is dispensed, push rod breaks through the foil on one face at the location of one of the individual compartments, contacting the tablet dosage form, and pushing it through the second seal on the opposite face of the disk cartridge, breaking through the second foil, and dispensing the tablet. In this manner, only a single tablet is dispensed, and the seals for the remaining tablets remain intact, protecting them from moisture and humidity. After the dispensing of the tablet, the disk indexes one location so that the next compartment containing the next tablet is in position to be dispensed next, for example, as shown and described with reference to FIGS. 15A and 15B.

Methods of Use of a Drug Dispensing Device of the Invention for Oral Transmucosal Drug Delivery Delivery of a single dosage form using a drug dispensing device of the invention may be accomplished as detailed in the figures described below.

FIG. 35 is a block diagram illustrating a dispensing device programming flow chart 372, wherein the process involves the steps of: loading a dosage form cartridge into the dispensing device. If loading is successful 374, the process goes to the next step. If unsuccessful 376, the process goes back to the first step of loading a dosage form cartridge into the dispensing device; closing and locking the dispensing device. If successful 378, the process goes to the next step. If unsuccessful 380, the process goes back to the previous step of closing and locking the dispensing device; docking the dispensing device into the PC. If successful 382, the process goes to the next step. If unsuccessful 384, the process goes back to the previous step; programming the dispensing device. If successful 386, the process goes to the next step. If unsuccessful 388, the process goes back to the previous step; recording a thumbprint or PIN to identify the appropriate user. If successful 390, the process goes to the next step. If unsuccessful 392, the process goes back to the previous step; and testing the dispensing device if a dispensing works properly. If successful 396, the programming ends 398. If unsuccessful 394, the process goes back to the first step to correct the programming.

FIG. 36 is a block diagram illustrating a dispensing device operation flow chart 400, wherein an example of stepwise operation of a drug dispensing device of the invention is provided. The detailed steps include: pressing any button to wake-up the dispensing device 402. The user verifies if a preprogrammed lock-out time is over. If the preprogrammed lock-out time is not over yet, the user goes back to the prior step of waking up the dispensing device and repeats the process. If the verification is satisfied, the dispensing device is unlocked for dispensing a drug dosage form. Inputting patient identification 404 using e.g., a thumbprint, or PIN verification, is performed. If patient identification 404 is incorrect 408, it results in lock-down of the device 426. If the patient identification 404 is correct 406, the process goes to the next step: detecting an RFID tag 410. If incorrect 414, it results in lock-down of the drug dispensing device 426. If detecting an RFID tag is successful 412, the user proceeds to the next step by which the user verifies if a lock-out device is not blocking delivery and dispensing is fine. Then a comparison is made of the (a) dispensing request, (b) dispensing history, and (c) programmed prescription 416. If (a), (b) and (c) are consistent with permission to dispense a dosage form from the drug dispensing device of the invention, dispensing is ready 418. If not ready, lock-down of the dispensing device is resulted in 420. Displaying dispensing device status and ID which indicates the drug dispensing device is ready 422. Dispensing a dosage form when the dispense button is pressed 424. The dispensing device begins to dispense the drug dosage form to a patient. Upon completion of dispensing the dosage form, the dispensing device lock-out is locked down for a preprogrammed period 426. The steps are repeated for a future dispensing of the drug dosage form.

FIG. 37 is a block diagram illustrating another exemplary dispensing device operation flow chart 428, wherein an example of stepwise operation of a drug dispensing device of the invention is provided. The method comprises the following steps: a user may press any button to wake-up the dispensing device 430. Then the device verifies if a preprogrammed lock-out time, such as 10 min, is over. If the preprogrammed lock-out time is over, patient identification is attempted, i.e. using 432, detecting an RFID tag is performed. If the preprogrammed lock-out time is not over yet 434, the user goes back to the prior step of waking up the dispensing device and repeats the process. If detecting an RFID tag is successful 436, the device proceeds to the next step and verifies that it is the mechanical dispensing is in functional condition. If detecting an RFID tag is unsuccessful 438, the user goes back to the first step. If the verification is satisfied 440, the dispensing device is unlocked for dispensing a drug dosage form. If the verification is not satisfied 442, an error message indicating a failure of the mechanical check is prompted 444. If the mechanical check is ok, then the motor-driven dispensing of a drug dosage form to a patient is performed. Upon completion of dispensing, the dosage form, the dispensing device lock-out is locked down for a preprogrammed period. The steps are repeated for a future dispensing of the dosage form 446.

In another example of the process of dispensing drug dosage forms using a drug delivery device of the present invention, the process includes the steps of: (1) load; (2) check; (3) position; and (4) deliver. This process comprises the following steps: (1) loading the drug dispensing device with a plurality of drug dosage forms; (2) checking the delivery status and verifying, for example, by a green light indicating that the lock-out mechanism is not blocking delivery and the device is armed with a drug dosage form; (3) positioning the device to deliver a dosage form of the invention under the tongue of the appropriate patient; and (4) delivering the dosage form to the patient by activating the device. The red light or other indicator is always visible when the device is not ready for delivery. The drug dispensing information is communicated to health care personnel such that the dosing regimen is adjusted to ensure that the patient is receiving the appropriate drug dose at the appropriate frequency to provide therapeutic efficacy.

FIG. 38 is a block diagram illustrating another exemplary dispenser operation flow chart 448, wherein an example of stepwise operation of a drug dispensing device of the invention is provided. The method comprises the following steps: a user presses any button to wake-up and unlock the dispenser 452 in sleep mode 450. Then the user verifies if a preprogrammed lock-out time, such as 10 min, is over. the preprogrammed lock-out time is over 454, the system verifies that the user is authorized for access, such as detecting a user identity (e.g. an RFID tag, fingerprint, etc.), is performed 458. If the preprogrammed lock-out time has not expired 456, the system returns to the first step of waking up the dispenser and repeats the process. If the user identity is detected and authorized 458, the system proceeds to the next step in which the system is unlocked for delivery 462. If the user identity is not detected or not authorized 460, the system returns to the first step of waking up the dispenser and repeats the process. Once the system is unlocked, it remains unlocked for 5 seconds before re-locking 464. If the user presses the second button before the 5 seconds has elapsed 466, the button will dispense a dosage form 468. Once the dispensing is completed, the system is locked 470 until the next dispensing attempt is made. The steps are repeated for a future dispensing of the dosage form 472.

FIG. 39 is a block diagram illustrating an exemplary dispenser disassembly flow chart by a healthcare professional 474, wherein an example of stepwise disassembly of a drug dispensing device of the invention is provided. As exemplified in FIG. 39, a healthcare professional may disassemble and dispose of the dispenser in a secure, controlled manner.

FIG. 40 is a block diagram illustrating an exemplary outpatient acute dispensing device operation flow chart 518, wherein an example of stepwise operation of a drug dispensing device of the invention is provided. FIG. 40 depicts a stepwise operation of an exemplary outpatient acute dispensing device.

FIG. 41 is a block diagram illustrating an exemplary inpatient dispenser assembly and preparation flow chart 550, wherein an example of stepwise assembly and preparation of a drug dispensing device of the invention is provided. FIG. 41 depicts a stepwise assembly and preparation of the inpatient dispenser.

FIG. 42 is a block diagram illustrating an exemplary outpatient chronic dispensing device operation flow chart 598, wherein an example of stepwise operation of a drug dispensing device of the invention is provided. FIG. 42 depicts a stepwise operation of the outpatient chronic dispensing device.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

IX. In Vivo Human Studies

Provided herein is pharmacokinetic data obtained in animals and humans based on studies where sufentanil and alfentanil were administered via the sublingual route using the claimed small volume dosage forms.

A human clinical study was performed using healthy volunteers. The study which is detailed in Example 1 below was performed with 12 subjects (6 men and 6 women) using sublingual sufentanil dosage forms containing either 2.5 mcg, 5 mcg or 10 mcg of sufentanil base corresponding to 3.7 mcg, 7.5 mcg or 15 mcg of sufentanil citrate, respectively (see Table 1). All excipients were "pharmaceutically acceptable" (inactive and have GRAS or "generally recognized as safe" status.

Sufentanil dosage forms designed for sublingual use were compared to IV sufentanil, administered through an IV catheter as a continuous infusion over 10 minutes. Plasma samples were drawn from a different IV catheter at a remote location. The assay demonstrated good inter-day precision and accuracy at the high, medium and low quality control sample concentrations.

The dosage forms for this study eroded over a period of 10-30 minutes in all subjects. After placement of each sufentanil dosage form in the sublingual cavity of the 12 healthy volunteers, a remarkably consistent pharmacokinetic profile was obtained (see FIG. 43 and Table 2). The bioavailability compared to IV administration for single administration of all three dosages averaged 91%, which is far superior to that measured for commercially available fentanyl transmucosal preparations, Actiq and Fentora (47% and 65%, respectively—Fentora package insert). Although this high bioavailability could be due to a number of factors including but not limited to erosion time, it is likely that the lack of saliva produced by the small size of the dosage forms limits the swallowing of the drug and avoids the low bioavailability typical of drug absorption via the GI route. Both Fentora and Actiq package inserts claim at least 50% and 75% of the drug dose, respectively, is swallowed via the saliva, and both exhibit lower bioavailability than the claimed dosage forms.

The dosage forms used in this clinical trial had a volume of approximately 5 microliters (mass of 5.5-5.85 mg), a small fraction of the size of Actiq or Fentora lozenges. The dog studies described in Example 4 demonstrate that sufentanil has very poor GI bioavailability (12%), therefore, given the high bioavailability of the sufentanil dosage forms, wherein drug is administered by the oral transmucosal route, the data supports the conclusion that greater than 75% of the drug is absorbed transmucosally. Therefore, less than 25% of the drug is swallowed, which is a much lower percentage than is swallowed with Fentora or Actiq.

Importantly, this bioavailability is also linked to the consistency of total drug delivered to the patient. For example, the total plasma drug area under the curve (AUC 0-infinity) for sufentanil dosage forms 10 mcg was 0.0705±0.0194 hr*ng/ml (mean±standard deviation (SD)). This SD is only 27.5% of the total AUC. Coefficient of variation (CV) is a term to describe the percent SD of the mean. The coefficient of variation for the fentanyl products, Fentora (AUC is 45%) and Actiq (AUC is 41%; Fentora package insert), while the coefficient of variation for the claimed sublingual sufentanil dosage forms is less than 40%. Therefore, the total dose delivered to the subject is not only more bioavailable for the sufentanil dosage forms but it is more consistent.

The sufentanil sublingual dosage forms are also superior in terms of consistent drug plasma levels early after administration. The $C_{max}$ obtained with the 10 mcg sufentanil dosage form was 27.5±7.7 pg/ml. The coefficient of variation of the $C_{max}$ is therefore only 28%. The $C_{max}$ for Fentora and Actiq suffer from variability of GI uptake of drug. Fentora reports a $C_{max}$ of 1.02±0.42 ng/ml, therefore the coefficient of variation of the $C_{max}$ is 41%. The range of coefficients of variation for the various doses of Fentora is from 41% to 56% (package insert). Actiq coefficient of variation of $C_{max}$ is reported as 33% (Fentora package insert).

In addition to superior bioavailability and consistency in plasma concentrations, the time to $C_{max}$, also referred to as $T_{max}$, is important since quick and consistent onset of pain relief is important in the treatment of acute pain. The $T_{max}$ for 10 mcg sufentanil dosage forms was 40.8±13.2 minutes (range 19.8-60 minutes). The reported average $T_{max}$ for Fentora is 46.8 with a range of 20-240 minutes. The $T_{max}$ for Actiq is 90.8 minutes, range 35-240 minutes (Fentora package insert). Therefore, the consistency in onset of analgesia for sufentanil dosage forms is markedly improved over Fentora and Actiq, with a 400% decrease in the slowest onset of $T_{max}$.

Important in the treatment of acute pain, especially acute breakthrough pain, is a consistent and relatively short half-life of the drug. The plasma elimination half-life of the 10 mcg sufentanil dosage form was 1.71±0.4 hours, which allows the drug to be titratable for various levels of pain. If the breakthrough pain event lasts longer than 1.5 hours then the patient can dose with another dosage form. The plasma elimination half-life of Actiq and Fentora are 3.2 hours and 2.63 hours, respectively, for the lowest doses. The half-lives for the higher doses increase substantially for these drugs, thereby limiting the titratability of these drugs.

Although still in development, published data allows comparison of the sufentanil pharmacokinetic data provided herein to that of Rapinyl, a fentanyl sublingual fast-dissolve lozenge. As previously mentioned, the observed bioavailability for the claimed sufentanil dosage averaged 91% as compared to the published bioavailability for Rapinyl which is approximately 70% (Bredenberg, New Concepts in Administration of Drugs in Tablet Form, Acta Universitatis Upsaliensis, Uppsala, 2003). The coefficient of variation of the AUC (0-infinity) for Rapinyl ranges from 25-42% depending on dose, whereas the coefficient of variation for the claimed 10 mcg sufentanil dosage forms is 27.5%. This high bioavailability would suggest that regardless of dose, the sufentanil dosage forms have a consistently low coefficient of variation of AUC, whereas this is not true for Rapinyl. In fact, the coefficient of variation around the AUC for all three doses of sufentanil exemplified herein (2, 5, and 10 mcg) averaged 28.6%, demonstrating that the observed low coefficient of variation is not dependent on dose.

The coefficient of variation of the $C_{max}$ for Rapinyl varies from 34-58% depending on dose. As shown by the data presented herein, administration of the 10 mcg sufentanil dosage form resulted in a $C_{max}$ variation of only 28%, and the average coefficient of variation of $C_{max}$ for the 2, 5, and 10 mcg doses was 29.4%, indicating minimal variability depending on dose. Similarly, the coefficient of variation for $T_{max}$ with Rapinyl ranges from 43-54% depending on dose, whereas for our sufentanil dosage forms, this coefficient of variation for $T_{max}$ averages only 29% over all three dosage strengths. This consistent onset of action achieved with sublingual sufentanil dosage forms allows a safer redosing window when compared to any of the three comparator drugs, since rising plasma levels are contained to a shorter period.

Additionally, as with Fentora and Actiq, Rapinyl demonstrates a longer plasma elimination half-life (5.4-6.3 hours, depending on dose) than the claimed sufentanil dosage forms. The plasma elimination half-life of sufentanil dosage forms ranged from 1.5-2 hours following a single oral transmucosal administration in humans (Table 2), which allows for more titratability and avoids overdosing. As will be understood by those of skill in the art, the half-life described herein for the exemplified dosage forms may be adjusted by modification of the component and relative amounts of the excipients in the formulation used to make a given dosage form. The ability to titrate to higher plasma levels by administering repetitive doses of the sublingual sufentanil dosage forms was also tested in this human study. Repeat dosing of 5 mcg dosage forms every 10 minutes for four dosings resulted in a bioavailability of 96%, indicating that repetitive dosing to achieve higher plasma levels while still maintaining high bioavailability is possible. Whether treating post-operative pain or cancer breakthrough pain, being able to efficiently titrate to an individual's own level of pain relief is important.

Another aspect of the PK curves generated by sublingual sufentanil dosage forms is the plateau phase, which allows for a period of consistent plasma levels, which is important for both safety and efficacy. Compared to either IV bolus administration (see Animal Studies Examples 2-5) or the 10 minute IV infusion in our human study (Example 1 and FIG. 43), the PK profile for the sufentanil dosage forms is clearly safer. Rapid, high $C_{max}$ plasma levels are avoided. Given the ability of opioids to produce respiratory depression, avoiding these high peaks in the PK profile is advantageous.

An important mathematical ratio that demonstrates the prolonged plateau phase of the measured blood plasma levels of sufentanil following administration of a dosage form is the time spent above 50% of $C_{max}$ divided by the known IV terminal elimination half-life of the drug:

$$\text{Therapeutic Time Ratio} = \frac{\text{Time of offset}\frac{C_{max}}{2} - \text{Time of onset of }\frac{C_{max}}{2}}{\text{IV Elimation Half-Life of the Drug}}$$

The elimination half-life is an intrinsic property of the molecule and is measured most reliably using the IV route to avoid contamination from continued uptake of drug from the sublingual route. The IV elimination half-life for 5 mcg of sufentanil in our human study was 71.4 minutes due to the detection limits of the assay at these low doses. The published IV elimination half-life for sufentanil at much higher doses is 148 minutes, due to detection of both the rapid alpha-elimination mechanism of redistribution and the longer beta phase of elimination via metabolism and excretion. This published elimination half-life is more accurate and more appropriate to use in the above equation. The time spent above 50% of $C_{max}$ on average for the 12 volunteers for the 2.5, 5 and 10 mcg dosage strengths was 110 minutes, 111 minutes and 106 minutes, respectively. Therefore, the Therapeutic Time Ratio for these specific sufentanil dosage forms ranged from 0.72-0.75. As the formulation of the dosage forms is varied, erosion time of the dosage form will be either decreased or increased, and one might see a range of Therapeutic Time Ratios from approximately 0.2-2.0 for sufentanil.

The Therapeutic Time Ratio is a measure of how successfully short-acting drugs are formulated to produce an increase in therapeutic time and increase safety by avoiding high peak plasma $C_{max}$ concentrations. For example, as a comparison, the sufentanil IV arm of the human study demonstrated a Therapeutic Time Ratio of 10 min/148 min=0.067. This low ratio value for the IV arm, therefore, is a measure of the high peak produced by IV infusion of sufentanil and demonstrates that this formulation does not produce a significant plateau phase. There is a 10-fold higher Therapeutic Time Ratio for the sufentanil formulations listed in Table 1 (the dosages used in the human study) versus IV sufentanil, indicating a prolonged therapeutic plateau profile for these formulations.

The uptake of transmucosal medications via small volume drug dosage forms results in a more consistent drug delivery between individual dosages and individual patients as compared to that of currently available oral transmucosal dosage forms for which a large fraction of drug uptake occurs via the GI route.

The methods and systems described herein are designed to work effectively in the unique environment of the oral cavity, providing for higher levels of drug absorption and pain relief than currently available systems. The claimed methods and systems are designed to avoid the high peak plasma levels of intravenous administration by entry into the circulation via the sublingual mucosa.

The claimed methods and systems further provide for independent control of bioadhesion, dosage form disintegration (erosion) and drug dissolution and release over time, together with administration using a device to provide a safe delivery profile. The device-administered oral transmucosal dosage forms provide individual, repetitive doses that include a defined amount of the active agent (e.g., sufentanil), thereby allowing the patient or care giver to accurately titrate the amount of drug delivered and to adjust the amount as appropriate in a safe and effective manner. The lock-out feature of the dispensing device adds to the safety of the drug delivery profile.

An advantage of the oral transmucosal dosage forms herein is that they exhibit high consistent bioavailability and can maintain the plasma drug concentration within a targeted therapeutic window with significantly lower variability for a longer duration than currently available medications or systems for treatment of pain. The high peak plasma levels typically observed for IV dosage forms are blunted following administration of sufentanil-counting dosage forms. In addition, a rapid decline in plasma levels is avoided since the drug is continually crossing from the oral cavity into the bloodstream during the length of time of erosion of the dosage form or longer, thus providing plasma pharmacokinetics with an extended plateau phase as compared to the IV route of administration. Further, treatment with the claimed methods and systems provides for improved safety by minimizing the potentially deleterious side effects of the peaks and troughs in the plasma drug pharmacokinetics, which are typical of currently available medications or systems for treatment of pain.

Advantages of the claimed sublingual dosage forms over various liquid forms for either sublingual or intranasal administration include local release of drug from the dosage form over time with minimal swallowing of liquid drug via either the nasal or oral/GI route. Published pharmacokinetic data following administration of intranasal sufentanil liquid (15 mcg) in humans demonstrates a bioavailability of 78% (Helmers et al., Canadian Journal of Anaesthesia 36:494-497, 1989). Sublingual liquid sufentanil administration (5 mcg) in Beagle dogs (see Example 4 below) resulted in a bioavailability of 40%. The aforementioned bioavailability data are less than the 91% average bioavailability that was obtained in human volunteers using sufentanil administered sublingually in the form of a small volume dosage form (see Example 1 below).

Due to the small size of the oral transmucosal dosage forms, repeated placement in the sublingual cavity over time is possible. Minimal saliva production and minimal physical discomfort occurs due to the small size, which allows for repetitive dosing over days to weeks to months. Given the lipid profile of the sublingual cavity, the sublingual route, also allows for slower release into the plasma for certain drugs, such as sufentanil, which may be due to utilization of a "depot" effect that further stabilizes plasma levels compared to buccal delivery.

The oral transmucosal dosage forms are designed to fit comfortably under the tongue such that the drug form erodes sufficiently slowly to avoid the immediate peak plasma levels followed by significant drop off seen in prior art formulations such as described in U.S. Pat. No. 6,759,059 (Rapinyl), wherein fentanyl was administered via tablets containing 400 mcg of fentanyl which resulted in a peak plasma level of 2.5 ng/ml followed by an immediate drop in plasma level. Fentora (fentanyl buccal tablet) also suffers from a lack of a plateau phase but rather has a steep incline up to the $C_{max}$ followed by a significant drop-off in plasma levels (Fentora package insert).

Animal Studies

A series of studies in awake, alert Beagle dogs was performed to more fully elucidate the properties of small volume oral transmucosal dosage forms using various drugs and formulations. A comparison of the claimed system for oral transmucosal administration of sufentanil relative to administration of liquid sublingual sufentanil or swallowed sufentanil dosage forms was made to evaluate various attributes of the drug dosage forms. The results support the claim that the small, volume drug dosage forms of the invention are well tolerated sublingually (as demonstrated by use in awake dogs) and result in higher bioavailability and more consistent pharmacokinetic data than other oral transmucosal dosage forms, including instilled liquids.

The first Beagle dog study was carried out to compare a sublingual 5 mcg sufentanil dosage form to IV sufentanil as described more fully in Example 2 below. A total of three Beagle dogs were studied and the results are graphed in FIG.

44 and tabulated in Table 3. The bioavailability of the sublingual sufentanil dosage forms was 75% compared to IV. Therefore, similar to the human data, this bioavailability data in dogs confirms the superior attributes of the dosage forms over larger dosage forms. Furthermore, similar to the human data, the coefficient of variation for the AUC was low, 14%, compared to the variation of other commercial transmucosal dosage forms. The Therapeutic Time Ratio of the sublingual sufentanil dosage forms is 0.28 whereas the Ratio for IV sufentanil is 0.05 (using the published IV elimination half-life of sufentanil in dogs of 139 minutes). Therefore, similar to humans, the 5 mcg dosage form in Table 1 resulted in a much higher Therapeutic Time Ratio (5.6-fold) compared to IV sufentanil in dogs.

Additional studies determined the effect of varying the formulation on the pharmacokinetic profile. This study is explained more fully in Example 3 below. By prolonging the erosion time of the dosage form, the plasma half-life was extended from 33 minutes for the medium disintegrating formulation (in Example 2) to 205 minutes. The Therapeutic Time Ratio was increased from 0.28 to 1.13 for the slow disintegrating dosage forms. This study illustrates the flexibility of the small volume dosage forms, and the ability based on excipient selection, to alter the PK of the drug. This flexibility is possible due to the small size of the dosage forms, which allows either short or prolonged contact time with the sublingual mucosa without dislodging or creating excess saliva which would prematurely wash the drug into the GI tract.

Another study in Beagle dogs was performed to evaluate the advantages of the sublingual dosage form over liquid administration sublingually. This study is described more fully in Example 4 below. The results indicate that although delivery of sufentanil (5 mcg) in an instilled liquid form to the sublingual cavity results in rapid $T_{max}$, this method of drug administration results in very low bioavailability (40%) compared to sublingual sufentanil dosage forms (75%). This is probably due to swallowing of the liquid drug. Moreover, the AUC is extremely variable, as shown by the high coefficient of variation (82%). The $C_{max}$ is also highly variable with this method of drug administration, demonstrating a coefficient of variation of 72%. The Therapeutic Time Ratio for instilled liquid sufentanil sublingually was calculated as 0.06, very similar to the IV sufentanil arm for this study which demonstrated a Ratio of 0.03. Therefore, this instilled sublingual liquid profile does not provide the advantageous therapeutic plateau observed with the sublingual dosage forms. These findings support that the high sublingual bioavailability observed from different formulations is not intrinsic to the molecule but rather it is a direct result of the unique design of the dosage form and its formulation. The strong adherence of the small dosage forms to the oral mucosa in the sublingual cavity minimizes the variability in the surface area available for absorption, as is the case of a liquid solution, thus improving delivery of the molecule to the systemic circulation. In addition, owing to its unique design and small dimensions, the dosage forms do not elicit significant saliva production, thus reducing the potential for ingestion of the released drug. Both factors contribute to the higher and more uniform drug absorption from the sublingual cavity.

An additional part of this study in Example 4 was the determination of the bioavailability of swallowed sufentanil dosage forms. Since there is little to no data on sufentanil GI bioavailability in the literature, it was important to further evaluate the low bioavailability of this route of administration to further support the observation that drug from the sublingual dosage forms could not be swallowed and maintain a high bioavailability. As indicated by the PK analysis data in Table 7, oral bioavailability of sufentanil from the swallowed dosage forms is very low, approximately 12%. In addition, as predicted from the known erratic GI uptake of fentanyl, the swallowed dosage forms demonstrated extremely high variability both in the amount of drug absorbed (AUC) and the pharmacokinetics of absorption ($C_{max}$, $T_{max}$) as shown in Table 7. These data support the conclusion that bioadhesive sublingual dosage forms strongly adhere in the sublingual cavity in such a manner that they don't dislodge, thus avoiding oral ingestion and avoiding the high variability of plasma levels which is typical when drug is absorbed via the GI route.

Additional studies evaluating alfentanil, formulated into small volume dosage forms were performed in Beagle dogs and are more fully described in Example 5 below.

Alfentanil dosage forms resulted in a bioavailability of 94% compared to IV alfentanil and a coefficient of variation of 5% for the AUC, 7% for $C_{max}$ and 28% for $T_{max}$ The Therapeutic Time Ratio was calculated as 0.33, compared to 0.04 for the IV alfentanil arm of this study (calculated using a published IV elimination half-life of 104 min for alfentanil in dogs). Therefore, the alfentanil formulation (as described in Example 5) produces an 8-fold improved Therapeutic Time Ratio over the IV alfentanil arm. The high bioavailability of this formulation again supports the claim that minimal swallowing of drug occurs with use of the dosage forms.

X. Utility of Small-Volume Oral Transmucosal Dosage Forms

The claimed dosage forms find utility in delivery of any drug that can be administered by the oral transmucosal route. The small volume of the oral transmucosal dosage forms is that they provide for high bioavailability, low variability in $T_{max}$, low variability in $C_{max}$ and low variability in AUC. The dosage forms also provide for prolonged plasma levels within the therapeutic window.

In one exemplary embodiment described in detail herein, the dosage forms find utility in treating a subject suffering from pain that may be associated with any of a variety of identifiable or unidentifiable etiologies. In this embodiment, the dosage forms find utility in suppression or mitigation of pain. The term "treatment" or "management" of pain is used here to generally describe regression, suppression, or mitigation of pain so as to make the subject more comfortable, as determined for example by pain score.

The invention finds utility in the treatment of both opioid naive patients and opioid tolerant patients.

The term "opioid naive patient" is used herein with reference to a patient who has not received repeated administration of an opioid substance over a period of weeks to months.

The term "opioid tolerant patient" as used herein means a physiological state characterized by a decrease in the effects of an opioid substance (e.g., analgesia, nausea or sedation) with chronic administration. An opioid substance is a drug, hormone, or other chemical substance that has analgesic, sedative and/or narcotic effects similar to those containing opium or its derivatives. If analgesic tolerance develops, the dose of opioid substance is increased to result in the same level of analgesia. This tolerance may not extend to side effects and side effects may not be well tolerated as the dose is increased.

The dosage forms find particular utility in the treatment of acute pain or other conditions "in the field", i.e., under highly sub-optimal conditions. Paramedics or military medics often are required to treat severe acute pain or other injuries or conditions in non-sterile situations, where needles used for IV or IM administration can result in unintended needle sticks, risk of infection, etc. Oral opioid tablets often take 60 minutes to provide relief which is too long for someone in severe pain. The claimed dosage forms find utility in addressing this need.

When the dosage forms are used for the treatment of pain, the claimed methods and systems find utility in administration of drugs to pediatric and adult populations and in treatment of human and non-human mammals, as well as in opioid tolerant and opioid naive patient populations.

Application of the claimed methods and systems is not limited to any particular therapeutic indication. As such, the claimed dosage forms find utility in administration of drugs to pediatric and adult populations and in the treatment of human and non-human mammals.

The dosage forms find utility in pediatric applications, since the comfortable and secure nature of the dosage form allows children to readily accept this mode of therapy and will reliably deliver drug transmucosally. Specific examples include, but are not limited to, treatment of pediatric acute pain when IV access is not available or inconvenient, treatment of pediatric asthma when the child is not able to use an inhaled route of administration effectively, treatment of nausea when a child can not or will not swallow a pill, pre-procedural sedation when a child is NPO (no oral intake allowed) or a more rapid onset is required.

The dosage forms find further utility in veterinary applications. Specific examples include, but are not limited to, any treatment of an acute condition for which IV administration is not readily available or inconvenient, such as pain relief, anxiety/stress relief, pre-procedural sedation, etc.

The following examples are provided to illustrate the invention and are not intended to limit any aspect of the invention as set forth above or in the claims below.

The dosage forms for the dosage forms described above can be tested for in vivo drug pharmacokinetics in both humans and a suitable animal model following sublingual administration.

The following examples demonstrate the ability of the dosage forms to allow a consistent absorption profile of sufentanil citrate following sublingual administration in human volunteers and awake, alert Beagle dog model.

Example 1

Sublingual Sufentanil Dosage Forms Administered Sublingually in Adult Human Volunteers

TABLE 1

| | Sufentanil Formulations Used in the Human Clinical Study | | | | | | | | |
|---|---|---|---|---|---|---|---|---|---|
| | #46 2.5 μg Sufentanil Base | | | #47 5.0 μg Sufentanil Base | | | #47 5.0 μg Sufentanil Base | | |
| Ingredient | Mass in Batch (g) | Mass in tablet, mg | % Mass in tablet, w/w | Mass in Batch (g) | Mass in tablet, mg | % Mass in tablet, w/w | Mass in Batch (g) | Mass in tablet, mg | % Mass in tablet, w/w |
| Sufentanil Citrate | 0.3750 | 0.00375 | 0.068 | 0.75 | 0.0075 | 0.068 | 1.5000 | 0.0150 | 0.273 |
| Mannitol 200SD | 406.60 | 4.066 | 79.931 | 406.30 | 4.063 | 79.931 | 405.500 | 4.055 | 73.727 |
| Poloxamer (Lutrol F68) | 11 | 0.110 | 2.000 | 11 | 0.110 | 2.000 | 11 | 0.110 | 2.000 |
| Polyox WSR 303 | 16.5 | 0.165 | 3.000 | 16.5 | 0.165 | 3.000 | 16.5 | 0.165 | 3.000 |
| PEG-8000 | 82.5 | 0.825 | 15.001 | 82.5 | 0.825 | 14.999 | 82.5 | 0.825 | 15.000 |
| Stearic Acid | 27.5 | 0.275 | 5.000 | 27.5 | 0.275 | 5.000 | 27.5 | 0.275 | 5.000 |
| Mg Stearate | 5.5 | 0.055 | 1.000 | 5.5 | 0.055 | 1.000 | 5.5 | 0.055 | 1.000 |
| Total | 549.975 | 5.49975 | 100 | 550.050 | 5.005 | 100 | 550.000 | 5.5 | 100 |
| Calculated Strength (Sufentanil base) | | | 0.002506159 | | | 0.005012 | | | 0.0100255? |

A human clinical study was performed using healthy volunteers. The study was performed with 12 subjects (6 men and 6 women) using Sufentanil dosage forms (formulations #46-#48 shown in Table 1) manufactured to have a volume of 5 μL, a mass of approximately 5.5 mg, and determined to have a uniform size for all dosage strengths with dimensions of approximately 3 mm in diameter and 0.8 mm in thickness. Sufentanil dosage forms contained either 2.5 mcg, 5 mcg or 10 mcg of sufentanil base corresponding to 3.7 mcg, 7.5 mcg or 15 mcg of sufentanil citrate, respectively. All excipients were inactive and have GRAS ("generally recognized as safe") status. The sufentanil dosage forms were tested for sublingual use. Study staff administered individual dosage forms to a subject by placing them directly at the base of the frenulum using blunt-tipped forceps.

For bioavailability calculations, intravenous sufentanil, 5 mcg was diluted in 0.9% saline to a total volume of 20 mL, and was administered through an IV catheter as a continuous infusion over 10 minutes. Plasma samples were drawn from a different IV catheter at a remote location. This human trial was a cross-over design with wash-out periods between transitions from higher to lower doses. Subjects were blocked with the opioid antagonist naltrexone daily to avoid opioid-induced side-effects. Day 0: IV sufentanil Infusion: Seventeen samples were collected: −5.0 (before the start of infusion), 2.5, 5, 7.5, 10, 12.5, 15, 20, 30, 45, 60, 90, 120, 160, 320, 480 and 640 minutes Day 2: sublingual 2.5 mcg sufentanil dosage forms; Seventeen samples: −5.0 (before dosage form administration), 2.5, 5, 7.5, 10, 12.5, 15, 20, 30, 45, 60, 90, 120, 160, 320, 480 and 640 minutes Day 3: sublingual 5.0 mcg sufentanil dosage forms; Seventeen samples: −5.0 (before dosage form administration), 2.5, 5, 7.5, 10, 12.5, 15, 20, 30, 45, 60, 90, 120, 160, 320, 480 and 640 minutes Day 4: sublingual 10.0 mcg sufentanil dosage forms; Seventeen samples: −5.0 (before dosage form administration), 2.5, 5, 7.5, 10, 12.5, 15, 20, 30, 45, 60, 90, 120, 160, 320, 480 and 640 minutes Day 7: sublingual 5.0 mcg sufentanil dosage forms repeated 4 times at 10 minute intervals; Twenty three samples: −5.0 (before the first dosage form administration), 5, 7.5 minutes 10 (immediately prior to the second dosage form administration), 15, 17.5 minutes 20 (immediately prior to the third dosage form administration), 25, 27.5 minutes 30 (immediately prior to the fourth dosage form administration), 35, 40, 45, 50, 55, 60, 90, 120, 150, 190, 350, 510 and 670 minutes.

The total volume of blood required for pharmacokinetic sampling was approximately 455 mL.

Sufentanil concentrations in plasma samples were determined using a validated LC-MS/MS sufentanil human plasma assay. The assay demonstrated good inter-day precision and accuracy at the high, medium and low quality control sample concentrations.

The dosage forms for this study eroded over a period of 10-30 minutes in all subjects. After placement of each sufentanil sublingual dosage forms in the sublingual cavity of the 12 healthy volunteers, a remarkably consistent pharmacokinetic profile was obtained for the three dosages (FIG. 43).

TABLE 2

PK Analyses of the IV (5 mcg) and Sublingual Sufentanil Dosing Arms in the Human Clinical Study using Three Dosage Strengths (2.5 mcg = #46, 5 mcg = #47, 10 mcg = #48)

| Group | AUC (hr * ng/ml) (mean ± SD) | F (%) | Absorption Variability (% CV) | $C_{max}$ (pg/mL) | $T_{max}$ (min) | Plasma Elimination Half-life (hr) | Therapeutic Time Ratio[1] |
|---|---|---|---|---|---|---|---|
| Intravenous Sufentanil | 0.0368 ± 0.0076 | — | 20.7 | 0.0813 ± 0.0281 | 9.6 ± 1.8 | 1.19 ± 0.18 | 0.067 |
| Sublingual Sufentanil dosage form (Formulation #46) | 0.0178 ± 0.0044 | 97.8 | 24.7 | 0.0068 ± 0.0021 | 43.8 ± 7.8 | 1.65 ± 0.43 | 0.74 |
| Sublingual Sufentanil dosage form (Formulation #47) | 0.273 ± 0.0093 | 76.7 | 34.1 | 0.0109 ± 0.0035 | 46.2 ± 17.4 | 1.54 ± 0.57 | 0.75 |
| Sublingual Sufentanil dosage form (Formulation #48) | 0.0705 ± 0.0194 | 98.2 | 27.5 | 0.0275 ± 0.0077 | 40.8 ± 13.2 | 1.71 ± 0.40 | 0.72 |
| Repeat Dosing of #47 Sufentanil dosage form every 10 min. x 4 | 0.1403 ± 0.0361 | 96.4 | 25.7 | 0.0464 ± 0.0124 | 62.4 ± 13.8 | 1.97 ± 0.30 | NA |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from literature and is 148 min in humans for sufentanil.

Example 2

In Vivo Evaluation of Sublingual Sufentanil Dosage Forms in a Dog Model

The following Examples 2-5 are using the Beagle dog model and the formulations for the dosage forms all are using a dosage form with a total mass of 5.5 mg. The in vivo pharmacokinetics (PK) of sufentanil following sublingual administration of the 5 mcg dosage forms (formulation #44 for dogs, which is the same as the human formulation #47) described above were evaluated in a healthy Beagle dog model. Briefly, single 5 mcg dosage forms described above were administered sublingually in fully awake healthy dogs by direct placement in the sublingual cavity. A total of three dogs were evaluated. Following administration, the position of the dosage form in the sublingual cavity was observed visually at 5-15 minute intervals following administration. The sublingual sufentanil PK was compared with that of IV administered sufentanil at the same dose level.

All dogs were catheterized via the cephalic vein for blood collections up to 2 hours post-dosing. Through the 2-hour post-dose blood collection, all dogs were fitted with an Elizabethan collar to prevent removal of the catheter. The catheter was removed following the 2-hour blood collection. The 4-, 8-, and 24-hour post-dose blood collection were collected from the cephalic or other suitable vein. Approximately 2 ml of blood were collected into pre-chilled tubes containing potassium EDTA at the following time points: prior to dosing and approximately 1, 3, 5, 10, 15, 30 min, 1, 2, 4, 8 and 24 hours post-dose. The samples were analyzed with the appropriately validated LC/MS/MS method for the determination of sufentanil citrate in dog plasma. The sufentanil plasma concentrations and the pharmacokinetic results are shown in FIG. 44 and Table 3.

TABLE 3

PK Analysis of the IV (5 mcg) and the Sublingual Sufentanil Dosing Arms in Beagle Dogs.

| Group | AUC (hr * ng/ml) (mean ± SD) | F (%) | Absorption Variability (% CV) | $C_{max}$ (pg/mL) | $T_{max}$ (min) | Plasma Elimination Half-life (min) | Therapeutic Time Ratio[1] |
|---|---|---|---|---|---|---|---|
| Intravenous Sufentanil | 211.5 ± 48.2 | — | 22.8 | 536.7 ± 186.1 | 1.6 ± 0.6 | 10.3 ± 4.5 | 0.05 ± 0.02 |
| Sublingual Sufentanil dosage form (Formulation #44) | 161.2 ± 23.1 | 74.8 ± 10.7 | 14.3 | 222.7 ± 25.9 | 11.7 ± 2.5 | 33.3 ± 5.8 | 0.28 ± 0.16 |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from literature and is 139 min in beagle dogs for sufentanil.

Example 3

Exemplary Sufentanil Dosage Forms to Control Drug Release and In Vivo Pharmacokinetics For purposes of illustration, a longer duration dosage form (formulation #58) was prepared with sufentanil citrate in order to evaluate a slower rate of drug release and in vivo pharmacokinetics of a longer-acting dosage form. This slower disintegrating sufentanil dosage form, as described in Table 4 was prepared by direct compression and tested as described above. The range of erosion times in dogs was 35-120 minutes and the bioadhesion of the placebo formulation was measured as described above and determined to be 0.18±0.08 N/cm².

Sample analysis was performed using a validated LC/MS/MS method for analysis of sufentanil in dog plasma. Pharmacokinetic analysis was performed using a non-compartmental model of absorption. The results of a limited PK analysis are shown in Table 5.

TABLE 4

Slow Disintegrating Sufentanil Formulation

| Composition | Formulation # 58 |
|---|---|
| Sufentanil citrate | 0.5456 |
| Mannitol | 40.3 |
| Carbopol 971 | 20.00 |
| PEG 8000 | 25.60 |
| HPMC | 10.00 |

TABLE 4-continued

Slow Disintegrating Sufentanil Formulation

| Composition | Formulation # 58 |
|---|---|
| Polyox 303 | 2.60 |
| Mg Stearate | 1.00 |
| Total | 100.00 |

TABLE 5

PK Analyses for the Slow-Disintegrating Sublingual Sufentanil Dosage Form in Beagle Dogs.

| Group | Plasma Elimination Half-life (min) | Therapeutic Time Ratio[1] |
|---|---|---|
| Sublingual formulation # 58 | 205 ± 93.1 | 1.13 ± 0.69 |

[1]Represents the relative time that the drug achieves therapeutic levels (above 50% of $C_{max}$) and is calculated by the formula: TTR = (Time spent above 50% of $C_{max}$)/(IV Terminal elimination half-life). The denominator is obtained from literature and is 139 min in beagle dogs for sufentanil.

Example 4

In Vivo Study of Sublingual Sufentanil Solution and Swallowing of Sufentanil Dosage Forms in a Dog Model A. Evaluation of Bioavailability of Sufentanil Following Sublingual Administration of a Solution Dosage Form The bioavailability of sufentanil following sublingual administration from a solution as compared to that intravenously was evaluated in a healthy, conscious Beagle dog animal model, as indicated in Table 6. In both arms of the study the commercially available formulation of sufentanil citrate (Sufenta® 50 μg/mL) was used and was dosed at the same total dose of 5 mcg of sufentanil base. Intravenous administrations (Group 1) were performed by single administration (n=3) of Sufenta® 50 μg/mL by bolus injection to the cephalic vein via a sterile needle and syringe of appropriate size. For the sublingual administrations (Group 2) the test article was prepared by appropriately diluting Sufenta® 50 μg/mL with 0.9% w/w to the same final dose of 5 mcg of sufentanil base and was administered twice sublingually (n=6 total), with each dose separated by a minimum of a 2-day washout. Doses were slowly applied under the tongue, adjacent to the frenulum via a sterile syringe. Blood samples were collected from a jugular or other suitable vein prior to dosing and approximately 1, 3, 5, 10, 15, 30 min, 1, 2, 4, 8 and 24 hours post-dose. Approximately 2 mL of blood were collected per time-point into pre-chilled tubes containing $K_2$ EDTA. The samples were centrifuged at 3,000.times.g for approximately 10 minutes in a refrigerated centrifuge. Plasma was collected and frozen within 20 minutes of centrifugation at approximately −70° C. and was maintained at the same temperature until analysis. Sample analysis was performed using a validated LC/MS/MS method for analysis of sufentanil in dog plasma.

Pharmacokinetic analysis was performed using a non-compartmental model of absorption. The sufentanil plasma concentrations are graphed in FIG. 45. The results of the PK analysis are shown in Table 7.

B. Evaluation of Bioavailability of Sufentanil Following Oral Ingestion of a Dosage Form The bioavailability of sufentanil following ingestion of a 5 mcg sufentanil dosage form (formulation #44, which is the same formulation as #47 used in the human study above) as compared to intravenous sufentanil administration was evaluated in a healthy, conscious Beagle dog animal model, as described in the previous example. A single 5 mcg dosage form was administered twice orally, with each dose separated by a minimum of a 2-day washout for a total of n=6 (Table 6). The dosage forms were placed manually as far back as possible in the throat and flushed with water to promote the swallow response in the animal. Pharmacokinetic analysis was performed using a non-compartmental model of absorption. The sufentanil plasma concentrations are shown graphed in FIG. 45. The results of the PK analysis are shown in Table 7.

TABLE 6

Organization of Test Groups

| Group | Treatment | Dose Level (μg)[a] | Route of Administration | Number of animals[b] | Total Number of Animals, n |
|---|---|---|---|---|---|
| 1 | Sufentanil solution | 5.0 | IV | 3 | 3 |
| 2 | Sufentanil solution | 5.0 | Sublingual | 3[c] | 6 |
| 3 | Ingested Sufentanil dosage form | 5.0 | Oral | 3[c] | 6 |

[a] = expressed as free base.
[b] = Same animals will be used for Groups 1 through 3 with a minimum 2-day washout period between dosing.
[c] = Groups 2 & 3 animals were dosed twice with a minimum 2-day washout period for a total of n = 6
[d] = Normal (0.9% w/w saline) was used to dilute the test article (Sufenta ® 50 μg/mL) to the desired concentration.

TABLE 7

PK Analyses of Intravenously Administered Sufentanil Compared to a Sublingually Instilled Sufentanil Solution and an Ingested Sufentanil Dosage Form in Beagle Dogs.

| Group | AUC (mean ± SD) | F (%) | Absorption Variability (% CV) | $T_{max}$ (min) | $C_{max}$ (pg/mL) | Plasma Elimination Half-life (min) | Therapeutic Time Ratio[1] |
|---|---|---|---|---|---|---|---|
| Intravenous Sufentanil | 123.3 ± 49.3 | — | 21.8 | 1.0 ± 0.0 | 536.7 ± 186.1 | 2.8 ± 0.4 | 0.02 ± 0.0 |
| Sublingual Sufentanil solution | 58.3 ± 36.4 | 40.0 ± 32.7 | 81.8 | 4.3 ± 1.0 | 236.4 ± 170.0 | 8.3 ± 4.5 | 0.04 ± 0.02 |
| Ingested dosage form | 15.9 ± 22.4 | 12.2 ± 15.3 | 134.2 | 14.6 ± 9.9 | 33.8 ± 33.2 | 22.5 ± 16.8 | 0.13 ± 0.09 |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from literature and is 139 min in beagle dogs for sufentanil.

Example 5

In Vivo Evaluation of Sublingual Alfentanil HCl Dosage Forms in a Dog Model

For purposes of illustration of another drug use for the dosage form, an additional dosage form was prepared with alfentanil HCl in order to demonstrate the ability of the dosage forms described in this application to effectively improve the PK of alfentanil compared to that of the IV route of administration. The formulation composition, a medium disintegrating dosage form, is described in Table 8. The erosion time in dogs of formulation #63 was 20 minutes and the bioadhesion was measured at 0.056±0.01 N/cm² for the placebo formulation.

The dosing parameters for this study are shown in Table 9. The alfentanil plasma concentrations are graphed in FIG. 46. PK analysis was performed using a non-compartmental absorption model. The results of the PK analysis are shown in Table 10. Blood sampling and storage mirrored the conditions described earlier; sample analysis was performed using a validated LC/MS/MS method for analysis of alfentanil in dog plasma.

TABLE 8

Exemplary Alfentanil Dosage Form

| Formulation # 63 | % composition |
|---|---|
| Alfentanil HCl | 5.00 |
| Mannitol | 52.00 |
| Carbopol 974 | 7.00 |
| PEG 8000 | 35.00 |
| Mg Stearate | 1.00 |
| Total | 100.00 |

TABLE 9

Dosing Parameters for Administration of Sublingual Alfentanil Dosage Forms and an Intravenous Alfentanil Solution in Beagle Dogs.

| Group | Treatment | Dose Level (μg)$^a$ | Route of Administration | Number of animals (Males) |
|---|---|---|---|---|
| 1 | Alfentanil solution | 253.0 | IV | 3 |
| 2 | Alfentanil dosage form | 239.0 ± 16.2 | Sublingual | 2 |

$^a$= expressed as free base.
$^b$= Same animals were used for Groups 1 and 2 with a minimum 2-day washout period between dosing.

TABLE 10

PK Analyses of Alfentanil Sublingual Dosage Forms compared to Intravenous Alfentanil in Beagle Dogs.

| Group | AUC (hr * ng/ml) (mean ± SD) | F (%) | Absorption Variability (% CV) | $T_{max}$ (min) | $C_{max}$ (pg/mL) | Plasma Half-life (min) | Therapeutic Time Ratio[1] |
|---|---|---|---|---|---|---|---|
| Intravenous Alfentanil | 15.3 ± 1.6 | — | 10.5 | 1 ± 0 | 139.1 ± 76.4 | 4.4 ± 2.4 | 0.04 ± 0.02 |
| Sublingual Alfentanil dosage form | 14.4 ± 0.7 | 94.1 ± 4.6 | 4.9 | 15.0 ± 4.2 | 35.5 ± 2.6 | 40.8 ± 8.5 | 0.33 ± 0.07 |

[1]Represents the relative time that the drug achieves therapeutic levels (above 50% of $C_{max}$) and it is calculated by the formula: TTR = (Time spent above 50% of $C_{max}$)/(IV Terminal elimination half-life). The denominator is obtained from literature and is 104 min. in beagle dogs.

Example 6

Acute Pain Management in the Outpatient Setting by Administering a Sufentanil-Containing Dosage Form Using a Device A pharmacist loads a drug dispensing device with a drug cartridge which includes 40 sufentanil dosage forms. Each cartridge has two colored initialization tablets (called "shipping tablets") arranged to be the first two tablets dispensed. The device has a means for loading the cartridge, which is either a port, hatch, or door that is secure and inaccessible to unauthorized users. Once the pharmacist has loaded the cartridge into the device, he locks the device access port, hatch or door. The pharmacist then docks the dispensing device for the first time to a dock that is connected to a personal or other computer, using the docking connector, and then programs the device. Programming involves uploading the dosage strength of the dosage forms, the number of dosage forms loaded in the device, the prescribed frequency of dosage form usage, the number of dosage forms to be used per day, the current date and time, the preferred language, a valid thumbprint or other identification for identifying the patient, and the physician's identification information, in case the device is lost and found.

Once the dispensing device is programmed, the pharmacist demonstrates proper usage and tests the device by dispensing a single shipping tablet. The pharmacist then gives the dispensing device to the patient and observes the patient dispense a shipping tablet to ensure proper usage and functionality. Along with the dispensing device, the pharmacist provides the patient with a radio frequency identification (RFID) tag that must be within approximately 5 inches of the device to allow the dispensing device to operate.

When the patient wants to administer a dose of the drug, he or she will hold the dispensing device, and push any button to wake the device up from its sleep mode. The device will query the user for either a thumbprint reading or a personal identification number (PIN). The device will then search for a validated RFID key within range. Once these conditions are met, the dispensing device will query its internal memory and clock to make sure that the dosage regimen programmed by the pharmacist is not being violated by the current usage request. At this point the device displays status information, such as the date and time, the number of doses left, the last time a dosage was used, the patient's name, etc., and the pharmacist informs the patient that the device is ready to dispense the dosage forms by a visual and/or audible signal.

The patient will hold the dispensing end of the device under his or her tongue and press the dispensing lever. When the dosage form is dispensed a tone will sound to inform the patient that the dosage form was properly delivered. At this point the device will lock down to prevent further dispensing until the preprogrammed lock-out time has passed, at which time the device will be ready to use again.

Example 7

Acute Pain Management in the Inpatient Setting by Administering a Sufentanil-Containing Dosage Form Using a Device A post operative patient requires acute pain treatment following surgery. The surgeon prescribes oral transmucosal sufentanil to be administered using the drug dispensing device. The attending nurse takes the prescription order to the pharmacist or automated pharmaceutical inventory management system (e.g. Pyxis) and obtains a sufentanil-containing drug cartridge for sublingual delivery. The cartridge is labeled and equipped with an RFID electronic tag containing drug label information. The cartridge is labeled and equipped with an RFID electronic tag containing drug label information.

The nurse then takes a disposable dispensing portion of the drug dispensing device from inventory, and proceeds to a base station to obtain a reusable controller portion of the drug dispensing device that has completed its recharge cycle and is ready for use. The nurse inserts the drug cartridge into the disposable dispensing portion, and then affixes this to the reusable controller portion of the drug dispensing device and locks the disposable portion into the reusable portion of the drug dispensing device. At this point the device reads the RFID tag on the drug cartridge and uploads the appropriate drug information, including the type of drug, the dosage strength, the programmed lockout period between doses, etc. The nurse confirms the proper drug cartridge information has been read by the drug dispensing device and gives the drug dispensing device to the patient for patient controlled dispensing of the pain medication.

When the patient requires pain medication, she takes the drug dispensing device in her hand, and places the dispensing tip in her mouth, under her tongue and presses the dispense button. The drug dispensing device then does an internal check to ensure that the proper lockout period has elapsed since the last dosage dispense. At this point the drug dispensing device dispenses a dosage form under the patient's tongue and provides feedback that dosing was successful. The patient removes the drug dispensing device from her mouth and allows the sublingual dosage form to dissolve under her tongue. The patient may attempt to dispense as frequently as she desires, but the drug dispensing device will only allow successful dosing after the appropriate lockout period has elapsed. The drug dispensing device electronically logs the dispensing attempts and successful dispenses in its dosing history.

Periodically the nurse checks on the patient and drug dispensing device. During such checks, the nurse inspects the drug dispensing device to see that there are no errors and to check the number of remaining dosage forms in the drug dispensing device, and returns it to the patient.

When the patient is discharged, the nurse takes the drug dispensing device and unlocks the reusable portion from the disposable portion, disposes of the cartridge and disposable portion of the drug dispensing device. The nurse then connects the reusable portion of the device to a computer and uploads the patient use information from the drug dispensing device to the computer for input into the patient's medical records. The nurse cleans the reusable controller portion and returns it to the base station for recharging.

Example 8

Acute Pain Management in the Inpatient Setting by Administering a Sufentanil-Containing Dosage Form Using a Device and a Portable Dock A post operative patient requires acute pain treatment following surgery. The surgeon prescribes oral transmucosal sufentanil to be administered using the drug dispensing device. The attending nurse takes the prescription order to the pharmacist or automated pharmaceutical inventory management system (e.g. Pyxis) and obtains a sufentanil-containing drug cartridge for sublingual delivery. The cartridge is labeled and equipped with an RFID electronic tag containing drug label information. The cartridge is labeled and equipped with an RFID electronic tag containing drug label information. The cartridge includes a shipping tablet or initialization tablet in the first to be dispensed location of the dosage form stack.

The nurse then takes a disposable dispensing portion of the drug dispensing device from inventory, and proceeds to a base station to obtain a reusable controller portion of the drug dispensing device that has completed its recharge cycle and is ready for use. The nurse inserts the drug cartridge into the disposable dispensing portion, and then affixes this to the reusable controller portion of the drug dispensing device. Next, the nurse takes a portable dock (or docking fob) from the base station where it has been recharging, and docks the assembled drug dispensing device to the portable dock. The portable dock and the assembled drug dispensing device communicate electronically and a setup menu comes up on the portable dock for setting up the drug dispensing device.

At this point the device locks the reusable and disposable portions together, reads the RFID-tag on the drug cartridge and uploads the appropriate drug information, including the type of drug, the dosage strength, the lockout period between doses, etc. The dispensing device writes a code to the RFID tag on the cartridge identifying it as a used cartridge. The nurse enters her fingerprint in the fingerprint reader on the portable dock to gain secured access and proceeds to set up the drug dispensing device for use. The set up procedure includes entering patient identification, the nurse's identification, confirming the proper time on the device, and confirming the proper drug cartridge information. The nurse then takes a disposable RFID bracelet and places this adjacent to the drug dispensing device at which point the drug dispensing device reads the tag and the nurse confirms that the proper bracelet tag has been read.

The nurse then confirms proper setup of the drug dispensing device by pressing the dispensing button once. The drug dispensing device actuates, dispensing the shipping tablet facsimile into the nurses hand, confirming proper operation. The drug dispensing device detects the dispensing of the shipping tablet, allowing for an internal system check of proper operation and internal calibration of the newly assembled system. If the internal dispensing check is successful, the portable dock queries the nurse to confirm that the shipping table was properly dispensed, and the nurse confirms the proper setup. The nurse then disengages the drug dispensing device from the portable dock, and proceeds to the patient's bedside for the final steps of setup.

The nurse places the RFID bracelet on the patient's wrist and affixes a theft resistant tether to the patient's bed and the other end to the drug dispensing device. The nurse then instructs the patient on proper use of the sublingual drug dispensing device, and gives the drug dispensing device to the patient for patient controlled dispensing of sufentanil.

When the patient requires pain medication, she takes the drug dispensing device in her hand, and places the dispensing tip in her mouth, under her tongue and presses the dispensing button. The drug dispensing device then does an internal check to ensure that the proper lockout period has elapsed since the last dosage dispense, and that the patient's RFID bracelet is present and readable. At this point the drug dispensing device dispenses a dosage form under the patient's tongue and provides a feedback that dosing was successful. The patient removes the drug dispensing device from her mouth and allows the sublingual dosage form to dissolve under her tongue. The patient may attempt to dispense as frequently as she desires, but the drug dispensing device will only allow successful dosing after the appropriate lockout period has elapsed. The drug dispensing device electronically logs the dispensing attempts and successful dispenses in its dosing history.

Periodically the nurse checks on the patient and device. During such a patient check in the nurse brings a portable docking FOB and docks the device to the FOB. The electronic connection enables the nurse to download the information from the drug dispensing device to the fob. This information includes the use history, drug information, number of remaining dosage forms and duration of use since initial set up. The nurse then enters her fingerprint in the finger print scanner to gain access to the information and to drug dispensing device. Because the patient is requiring an additional dose of drug prior to the lockout period expiring, the nurse overrides the lockout period and then returns the drug dispensing device to the patient at which point the patient is able to take another dose.

The nurse leaves the patient's room with the portable docking FOB and returns to the nurse's station to record the dosing history in the patient's records. When finished the nurse returns the FOB to the base station for recharging.

When the patient has used all of the dosage forms in the drug dispensing device, the nurse brings the portable docking fob into the patient's room and docks the drug dispensing device to the FOB. The nurse then enters her fingerprint in the fingerprint scanner on the fob to gain secured access to the drug dispensing device. Next, the nurse unlocks the security tether and disconnects the drug dispensing device from the bed. She then unlocks the drug dispensing device and removes it from the fob for disassembly. The nurse disconnects the disposable portion from the reusable portion, and removes the cartridge from the disposable portion. The nurse disposes of the disposable portion and the cartridge, and wipes the reusable controller portion with an antiseptic wipe to clean it before returning it to the base station. The reusable controller portion requires that the nurse return it to the base station where it recharges and runs an internal diagnostic test before being ready for use again.

The nurse then proceeds to set up a new drug dispensing device as described above and provides this to the patient.

Although the foregoing invention has been described in some detail by way of illustration and example for purposes of clarity and understanding, it will be apparent to those skilled in the art that certain changes and modifications may be practiced. Various aspects of the invention have been achieved by a series of experiments, some of which are described by way of the following non-limiting examples. Therefore, the description and examples should not be construed as limiting the scope of the invention, which is delineated by the appended description of exemplary embodiments.

The invention claimed is:

1. An apparatus, comprising:
a dispensing mechanism of a delivery device being rotatable in a first direction, the delivery device configured to dispense a drug-containing tablet to an oral mucosal membrane of a patient, the dispensing mechanism being configured to move a push rod within a delivery passage of the delivery device when the dispensing mechanism is rotated in the first direction to dispense the drug-containing tablet from the delivery device; and
a processor operatively coupled to the dispensing mechanism, the processor configured to control the dispensing mechanism to inhibit delivery of the drug-containing tablet during a predetermined lockout period.

2. The apparatus of claim 1, wherein the lockout period includes at least one of a fixed time interval, a predetermined time interval, a predetermined variable time interval, a time interval determined by an algorithm or a variable time interval communicated to the device from a remote computer, docking station or other device.

3. The apparatus of claim 1, wherein the lockout period has a duration within the range of about 1 minute to about 60 minutes.

4. The apparatus of claim 1, wherein the lockout period is programmable.

5. The apparatus of claim 1, wherein the delivery device emits a first light when the delivery device is in the lockout period, the delivery device emits a second light when the delivery device is not in the lockout period and is ready to dispense the drug-containing tablet.

6. The apparatus of claim 1, wherein the drug-containing tablet is a first drug-containing tablet, the lockout period configured to end upon expiration of a predetermined duration of time after a second drug-containing tablet was dispensed from the delivery device.

7. The apparatus of claim 1, wherein the delivery device is associated with a patient, a duration of the lockout period is determined based at least in part on at least one of a dosing history of the patient, one or more dosing requests received from the patient by the delivery device, or a pharmacokinetic property of the drug-containing tablet.

8. The apparatus of claim 1, wherein the dispensing mechanism includes a hub coupled to a first end portion of the push rod, rotation of the hub in the first direction acting to move a second end portion of the push rod from a first position with respect to the delivery passage to a second position with respect to the delivery passage.

9. The apparatus of claim 1, wherein:
the dispensing mechanism includes a hub and a motor configured to rotate the hub, and
the processor is configured to send a signal to the motor to rotate the hub when (1) a dispensing request is received by the processor, and (2) the lockout period has expired.

10. The apparatus of claim 1, wherein the delivery device emits at least one of an audible or tactile indication associated with dispensing the tablet from the delivery device.

11. The apparatus of claim 1, wherein the tablet includes a dosage of sufentanil.

12. An apparatus, comprising:
a housing of a delivery device including a dispensing end configured to facilitate delivery of a first drug-containing tablet into the mouth of a patient, the dispensing end defining a delivery pathway through which the first drug-containing tablet may be passed for dispensing of the first drug-containing tablet;

a push rod, at least a portion of the push rod being movably disposed within the delivery pathway of the dispensing end of the delivery device;

a rotary actuator coupled to the push rod, the rotary actuator configured to move a first end portion of the push rod within the delivery pathway to dispense the first drug-containing tablet from the delivery device; and a lockout mechanism configured to control the rotary actuator to prevent dispensing of a second drug-containing tablet during a lockout period after the first drug dosage tablet is dispensed.

13. The apparatus of claim 12, wherein the lockout mechanism includes a processor configured to send a signal to actuate the rotary actuator for dispensing the second drug-containing tablet from the delivery device, the processor configured to not send the signal during the lockout period.

14. The apparatus of claim 12, wherein the rotary actuator includes a hub configured to be driven by a motor.

15. The apparatus of claim 12, wherein the lockout period includes at least one of a fixed time interval, a predetermined time interval, a predetermined variable time interval, a time interval determined by an algorithm or a variable time interval communicated to the device from a remote computer, docking station or other device.

16. The apparatus of claim 12, wherein the lockout period has a duration within the range of about 1 minute to about 60 minutes.

17. The apparatus of claim 12, wherein the lockout period is programmable.

18. The apparatus of claim 12, wherein the delivery device emits a first light when the delivery device is in the lockout period, the delivery device emits a second light when the delivery device is not in the lockout period and is ready to dispense the drug-containing tablet.

19. The apparatus of claim 12, wherein the delivery device emits at least one of an audible or tactile indication associated with dispensing the tablet from the delivery device.

20. The apparatus of claim 12, wherein the delivery device is associated with a patient, a duration of the lockout period is determined based at least in part on at least one of a dosing history of the patient, one or more dosing requests received from the patient by the delivery device, or a pharmacokinetic property of the drug-containing tablet.

21. The apparatus of claim 12, wherein:

the rotary actuator is coupled to a second end portion of the push rod, and in response to a signal sent by the lockout mechanism, the rotary actuator rotates the second end portion of the push rod to move a first end portion of the push rod from a first position within the delivery pathway to a second position within the delivery pathway.

22. A method, comprising:

determining at a processor of a delivery device whether the delivery device is in a lockout period, the processor configured to send a signal when the delivery device is not in the lockout period to actuate a rotary actuator of the delivery device for dispensing a drug-containing tablet from the delivery device, the rotary actuator configured upon actuation to move a first end portion of a flexible push rod within a delivery passage of the delivery device, the first end portion of the push rod configured to deliver the drug-containing tablet from the delivery passage of the delivery device; and after the determining, (1) when the delivery device is determined to not be in the lockout period, sending the signal, or (2) when the delivery device is determined to be in the lockout period, inhibiting dispensing of the drug-containing tablet from the delivery device by not sending the signal.

23. The method of claim 22, further comprising:

receiving at the processor of the delivery device a request to dispense the drug-containing tablet, the determining being performed in response to the receiving the request to dispense the drug-containing tablet.

24. The method of claim 22, wherein the lockout period includes at least one of a fixed time interval, a predetermined time interval, a predetermined variable time interval, a time interval determined by an algorithm or a variable time interval communicated to the device from a remote computer, docking station or other device.

25. The method of claim 22, wherein the tablet includes a dosage of sufentanil.

26. The method of claim 22, further comprising:

rotating the rotary actuator in a first direction, the rotating acting to move the first end portion of the push rod within a nonlinear portion of the delivery passage of the delivery device.

27. The method of claim 22, further comprising:

emitting via the delivery device at least one of an audible or tactile indication associated with dispensing the tablet from the delivery device.

* * * * *

UNITED STATES PATENT AND TRADEMARK OFFICE
CERTIFICATE OF CORRECTION

| | | |
|---|---|---|
| PATENT NO. | : 9,642,996 B2 | Page 1 of 1 |
| APPLICATION NO. | : 14/305422 | |
| DATED | : May 9, 2017 | |
| INVENTOR(S) | : Palmer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 195 days.

Signed and Sealed this
Twenty-fifth Day of June, 2019

Andrei Iancu
*Director of the United States Patent and Trademark Office*